(12) United States Patent
Lim et al.

(10) Patent No.: US 12,090,170 B2
(45) Date of Patent: Sep. 17, 2024

(54) METHODS OF TREATING GLIOBLASTOMAS

(71) Applicant: The Regents of the University of California, Oakland, CA (US)

(72) Inventors: Wendell A. Lim, San Francisco, CA (US); Hideho Okada, San Francisco, CA (US); Kole T. Roybal, San Francisco, CA (US); Joseph H. Choe, San Francisco, CA (US); Payal B. Watchmaker, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 908 days.

(21) Appl. No.: 17/042,032

(22) PCT Filed: Apr. 4, 2019

(86) PCT No.: PCT/US2019/025860
§ 371 (c)(1),
(2) Date: Sep. 25, 2020

(87) PCT Pub. No.: WO2019/195596
PCT Pub. Date: Oct. 10, 2019

(65) Prior Publication Data
US 2021/0023139 A1 Jan. 28, 2021

Related U.S. Application Data

(60) Provisional application No. 62/653,929, filed on Apr. 6, 2018.

(51) Int. Cl.
*A61K 35/17* (2015.01)
*A61K 38/17* (2006.01)

(52) U.S. Cl.
CPC .......... *A61K 35/17* (2013.01); *A61K 38/1793* (2013.01)

(58) Field of Classification Search
CPC ................ A61K 35/17; A61K 38/1793; A61K 2039/5156; A61K 2039/5158; A61K 39/0011; A61P 35/00; C07K 14/7051; C07K 2319/03; C07K 16/28
See application file for complete search history.

(56) References Cited

U.S. PATENT DOCUMENTS

| | | |
|---|---|---|
| 9,493,568 B2 | 11/2016 | Reilly et al. |
| 2016/0264665 A1* | 9/2016 | Lim .................... A61K 39/0011 |
| 2017/0210811 A1 | 7/2017 | Wong et al. |
| 2017/0309025 A1 | 10/2017 | O'Rourke et al. |
| 2018/0079812 A1 | 3/2018 | Lim et al. |
| 2018/0085401 A1 | 3/2018 | Wu et al. |
| 2021/0023136 A1 | 1/2021 | Lim et al. |
| 2021/0023138 A1 | 1/2021 | Lim et al. |

FOREIGN PATENT DOCUMENTS

| | | |
|---|---|---|
| WO | WO 2014/130657 A1 | 8/2014 |
| WO | WO 2016/138034 A1 | 9/2016 |
| WO | WO 2017/025038 A1 | 2/2017 |
| WO | WO 2017/087723 A1 | 5/2017 |
| WO | WO 2017/193059 A1 | 11/2017 |
| WO | WO 2018/039247 A1 | 3/2018 |
| WO | WO 2019/195576 A1 | 10/2019 |
| WO | WO 2019/195586 A1 | 10/2019 |

OTHER PUBLICATIONS

Bielamowicz, K et. al. "Trivalent CAR T cells overcome interpatient antigenic variability in glioblastoma", 2017, Neuro-Oncology, 20(4), 506-518. (Year: 2017).*
Bielamowicz, K et. al. "Trivalent CAR T cells overcome interpatient antigenic variability in glioblastoma", 2017, Neuro-Oncology, 20(4), Supplemental Tables 1-3, pp. 1-3. (Year: 2017).*
Genbler, S et. al. "Dual targeting of glioblastoma with chimeric antigen receptor-engineered natural killer cells overcomes heterogeneity of target antigen expression and enhances antitumor activity and survival", 2016, OncoImmunology, 5(4), 1-12. (Year: 2016).*
Hedge, M et. al. "Combinational Targeting Offsets Antigen Escape and Enhances Effector Functions of Adoptively Transferred T Cells in Glioblastoma", 2013, Molecular Therapy, 21(11), 2087-2101. (Year: 2013).*
Suryadevara, CM et. al. "Are BiTEs the 'missing link' in cancer therapy?", 2015, OncoImmunology, 4(6), 1-10. (Year: 2015).*
Dutoit, V et. al. "Exploiting the glioblastoma peptidome to discover novel tumour-associated antigens for immunotherapy", 2012, Brain, 135, 1042-1054. (Year: 2012).*
Johnson et al., "Rational development and characterization of humanized anti-EGFR variant III chimeric antigen receptor T cells for glioblastoma", Science Translational Medicine, 2015, 7(275): 1-16.

(Continued)

*Primary Examiner* — Nelson B Moseley, II
*Assistant Examiner* — Alyssa Rae Stonebraker
(74) *Attorney, Agent, or Firm* — James S. Keddie; Bozicevic, Field & Francis LLP

(57) ABSTRACT

Methods are provided for treating a subject for glioblastoma, including e.g., an EGFRvIII negative glioblastoma. The methods of the present disclosure involve administering to a subject a molecular circuit that includes a binding triggered transcriptional switch (BTTS) that binds to a priming antigen expressed by the subjects glioblastoma multiforme (GBM) that, when bound to the priming antigen, induces one or more encoded therapeutics specific for one or more antigens expressed by the GBM. Nucleic acids containing sequences encoding all or portions of such circuits are also provided, as well as cells, expression cassettes and vectors that contain such nucleic acids. Also provided are kits for practicing the described methods.

13 Claims, 5 Drawing Sheets
Specification includes a Sequence Listing.

(56) References Cited

OTHER PUBLICATIONS

Montano et al., "Expression of EGFRvIII in Glioblastoma: Prognostic Significance Revisited", Neoplasia, 2011, 13(12): 1113-1121.
Sattiraju et al., "IL13RA2 targeted alpha particle therapy against glioblastomas", Oncotarget, 2017, 8(26): 42997-43007.
Chow et al., "T Cells Redirected to EphA2 for the Immunotherapy of Glioblastoma", Molecular Therapy, 2013, 21(3): 629-637.
Migliorini et al. (2018) "CART-Cell Therapies in Glioblastoma: A First Look" Clinical Cancer Research, 24(3): 535-540.
O'Rourke et al. (2017) "A single dose of peripherally infused EGFRvIII-directed CART cells mediates antigen loss and induces adaptive resistance in patients with recurrent glioblastoma" Science Translational Medicine, 9(399):1-15.
Cajal et al., "Beyond molecular tumor heterogeneity: protein synthesis takes control", Oncogene, 2018, 37(19): 2490-2501.
Ding et al., "Clonal evolution in relapsed acute myeloid leukemia revealed by whole genome sequencing", Nature, 2012, 481(7382): 506-510.
Gerlinger et al., "Genomic architecture and evolution of clear cell renal cell carcinomas defined by multiregion sequencing", Nat Genet., 2014, 46(3): 225-233.
Kortum et al., "Targeted sequencing of refractory myeloma reveals a high incidence of mutations in CRBN and Ras pathway genes", Blood, 2016, 128(9): 1226-1233.
Landau et al., "Evolution and Impact of Subclonal Mutations in Chronic Lymphocytic Leukemia", Cell, 2013, 152: 714-726.
Liang et al., "Complex roles of the stroma in the intrinsic resistance to gemcitabine in pancreatic cancer: where we are and where we are going", Experimental & Molecular Medicine, 2017, 49: e406.
Lim et al., "The Principles of Engineering Immune Cells to Treat Cancer", Cell, 2017, 168(4): 724-740.
Rathore et al., "Radiomic MRI signature reveals three distinct subtypes of glioblastoma with different clinical and molecular characteristics, offering prognostic value beyond IDH1", Scientific Reports, 2018, 8: 5087.
Roybal et al., "Synthetic Immunology: Hacking Immune Cells to Expand Their Therapeutic Capabilities", Annu Rev Immunol, 2017, 35: 229-253.
Wang et al., "Clonal Evolution in Breast Cancer Revealed by Single Nucleus Genome Sequencing", Nature, 2014, 512(7513): 155-160.
Akhavan et al., "CAR T cells for brain tumors: Lessons learned and road ahead", Immunol Rev. Jul. 2019, 290(1): 60-84.
Choe et al., "SynNotch-CAR T cells overcome challenges of specificity, heterogeneity, and persistence in treating glioblastoma", Science Translational Medicine, Apr. 28, 2021, 13, eabe7378, 15 pages.
Choi et al., "Engineering Chimeric Antigen Receptor T cells to Treat Glioblastoma", J Target Ther Cancer., Aug. 2017, 6(4): 22-25.
Dauth et al., "Extracellular Matrix Protein Expression Is Brain Region Dependent", The Journal of Comparative Neurology, 2016, 524:1309-1336.
Ferrerosa et al., "IMMU-14. Synnotch Chimeric Antigen Receptor (CAR) T-Cells as a Potential Treatment for Diffuse Intrinsic Pontine Glioma (DIPG)/Diffuse Midline Glioma (DMG)", Jun. 2022, 24(Suppl 1): i84, doi: 10.1093/neuonc/noac079.307.
Mao et al., "Updates On Chimeric Antigen Receptor-Mediated Glioblastoma Immunotherapy", Rhode Island Medical Journal, 2017, 100(6): 39-42.
Nakagawa et al., "Identification of glioblastoma-specific antigens expressed in patient-derived tumor cells as candidate targets for chimeric antigen receptor T cell therapy", Neuro-Oncology Advances, Nov. 15, 2022, 5(1): 1-9.
Nehama et al., "B7-H3-redirected chimeric antigen receptor T cells target glioblastoma and neurospheres", EBioMedicine, 2019, 47: 33-43.
Razpotnik et al., "Targeting Malignant Brain Tumors with Antibodies", Frontiers in Immunology, 2017, 8(1181), pp. 1-14.
Shraibman et al., "Identification of Tumor Antigens Among the HLA Peptidomes of Glioblastoma Tumors and Plasma", Molecular & Cellular Proteomics, Jun. 2019, 18(6): 1255-1268.
Szeto et al., "TCR Recognition of Peptide-MHC-I: Rule Makers and Breakers", International Journal of Molecular Sciences, Dec. 2020, 22(1):68, 26 pages.
Wang et al., "Identification of tumor-associated antigens and immune subtypes of lower-grade glioma and glioblastoma for mRNA vaccine development", Chinese Neurosurgical Journal, Oct. 28, 2022, 8:34, 14 pages.
Watchmaker et al., "EXTH-33. Priming of Synnotch CAR T Cells Via CNS-Specific Antigen Allows Spatial and Temporal Regulation of CAR Expression, Effective Homing and Persistence of T Cells in the CNS", Neuro-Oncology, Nov. 2022, vol. 24, Issue Supplement_7, Nov. 2022, p. vii216, https://doi.org/10.1093/neuonc/noac209.831.
Wu et al., "Tumor antigens and immune subtypes of glioblastoma: the fundamentals of mRNA vaccine and individualized immunotherapy development", Journal of Big Data, Jul. 14, 2022, 9:92, 25 pages.
Yamada et al., "Molecular Cloning of Brevican, a Novel Brain Proteoglycanof the Aggrecadersican Family", The Journal of Biological Chemistry, 1994, 269(13): 10119-10126.
Yang et al., "Targeting EGFRvIII for glioblastoma multiforme", Cancer Letters, 2017, 403: 224-230.
Yang et al., "T cells expressing NKG2D chimeric antigen receptors efficiently eliminate glioblastoma and cancer stem cells", Journal for ImmunoTherapy of Cancer, 2019, 7:171, 13 pages.

* cited by examiner heterogeneous expression of A
homogeneous expression of B

A: priming antigen
B: killing antigen synNotch→CAR
short radius of killing synNotch→diffusible CAR
wider radius of killing priming cells    non-priming cancer cells Glioblastoma SynNotch --> CAR Killing
(GBM synNotch --> Gal4UAS IL13Ra2/EphA2 CAR GFP PGK BFP)

Antigen A
Antigen C (A) and (C)

*If A then kill C*

| Antigen A | Priming |
| Antigen C OR Antigen D | Killing |

(A) and (C or D)

*If A then kill C or D*

| Antigen A OR Antigen B | Priming |
| Antigen C | Killing |

(A or B) and (C)

*If A or B then kill C*

| Antigen A OR Antigen B | Priming |
| Antigen C OR Antigen D | Killing |

(A or B) and (C or D)

*If A or B then kill C or D*

"METHODS OF TREATING GLIOBLASTOMAS

CROSS-REFERENCE TO RELATED APPLICATIONS

This application is a § 371 national phase of International Application No. PCT/US2019/025860, filed on Apr. 4, 2019, which claims the benefit of United States Provisional Patent Application Serial Nos. 62/653,929 filed Apr. 6, 2018; the disclosure of which application is herein incorporated by reference.

STATEMENT REGARDING FEDERALLY SPONSORED RESEARCH

This invention was made with government support under grant nos. R01 CA196277, P50 GM081879 and R35 NS105068 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "UCSF-565WO_SeqList_ST25.txt" created on Apr. 2, 2019 and having a size of 491 KB. The contents of the text file are incorporated by reference herein in their entirety.

INTRODUCTION

Among neuroepithelial tumors, the most frequent (50-60%) is glioblastoma. Glioblastoma multiforme (GBM) is highly anaplastic and develops from a diffuse astrocytoma or de novo. GBM is often found in the cerebral hemispheres and its peak incidence occurs at an age of 45-70 years. The median survival of patients with GBM is typically less than 2 years. GBM tumors commonly appear as a heterogeneous mixture containing cells of various phenotypes and polymorphisms. Heterogeneity in GBM tumors at the cellular level undoubtedly contributes to the aggressive pathology of the disease and may play a role in tumor recurrences following treatment (see e.g., Soeda et al., Scientific Reports (2015) 5:7979). Epidermal growth factor receptor (EGFR) is over expressed in approximately 50-60% of glioblastoma (GBM) tumors. Moreover, mutation of EGFR giving rise to detrimental EGFR variants, e.g., such as EGFR variant III (EGFRvIII), is common and, when present, appears to occur in the early stages of cancer progression consistent with a cancer stem cell model for GBM. In some subjects, EGFRvIII may not arise at all during GBM disease progression, meaning therapies specifically directed to this variant would not be indicated in certain patients.

SUMMARY

Methods are provided for treating a subject for glioblastoma, including e.g., an EGFRvIII negative glioblastoma. The methods of the present disclosure involve administering to a subject a molecular circuit that includes a binding triggered transcriptional switch (BTTS) that binds to a priming antigen expressed by the subject's glioblastoma multiforme (GBM) that, when bound to the priming antigen, induces one or more encoded therapeutics specific for one or more antigens expressed by the GBM. Nucleic acids containing sequences encoding all or portions of such circuits are also provided, as well as cells, expression cassettes and vectors that contain such nucleic acids. Also provided are kits for practicing the described methods.

DEFINITIONS

Figure 1A:
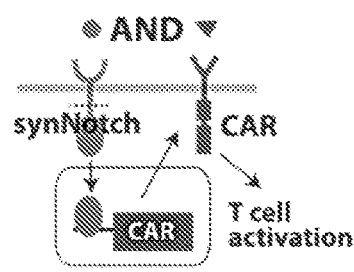
FIG. 1A-1D depict examples of prime/kill circuits, with or without diffusible components, and employing antigen recognition and therapeutic targeting using priming antigen and targeting antigen expressed on EGFRvIII(−) GBM cells.

As used herein, the term "heterogeneous", when used in reference to cancer, generally refers to a cancer displaying some level of intracancer or intratumor heterogeneity, e.g., at the molecular, cellular, tissue or organ level. A heterogeneous cancer is composed of at least two different cell types, where different cell types may be defined in variety of ways. For example, different cell types may differ genomically (e.g., through the presence of a mutation in one cell type that is absent in another), transcriptionally (e.g., through expression of a gene in one cell type that is not expressed in another, through enhanced or reduced expression of a gene in one cell type as compared to another, etc.), or proteomically (e.g., through expression of a protein in one cell type that is not expressed in another, through enhanced or reduced expression of a protein in one cell type as compared to another, etc.). In some instances, cancer heterogeneity may be identified based on the presence of two or more phenotypically different cells present in a cancer, including e.g., where such phenotypically different cells are identified through clinical testing (e.g., histology, immunohistochemistry, in situ hybridization, cytometry, transcriptomics, mutational analysis, whole genome sequencing, proteomics, etc.).

As such, a heterogeneous cancer, as defined herein, will generally include at least one cancerous cell type and at least one other cell type, where the one other cell type may be a second cancerous cell type or a non-cancerous cell type. For example, a heterogeneous cancer may include a first cancerous cell type and a second cancerous cell type. Alternatively, a heterogeneous cancer may include a cancerous cell type and a non-cancerous cell type. Although a heterogeneous cancer will include at least two different cell types, such cancers are not so limited and may include e.g., more than two different cell types, three or more different cell types, four or more different cell types, five or more different cell types, etc., where at least one cell type is cancerous and the additional cell types may each be cancerous or non-cancerous.

As summarized above, heterogeneity of a cancer may be defined by differing gene or protein expression by different subpopulations of cells of the cancer. For example, in some instances, a first subpopulation of cells may express a first gene product from a first gene that is not expressed by a second subpopulation of cells, where such a second cell population may or may not express a second gene product from a second gene that defines the second population. Put another way, subpopulations of cells within a heterogeneous cancer may, in some instances, each be defined by the presence or absence (or relative levels) of one or more expressed gene products, where useful expressed gene products for defining cell types may include but are not limited to biomarkers, antigens, wild-type proteins, mutated proteins, wild-type transcripts, mutated transcripts, etc.

Cancer heterogeneity, in some instances, may include or exclude heterogeneity at the subject level, i.e., intrapatient heterogeneity. As used herein, the term "intrapatient heterogeneity" generally refers to heterogeneity observed between multiple cancers, e.g., multiple tumors, present in a single subject. For example, a primary tumor and a metastasis with a subject may be heterogeneous, e.g., differentially expressing a particular gene product, such as a biomarker, an antigen or a mutated protein. Multiple heterogeneous cancers may arise in a subject through various mechanisms including but not limited to mutation, clonal expansion, metastasis, selection, and combinations thereof. For example, two different intrapatient heterogeneous cancers arising by metastasis of a primary tumor may be heterogeneous with respect to the tissues in which they reside. Alternatively, two different intrapatient heterogeneous cancers derived from the same primary tumor may arise due to mutation and clonal expansion, where one cancer is a subclone of the other. Various other mechanism by which different intrapatient heterogeneous cancers may arise are possible and fall within the scope of the term as used herein.

Cancer heterogeneity, in some instances as used herein, may exclude heterogeneity at the population level, i.e., interpatient heterogeneity. As used herein, the term "interpatient heterogeneity" generally refers to differences observed between two cancers or two tumors present in separate subjects or patients.

As used herein, the terms "treatment," "treating," "treat" and the like, refer to obtaining a desired pharmacologic and/or physiologic effect and/or a response related to the treatment. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

A "therapeutically effective amount" or "efficacious amount" refers to the amount of an agent (including biologic agents, such as cells), or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

The terms "individual," "subject," "host," and "patient," used interchangeably herein, refer to a mammal, including, but not limited to, murines (e.g., rats, mice), non-human primates, humans, canines, felines, ungulates (e.g., equines, bovines, ovines, porcines, caprines), lagomorphs, etc. In some cases, the individual is a human. In some cases, the individual is a non-human primate. In some cases, the individual is a rodent, e.g., a rat or a mouse. In some cases, the individual is a lagomorph, e.g., a rabbit.

The term "refractory", used herein, refers to a disease or condition that does not respond to treatment. With regard to cancer, "refractory cancer", as used herein, refers to cancer that does not respond to treatment. A refractory cancer may be resistant at the beginning of treatment or it may become resistant during treatment. Refractory cancer may also called resistant cancer.

The term "histology" and "histological" as used herein generally refers to microscopic analysis of the cellular anatomy and/or morphology of cells obtained from a multicellular organism including but not limited to plants and animals.

The term "cytology" and "cytological" as used herein generally refers to a subclass of histology that includes the microscopic analysis of individual cells, dissociated cells, loose cells, clusters of cells, etc. Cells of a cytological sample may be cells in or obtained from one or more bodily fluids or cells obtained from a tissue that have been dissociated into a liquid cellular sample.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional heterodimerization of the two portions of the split CAR is pharmacologically controlled (e.g., as described in PCT publication no. WO 2014/127261 A1 and US Patent Application No. 2015/0368342 A1, the disclosures of which are incorporated herein by reference in their entirety). CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety. Useful CARs also include the anti-CD19-4-1BB-CD3ζ CAR expressed by lentivirus loaded CTL019 (Tisagenlecleucel-T) CAR-T cells as commercialized by Novartis (Basel, Switzerland).

The terms "T cell receptor" and "TCR" are used interchangeably and will generally refer to a molecule found on the surface of T cells, or T lymphocytes, that is responsible for recognizing fragments of antigen as peptides bound to major histocompatibility complex (MHC) molecules. The TCR complex is a disulfide-linked membrane-anchored heterodimeric protein normally consisting of the highly variable alpha (α) and beta (β) chains expressed as part of a complex with CD3 chain molecules. Many native TCRs exist in heterodimeric αβ or γδ forms. The complete endogenous TCR complex in heterodimeric αβ form includes eight chains, namely an alpha chain (referred to herein as TCRα or TCR alpha), beta chain (referred to herein as TCRβ or TCR beta), delta chain, gamma chain, two epsilon chains and two zeta chains. In some instance, a TCR is generally referred to by reference to only the TCRα and TCRβ chains, however, as the assembled TCR complex may associate with endogenous delta, gamma, epsilon and/or zeta chains an ordinary skilled artisan will readily understand that reference to a TCR as present in a cell membrane may include reference to the fully or partially assembled TCR complex as appropriate.

Recombinant or engineered individual TCR chains and TCR complexes have been developed. References to the use of a TCR in a therapeutic context may refer to individual recombinant TCR chains. As such, engineered TCRs may include individual modified TCRα or modified TCRβ chains as well as single chain TCRs that include modified and/or unmodified TCRα and TCRβ chains that are joined into a single polypeptide by way of a linking polypeptide.

As used herein, by "chimeric bispecific binding member" is meant a chimeric polypeptide having dual specificity to two different binding partners (e.g., two different antigens). Non-limiting examples of chimeric bispecific binding members include bispecific antibodies, bispecific conjugated monoclonal antibodies (mab)$_2$, bispecific antibody fragments (e.g., F(ab)$_2$, bispecific scFv, bispecific diabodies, single chain bispecific diabodies, etc.), bispecific T cell engagers (BiTE), bispecific conjugated single domain antibodies, micabodies and mutants thereof, and the like. Non-limiting examples of chimeric bispecific binding members also include those chimeric bispecific agents described in Kontermann. *MAbs*. (2012) 4(2): 182-197; Stamova et al. *Antibodies* 2012, 1(2), 172-198; Farhadfar et al. *Leuk Res*. (2016) 49:13-21; Benjamin et al. *Ther Adv Hematol*. (2016) 7(3):142-56; Kiefer et al. *Immunol Rev*. (2016) 270(1):178-92; Fan et al. *J Hematol Oncol*. (2015) 8:130; May et al. *Am J Health Syst Pharm*. (2016) 73(1):e6-e13; the disclosures of which are incorporated herein by reference in their entirety.

A "biological sample" encompasses a variety of sample types obtained from an individual or a population of individuals and can be used in various ways, including e.g., the isolation of cells or biological molecules, diagnostic assays, etc. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by mixing or pooling of individual samples, treatment with reagents, solubilization, or enrichment for certain components, such as cells, polynucleotides, polypeptides, etc. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples (e.g., biopsy samples), and cellular samples. Accordingly, biological samples may be cellular samples or acellular samples.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, nanobodies, single-domain antibodies, and fusion proteins comprising an antigen-binding portion of an antibody and a non-antibody protein.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids (Hamers-Casterman et al. (1993) *Nature* 363:446; Desmyter et al. (2015) *Curr. Opin. Struct. Biol.* 32:1). In the family of "camelids" immunoglobulins devoid of light polypeptide chains are found. "Camelids" comprise old world camelids (*Camelus bactrianus* and *Camelus dromedarius*) and new world camelids (for example, Llama *paccos*, Llama *glama*, Llama *guanicoe* and Llama *vicugna*). A single variable domain heavy chain antibody is referred to herein as a nanobody or a $V_{HH}$ antibody.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

A "orthogonal" or "orthogonalized" member or members of a binding pair are modified from their original or wild-type forms such that the orthogonal pair specifically bind one another but do not specifically or substantially bind the non-modified or wild-type components of the pair. Any binding partner/specific binding pair may be orthogonalized, including but not limited to e.g., those binding partner/specific binding pairs described herein.

The terms "domain" and "motif", used interchangeably herein, refer to both structured domains having one or more particular functions and unstructured segments of a polypeptide that, although unstructured, retain one or more particular functions. For example, a structured domain may encompass but is not limited to a continuous or discontinuous plurality of amino acids, or portions thereof, in a folded polypeptide that comprise a three-dimensional structure which contributes to a particular function of the polypeptide. In other instances, a domain may include an unstructured segment of a polypeptide comprising a plurality of two or more amino acids, or portions thereof, that maintains a particular function of the polypeptide unfolded or disordered. Also encompassed within this definition are domains that may be disordered or unstructured but become structured or ordered upon association with a target or binding partner. Non-limiting examples of intrinsically unstructured domains and domains of intrinsically unstructured proteins are described, e.g., in Dyson & Wright. *Nature Reviews Molecular Cell Biology* 6:197-208.

The terms "synthetic", "chimeric" and "engineered" as used herein generally refer to artificially derived polypeptides or polypeptide encoding nucleic acids that are not naturally occurring. Synthetic polypeptides and/or nucleic acids may be assembled de novo from basic subunits including, e.g., single amino acids, single nucleotides, etc., or may be derived from pre-existing polypeptides or polynucleotides, whether naturally or artificially derived, e.g., as through recombinant methods. Chimeric and engineered polypeptides or polypeptide encoding nucleic acids will generally be constructed by the combination, joining or fusing of two or more different polypeptides or polypeptide encoding nucleic acids or polypeptide domains or polypeptide domain encoding nucleic acids. Chimeric and engineered polypeptides or polypeptide encoding nucleic acids include where two or more polypeptide or nucleic acid "parts" that are joined are derived from different proteins (or nucleic acids that encode different proteins) as well as where the joined parts include different regions of the same protein (or nucleic acid encoding a protein) but the parts are joined in a way that does not occur naturally.

The term "recombinant", as used herein describes a nucleic acid molecule, e.g., a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide means a polypeptide produced by expression from a recombinant polynucleotide. The term recombinant as used with respect to a host cell or a virus means a host cell or virus into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "operably linked" refers to a juxtaposition wherein the components so described are in a relationship permitting them to function in their intended manner. For instance, a promoter is operably linked to a coding sequence if the promoter affects its transcription or expression. Operably linked nucleic acid sequences may but need not necessarily be adjacent. For example, in some instances a coding sequence operably linked to a promoter may be adjacent to the promoter. In some instances, a coding sequence operably linked to a promoter may be separated by one or more intervening sequences, including coding and non-coding sequences. Also, in some instances, more than two sequences may be operably linked including but not limited to e.g., where two or more coding sequences are operably linked to a single promoter.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "vector" or "expression vector" is a replicon, such as plasmid, phage, virus, or cosmid, to which another DNA segment, i.e. an "insert", may be attached so as to bring about the replication of the attached segment in a cell.

The term "Heterologous", as used herein, means a nucleotide or polypeptide sequence that is not found in the native (e.g., naturally-occurring) nucleic acid or protein, respectively. Heterologous nucleic acids or polypeptide may be derived from a different species as the organism or cell within which the nucleic acid or polypeptide is present or is expressed. Accordingly, a heterologous nucleic acids or polypeptide is generally of unlike evolutionary origin as compared to the cell or organism in which it resides.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, the present disclosure provides methods of treating a subject for a glioblastoma, including an EGFRvIII negative glioblastoma. The methods of the present disclosure involve administering to the subject a molecular circuit that is primed by priming antigen to induce one or more encoded therapeutics specific for one or more antigens expressed by the glioblastoma. The circuit may be administered in the form of cells encoding the molecular circuit, vector(s) that deliver nucleic acids encoding the circuit to cells of the subject, or the like. Accordingly, nucleic acids containing sequences encoding all or portions of such circuits are also provided, as well as cells, expression cassettes and vectors that contain such nucleic acids. Also provided are kits for practicing the described methods.

The subject circuits may integrate the expression of a priming antigen on a glioblastoma multiforme (GBM) cell and at least a second antigen expressed on a second cell of the GBM to produce a desired outcome with respect to the second cell. In some instances, the subject circuits may integrate the expression of a priming antigen on an EGFRvIII-negative ("EGFRvIII(−)") glioblastoma multiforme (GBM) cell and at least a second antigen expressed on a second cell of the EGFRvIII(−) GBM to produce a desired outcome with respect to the second cell. The integration of two antigens expressed by different cells of a heterogeneous cell population to result in a desired targeting event may be referred to herein as "trans-targeting".

For example, an employed circuit may integrate "priming antigen" expressed by a first GBM cell (e.g., an EGFRvIII(−) GBM cell), referred to as a "priming cell", and a second antigen (e.g., a "targeting antigen" or "targeted antigen" or "killing antigen") expressed by a second cell, e.g., a nearby cell, of the GBM (e.g., EGFRvIII(−) GBM), referred to as a "targeted cell", to target the second cell type in trans. A therapeutic cell modified with such a circuit is primed by the presence of the priming antigen on the first cell to then target the targeted cell.

For comparison, in this context cis-targeting refers to integrating of two antigens to target a single cell which expresses both a priming antigen and a targeting antigen to produce a desired outcome with respect to the single cell. Thus, in cis-targeting, the targeted cell expresses both the priming antigen and the targeting antigen such that the two antigens are expressed in cis with respect to the cell. In trans-targeting, the targeted cell expresses only the targeting antigen and not the priming antigen such that the two antigens are expressed in trans with respect to the two cells. As such, trans targeting may be employed to target a cell that does not express a priming antigen. In some instances, a circuit of the present disclosure may employ both transtargeting and cis-targeting, i.e., cis- and trans-targeting may be combined in a single circuit. In some instances, a circuit of the present disclosure may employ only trans-targeting and may e.g., exclude cis-targeting.

The circuits of the present disclosure will generally employ at least one binding triggered transcriptional switch (BTTS) as described in more detail below. A therapeutic cell may be modified to express a BTTS responsive to a priming antigen. The BTTS may be expressed in the plasma membrane of the cell. Binding of the BTTS to priming antigen may induce expression of a protein in the BTTS expressing cell. The induced protein may be a heterologous antigen-specific protein, such as a second BTTS or a heterologous antigen-specific therapeutic, as described in more detail below. In the context of cis-targeting, binding of the BTTS to priming antigen expressed on a GBM priming cell (e.g., an EGFRvIII(−) GBM priming cell) induces expression of an antigen specific protein that is specific for a targeting antigen that is also expressed by the GBM priming cell (e.g., EGFRvIII(−) GBM priming cell) (i.e., the GBM cell is both the priming cell and the targeted cell). In the context of trans-targeting, binding of the BTTS to priming antigen expressed on a GBM priming cell (e.g., EGFRvIII(−) GBM priming cell) induces expression of an antigen specific protein that is specific for a targeting antigen that is expressed on a GBM cell (e.g., an EGFRvIII(−) GBM cell) that does not express the priming antigen (i.e., a GBM cell (e.g., EGFRvIII(−) GBM cell) other than the priming cell).

In this manner, trans-targeting allows for targeting of cells by an antigen specific protein, such as an antigen-specific therapeutic, only in the presence of priming cells. Correspondingly, trans-targeting allows for targeting of cells with an antigen specific protein, such as an antigen-specific therapeutic, in a heterogeneous cell population, such as a heterogeneous cancer, where the targeted cells do not express priming antigen, i.e., are priming-antigen(−) cells.

Accordingly, such targeted priming antigen(−) GBM cells (e.g., priming-antigen(−)/EGFRvIII(−) GBM cells) may be spatially associated with priming-antigen-positive ("priming-antigen(+)") GBM cells (e.g., priming-antigen(+)/EGFRvIII(−) GBM cells), i.e., cells that that do express priming antigen.

While the subject methods are described primarily herein with respect to EGFRvIII(−) GBM cells (i.e., EGFRvIII(−) GBM priming cells and EGFRvIII(−) GBM targeted cells), in some instances the described circuits may be employed in methods of trans-targeting of a GBM cell in a subject that is a EGFRvIII(+) cell and/or a cell present in an EGFRvIII-positive ("EGFRvIII(+)") GBM. In such instances, the priming antigen employed will generally not be EGFRvIII (i.e., the priming antigen may be a non-EGFRvIII priming antigen). Accordingly, the present disclosure includes methods of treating a subject, as described in more detail below, for a GBM, which may be EGFRvIII(+) or EGFRvIII(−), that include administering to the subject an immune cell genetically modified with: (a) a nucleic acid sequence encoding a binding triggered transcriptional switch (BTTS) that binds to a priming antigen other than EGFRvIII (i.e., a non-EGFRvIII priming antigen); (b) a nucleic acid sequence encoding an antigen-specific therapeutic that binds to a killing antigen expressed by the GBM; (c) a regulatory sequence operably linked to (b) that is responsive to the BTTS; wherein binding of the BTTS to the priming antigen activates expression of the antigen-specific therapeutic which binds the killing antigen thereby inducing killing of GBM cells expressing the killing antigen.

Useful non-EGFRvIII priming antigens for cis- or trans-targeting of EGFRvIII(+) GBM cells include but are not limited to those priming antigens described below for targeting EGFRvIII(−) GBM cells. Moreover, the use of a non-EGFRvIII priming antigen in a method of the present disclosure does not necessarily preclude the use of EGFRvIII as a targeting antigen; however, in some instances, the subject methods may specifically exclude the use of EGFRvIII as a targeting/killing antigen. As will be readily recognized, wherein methods and/or components of methods are described below with respect to targeting EGFRvIII(−) GBM cells and/or treating a subject for a EGFRvIII(−) GBM, such methods may be equally applied or adapted in many cases to targeting EGFRvIII(+) GBM cells using a non-EGFRvIII priming antigen and/or treating a subject for a EGFRvIII(−) GBM using a non-EGFRvIII priming antigen.

Methods

As summarized above, the present disclosure provides methods of targeting priming-antigen(−) cells in a heterogeneous EGFRvIII(−) GBM, including where such cells are targeted in trans. Such methods may include administering, to a subject in need thereof, a circuit encoding a BTTS responsive to priming antigen that induces expression of an antigen-specific therapeutic, where the antigen-specific therapeutic may be responsive to one or more antigens other than the priming antigen. Such circuits, when expressed on a therapeutic immune cell, may activate the immune cell to mediate the targeted killing of priming-antigen(−)/EGFRvIII(−) GBM cells in a EGFR(−) GBM tumor where at least some of the cells heterogeneously express the priming antigen.

Methods of Treatment

As summarized above, the methods of the present disclosure find use in treating a subject for an EGFRvIII(−) GBM. Such treatments may include obtaining a desired effect with respect to at least one EGFRvIII(−) GBM cell type (or subpopulation thereof) of a GMB tumor heterogeneously positive for priming antigen. The term "heterogeneously positive", as used herein, is generally meant a GBM tumor containing at least some cells that express the priming antigen and at least some cells that do not express the priming antigen. Such tumors may, in some instances, include a subpopulation of cells that does not express the priming antigen that was derived from a parent population expressing the priming antigen. In some instances, a subpopulation of a tumor may begin expressing a priming antigen de novo from a parent population that does not express the priming antigen. In some instances, antigen expression of GBM cells may change or evolve over the course of tumor progression.

In some instances, treatments may include obtaining a desired effect with respect to one cell type or more than one cell type (or subpopulation of cells) of the heterogeneous EGFRvIII(−) GBM, including two or more, three or more, four or more, five or more, etc., cell types or subpopulations of cells of the heterogeneous EGFRvIII(−) GBM. Desired effects of the treatments, as described in more detail below, will vary. For example, with respect to one or more targeted cell types, desired effects will vary and may include but are not limited to e.g., killing of the one or more targeted cell types, reducing the proliferation of the one or more targeted cell types, and the like.

The subject methods may include introducing into a subject in need thereof, cells that contain nucleic acid sequences encoding a circuit for trans-targeting of a cell of a heterogeneous EGFRvIII(−) GBM. The introduced cells may be immune cells, including e.g., myeloid cells or lymphoid cells.

In some instances, the instant methods may include contacting a cell with one or more nucleic acids encoding a circuit wherein such contacting is sufficient to introduce the nucleic acid(s) into the cell. Any convenient method of introducing nucleic acids into a cell may find use herein including but not limited viral transfection, electroporation, lipofection, bombardment, chemical transformation, use of a transducible carrier (e.g., a transducible carrier protein), and the like. Nucleic acids may be introduced into cells maintained or cultured in vitro or ex vivo. Nucleic acids may also be introduced into a cell in a living subject in vivo, e.g., through the use of one or more vectors (e.g., viral vectors) that deliver the nucleic acids into the cell without the need to isolate, culture or maintain the cells outside of the subject.

Introduced nucleic acids may be maintained within the cell or transiently present. As such, in some instance, an introduced nucleic acid may be maintained within the cell, e.g., integrated into the genome. Any convenient method of nucleic acid integration may find use in the subject methods, including but not limited to e.g., viral-based integration, transposon-based integration, homologous recombination-based integration, and the like. In some instance, an introduced nucleic acid may be transiently present, e.g., extrachromosomally present within the cell. Transiently present nucleic acids may persist, e.g., as part of any convenient transiently transfected vector.

An introduced nucleic acid encoding a circuit may be introduced in such a manner as to be operably linked to a regulatory sequence, such as a promoter, that drives the expression of one or more components of the circuit. The source of such regulatory sequences may vary and may include e.g., where the regulatory sequence is introduced with the nucleic acid, e.g., as part of an expression construct or where the regulatory sequence is present in the cell prior to introducing the nucleic acid or introduced after the nucleic acid. As described in more detail herein, useful regulatory sequence can include e.g., endogenous promoters and heterologous promoters. For example, in some instances, a nucleic acid may be introduced as part of an expression construct containing a heterologous promoter operably linked to a nucleic acid sequence. In some instances, a nucleic acid may be introduced as part of an expression construct containing a copy of a promoter that is endogenous to the cell into which the nucleic acid is introduced. In some instances, a nucleic acid may be introduced without a regulatory sequence and, upon integration into the genome of the cell, the nucleic acid may be operably linked to an endogenous regulatory sequence already present in the cell. Depending on the confirmation and/or the regulatory sequence utilized, expression of each component of the circuit from the nucleic acid may be configured to be constitutive, inducible, tissue-specific, cell-type specific, etc., including combinations thereof.

Any convenient method of delivering the circuit encoding components may find use in the subject methods. In some instances, the subject circuit may be delivered by administering to the subject a cell expressing the circuit. In some instances, the subject circuit may be delivered by administering to the subject a nucleic acid comprising one or more nucleotide sequences encoding the circuit. Administering to a subject a nucleic acid encoding the circuit may include administering to the subject a cell containing the nucleic acid where the nucleic acid may or may not yet be expressed. In some instances, administering to a subject a nucleic acid encoding the circuit may include administering to the subject a vector designed to deliver the nucleic acid to a cell.

Accordingly, in the subject methods of treatment, nucleic acids encoding a circuit or components thereof may be administered in vitro, ex vivo or in vivo. In some instances, cells may be collected from a subject and transfected with nucleic acid and the transfected cells may be administered to the subject, with or without further manipulation including but not limited to e.g., in vitro expansion. In some instances, the nucleic acid, e.g., with or without a delivery vector, may be administered directly to the subject.

Priming cells and targeted cells of a subject circuit will generally differ in at least the expression of priming antigen and targeting antigen. In some instances, priming cells and targeted cells may differ in the expression of at least one surface expressed epitope, e.g., a surfaced expressed protein, an antigen presented in the context of MHC, etc., including e.g., where the surface expressed epitope is a molecule other than the priming antigen and/or the targeting antigen. In some instances, two different targeted cells may differ in the expression of at least one surface expressed epitope, e.g., a surfaced expressed protein, an antigen presented in the context of MHC, etc.

Differential expression between two cells or two cell types of a EGFRvIII(−) GBM will vary. For example, in some instances, a cell expresses one surface epitope not expressed by the other. In some instances, a cell expresses one surface epitope more highly than the surface epitope is expressed by the other cell. Where cells differ in the level, e.g., as compared to the presence/absence, of expression of a surface epitope the difference in level may vary but will generally be substantially different, e.g., sufficiently different to allow for practical targeting of one cell versus the other. Differences in expression between cells may range from less than one order of magnitude of expression to ten orders of magnitude of expression or more, including but not limited to e.g., 1 order of magnitude, 2 orders of magnitude, 3 orders of magnitude, 4 orders of magnitude, 5 orders of magnitude, 6 orders of magnitude, 7 orders of magnitude, 8 orders of magnitude, 9 orders of magnitude, 10 orders of magnitude, etc. In some instances, two cell types differing in level of expression of a particular epitope may be said to be "high" and "low" for the epitope, respectively, where high versus low expression may be differentiated using conventional methods known to the relevant artisan.

In some instances, the presence or absence of a particular epitope will be defined by the limit of detection of the method employed to detect the epitope, including e.g., where such limit of detection may or may not be based on an appropriate reference standard or positive or negative control. For example, where the epitope is present below the limit of detection the cell may be said to be "negative" for the epitope. Correspondingly, where the epitope is present below the level detected in a reference standard or appropriate control the cell may be said to be negative for the epitope. Where the epitope is present above the limit of detection the cell may be said to be "positive" for the epitope. Correspondingly, where the epitope is present above the level detected in a reference standard or appropriate control the cell may be said to be positive for the epitope.

As summarized above, priming cells and targeted cells in a heterogeneous GBM will generally be in sufficient proximity to allow for recognition of a targeted cell expressing a targeting antigen, but not the priming antigen, by a primed immune cell. Relative proximity between a priming cell and a targeted cell sufficient for trans-targeting of the targeted cell will vary and, as described herein, may be modified as desired depending on how the subject circuit is designed (e.g., through the use of a more or less stable antigen-specific therapeutic, through the use of a diffusible payload, etc.). In some instances, the priming cell and the targeted cell may be adjacent. In some instances, the priming cell and the targeted cell may be non-adjacent. As such, the proximity, expressed in this context as the distance between, a priming cell and a targeted cell may range from about 1 cell diameter to 100 cell diameters or more, including but not limited to e.g., 1 to 100 cell diameters, 2 to 100 cell diameters, 5 to 100 cell diameters, 10 to 100 cell diameters, 1 to 50 cell diameters, 2 to 50 cell diameters, 5 to 50 cell diameters, 10 to 50 cell diameters, 1 to 25 cell diameters, 2 to 25 cell diameters, 5 to 25 cell diameters, 10 to 25 cell diameters, etc.

Heterogeneity of EGFRvIII(−) GBM tumors treated using the methods described herein will vary. For example, in some instances, the degree of heterogeneity in a heterogeneous EGFRvIII(−) GBM will vary. For example, with respect to each individual cell type present in a heterogeneous GBM, a subject cell type (e.g., a priming cell, a first targeted cell type, a second targeted cell type, or another cell type) will represent less than 100% of the cells of the EGFRvIII(−) GBM including but not limited to e.g., less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 4%, less than 3%, less than 2%, or less than 1% of the cells of the heterogeneous EGFRvIII(−) GBM.

In some instances, 75% or less of the cells of a heterogeneous EGFRvIII(−) GBM express the relevant priming antigen, including but not limited to e.g., 70% or less, 65% or less, 60% or less, 55% or less, 50% or less, 45% or less, 40% or less, 35% or less, 30% or less, 25% or less, or 20% or less. In some instances, methods of the present disclosure find use in treating a heterogeneous EGFRvIII(−) GBM in a subject where the percentage of cells of the EGFRvIII(−) GBM that express the relevant priming antigen ranges from 1% or more than 1% to 99% or less than 99%, including but not limited to e.g., from 1% to 99%, from 5% to 90%, from 10% to 85%, from 20% to 80%, from 25% to 75% and the like.

In some instances, a targeted cell (e.g., a targeting antigen-positive, EGFR(−) cell of the tumor) of a herein disclosed methods may represent less than 50% of the cells of the heterogeneous cancer or heterogeneous tumor, including but not limited to e.g., less than 45%, less than 40%, less than 35%, less than 30%, less than 25%, less than 20%, less than 15%, less than 10%, less than 5%, less than 4%, less than 3%, less than 2%, or less than 1% of the cells of the heterogeneous cancer or a heterogeneous tumor.

In some instances, a particular cell type present in a heterogeneous EGFR(−) GBM (e.g., a priming cell type, a targeted cell type or another cell type) may be a majority cell type of the heterogeneous cancer, including e.g., where the particular cell type represents 50% or greater, including e.g., 60% or greater, 70% or greater, 80% or greater, 90% or greater, 95% or greater, of the cells of the heterogeneous GBM. In some instances, a priming cell of a herein disclosed method may represent 50% or greater of the cells of the heterogeneous GBM, including but not limited to e.g., 60% or greater, 70% or greater, 80% or greater, 90% or greater, 95% or greater, of the cells of the heterogeneous GBM. In some instances, a EGFRvIII(−) targeted cell expressing targeting antigen of a herein disclosed method may represent 50% or greater of the cells of the heterogeneous GBM, including but not limited to e.g., 60% or greater, 70% or greater, 80% or greater, 90% or greater, 95% or greater, of the cells of the heterogeneous GBM.

The methods of the present disclosure may be employed to target and treat a variety of GBM tumors, including e.g., primary GBM, secondary GBM tumors, re-growing GBM tumors, recurrent GBM tumors, refractory GBM tumors and the like. For example, in some instances, the methods of the present disclosure may be employed as an initial treatment of a primary GBM identified in a subject, including where the primary GBM is identified as EGFRvIII(−). In some instances, the methods of the present disclosure may be employed as a non-primary (e.g., secondary or later) treatment, e.g., in a subject with a GBM that is refractory to at least one prior treatment, in a subject with a GBM that is re-growing following at least one prior treatment, in a subject with a mixed response to at least one prior treatment (e.g., a positive response in at least one tumor in the subject and a negative or neutral response in at least a second tumor in the subject, including e.g., a mixed response to a treatment for multiple GBM), and the like.

In some instances, the method of the present disclosure may be employed to target, treat or clear a subject for minimal residual disease (MRD) remaining after a prior GBM therapy. Targeting, treating and/or clearance of EGFRvIII(−) GBM MRD may be pursued using the instant methods whether or not the MRD is or has been determined to be refractory to the prior treatment. In some instances, a method of the present disclosure may be employed to target, treat and/or clear a subject of MRD following a determination that the MRD is refractory to a prior treatment or one or more available treatment options other than those employing the herein described circuits.

In some instances, the instant methods may be employed prophylactically for surveillance. For example, a subject in need thereof may be administered a treatment involving one or more of the herein described circuits when the subject does not have detectable disease but is at risk of developing a GBM or a recurrent GBM. In some instances, a prophylactic approach may be employed when a subject is at particularly high risk of developing a primary GBM that would be predicted to be a heterogeneous GBM and may, e.g., be predicted to be EGFRvIII(−). In some instances, a prophylactic approach may be employed when a subject has been previously treated for a GBM and is at risk of reoccurrence. Essentially any combination of priming antigen and targeting antigen may be employed in prophylactic treatments, including those described herein.

In some instances, the herein described methods may be used to prophylactically surveil a subject for GBM cells expressing one or more mutations commonly present in GBM tumors, including mutations found in recurrent and/or refractory GBM or that occur in primary GBM. Mutations found in primary, recurrent and/or refractory GBM (and subtypes thereof) include but are not limited to e.g., IDH1 mutation, TP53 mutation, ALK mutation, RRM1 mutation, TUBB3 mutation, ATRX mutation, BRAF mutation, PTEN mutation, PDGFRA mutation, PTPN11 mutation, and SMARCA4 mutation. In some instances, methods may employ an antigen-specific therapeutic specific for one or more killing antigens, where the one or more killing antigens include one or more commonly mutated proteins, including surface expressed proteins.

In some instances, methods of the present disclosure may be employed to treat subjects that do not necessarily present with a heterogeneous GBM, including primary and non-primary GBMs, but are at an increased risk of developing such a heterogeneous GBM. For example, a subject having an apparently homogeneous EGFRvIII(−) GBM may be treated with a circuit to prophylactically surveil a subject for GBM cells expressing one or more mutations that occur in GBM (where such mutations may exclude, in some instances, mutations resulting in production of a EGFRvIII variant).

The methods of treating described herein may, in some instances, be performed in a subject that has previously undergone one or more conventional treatments. For example, in the case of oncology, the methods described herein may, in some instances, be performed following a conventional cancer therapy including but not limited to e.g., conventional chemotherapy, conventional radiation therapy, conventional immunotherapy, surgery, etc. In some instances, the methods described herein may be used when a subject has not responded to or is refractory to a conventional therapy.

With respect to the GBM as a whole, desired effects of the described treatments may result in a reduction in the number of cells in the GBM, a reduction in the size of a GBM tumor, a reduction in the overall proliferation of the GBM, a reduction in the overall growth rate of a GBM tumor, etc. For example, an effective treatment is in some cases a treatment that, when administered in one or more doses to an individual in need thereof, reduces the number of cancer cells in the individual and/or reduces tumor mass in the individual, by at least about 10%, at least about 15%, at least about 20%, at least about 25%, at least about 30%, at least about 40%, at least about 50%, at least about 75%, or more than 75%, compared to the number of cancer cells and/or tumor mass in the absence of the treatment. Reductions in the number of cancer cells or the size of the tumor mass may be defined with respect to the heterogeneous tumor as a whole or with respect to the targeted cells of the GBM.

In some embodiments, an effective treatment is a treatment that, when administered alone (e.g., in monotherapy)

or in combination (e.g., in combination therapy) with one or more additional therapeutic agents, in one or more doses, is effective to reduce one or more of tumor growth rate, GBM cell number, and tumor mass, by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the tumor growth rate, GBM cell number, or tumor mass in the absence of the treatment. Reductions in the tumor growth rate, GBM cell number, or tumor mass may be defined with respect to the heterogeneous tumor as a whole or with respect to the targeted cells of the GBM.

In some instances, treatment may involve activation of an immune cell containing nucleic acid sequences encoding a circuit as described herein. Accordingly, the present disclosure correspondingly presents methods of activating an immune cell, e.g., where the immune cell expresses a priming/targeting circuit as described herein and is contacted with a first cell of a EGFRvIII(−) GBM expressing a priming antigen and a second cell of the GBM expressing a targeting antigen.

Immune cell activation, as a result of the methods described herein, may be measured in a variety of ways, including but not limited to e.g., measuring the expression level of one or more markers of immune cell activation. Useful markers of immune cell activation include but are not limited to e.g., CD25, CD38, CD40L (CD154),CD69, CD71, CD95, HLA-DR, CD137 and the like. For example, in some instances, upon antigen binding by an immune cell receptor an immune cell may become activated and may express a marker of immune cell activation (e.g., CD69) at an elevated level (e.g., a level higher than a corresponding cell not bound to antigen). Levels of elevated expression of activated immune cells of the present disclosure will vary and may include an increase, such as a 1-fold or greater increase in marker expression as compared to un-activated control, including but not limited to e.g., a 1-fold increase, a 2-fold increase, a 3-fold increase, a 4-fold increase, etc.

In some instances, an immune cell modified to encode a circuit of the present disclosure, when bound to a targeted antigen, may have increased cytotoxic activity, e.g., as compared to an un-activated control cell. In some instances, activated immune cells encoding a subject circuit may show 10% or greater cell killing of antigen expressing target cells as compared to un-activated control cells. In some instances, the level of elevated cell killing of activated immune cells will vary and may range from 10% or greater, including but not limited to e.g., 20% or greater, 30% or greater, 40% or greater, 50% or greater, 60% or greater, 70% or greater, 80% or greater, 90% or greater, etc., as compared to an appropriate control.

In some instances, treatment may involve modulation, including induction, of the expression and/or secretion of a cytokine by an immune cell containing nucleic acid sequences encoding a circuit as described herein. Non-limiting examples of cytokines, the expression/secretion of which may be modulated, include but are not limited to e.g., Interleukins and related (e.g., IL-1-like, IL-1α, IL-1β, IL-1RA, IL-18, IL-2, IL-4, IL-7, IL-9, IL-13, IL-15, IL-3, IL-5, GM-CSF, IL-6-like, IL-6, IL-11, G-CSF, IL-12, LIF, OSM, IL-10-like, IL-10, IL-20, IL-14, IL-16, IL-17, etc.), Interferons (e.g., IFN-α, IFN-β, IFN-γ, etc.), TNF family (e.g., CD154, LT-β, TNF-α, TNF-β, 4-1BBL, APRIL, CD70, CD153, CD178, GITRL, LIGHT, OX40L, TALL-1, TRAIL, TWEAK, TRANCE, etc.), TGF-β family (e.g., TGF-β1, TGF-β2, TGF-β3, etc.) and the like.

In some instances, activation of an immune cell through a circuit of the present disclosure may induce an increase in cytokine expression and/or secretion relative to that of a comparable cell where the circuit is not present or otherwise inactive. The amount of the increase may vary and may range from a 10% or greater increase, including but not limited to e.g., 10% or greater, 25% or greater, 50% or greater, 75% or greater, 100% or greater, 150% or greater, 200% or greater, 250% or greater, 300% or greater, 350% or greater 400% or greater, etc.

Conventional Treatments and Combination Therapy

As will be readily understood, the methods of treating described herein may, in some instances, be combined with one or more conventional treatments. For example, in the case of oncology for GBM, the methods described herein may, in some instances, be combined with a conventional GBM therapy including but not limited to e.g., conventional chemotherapy, conventional radiation therapy, conventional immunotherapy, surgery, etc. Also as described above, in some instances, the methods of treating described herein may be employed following conventional therapy, e.g., to treat a heterogeneous EGFRvIII(−) GBM that is refractory to a conventional therapy, to treat a heterogeneous EGFRvIII (−) GBM that is recurrent after a conventional therapy, to treat a subject for MRD following conventional therapy, and the like.

In some instances, the methods described herein may be used before or after a conventional therapy. For example, the methods described herein may be used as an adjuvant therapy, e.g., after a subject has seen improvement from a conventional therapy, or may be used when a subject has not responded to a conventional therapy. In some instances, the methods described herein may be used prior to an additional therapy, e.g., to prepare a subject for an additional therapy, e.g., a conventional therapy as described herein.

Standard GBM therapies include surgery (e.g., surgical removal of cancerous tissue), radiation therapy, chemotherapeutic treatment, antibody treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Antibodies suitable for use in, or under investigation for, GBM treatment include, but are not limited to, naked antibodies, e.g., trastuzumab (Herceptin), bevacizumab (Avastin™) cetuximab (Erbitux™), panitumumab (Vectibix™), Ipilimumab (Yervoy™), rituximab (Rituxan), alemtuzumab (Lemtrada™), Oregovomab (OvaRex™), Lambrolizumab (pembrolizumab, MK-3475, Keytruda™), ranibizumab (Lucentis™) etc., and conjugated antibodies, e.g., conjugated antibodies of those listed above and the like.

Conventional cancer therapies also include targeted therapies for cancer including but not limited to e.g., Bevacizumab (Avastin) targeting VEGF ligand (approved for use in Glioblastoma) and the like.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from Taxus brevifolia; or T-1912 from Taxus yannanensis).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In some instances, methods of treating a subject for cancer may further include administering an agent which enhances the activity of the treatment. Such agents that enhance the activity of the treatment will vary widely and may include but are not limited to e.g., agents that inhibit an inhibitor molecule. Suitable inhibitory molecules that may be targeted include but are not limited to e.g., PD1, PD-L1, CTLA4, TIM3, LAG3, VISTA, BTLA, TIGIT, LAIR1, CD160, 2B4 and TGFR beta.

Inhibiting of inhibitory molecules may be achieved by any convenient method including but not limited to e.g., the administration of a direct inhibitor of the inhibitory molecule (e.g., an antibody that binds the inhibitory molecule, a small molecule antagonist of the inhibitory molecule, etc.), administration of an agent that inhibits expression of the inhibitory molecule (e.g., an inhibitory nucleic acid, e.g., a dsRNA, e.g., an siRNA or shRNA targeting a nucleic acid encoding the inhibitory molecule), an indirect inhibitor of the inhibitory signaling, and the like. In some instances, an agent that may be administered may be an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy (Bristol-Myers Squibb)), Tremelimumab (Pfizer, formerly known as ticilimumab, CP-675, 206)), TIM3, LAG3, or the like.

In some instances, the methods of the instant disclosure may be used without any additional conventional therapy including e.g., where the method described herein is the sole method used to treat the subject. For example, in the case of oncology, the methods described herein may, in some instances, be the sole method used to treat the subject for a GBM, including e.g., a primary GBM, a recurrent GBM, and the like.

Determining when combination therapies, e.g., involving the administration of one or more agents that ameliorates one or more side effects of a therapy described herein or involving the administration of one or more agents that enhances a therapy described herein, are indicated and the specifics of the administration of such combination therapies are within the skill of the relevant medical practitioner. In some instances, dosage regimens and treatment schedules of combination therapies may be determined through clinical trials.

Testing

As summarized above, the methods of the present disclosure may, in some instances, include testing, where such testing may include but is not limited to e.g., testing of the subject, testing of a biological sample obtained from the subject, and the like. In some instances, methods of the present disclosure may include testing and/or evaluating a subject for a heterogeneous GBM. In some instances, methods of the present disclosure may include testing and/or evaluating a subject for a heterogeneous EGFRvIII(−) GBM. Testing may be employed, in some instances, to determine or identify whether a subject has a heterogeneous GBM or whether a GBM (e.g., an EGFRvIII(−) GBM), in a subject known to have such, is a heterogeneous GBM.

In some instances, a GBM of a subject may be tested or evaluated to determine, detect or identify whether the GBM expresses one or more particular antigens, including but not limited to e.g., an EGFRvIII antigen, a priming antigen (including but not limited to e.g., Interleukin-13 receptor subunit alpha-2 (IL13RA2), Interleukin-13 receptor subunit alpha-1 (IL13RA1), Neuroligin(s), Neurexin-1-beta (NRXN1), Receptor-type tyrosine-protein phosphatase zeta (PTPRZ1), Neuronal cell adhesion molecule (NRCAM), Cadherin-10 (CDH10) and Protocadherin gamma-05 (PCDHGC5), CD70 antigen (CD70), Chondroitin sulfate proteoglycan 5 (CSPG5), Brevican core protein (BCAN), Metabotropic glutamate receptor 3 (GRM3), Protein crumbs homolog 1 (CRB1), Neuromodulin (GAP43), Sodium/potassium-transporting ATPase subunit beta-2 (ATP1B2), Ran-binding protein MOG1 (MOG1), and a Receptor-type tyrosine-protein phosphatase zeta-Hepatocyte growth factor receptor fusion (PTPRZ1-MET), combinations thereof and the like) and/or a targeting antigen (including but not limited to e.g., Ephrin type-A receptor 2 (EphA2), Ephrin type-A receptor 3 (EphA3), Interleukin-13 receptor (IL13R) (e.g., IL13RA1 or IL13RA2), Epidermal growth factor receptor (EGFR), erb-b2 receptor tyrosine kinase 2 (ERBB2), combinations thereof and the like). In some instances, whether a method of the present disclosure is employed and/or the particular combination of priming antigen(s) and targeting antigen(s) employed in a subject circuit may be determined based on testing the subject for particular antigen expression in the cells of the subject's GBM.

Subjects suitable for testing will include those that have or have not been previously treated for a GBM including a heterogeneous GBM and/or a EGFRvIII(−) GBM. For example, in some instances, a subject may have been recently diagnosed with a GBM and the subject may be tested, e.g., to evaluate the presence of EGFRvIII, one or more priming antigens and/or one or more targeting antigens, before any treatment of the diagnosed GBM. In some instances, the subject may have been previously treated for a GBM and the subject may be tested, e.g., to evaluate the presence of EGFRvIII, one or more priming antigens and/or one or more targeting antigens, after treatment of the diagnosed GBM, including e.g., where the subject's GBM is responsive or refractory to the prior treatment. In some instances, the subject may be undergoing treatment for a GBM and the subject may be tested, e.g., to evaluate the presence of EGFRvIII, one or more priming antigens and/or one or more targeting antigens, during the treatment of the diagnosed GBM, including e.g., where the subject's GBM is responsive or refractory to the ongoing treatment or where the subject's response is as yet unknown.

Testing of a subject may include assaying a biological sample obtained from the subject. Useful biological samples may include but are not limited to e.g., biopsy (e.g., a GBM tumor biopsy, etc.), blood samples, and the like. Any convenient method of collecting a biological sample may find use in the herein described methods including but not limited to e.g., needle biopsy, stereotactic biopsy, open biopsy, and the like.

In a brain tumor needle biopsy, a small cut may be made and a small hole, called a burr hole, may be drilled in the skull. A narrow, hollow needle may be inserted through the hole, and tumor tissue may be removed from the core of the needle. In a stereotactic biopsy (a.k.a. a "closed" biopsy) of a brain tumor, the same general procedure may be employed as described for a needle biopsy; however, a computer-assisted guidance system that aids in the location and diagnosis of the tumor may be employed. A computer, using information from a CT or MRI scan, may provide precise information about a tumor's location and its position relative to other structures in the brain. Stereotactically guided equipment might be moved into the burr hole to remove a sample of the tumor. In an open biopsy of a brain tumor a tissue sample is taken during an operation while the tumor is exposed. The sample, regardless of the biopsy method employed for collection, may then be sent for study and review, e.g., by a pathologist.

Any convenient method of assaying a biological sample may find use in the herein described methods including but not limited to e.g., a blood chemistry test, cancer gene mutation testing, complete blood count (CBC), cytogenetic analysis, immunophenotyping, tumor marker tests, histology, cytology (including e.g., flow cytometry, including FACS), immunohistochemistry, gene expression analysis, proteomics, in situ hybridization, and the like. For example, in some instances, immunohistochemistry and/or in situ hybridization may be performed on a biopsy sample obtained from the subject, e.g., to detect the expression of one or more antigens. In some instances, cytology may be performed on a blood sample from the subject, e.g., to detect circulating tumor cells (CTCs).

In some instances, antigen detection in a biological sample may include molecular detection of antigen transcript. Any convenient method of transcript detection may be employed including but not limited to PCR-based assays. Antigen transcript detection may find use in various embodiments of the herein described methods, including but not limited to e.g., where the methods include determining whether one of more cells from a sample of a subject express EGFRvIII, EGFR or both EGFRvIII and EGFR and/or performing quantification of the level(s) of expression thereof.

In some instances, immunohistochemistry methods (including e.g., colorimetric or immunofluorescence assays thereof) may be employed to evaluate the presence or absence of EGFRvIII, EGFR or both EGFRvIII and EGFR and/or quantify of the level(s) of expression thereof. Essentially any convenient and appropriate method for detecting and/or quantifying EGFRvIII, EGFR or both EGFRvIII and EGFR may be employed in the methods described herein, e.g., methods employing a specific binding member for EGFRvIII, a specific binding member for EGFR or both. Specific binding members that specifically bind EGFRvIII or EGFR for use in the present methods may, in some instances, specifically bind to an EGFRvIII or an EGFR represented, respectively, by a human amino acid sequence of the subject protein provided or described herein.

The amino acid sequence of EGFRvIII may vary, e.g., depending on the particular mutation and/or rearrangement from which a particular EGFRvIII is derived. A non-limiting example of an EGFRvIII amino acid sequence is as follows:

(SEQ ID NO: 1)
MRPSGTAGAAFLALLAALCPASRALEEKKGNYVVTDHGSCVRACGADSY

EMEEDGVRKCKKCEGPCRKVCNGIGIGEFKDSLSINATNIKHFKNCTSI

SGDLHILPVAFRGDSFTHTPPLDPQELDILKTVKEITGFLLIQAWPENR

TDLHAFENLEIIRGRTKQHGQFSLAVVSLNITSLGLRSLKEISDGDVII

SGNKNLCYANTINWKKLFGTSGQKTKIISNRGENSCKATGQVCHALCSP

EGCWGPEPRDCVSCRNVSRGRECVDKCNLLEGEPREFVENSECIQCHPE

CLPQAMNITCTGRGPDNYIQCAHYIDGPHCVKTCPAGVMGENNTLVWKY

ADAGHVCHLCHPNCTYGCTGPGLEGCPTNGPKIPSIATGMVGALLLLLV

VALGIGLFMRRRHIVRKRTLRRLLQERELVEPLTPSGEAPNQALLRILK

ETEFKKIKVLGSGAFGTVYKGLWIPEGEKVKIPVAIKELREATSPKANK

EILDEAYVMASVDNPHVCRLLGICLTSTVQLITQLMPFGCLLDYVREHK

DNIGSQYLLNWCVQIAKGMNYLEDRRLVHRDLAARNVLVKTPQHVKITD

FGLAKLLGAEEKEYHAEGGKVPIKWMALESILHRIYTHQSDVWSYGVTV

WELMTFGSKPYDGIPASEISSILEKGERLPQPPICTIDVYMIMVKCWMI

DADSRPKFRELIIEFSKMARDPQRYLVIQGDERMHLPSPTDSNFYRALM

DEEDMDDVVDADEYLIPQQGFFSSPSTSRTPLLSSLSATSNNSTVACID

RNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNS

TFDSPAHWAQKGSHQISLDNPDYQQDFFPKEAKPNGIFKGSTAENAEYL

RVAPQSSEFIGA.

EGFRvIII proteins, and the amino acid sequences thereof, may vary from that provided above. For example, in some instances, a subject EGFRvIII variant may include one or more mutations relative to the sequence provided above, including but not limited to e.g., 1 mutation, 2 or less, 3 or less, 4 or less, 5 or less mutations, etc. In some instances, a subject EGFRvIII variant may share 80% or greater sequence identity with the amino acid sequence provided above, including but not limited to e.g., 85% or greater, 90% or greater, 95% or greater, 96% or greater, 97% or greater, 98% or greater, 99% or greater, or 100% sequence identity with the above EGFRvIII sequence.

EGFR proteins, and the amino acid sequences thereof, may vary, including from those provided herein. For example, in some instances, a subject EGFR variant may include one or more mutations relative to the sequence provided herein, including but not limited to e.g., 1 mutation, 2 or less, 3 or less, 4 or less, 5 or less mutations, etc. In some instances, a subject EGFR variant may share 80% or greater sequence identity with the amino acid sequence provided herein, including but not limited to e.g., 85% or greater, 90% or greater, 95% or greater, 96% or greater, 97% or greater, 98% or greater, 99% or greater, or 100% sequence identity with a herein provided EGFR sequence.

In some instances, testing of a subject may include multi-sampling. Multi-sampling, as used herein, generally refers to the process of taking multiple samples of a suspected tumor and/or multiple samples of multiple tumors present in a subject. Multi-sampling may be performed at one instance, e.g., where multiple samples are collected from various locations during one period of collection, or over multiple instances, e.g., were one or more sites are sampled over at multiple instances over a period of time. Multi-sampling may find use in subject with heterogeneous cancers, e.g., to ensure that the heterogeneity of a cancer or tumor is sufficiently sampled, e.g., to detect the cellular distribution and/or antigen distribution of a particular cancer or tumor.

In some instances, a subject may be evaluated, in certain contexts, through one or more of the following diagnostics procedures: 3D CT angiography, Angiography, Anoscopy, Autofluorescence bronchoscopy/fluorescence bronchoscopy, Barium swallow or enema, Biopsy, Bone Marrow Aspiration and Biopsy, Bone Scan, Bronchoscopy, CA-125 test, CAD for mammography, CTC Test, Chest x-ray, Colonoscopy, Complete Blood Count Test, Computed Tomography Scan, CT-guided biopsy, DEXA scan, Digital Breast Tomosynthesis, Electrocardiogram, Endobronchial ultrasound, Endoscopic ultrasound, ERCP, Flow cytometry, Full-field digital mammography, Genetic testing, Large bore CT scanner/RT with simulation, Lumbar puncture, Magnetic Resonance Imaging, Mammography, Miraluma breast imaging, MRI-Guided Breast Biopsy, Multi-detector CT scanner, Multiple-gated acquisition (MUGA) scan, Navigational Bronchoscopy, Nuclear Medicine Imaging, Oncotype DX Test, Pap test, Pelvic exam, PET Scan, PET-CT Scan, Radiofrequency ablation, Sentinel lymph node biopsy, Spiral CT, Tumor marker testing, Tumor molecular profiling, Ultrasound, Video Capsule Endoscopy, X-ray, and the like.

Diagnostic procedures may be performed for a variety of reasons including but not limited to e.g., to screen for GBM or precancerous conditions indicative of increased risk of GBM (e.g., CMV infection) before a person has any symptoms of disease; to help diagnose GBM; to provide information about the stage of a GBM; to provide information about the malignancy of a GBM; to provide information about the size and/or extent of a primary GBM; to provide information about whether or not a GBM has metastasized; to plan treatment; to monitor a patient's general health during treatment; to check for potential side effects of the treatment; to determine whether a GBM is responding to treatment; to find out whether a GBM has recurred; etc.

Antigens

Antigens employed in the present methods include, as described above, a priming antigen and one or more targeting antigens and others in some instances. In instances where the targeted cell is targeted for killing, the subject targeting antigen may be referred to herein as a "killing antigen". Such terms may, but need not necessarily, be used interchangeably where appropriate.

As described herein with regards to cancer heterogeneity, the relative presence of an antigen and/or the relative presence of cells expressing an antigen will vary. In general, less than 100% of the cells of a heterogeneous cancer treated with the described methods will express a priming antigen, including but not limited to e.g., where less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20% of cells of the heterogeneous cancer express the priming antigen.

Useful priming antigens will vary and may include but are not limited to e.g., Interleukin-13 receptor subunit alpha-2 (IL13RA2), Interleukin-13 receptor subunit alpha-1 (IL13RA1), Neuroligin(s), Neurexin-1-beta (NRXN1), Receptor-type tyrosine-protein phosphatase zeta (PTPRZ1), Neuronal cell adhesion molecule (NRCAM), Cadherin-10 (CDH10) and Protocadherin gamma-05 (PCDHGC5). Useful priming antigens may also include but are not limited to e.g., CD70 antigen (CD70), Chondroitin sulfate proteoglycan 5 (CSPG5), Brevican core protein (BCAN), Metabotropic glutamate receptor 3 (GRM3), Protein crumbs homolog 1 (CRB1), Neuromodulin (GAP43), Sodium/potassium-transporting ATPase subunit beta-2 (ATP1B2), Ran-binding protein MOG1 (MOG1), and a Receptor-type tyrosine-protein phosphatase zeta-Hepatocyte growth factor receptor fusion (PTPRZ1-MET).

In some instances, useful priming antigens may include Interleukin-13 receptor subunit alpha-2 (IL13RA2). IL13RA2 is encoded by the interleukin 13 receptor subunit alpha 2 gene, located in humans at Xq23, and is a subunit of the interleukin 13 receptor complex. IL13RA2 binds IL13 with high affinity, but lacks cytoplasmic domain. IL13RA2 protein may be found in at least one isoform in humans, including IL13RA2 having the following amino acid sequence:

```
                                          (SEQ ID NO: 2)
MAFVCLAIGCLYTFLISTTFGCTSSSDTEIKVNPPQDFEIVDPGYLGYL

YLQWQPPLSLDHFKECTVEYELKYRNIGSETWKTIITKNLHYKDGFDLN

KGIEAKIHTLLPWQCTNGSEVQSSWAETTYWISPQGIPETKVQDMDCVY

YNWQYLLCSWKPGIGVLLDTNYNLFYWYEGLDHALQCVDYIKADGQNIG

CRFPYLEASDYKDFYICVNGSSENKPIRSSYFTFQLQNIVKPLPPVYLT

FTRESSCEIKLKWSIPLGPIPARCFDYEIEIREDDTTLVTATVENETYT

LKTTNETRQLCFVVRSKVNIYCSDDGIWSEWSDKQCWEGEDLSKKTLLR

FWLPFGFILILVIFVTGLLLRKPNTYPKMIPEFFCDT.
```

In some instances, the methods described herein may employ a BTTS that specifically binds IL13RA2, including e.g., human IL13RA2.

In some instances, useful priming antigens may include Interleukin-13 receptor subunit alpha-1 (IL13RA1). IL13RA1 is encoded by the interleukin 13 receptor subunit alpha 1 gene, located in humans at Xq24, and is a subunit of the interleukin 13 receptor which forms a receptor complex with IL4 receptor alpha, a subunit shared by IL13 and IL4 receptors. IL13RA1 is a primary IL13-binding subunit of the IL13 receptor. IL13RA1 protein may be found in at least one isoform in humans, including IL13RA1 Isoform 1 having the following amino acid sequence:

```
                                          (SEQ ID NO: 3)
MEWPARLCGLWALLLCAGGGGGGGAAPTETQPPVTNLSVSVENLCTVI

WTWNPPEGASSNCSLWYFSHFGDKQDKKIAPETRRSIEVPLNERICLQV

GSQCSTNESEKPSILVEKCISPPEGDPESAVTELQCIWHNLSYMKCSWL

PGRNTSPDTNYTLYYWHRSLEKIHQCENIFREGQYFGCSFDLTKVKDSS

FEQHSVQIMVKDNAGKIKPSFNIVPLTSRVKPDPPHIKNLSFHNDDLYV

QWENPQNFISRCLFYEVEVNNSQTETHNVFYVQEAKCENPEFERNVENT

SCFMVPGVLPDTLNTVRIRVKTNKLCYEDDKLWSNWSOEMSIGKKRNST

LYITMLLIVPVIVAGAIIVLLLYLKRLKIIIFPPIPDPGKIFKEMFGDq

NDDTLHWKKYDIYEKOTKEETDSVVLIENLKKASQ;
``` and IL13RA1 Isoform 2 having the following amino acid sequence:

```
                                          (SEQ ID NO: 4)
MEWPARLCGLWALLLCAGGGGGGGAAPTETQPPVTNLSVSVENLCTVI

WTWNPPEGASSNCSLWYFSHFGDKQDKKIAPETRRSIEVPLNERICLQV

GSQCSTNESEKPSILVEKCISPPEGDPESAVTELQCIWHNLSYMKCSWL

PGRNTSPDTNYTLYYWHRSLEKIHQCENIFREGQYFGCSFDLTKVKDSS

FEQHSVQIMVKDNAGKIKPSFNIVPLTSRVKPDPPHIKNLSFHNDDLYV

QWENPQNFISRCLFYEVEVNNSQTETHNVFYVRF.
```

In some instances, the methods described herein may employ a BTTS that specifically binds IL13RA1, including e.g., human IL13RA1 Isoform 1, human IL13RA1 Isoform 2, or both human IL13RA1 Isoform 1 and human IL13RA1 Isoform 2.

In some instances, useful priming antigens may include neuroligins. Neuroligins include e.g., Neuroligin-4, X-linked (NLGN4X) encoded by the neuroligin 4, X-linked gene at Xp22.32-p22.31 in humans. The NLGN4X protein may be found in at least one isoform in humans, including but not limited to e.g., NLGN4X Isoform 1 having the following amino acid sequence:

```
                                          (SEQ ID NO: 5)
MSRPQGLLWLPLLFTPVCVMLNSNVLLWLTALAIKFTLIDSQAQYPVVNT

NYGKIRGLRTPLPNEILGPVEQYLGVPYASPPTGERRFQPPEPPSSWTGI

RNTTQFAAVCPQHLDERSLLHDMLPIWFTANLDTLMTYVQDQNEDCLYLN

IYVPTEDDIHDQNSKKPVMVYIHGGSYMEGTGNMIDGSILASYGNVIVIT

INYRLGILGFLSTGDQAAKGNYGLLDQIQALRWIEENVGAFGGDPKRVTI

FGSGAGASCVSLLTLSHYSEGLFQKAIIQSGTALSSWAVNYQPAKYTRIL
```

-continued

ADKVGCNMLDTTDMVECLRNKNYKELIQQTITPATYHIAFGPVIDGDVIP

DDPQILMEQGEFLNYDIMLGVNQGEGLKFVDGIVDNEDGVTPNDFDFSVS

NFVDNLYGYPEGKDTLRETIKFMYTDWADKENPETRRKTLVALFTDHQWV

APAVATADLHAQYGSPTYFYAFYHHCQSEMKPSWADSAHGDEVPYVFGIP

MIGPTELFSCNFSKNDVMLSAVVMTYWTNFAKTGDPNQPVPQDTKFIHTK

PNRFEEVAWSKYNPKDQLYLHIGLKPRVRDHYRATKVAFWLELVPHLHNL

NEIFQYVSTTTKVPPPDMTSFPYGTRRSPAKIWPTTKRPAITPANNPKHS

KDPHKTGPEDTTVLIETKRDYSTELSVTIAVGASLLFLNILAFAALYYKK

DKRRHETHRRPSPQRNTTNDIAHIQNEEIMSLQMKQLEHDHECESLQAHD

TLRLTCPPDYTLTLRRSPDDIPLMTPNTITMIPNTLTGMQPLHTFNTFSG

GQNSTNLPHGHSTTRV, and NLGN4X Isoform 2 having the following amino acid sequence:

(SEQ ID NO: 6)
MSRPQGLLWLPLLFTPVCVMLNSNVLLWLTALAIKFTLIDSQAQYPVVNT

NYGKIRGLRTPLPNEILGPVEQYLGVPYASPPTGERRFQPPEPPSSWTGI

RNTTQFAAVCPQHLDERSLLHDMLPIWFTANLDTLMTYVQDQNEDCLYLN

IYVPTEDGANTKKNADDITSNDRGEDEDIHDQNSKKPVMVYIHGGSYMEG

TGNMIDGSILASYGNVIVITINYRLGILGFLSTGDQAAKGNYGLLDQIQA

LRWIEENVGAFGGDPKRVTIFGSGAGASCVSLLTLSHYSEGLFQKAIIQS

GTALSSWAVNYQPAKYTRILADKVGCNMLDTTDMVECLRNKNYKELIQQT

ITPATYHIAFGPVIDGDVIPDDPQILMEQGEFLNYDIMLGVNQGEGLKFV

DGIVDNEDGVTPNDFDFSVSNFVDNLYGYPEGKDTLRETIKFMYTDWADK

ENPETRRKTLVALFTDHQWVAPAVATADLHAQYGSPTYFYAFYHHCQSEM

KPSWADSAHGDEVPYVFGIPMIGPTELFSCNFSKNDVMLSAVVMTYWTNF

AKTGDPNQPVPQDTKFIHTKPNRFEEVAWSKYNPKDQLYLHIGLKPRVRD

HYRATKVAFWLELVPHLHNLNEIFQYVSTTTKVPPPDMTSFPYGTRRSPA

KIWPTTKRPAITPANNPKHSKDPHKTGPEDTTVLIETKRDYSTELSVTIA

VGASLLFLNILAFAALYYKKDKRRHETHRRPSPQRNTTNDIAHIQNEEIM

SLQMKQLEHDHECESLQAHDTLRLTCPPDYTLTLRRSPDDIPLMTPNTIT

MIPNTLTGMQPLHTFNTFSGGQNSTNLPHGHSTTRV.

In some instances, the methods described herein may employ a BTTS that specifically binds NLGN4X, including e.g., human NLGN4X Isoform 1, human NLGN4X Isoform 2, or both human NLGN4X Isoform 1 and human NLGN4X Isoform 2.

Neuroligins also include e.g., Neuroligin-4, Y-linked (NLGN4Y) encoded by the neuroligin 4, Y-linked gene at Yq11.221 in humans. The NLGN4Y protein may be found in at least one isoform in humans, including but not limited to e.g., NLGN4Y Isoform 1 having the following amino acid sequence:

(SEQ ID NO: 7)
MLRPQGLLWLPLLFTSVCVMLNSNVLLWITALAIKFTLIDSQAQYPVVN

TNYGKIQGLRTPLPSEILGPVEQYLGVPYASPPTGERRFQPPESPSSWT

GIRNATQFSAVCPQHLDERFLLHDMLPIWFTTSLDTLMTYVQDQNEDCL

YLNIYVPMEDDIHEQNSKKPVMVYIHGGSYMEGTGNMIDGSILASYGNV

IVITINYRLGILGFLSTGDQAAKGNYGLLDQIQALRWIEENVGAFGGDP

KRVTIFGSGAGASCVSLLTLSHYSEGLFQKAIIQSGTALSSWAVNYQPA

KYTRILADKVGCNMLDTTDMVECLKNKNYKELIQQTITPATYHIAFGPV

IDGDVIPDDPQILMEQGEFLNYDIMLGVNQGEGLKFVDGIVDNEDGVTP

NDFDFSVSNFVDNLYGYPEGKDTLRETIKFMYTDWADKENPETRRKTLV

ALFTDHQWVAPAVATADLHAQYGSPTYFYAFYHHCQSEMKPSWADSAHG

DEVPYVFGIPMIGPTELFSCNFSKNDVMLSAVVMTYWTNFAKTGDPNQP

VPQDTKFIHTKPNRFEEVAWSKYNPKDQLYLHIGLKPRVRDHYRATKVA

FWLELVPHLHNLNEIFQYVSTTTKVPPPDMTSFPYGTRRSPAKIWPTTK

RPAITPANNPKHSKDPHKTGPEDTTVLIETKRDYSTELSVTIAVGASLL

FLNILAFAALYYKKDKRRHETHRHPSPQRNTTNDITHIQNEEIMSLQMK

QLEHDHECESLQAHDTLRLTCPPDYTLTLRRSPDDIPFMTPNTITMIPN

TLMGMQPLHTFKTFSGGQNSTNLPHGHSTTRV,

NLGN4Y Isoform 2 having the following amino acid sequence:

(SEQ ID NO: 8)
MVYIHGGSYMEGTGNMIDGSILASYGNVIVITINYRLGILGFLSTGDQA

AKGNYGLLDQIQALRWIEENVGAFGGDPKRVTIFGSGAGASCVSLLTLS

HYSEGLFQKAIIQSGTALSSWAVNYQPAKYTRILADKVGCNMLDTTDMV

ECLKNKNYKELIQQTITPATYHIAFGPVIDGDVIPDDPQILMEQGEFLN

YDIMLGVNQGEGLKFVDGIVDNEDGVTPNDFDFSVSNFVDNLYGYPEGK

DTLRETIKFMYTDWADKENPETRRKTLVALFTDHQWVAPAVATADLHAQ

YGSPTYFYAFYHHCQSEMKPSWADSAHGDEVPYVFGIPMIGPTELFSCN

FSKNDVMLSAVVMTYWTNFAKTGDPNQPVPQDTKFIHTKPNRFEEVAWS

KYNPKDQLYLHIGLKPRVRDHYRATKVAFWLELVPHLHNLNEIFQYVST

TTKVPPPDMTSFPYGTRRSPAKIWPTTKRPAITPANNPKHSKDPHKTGP

EDTTVLIETKRDYSTELSVTIAVGASLLFLNILAFAALYYKKDKRRHET

HRHPSPQRNTTNDITHIQNEEIMSLQMKQLEHDHECESLQAHDTLRLTC

PPDYTLTLRRSPDDIPFMTPNTITMIPNTLMGMQPLHTFKTFSGGQNST

NLPHGHSTTRV,

NLGN4Y Isoform 3 having the following amino acid sequence:

```
                                              (SEQ ID NO: 9)
MLPIWFTTSLDTLMTYVQDQNEDCLYLNIYVPMEDGTNIKRNADDITSN

DHGEDKDIHEQNSKKPVMVYIHGGSYMEGTGNMIDGSILASYGNVIVIT

INYRLGILGMQEARLCGSSKMFNYFKSPFTNLINFF,
``` and NLGN4Y Isoform 4 having the following amino acid sequence:

```
                                              (SEQ ID NO: 10)
MLRPQGLLWLPLLFTSVCVMLNSNVLLWITALAIKFTLIDSQAQYPVVN

TNYGKIQGLRTPLPSEILGPVEQYLGVPYASPPTGERRFQPPESPSSWT

GIRNATQFSAVCPQHLDERFLLHDMLPIWFTTSLDTLMTYVQDQNEDCL

YLNIYVPMEDGTNIKRNADDITSNDHGEDKDIHEQNSKKPVMVYIHGGS

YMEGTGNMIDGSILASYGNVIVITINYRLGILGMQEARLCGSSKMFNYF

KSPFTNLINFF.
```

In some instances, the methods described herein may employ a BTTS that specifically binds NLGN4Y, including e.g., human NLGN4Y Isoform 1, human NLGN4Y Isoform 2, human NLGN4Y Isoform 3, human NLGN4Y Isoform 4, or any combination thereof.

Neuroligins also include e.g., Neuroligin-3 (NLGN3) encoded by the neuroligin 3 gene at Xq13.1 in humans. The NLGN3protein may be present in at least one isoform in humans, including but not limited to e.g., NLGN3 Isoform 1 having the following amino acid sequence:

```
                                              (SEQ ID NO: 11)
MWLRLGPPSLSLSPKPTVGRSLCLTLWFLSLALRASTQAPAPTVNTHFG

KLRGARVPLPSEILGPVDQYLGVPYAAPPIGEKRFLPPEPPPSWSGIRN

ATHFPPVCPQNIHTAVPEVMLPVWFTANLDIVATYIQEPNEDCLYLNVY

VPTEDVKRISKECARKPNKKICRKGGSGAKKQGEDLADNDGDEDEDIRD

SGAKPVMVYIHGGSYMEGTGNMIDGSILASYGNVIVITLNYRVGVLGFL

STGDQAAKGNYGLLDQIQALRWVSENIAFFGGDPRRITVFGSGIGASCV

SLLTLSHHSEGLFQRAIIQSGSALSSWAVNYQPVKYTSLLADKVGCNVL

DTVDMVDCLRQKSAKELVEQDIQPARYHVAFGPVIDGDVIPDDPEILME

QGEFLNYDIMLGVNQGEGLKFVEGVVDPEDGVSGTDFDYSVSNFVDNLY

GYPEGKDTLRETIKFMYTDWADRDNPETRRKTLVALFTDHQWVEPSVVT

ADLHARYGSPTYFYAFYHHCQSLMKPAWSDAAHGDEVPYVFGVPMVGPT

DLFPCNFSKNDVMLSAVVMTYWTNFAKTGDPNKPVPQDTKFIHTKANRF

EEVAWSKYNPRDQLYLHIGLKPRVRDHYRATKVAFWKHLVPHLYNLHDM

FHYTSTTTKVPPPDTTHSSHITRRPNGKTWSTKRPAISPAYSNENAQGS

WNGDQDAGPLLVENPRDYSTELSVTIAVGASLLFLNVLAFAALYYRKDK

RRQEPLRQPSPQRGAGAPELGAAPEEELAALQLGPTHHECEAGPPHDTL

RLTALPDYTLTLRRSPDDIPLMTPNTITMIPNSLVGLQTLHPYNTFAAG

FNSTGLPHSHSTTRV,
```

NLGN3 Isoform 2 having the following amino acid sequence:

```
                                              (SEQ ID NO: 12)
MWLRLGPPSLSLSPKPTVGRSLCLTLWFLSLALRASTQAPAPTVNTHFG

KLRGARVPLPSEILGPVDQYLGVPYAAPPIGEKRFLPPEPPPSWSGIRN

ATHFPPVCPQNIHTAVPEVMLPVWFTANLDIVATYIQEPNEDCLYLNVY

VPTEDGSGAKKQGEDLADNDGDEDEDIRDSGAKPVMVYIHGGSYMEGTG

NMIDGSILASYGNVIVITLNYRVGVLGFLSTGDQAAKGNYGLLDQIQAL

RWVSENIAFFGGDPRRITVFGSGIGASCVSLLTLSHHSEGLFQRAIIQS

GSALSSWAVNYQPVKYTSLLADKVGCNVLDTVDMVDCLRQKSAKELVEQ

DIQPARYHVAFGPVIDGDVIPDDPEILMEQGEFLNYDIMLGVNQGEGLK

FVEGVVDPEDGVSGTDFDYSVSNFVDNLYGYPEGKDTLRETIKFMYTDW

ADRDNPETRRKTLVALFTDHQWVEPSVVTADLHARYGSPTYFYAFYHHC

QSLMKPAWSDAAHGDEVPYVFGVPMVGPTDLFPCNFSKNDVMLSAVVMT

YWTNFAKTGDPNKPVPQDTKFIHTKANRFEEVAWSKYNPRDQLYLHIGL

KPRVRDHYRATKVAFWKHLVPHLYNLHDMFHYTSTTTKVPPPDTTHSSH

ITRRPNGKTWSTKRPAISPAYSNENAQGSWNGDQDAGPLLVENPRDYST

ELSVTIAVGASLLFLNVLAFAALYYRKDKRRQEPLRQPSPQRGAGAPEL

GAAPEEELAALQLGPTHHECEAGPPHDTLRLTALPDYTLTLRRSPDDIP

LMTPNTITMIPNSLVGLQTLHPYNTFAAGFNSTGLPHSHSTTRV,
``` and NLGN3 Isoform 3 having the following amino acid sequence:

```
                                              (SEQ ID NO: 13)
MWLRLGPPSLSLSPKPTVGRSLCLTLWFLSLALRASTQAPAPTVNTHF

GKLRGARVPLPSEILGPVDQYLGVPYAAPPIGEKRFLPPEPPPSWSGI

RNATHFPPVCPQNIHTAVPEVMLPVWFTANLDIVATYIQEPNEDCLYL

NVYVPTEDDIRDSGAKPVMVYIHGGSYMEGTGNMIDGSILASYGNVIV

ITLNYRVGVLGFLSTGDQAAKGNYGLLDQIQALRWVSENIAFFGGDPR

RITVFGSGIGASCVSLLTLSHHSEGLFQRAIIQSGSALSSWAVNYQPV

KYTSLLADKVGCNVLDTVDMVDCLRQKSAKELVEQDIQPARYHVAFGP

VIDGDVIPDDPEILMEQGEFLNYDIMLGVNQGEGLKFVEGVVDPEDGV

SGTDFDYSVSNFVDNLYGYPEGKDTLRETIKFMYTDWADRDNPETRRK

TLVALFTDHQWVEPSVVTADLHARYGSPTYFYAFYHHCQSLMKPAWSD

AAHGDEVPYVFGVPMVGPTDLFPCNFSKNDVMLSAVVMTYWTNFAKTG

DPNKPVPQDTKFIHTKANRFEEVAWSKYNPRDQLYLHIGLKPRVRDHY

RATKVAFWKHLVPHLYNLHDMFHYTSTTTKVPPPDTTHSSHITRRPNG

KTWSTKRPAISPAYSNENAQGSWNGDQDAGPLLVENPRDYSTELSVTI

AVGASLLFLNVLAFAALYYRKDKRRQEPLRQPSPQRGAGAPELGAAPE

EELAALQLGPTHHECEAGPPHDTLRLTALPDYTLTLRRSPDDIPLMTP

NTITMIPNSLVGLQTLHPYNTFAAGFNSTGLPHSHSTTRV.
```

In some instances, the methods described herein may employ a BTTS that specifically binds NLGN3, including e.g., human NLGN3 Isoform 1, human NLGN3 Isoform 2, human NLGN3 Isoform 3, or any combination thereof.

In some instances, useful priming antigens may include Neurexin-1-beta (NRXN1). NRXN1 is a single-pass type I membrane protein involved in cell-cell-interactions, exocytosis of secretory granules and regulation of signal transmission encoded by the neurexin 1 gene located at 2p16.3 in humans. Various variants of Neurexin family members are produced through the use of multiple alternative promoters (e.g., at least alpha and beta promoters) and extensive alternative splicing. NRXN1 protein may be found in at least one isoform in humans, including NRXN1 Isoform 1b having the following amino acid sequence:

```
                                        (SEQ ID NO: 14)
MYQRMLRCGAELGSPGGGGGGGGGGAGGRLALLWIVPLTLSGLLGVAW

GASSLGAHHIHHFHGSSKHHSVPIAIYRSPASLRGGHAGTTYIFSKGGG

QITYKWPPNDRPSTRADRLAIGFSTVQKEAVLVRVDSSSGLGDYLELHI

HQGKIGVKFNVGTDDIAIEESNAIINDGKYHVVRFTRSGGNATLQVDSW

PVIERYPAGNNDNERLAIARQRIPYRLGRVVDEWLLDKGRQLTIFNSQA

TIIIGGKEQGQPFQGQLSGLYYNGLKVLNMAAENDANIAIVGNVRLVGE

VPSSMTTESTATAMQSEMSTSIMETTTTLATSTARRGKPPTKEPISQTT

DDILVASAECPSDDEDIDPCEPSSGGLANPTRAGGREPYPGSAEVIRES

SSTTGMVVGIVAAAALCILILLYAMYKYRNRDEGSYHVDESRNYISNSA

QSNGAVVKEKQPSSAKSSNKNKKNKDKEYYV,
```

NRXN1 Isoform 3b having the following amino acid sequence:

```
                                        (SEQ ID NO: 15)
MYQRMLRCGAELGSPGGGGGGGGGGAGGRLALLWIVPLTLSGLLGVAW

GASSLGAHHIHHFHGSSKHHSVPIAIYRSPASLRGGHAGTTYIFSKGGG

QITYKWPPNDRPSTRADRLAIGFSTVQKEAVLVRVDSSSGLGDYLELHI

HQGKIGVKFNVGTDDIAIEESNAIINDGKYHVVRFTRSGGNATLQVDSW

PVIERYPAGRQLTIFNSQATIIIGGKEQGQPFQGQLSGLYYNGLKVLNM

AAENDANIAIVGNVRLVGEVPSSMTTESTATAMQSEMSTSIMETTTTLA

TSTARRGKPPTKEPISQTTDDILVASAECPSDDEDIDPCEPSSGGLANP

TRAGGREPYPGSAEVIRESSSTTGMVVGIVAAAALCILILLYAMYKYRN

RDEGSYHVDESRNYISNSAQSNGAVVKEKQPSSAKSSNKNKKNKDKEYY

V,
```

NRXN1 Isoform 1a having the following amino acid sequence:

```
                                        (SEQ ID NO: 16)
MGTALLQRGGCFLLCLSLLLLGCWAELGSGLEFPGAEGQWTRFPKWNAC

CESEMSFQLKTRSARGLVLYFDDEGFCDFLELILTRGGRLQLSFSIFCA

EPATLLADTPVNDGAWHSVRIRRQFRNTTLFIDQVEAKWVEVKSKRRDM

TVFSGLFVGGLPPELRAAALKLTLASVREREPFKGWIRDVRVNSSQVLP

VDSGEVKLDDEPPNSGGGSPCEAGEEGEGGVCLNGGVCSVVDDQAVCDC

SRTGFRGKDCSQEDNNVEGLAHLMMGDQGKSKGKEEYIATFKGSEYFCY

DLSQNPIQSSSDEITLSFKTLQRNGLMLHTGKSADYVNLALKNGAVSLV

INLGSGAFEALVEPVNGKFNDNAWHDVKVTRNLRQHSGIGHAMVTISVD

GILTTTGYTQEDYTMLGSDDFFYVGGSPSTADLPGSPVSNNFMGCLKEV

VYKNNDVRLELSRLAKQGDPKMKIHGVVAFKCENVATLDPITFETPESF

ISLPKWNAKKTGSISFDFRTTEPNGLILFSHGKPRHQKDAKHPQMIKVD

FFAIEMLDGHLYLLLDMGSGTIKIKALLKKVNDGEWYHVDFQRDGRSGT

ISVNTLRTPYTAPGESEILDLDDELYLGGLPENKAGLVFPTEVWTALLN

YGYVGCIRDLFIDGQSKDIRQMAEVQSTAGVKPSCSKETAKPCLSNPCK

NNGMCRDGWNRYVCDCSGTGYLGRSCEREATVLSYDGSMFMKIQLPVVM

HTEAEDVSLRFRSQRAYGILMATTSRDSADTLRLELDAGRVKLTVNLDC

IRINCNSSKGPETLFAGYNLNDNEWHTVRVVRRGKSLKLTVDDQQAMTG

QMAGDHTRLEFHNIETGIITERRYLSSVPSNFIGHLQSLTFNGMAYIDL

CKNGDIDYCELNARFGFRNIIADPVTFKTKSSYVALATLQAYTSMHLFF

QFKTTSLDGLILYNSGDGNDFIVVELVKGYLHYVFDLGNGANLIKGSSN

KPLNDNQWHNVMISRDTSNLHTVKIDTKITTQITAGARNLDLKSDLYIG

GVAKETYKSLPKLVHAKEGFQGCLASVDLNGRLPDLISDALFCNGQIER

GCEGPSTTCQEDSCSNQGVCLQQWDGFSCDCSMTSFSGPLCNDPGTTYI

FSKGGGQITYKWPPNDRPSTRADRLAIGFSTVQKEAVLVRVDSSSGLGD

YLELHIHQGKIGVKFNVGTDDIAIEESNAIINDGKYHVVRFTRSGGNAT

LQVDSWPVIERYPAGRQLTIFNSQATIIIGGKEQGQPFQGQLSGLYYNG

LKVLNMAAENDANIAIVGNVRLVGEVPSSMTTESTATAMQSEMSTSIME

TTTTLATSTARRGKPPTKEPISQTTDDILVASAECPSDDEDIDPCEPSS

GGLANPTRAGGREPYPGSAEVIRESSSTTGMVVGIVAAAALCILILLYA

MYKYRNRDEGSYHVDESRNYISNSAQSNGAVVKEKQPSSAKSSNKNKKN

KDKEYYV,
```

NRXN1 Isoform 2a having the following amino acid sequence:

```
                                        (SEQ ID NO: 17)
MGTALLQRGGCFLLCLSLLLLGCWAELGSGLEFPGAEGQWTRFPKWNAC

CESEMSFQLKTRSARGLVLYFDDEGFCDFLELILTRGGRLQLSFSIFCA

EPATLLADTPVNDGAWHSVRIRRQFRNTTLFIDQVEAKWVEVKSKRRDM

TVFSGLFVGGLPPELRAAALKLTLASVREREPFKGWIRDVRVNSSQVLP

VDSGEVKLDDEPPNSGGGSPCEAGEEGEGGVCLNGGVCSVVDDQAVCDC

SRTGFRGKDCSQEDNNVEGLAHLMMGDQGKSKGKEEYIATFKGSEYFCY

DLSQNPIQSSSDEITLSFKTLQRNGLMLHTGKSADYVNLALKNGAVSLV

INLGSGAFEALVEPVNGKFNDNAWHDVKVTRNLRQVTISVDGILTTTGY

TQEDYTMLGSDDFFYVGGSPSTADLPGSPVSNNFMGCLKEVVYKNNDVR

LELSRLAKQGDPKMKIHGVVAFKCENVATLDPITFETPESFISLPKWNA

KKTGSISFDFRTTEPNGLILFSHGKPRHQKDAKHPQMIKVDFFAIEMLD

GHLYLLLDMGSGTIKIKALLKKVNDGEWYHVDFQRDGRSGTISVNTLRT
```

-continued

PYTAPGESEILDLDDELYLGGLPENKAGLVFPTEVWTALLNYGYVGCIR

DLFIDGQSKDIRQMAEVQSTAGVKPSCSKETAKPCLSNPCKNNGMCRDG

WNRYVCDCSGTGYLGRSCEREATVLSYDGSMFMKIQLPVVMHTEAEDVS

LRFRSQRAYGILMATTSRDSADTLRLELDAGRVKLTVNLDCIRINCNSS

KGPETLFAGYNLNDNEWHTVRVVRRGKSLKLTVDDQQAMTGQMAGDHTR

LEFHNIETGIITERRYLSSVPSNFIGHLQSLTFNGMAYIDLCKNGDIDY

CELNARFGFRNIIADPVTFKTKSSYVALATLQAYTSMHLFFQFKTTSLD

GLILYNSGDGNDFIVVELVKGYLHYVFDLGNGANLIKGSSNKPLNDNQW

HNVMISRDTSNLHTVKIDTKITTQITAGARNLDLKSDLYIGGVAKETYK

SLPKLVHAKEGFQGCLASVDLNGRLPDLISDALFCNGQIERGCEGPSTT

CQEDSCSNQGVCLQQWDGFSCDCSMTSFSGPLCNDPGTTYIFSKGGGQI

TYKWPPNDRPSTRADRLAIGFSTVQKEAVLVRVDSSSGLGDYLELHIHQ

GKIGVKFNVGTDDIAIEESNAIINDGKYHVVRFTRSGGNATLQVDSWPV

IERYPAGNNDNERLAIARQRIPYRLGRVVDEWLLDKGRQLTIFNSQATI

IIGGKEQGQPFQGQLSGLYYNGLKVLNMAAENDANIAIVGNVRLVGEVP

SSMTTESTATAMQSEMSTSIMETTTTLATSTARRGKPPTKEPISQTTDD

ILVASAECPSDDEDIDPCEPSSANPTRAGGREPYPGSAEVIRESSSTTG

MVVGIVAAAALCILILLYAMYKYRNRDEGSYHVDESRNYISNSAQSNGA

VVKEKQPSSAKSSNKNKKNKDKEYYV,

NRXN1 Isoform 3a having the following amino acid sequence:

(SEQ ID NO: 18)
MGTALLQRGGCFLLCLSLLLLGCWAELGSGLEFPGAEGQWTRFPKWNAC

CESEMSFQLKTRSARGLVLYFDDEGFCDFLELILTRGGRLQLSFSIFCA

EPATLLADTPVNDGAWHSVRIRRQFRNTTLFIDQVEAKWVEVKSKRRDM

TVFSGLFVGGLPPELRAAALKLTLASVREREPFKGWIRDVRVNSSQVLP

VDSGEVKLDDEPPNSGGGSPCEAGEEGEGGVCLNGGVCSVVDDQAVCDC

SRTGFRGKDCSQEIKFGLQCVLPVLLHDNDQGKYCCINTAKPLTEKDNN

VEGLAHLMMGDQGKSKGKEEYIATFKGSEYFCYDLSQNPIQSSSDEITL

SFKTLQRNGLMLHTGKSADYVNLALKNGAVSLVINLGSGAFEALVEPVN

GKFNDNAWHDVKVTRNLRQHSGIGHAMVNKLHCSVTISVDGILTTTGYT

QEDYTMLGSDDFFYVGGSPSTADLPGSPVSNNFMGCLKEVVYKNNDVRL

ELSRLAKQGDPKMKIHGVVAFKCENVATLDPITFETPESFISLPKWNAK

KTGSISFDFRTTEPNGLILFSHGKPRHQKDAKHPQMIKVDFFAIEMLDG

HLYLLLDMGSGTIKIKALLKKVNDGEWYHVDFQRDGRSGTISVNTLRTP

YTAPGESEILDLDDELYLGGLPENKAGLVFPTEVWTALLNYGYVGCIRD

LFIDGQSKDIRQMAEVQSTAGVKPSCSKETAKPCLSNPCKNNGMCRDGW

NRYVCDCSGTGYLGRSCEREATVLSYDGSMFMKIQLPVVMHTEAEDVSL

RFRSQRAYGILMATTSRDSADTLRLELDAGRVKLTVNLDCIRINCNSSK

GPETLFAGYNLNDNEWHTVRVVRRGKSLKLTVDDQQAMTGQMAGDHTRL

EFHNIETGIITERRYLSSVPSNFIGHLQSLTFNGMAYIDLCKNGDIDYC

-continued

ELNARFGFRNIIADPVTFKTKSSYVALATLQAYTSMHLFFQFKTTSLDG

LILYNSGDGNDFIVVELVKGYLHYVFDLGNGANLIKGSSNKPLNDNQWH

NVMISRDTSNLHTVKIDTKITTQITAGARNLDLKSDLYIGGVAKETYKS

LPKLVHAKEGFQGCLASVDLNGRLPDLISDALFCNGQIERGCEGPSTTC

QEDSCSNQGVCLQQWDGFSCDCSMTSFSGPLCNDPGTTYIFSKGGGQIT

YKWPPNDRPSTRADRLAIGFSTVQKEAVLVRVDSSSGLGDYLELHIHQG

KIGVKFNVGTDDIAIEESNAIINDGKYHVVRFTRSGGNATLQVDSWPVI

ERYPAGNNDNERLAIARQRIPYRLGRVVDEWLLDKGRQLTIFNSQATII

IGGKEQGQPFQGQLSGLYYNGLKVLNMAAENDANIAIVGNVRLVGEVPS

SMTTESTATAMQSEMSTSIMETTTTLATSTARRGKPPTKEPISQTTDDI

LVASAECPSDDEDIDPCEPSSGGLANPTRAGGREPYPGSAEVIRESSST

TGMVVGIVAAAALCILILLYAMYKYRNRDEGSYHVDESRNYISNSAQSN

GAVVKEKQPSSAKSSNKNKKNKDKEYYV, and NRXN1 Isoform 4 having the following amino acid sequence:

(SEQ ID NO: 19)
MDMRWHCENSQTTDDILVASAECPSDDEDIDPCEPSSANPTRAGGREPY

PGSAEVIRESSSTTGMVVGIVAAAALCILILLYAMYKYRNRDEGSYHVD

ESRNYISNSAQSNGAVVKEKQPSSAKSSNKNKKNKDKEYYV.

In some instances, the methods described herein may employ a BTTS that specifically binds NRXN1, including e.g., human NRXN1 Isoform 1b, human NRXN1 Isoform 3b, human NRXN1 Isoform 1a, human NRXN1 Isoform 2a, human NRXN1 Isoform 3a, human NRXN1 Isoform 4, or any combination thereof.

In some instances, useful priming antigens may include receptor-type tyrosine-protein phosphatase zeta (PTPRZ1), also known as Protein-tyrosine phosphatase receptor type Z polypeptide 1, R-PTP-zeta HTPZP2, PTPRZ, PTPRZ2, and PTPZ. PTPRZ1 is a receptor protein tyrosine phosphatase encoded by the protein tyrosine phosphatase, receptor type Z1 gene in humans, located in humans at 7q31.32. PTPRZ1 protein may be found in at least one isoform in humans, including PTPRZ1 Isoform 1 having the following amino acid sequence:

(SEQ ID NO: 20)
MRILKRFLACIQLLCVCRLDWANGYYRQQRKLVEEIGWSYTGALNQKNWG

KKYPTCNSPKQSPINIDEDLTQVNVNLKKLKFQGWDKTSLENTFIHNTGK

TVEINLTNDYRVSGGVSEMVFKASKITFHWGKCNMSSDGSEHSLEGQKFP

LEMQIYCFDADRFSSFEEAVKGKGKLRALSILFEVGTEENLDFKAIIDGV

ESVSRFGKQAALDPFILLNLLPNSTDKYYIYNGSLTSPPCTDTVDWIVFK

DTVSISESQLAVFCEVLTMQQSGYVMLMDYLQNNFREQQYKFSRQVFSSY

TGKEEIHEAVCSSEPENVQADPENYTSLLVTWERPRVVYDTMIEKFAVLY

QQLDGEDQTKHEFLTDGYQDLGAILNNLLPNMSYVLQIVAICTNGLYGKY

SDQLIVDMPTDNPELDLFPELIGTEEIIKEEEEGKDIEEGAIVNPGRDSA

TNQIRKKEPQISTTTHYNRIGTKYNEAKTNRSPTRGSEFSGKGDVPNTSL

-continued

NSTSQPVTKLATEKDISLTSQTVTELPPHTVEGTSASLNDGSKTVLRSPH

MNLSGTAESLNTVSITEYEEESLLTSFKLDTGAEDSSGSSPATSAIPFIS

ENISQGYIFSSENPETITYDVLIPESARNASEDSTSSGSEESLKDPSMEG

NVWFPSSTDITAQPDVGSGRESFLQTNYTEIRVDESEKTTKSFSAGPVMS

QGPSVTDLEMPHYSTFAYFPTEVTPHAFTPSSRQQDLVSTVNVVYSQTTQ

PVYNGETPLQPSYSSEVFPLVTPLLLDNQILNTTPAASSSDSALHATPVF

PSVDVSFESILSSYDGAPLLPFSSASFSSELFRHLHTVSQILPQVTSATE

SDKVPLHASLPVAGGDLLLEPSLAQYSDVLSTTHAASETLEFGSESGVLY

KTLMFSQVEPPSSDAMMHARSSGPEPSYALSDNEGSQHIFTVSYSSAIPV

HDSVGVTYQGSLFSGPSHIPIPKSSLITPTASLLQPTHALSGDGEWSGAS

SDSEFLLPDTDGLTALNISSPVSVAEFTYTTSVFGDDNKALSKSEIIYGN

ETELQIPSFNEMVYPSESTVMPNMYDNVNKLNASLQETSVSISSTKGMFP

GSLAHTTTKVFDHEISQVPENNFSVQPTHTVSQASGDTSLKPVLSANSEP

ASSDPASSEMLSPSTQLLFYETSASFSTEVLLQPSFQASDVDTLLKTVLP

AVPSDPILVETPKVDKISSTMLHLIVSNSASSENMLHSTSVPVFDVSPTS

HMHSASLQGLTISYASEKYEPVLLKSESSHQVVPSLYSNDELFQTANLEI

NQAHPPKGRHVFATPVLSIDEPLNTLINKLIHSDEILTSTKSSVTGKVFA

GIPTVASDTFVSTDHSVPIGNGHVAITAVSPHRDGSVTSTKLLFPSKATS

ELSHSAKSDAGLVGGGEDGDTDDDGDDDDDRGSDGLSIHKCMSCSSYRE

SQEKVMNDSDTHENSLMDQNNPISYSLSENSEEDNRVTSVSSDSQTGMDR

SPGKSPSANGLSQKHNDGKEENDIQTGSALLPLSPESKAWAVLTSDEESG

SGQGTSDSLNENETSTDFSFADTNEKDADGILAAGDSEITPGFPQSPTSS

VTSENSEVFHVSEAEASNSSHESRIGLAEGLESEKKAVIPLVIVSALTFI

CLVVLVGILIYWRKCFQTAHFYLEDSTSPRVISTPPTPIFPISDDVGAIP

IKHFPKHVADLHASSGFTEEFETLKEFYQEVQSCTVDLGITADSSNHPDN

KHKNRYINIVAYDHSRVKLAQLAEKDGKLTDYINANYVDGYNRPKAYIAA

QGPLKSTAEDFWRMIWEHNVEVIVMITNLVEKGRRKCDQYWPADGSEEYG

NFLVTQKSVQVLAYYTVRNFTLRNTKIKKGSQKGRPSGRVVTQYHYTQWP

DMGVPEYSLPVLTFVRKAAYAKRHAVGPVVVHCSAGVGRTGTYIVLDSML

QQIQHEGTVNIFGFLKHIRSQRNYLVQTEEQYVFIHDTLVEAILSKETEV

LDSHIFIAYVNALLIPGPAGKTKLEKQFQLLSQSNIQQSDYSAALKQCNR

EKNRTSSIIPVERSRVGISSLSGEGTDYINASYIMGYYQSNEFIITQHPL

LHTIKDFWRMIWDHNAQLVVMIPDGQNMAEDEFVYWPNKDEPINCESFKV

TLMAEEHKCLSNEEKLIIQDFILEATQDDYVLEVRHFQCPKWPNPDSPIS

KTFELISVIKEEAANRDGPMIVHDEHGGVTAGTFCALTTLMHQLEKENSV

DVYQVAKMINLMRPGVFADIEQYQFLYKVILSLVSTRQEENPSTSLDSNG

AALPDGNIAESLESLV,

PTPRZ1 Isoform 2 having the following amino acid sequence:

(SEQ ID NO: 21)
MRILKRFLACIQLLCVCRLDWANGYYRQQRKLVEEIGWSYTGALNQKNWG

KKYPTCNSPKQSPINIDEDLTQVNVNLKKLKFQGWDKTSLENTFIHNTGK

TVEINLTNDYRVSGGVSEMVFKASKITFHWGKCNMSSDGSEHSLEGQKFP

LEMQIYCFDADRFSSFEEAVKGKGKLRALSILFEVGTEENLDFKAIIDGV

ESVSRFGKQAALDPFILLNLLPNSTDKYYIYNGSLTSPPCTDTVDWIVFK

DTVSISESQLAVFCEVLTMQQSGYVMLMDYLQNNFREQQYKFSRQVFSSY

TGKEEIHEAVCSSEPENVQADPENYTSLLVTWERPVVVYDTMIEKFAVLY

QQLDGEDQTKHEFLTDGYQDLGAILNNLLPNMSYVLQIVAICTNGLYGKY

SDQLIVDMPTDNPELDLFPELIGTEEIIKEEEEGKDIEEGAIVNPGRDSA

TNQIRKKEPQISTTTHYNRIGTKYNEAKTNRSPTRGSEFSGKGDVPNTSL

NSTSQPVTKLATEKDISLTSQTVTELPPHTVEGTSASLNDGSKTVLRSPH

MNLSGTAESLNTVSITEYEEESLLTSFKLDTGAEDSSGSSPATSAIPFIS

ENISQGYIFSSENPETITYDVLIPESARNASEDSTSSGSEESLKDPSMEG

NVWFPSSTDITAQPDVGSGRESFLQTNYTEIRVDESEKTTKSFSAGPVMS

QGPSVTDLEMPHYSTFAYFPTEVTPHAFTPSSRQQDLVSTVNVVYSQTTQ

PVYNGETPLQPSYSSEVFPLVTPLLLDNQILNTTPAASSSDSALHATPVF

PSVDVSFESILSSYDGAPLLPFSSASFSSELFRHLHTVSQILPQVTSATE

SDKVPLHASLPVAGGDLLLEPSLAQYSDVLSTTHAASETLEFGSESGVLY

KTLMFSQVEPPSSDAMMHARSSGPEPSYALSDNEGSQHIFTVSYSSAIPV

HDSVGVTYQGSLFSGPSHIPIPKSSLITPTASLLQPTHALSGDGEWSGAS

SDSEFLLPDTDGLTALNISSPVSVAEFTYTTSVFGDDNKALSKSEIIYGN

ETELQIPSFNEMVYPSESTVMPNMYDNVNKLNASLQETSVSISSTKGMFP

GSLAHTTTKVFDHEISQVPENNFSVQPTHTVSQASGDTSLKPVLSANSEP

ASSDPASSEMLSPSTQLLFYETSASFSTEVLLQPSFQASDVDTLLKTVLP

AVPSDPILVETPKVDKISSTMLHLIVSNSASSENMLHSTSVPVFDVSPTS

HMHSASLQGLTISYASEKYEPVLLKSESSHQVVPSLYSNDELFQTANLEI

NQAHPPKGRHVFATPVLSIDEPLNTLINKLIHSDEILTSTKSSVTGKVFA

GIPTVASDTFVSTDHSVPIGNGHVAITAVSPHRDGSVTSTKLLFPSKATS

ELSHSAKSDAGLVGGGEDGDTDDDGDDDDDRGSDGLSIHKCMSCSSYRE

SQEKVMNDSDTHENSLMDQNNPISYSLSENSEEDNRVTSVSSDSQTGMDR

SPGKSPSANGLSQKHNDGKEENDIQTGSALLPLSPESKAWAVLTSDEESG

SGQGTSDSLNENETSTDFSFADTNEKDADGILAAGDSEITPGFPQSPTSS

VTSENSEVFHVSEAEASNSSHESRIGLAEGLESEKKAVIPLVIVSALTFI

CLVVLVGILIYWRKCFQTAHFYLEDSTSPRVISTPPTPIFPISDDVGAIP

IKHFPKHVADLHASSGFTEEFEEVQSCTVDLGITADSSNHPDNKHKNRYI

NIVAYDHSRVKLAQLAEKDGKLTDYINANYVDGYNRPKAYIAAQGPLKST

AEDFWRMIWEHNVEVIVMITNLVEKGRRKCDQYWPADGSEEYGNFLVTQK

SVQVLAYYTVRNFTLRNTKIKKGSQKGRPSGRVVTQYHYTQWPDMGVPEY

-continued

SLPVLTFVRKAAYAKRHAVGPVVVHCSAGVGRTGTYIVLDSMLQQIQHEG

TVNIFGFLKHIRSQRNYLVQTEEQYVFIHDTLVEAILSKETEVLDSHIHA

YVNALLIPGPAGKTKLEKQFQLLSQSNIQQSDYSAALKQCNREKNRTSSI

IPVERSRVGISSLSGEGTDYINASYIMGYYQSNEFIITQHPLLHTIKDFW

RMIWDHNAQLVVMIPDGQNMAEDEFVYWPNKDEPINCESFKVTLMAEEHK

CLSNEEKLIIQDFILEATQDDYVLEVRHFQCPKWPNPDSPISKTFELISV

IKEEAANRDGPMIVHDEHGGVTAGTFCALTTLMHQLEKENSVDVYQVAKM

INLMRPGVFADIEQYQFLYKVILSLVSTRQEENPSTSLDSNGAALPDGNI

AESLESLV, and PTPRZ1 Isoform 3 having the following amino acid sequence:

(SEQ ID NO: 22)
MRILKRFLACIQLLCVCRLDWANGYYRQQRKLVEEIGWSYTGALNQKNWG

KKYPTCNSPKQSPINIDEDLTQVNVNLKKLKFQGWDKTSLENTFIHNTGK

TVEINLTNDYRVSGGVSEMVFKASKITFHWGKCNMSSDGSEHSLEGQKFP

LEMQIYCFDADRFSSFEEAVKGKGKLRALSILFEVGTEENLDFKAIIDGV

ESVSRFGKQAALDPFILLNLLPNSTDKYYIYNGSLTSPPCTDTVDWIVFK

DTVSISESQLAVFCEVLTMQQSGYVMLMDYLQNNFREQQYKFSRQVFSSY

TGKEEIHEAVCSSEPENVQADPENYTSLLVTWERPRVVYDTMIEKFAVLY

QQLDGEDQTKHEFLTDGYQDLGAILNNLLPNMSYVLQIVAICTNGLYGKY

SDQLIVDMPTDNPELDLFPELIGTEEIIKEEEEGKDIEEGAIVNPGRDSA

TNQIRKKEPQISTTTHYNRIGTKYNEAKTNRSPTRGSEFSGKGDVPNTSL

NSTSQPVTKLATEKDISLTSQTVTELPPHTVEGTSASLNDGSKTVLRSPH

MNLSGTAESLNTVSITEYEEESLLTSFKLDTGAEDSSGSSPATSAIPFIS

ENISQGYIFSSENPETITYDVLIPESARNASEDSTSSGSEESLKDPSMEG

NVWFPSSTDITAQPDVGSGRESFLQTNYTERVDESEKTTKSFSAGPVMSQ

GPSVTDLEMPHYSTFAYFPTEVTPHAFTPSSRQQDLVSTVNVVYSQTTQP

VYNEASNSSHESRIGLAEGLESEKKAVIPLVIVSALTFICLVVLVGILIY

WRKCFQTAHFYLEDSTSPRVISTPPTPIFPISDDVGAIPIKHFPKHVADL

HASSGFTEEFEEVQSCTVDLGITADSSNHPDNKHKNRYINIVAYDHSRVK

LAQLAEKDGKLTDYINANYVDGYNRPKAYIAAQGPLKSTAEDFWRMIWEH

NVEVIVMITNLVEKGRRKCDQYWPADGSEEYGNFLVTQKSVQVLAYYTVR

NFTLRNTKIKKGSQKGRPSGRVVTQYHYTQWPDMGVPEYSLPVLTFVRKA

AYAKRHAVGPVVVHCSAGVGRTGTYIVLDSMLQQIQHEGTVNIFGFLKHI

RSQRNYLVQTEEQYVFIHDTLVEAILSKETEVLDSHIHAYVNALLIPGPA

GKTKLEKQFQLLSQSNIQQSDYSAALKQCNREKNRTSSIIPVERSRVGIS

SLSGEGTDYINASYIMGYYQSNEFIITQHPLLHTIKDFWRMIWDHNAQLV

VMIPDGQNMAEDEFVYWPNKDEPINCESFKVTLMAEEHKCLSNEEKLIIQ

DFILEATQDDYVLEVRHFQCPKWPNPDSPISKTFELISVIKEEAANRDGP

MIVHDEHGGVTAGTFCALTTLMHQLEKENSVDVYQVAKMINLMRPGVFAD

IEQYQFLYKVILSLVSTRQEENPSTSLDSNGAALPDGNIAESLESLV.

In some instances, the methods described herein may employ a BTTS that specifically binds PTPRZ1, including e.g., human PTPRZ1 Isoform 1, human PTPRZ1 Isoform 2, human PTPRZ1 Isoform 3, or any combination thereof.

In some instances, useful priming antigens may include neuronal cell adhesion molecule (NRCAM). NRCAM is a cell adhesion molecule member of the immunoglobulin superfamily with multiple immunoglobulin-like C2-type domains and fibronectin type-III domains encoded by the neuronal cell adhesion molecule gene, located in humans at 7q31.1. NRCAM protein may be found in at least one isoform in humans, including NRCAM Isoform 1 having the following amino acid sequence:

(SEQ ID NO: 23)
MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISVDELNDTIAA

NLSDTEFYGAKSSRERPPTFLTPEGNASNKEELRGNVLSLECIAEGLPTP

IIYWAKEDGMLPKNRTVYKNFEKTLQIIHVSEADSGNYQCIAKNALGAIH

HTISVRVKAAPYWITAPQNLVLSPGEDGTLICRANGNPKPRISWLTNGVP

IEIAPDDPSRKIDGDTIIFSNVQERSSAVYQCNASNEYGYLLANAFVNVL

AEPPRILTPANTLYQVIANRPALLDCAFFGSPLPTIEWFKGAKGSALHED

IYVLHENGTLEIPVAQKDSTGTYTCVARNKLGMAKNEVHLEIKDPTWIVK

QPEYAVVQRGSMVSFECKVKHDHTLSLTVLWLKDNRELPSDERFTVDKDH

LVVADVSDDDSGTYTCVANTTLDSVSASAVLSVVAPTPTPAPVYDVPNPP

FDLELTDQLDKSVQLSWTPGDDNNSPITKFIIEYEDAMHKPGLWHHQTEV

SGTQTTAQLKLSPYVNYSFRVMAVNSIGKSLPSEASEQYLTKASEPDKNP

TAVEGLGSEPDNLVITWKPLNGFESNGPGLQYKVSWRQKDGDDEWTSVVV

ANVSKYIVSGTPTFVPYLIKVQALNDMGFAPEPAVVMGHSGEDLPMVAPG

NVRVNVVNSTLAEVHWDPVPLKSIRGHLQGYRIYYWKTQSSSKRNRRHIE

KKILTFQGSKTHGMLPGLEPFSHYTLNVRVVNGKGEGPASPDRVFNTPEG

VPSAPSSLKIVNPTLDSLTLEWDPPSHPNGILTEYTLKYQPINSTHELGP

LVDLKIPANKTRWTLKNLNFSTRYKFYFYAQTSAGSGSQITEEAVTTVDE

AGILPPDVGAGKVQAVNPRISNLTAAAAETYANISWEYEGPEHVNFYVEY

GVAGSKEEWRKEIVNGSRSFFGLKGLMPGTAYKVRVGAVGDSGFVSSEDV

FETGPAMASRQVDIATQGWFIGLMCAVALLILILLIVCFIRRNKGGKYPV

KEKEDAHADPEIQPMKEDDGTFGEYSDAEDHKPLKKGSRTPSDRTVKKED

SDDSLVDYGEGVNGQFNEDGSFIGQYSGKKEKEPAEGNESSEAPSPVNAM

NSFV,

NRCAM Isoform 2 having the following amino acid sequence:

(SEQ ID NO: 24)
MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISVDELNDTIAA

NLSDTEFYGAKSSRERPPTFLTPEGNASNKEELRGNVLSLECIAEGLPTP

IIYWAKEDGMLPKNRTVYKNFEKTLQIIHVSEADSGNYQCIAKNALGAIH

HTISVRVKAAPYWITAPQNLVLSPGEDGTLICRANGNPKPRISWLTNGVP

IEIAPDDPSRKIDGDTIIFSNVQERSSAVYQCNASNEYGYLLANAFVNVL

AEPPRILTPANTLYQVIANRPALLDCAFFGSPLPTIEWFKGAKGSALHED

IYVLHENGTLEIPVAQKDSTGTYTCVARNKLGMAKNEVHLEIKDPTWIVK

QPEYAVVQRGSMVSFECKVKHDHTLSLTVLWLKDNRELPSDERFTVDKDH

LVVADVSDDDSGTYTCVANTTLDSVSASAVLSVVAPTPTPAPVYDVPNPP

FDLELTDQLDKSVQLSWTPGDDNNSPITKFIIEYEDAMHKPGLWHHQTEV

SGTQTTAQLKLSPYVNYSFRVMAVNSIGKSLPSEASEQYLTKASEPDKNP

TAVEGLGSEPDNLVITWKPLNGFESNGPGLQYKVSWRQKDGDDEWTSVVV

ANVSKYIVSGTPTFVPYLIKVQALNDMGFAPEPAVVMGHSGEDLPMVAPG

NVRVNVVNSTLAEVHWDPVPLKSIRGHLQGYRIYYWKTQSSSKRNRRHIE

KKILTFQGSKTHGMLPGLEPFSHYTLNVRVVNGKGEGPASPDRVFNTPEG

VPSAPSSLKIVNPTLDSLTLEWDPPSHPNGILTEYTLKYQPINSTHELGP

LVDLKIPANKTRWTLKNLNFSTRYKFYFYAQTSAGSGSQITEEAVTTVDE

AGILPPDVGAGKVQAVNPRISNLTAAAAETYANISWEYEGPEHVNFYVEY

GVAGSKEEWRKEIVNGSRSFFGLKGLMPGTAYKVRVGAVGDSGFVSSEDV

FETGPAMASRQVDIATQGWFIGLMCAVALLILILLIVCFIRRNKGGKYPV

KEKEDAHADPEIQPMKEDDGTFGEYRLFSFVSSASF,

NRCAM Isoform 3 having the following amino acid sequence:

(SEQ ID NO: 25)
MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISAKSSRERPPT

FLTPEGNASNKEELRGNVLSLECIAEGLPTPIIYWAKEDGMLPKNRTVYK

NFEKTLQIIHVSEADSGNYQCIAKNALGAIHHTISVRVKAAPYWITAPQN

LVLSPGEDGTLICRANGNPKPRISWLTNGVPIEIAPDDPSRKIDGDTIIF

SNVQERSSAVYQCNASNEYGYLLANAFVNVLAEPPRILTPANTLYQVIAN

RPALLDCAFFGSPLPTIEWFKGAKGSALHEDIYVLHENGTLEIPVAQKDS

TGTYTCVARNKLGMAKNEVHLEIKDPTWIVKQPEYAVVQRGSMVSFECKV

KHDHTLSLTVLWLKDNRELPSDERFTVDKDHLVVADVSDDDSGTYTCVAN

TTLDSVSASAVLSVVAPTPTPAPVYDVPNPPFDLELTDQLDKSVQLSWTP

GDDNNSPITKFIIEYEDAMHKPGLWHHQTEVSGTQTTAQLKLSPYVNYSF

RVMAVNSIGKSLPSEASEQYLTKASEPDKNPTAVEGLGSEPDNLVITWKP

LNGFESNGPGLQYKVSWRQKDGDDEWTSVVVANVSKYIVSGTPTFVPYLI

KVQALNDMGFAPEPAVVMGHSGEDLPMVAPGNVRVNVVNSTLAEVHWDPV

PLKSIRGHLQGYRIYYWKTQSSSKRNRRHIEKKILTFQGSKTHGMLPGLE

PFSHYTLNVRVVNGKGEGPASPDRVFNTPEGVPSAPSSLKIVNPTLDSLT

LEWDPPSHPNGILTEYTLKYQPINSTHELGPLVDLKIPANKTRWTLKNLN

FSTRYKFYFYAQTSAGSGSQITEEAVTTVDEAMASRQVDIATQGWFIGLM

CAVALLILILLIVCFIRRNKGGKYPVKEKEDAHADPEIQPMKEDDGTFGE

YSDAEDHKPLKKGSRTPSDRTVKKEDSDDSLVDYGEGVNGQFNEDGSFIG

QYSGKKEKEPAEGNESSEAPSPVNAMNSFV,

NRCAM Isoform 4 having the following amino acid sequence:

(SEQ ID NO: 26)
MQLKIMPKKKRLSAGRVPLILFLCQMISALEVPLDLVQPPTITQQSPKDY

IIDPRENIVIQCEAKGKPPPSFSWTRNGTHFDIDKDPLVTMKPGTGTLII

NIMSEGKAETYEGVYQCTARNERGAAVSNNIVVRPSRSPLWTKEKLEPIT

LQSGQSLVLPCRPPIGLPPPIIFWMDNSFQRLPQSERVSQGLNGDLYFSN

VLPEDTREDYICYARFNHTQTIQQKQPISVKVISVDELNDTIAANLSDTE

FYGAKSSRERPPTFLTPEGNASNKEELRGNVLSLECIAEGLPTPIIYWAK

EDGMLPKNRTVYKNFEKTLQIIHVSEADSGNYQCIAKNALGAIHHTISVR

VKAAPYWITAPQNLVLSPGEDGTLICRANGNPKPRISWLTNGVPIEIAPD

DPSRKIDGDTIIFSNVQERSSAVYQCNASNEYGYLLANAFVNVLAEPPRI

LTPANTLYQVIANRPALLDCAFFGSPLPTIEWFKGAKGSALHEDIYVLHE

NGTLEIPVAQKDSTGTYTCVARNKLGMAKNEVHLEIKDPTWIVKQPEYAV

VQRGSMVSFECKVKHDHTLSLTVLWLKDNRELPSDERFTVDKDHLVVADV

SDDDSGTYTCVANTTLDSVSASAVLSVVDVPNPPFDLELTDQLDKSVQLS

WTPGDDNNSPITKFIIEYEDAMHKPGLWHHQTEVSGTQTTAQLKLSPYVN

YSFRVMAVNSIGKSLPSEASEQYLTKASEPDKNPTAVEGLGSEPDNLVIT

WKPLNGFESNGPGLQYKVSWRQKDGDDEWTSVVVANVSKYIVSGTPTFVP

YLIKVQALNDMGFAPEPAVVMGHSGEDLPMVAPGNVRVNVVNSTLAEVHW

DPVPLKSIRGHLQGYRIYYWKTQSSSKRNRRHIEKKILTFQGSKTHGMLP

GLEPFSHYTLNVRVVNGKGEGPASPDRVFNTPEGVPSAPSSLKIVNPTLD

SLTLEWDPPSHPNGILTEYTLKYQPINSTHELGPLVDLKIPANKTRWTLK

NLNFSTRYKFYFYAQTSAGSGSQITEEAVTTVDEAMASRQVDIATQGWFI

GLMCAVALLILILLIVCFIRRNKGGKYPVKEKEDAHADPEIQPMKEDDGT

FGEYSDAEDHKPLKKGSRTPSDRTVKKEDSDDSLVDYGEGVNGQFNEDGS

FIGQYSGKKEKEPAEGNESSEAPSPVNAMNSFV,

NRCAM Isoform 5 having the following amino acid sequence:

(SEQ ID NO: 27)
MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISVDELNDTIAA

NLSDTEFYGAKSSRERPPTFLTPEGNASNKEELRGNVLSLECIAEGLPTP

IIYWAKEDGMLPKNRTVYKNFEKTLQIIHVSEADSGNYQCIAKNALGAIH

HTISVRVKAAPYWITAPQNLVLSPGEDGTLICRANGNPKPRISWLTNGVP

IEIAPDDPSRKIDGDTIIFSNVQERSSAVYQCNASNEYGYLLANAFVNVL

AEPPRILTPANTLYQVIANRPALLDCAFFGSPLPTIEWFKGAKGSALHED

IYVLHENGTLEIPVAQKDSTGTYTCVARNKLGMAKNEVHLEIKDPTWIVK

QPEYAVVQRGSMVSFECKVKHDHTLSLTVLWLKDNRELPSDERFTVDKDH

LVVADVSDDDSGTYTCVANTTLDSVSASAVLSVVAPTPTPAPVYDVPNPP

FDLELTDQLDKSVQLSWTPGDDNNSPITKFIIEYEDAMHKPGLWHHQTEV

SGTQTTAQLKLSPYVNYSFRVMAVNSIGKSLPSEASEQYLTKASEPDKNP

TAVEGLGSEPDNLVITWKPLNGFESNGPGLQYKVSWRQKDGDDEWTSVVV

ANVSKYIVSGTPTFVPYLIKVQALNDMGFAPEPAVVMGHSGEDLPMVAPG

NVRVNVVNSTLAEVHWDPVPLKSIRGHLQGYRIYYWKTQSSSKRNRRHIE

KKILTFQGSKTHGMLPGLEPFSHYTLNVRVVNGKGEGPASPDRVFNTPEG

VPSAPSSLKIVNPTLDSLTLEWDPPSHPNGILTEYTLKYQPINSTHELGP

LVDLKIPANKTRWTLKNLNFSTRYKFYFYAQTSAGSGSQITEEAVTTVDE

AGILPPDVGAGKVQAVNPRISNLTAAAAETYANISWEYEGPEHVNFYVEY

GVAGSKEEWRKEIVNGSRSFFGLKGLMPGTAYKVRVGAVGDSGFVSSEDV

FETGPAMASRQVDIATQGWFIGLMCAVALLILLLIVCFIRRNKGGKYPV

KEKEDAHADPEIQPMKEDDGTFGEYRSLESDAEDHKPLKKGSRTPSDRTV

KKEDSDDSLVDYGEGVNGQFNEDGSFIGQYSGKKEKEPAEGNESSEAPSP

VNAMNSFV and NRCAM Isoform 6 having the following amino acid sequence:

(SEQ ID NO: 28)
MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISAKSSRERPPT

FLTPEGNASNKEELRGNVLSLECIAEGLPTPIIYWAKEDGMLPKNRTVYK

NFEKTLQIIHVSEADSGNYQCIAKNALGAIHHTISVRVKAAPYWITAPQN

LVLSPGEDGTLICRANGNPKPRISWLTNGVPIEIAPDDPSRKIDGDTIIF

SNVQERSSAVYQCNASNEYGYLLANAFVNVLAEPPRILTPANTLYQVIAN

RPALLDCAFFGSPLPTIEWFKGAKGSALHEDIYVLHENGTLEIPVAQKDS

TGTYTCVARNKLGMAKNEVHLEIKDPTWIVKQPEYAVVQRGSMVSFECKV

KHDHTLSLTVLWLKDNRELPSDERFTVDKDHLVVADVSDDDSGTYTCVAN

TTLDSVSASAVLSVVAPTPTPAPVYDVPNPPFDLELTDQLDKSVQLSWTP

GDDNNSPITKFIIEYEDAMHKPGLWHHQTEVSGTQTTAQLKLSPYVNYSF

RVMAVNSIGKSLPSEASEQYLTKASEPDKNPTAVEGLGSEPDNLVITWKP

LNGFESNGPGLQYKVSWRQKDGDDEWTSVVVANVSKYIVSGTPTFVPYLI

KVQALNDMGFAPEPAVVMGHSGEDLPMVAPGNVRVNVVNSTLAEVHWDPV

PLKSIRGHLQGYRIYYWKTQSSSKRNRRHIEKKILTFQGSKTHGMLPGLE

PFSHYTLNVRVVNGKGEGPASPDRVFNTPEGVPSAPSSLKIVNPTLDSLT

LEWDPPSHPNGILTEYTLKYQPINSTHELGPLVDLKIPANKTRWTLKNLN

FSTRYKFYFYAQTSAGSGSQITEEAVTTVDEAGILPPDVGAGKAMASRQV

DIATQGWFIGLMCAVALLILLLIVCFIRRNKGGKYPVKEKEDAHADPEI

QPMKEDDGTFGEYSDAEDHKPLKKGSRTPSDRTVKKEDSDDSLVDYGEGV

NGQFNEDGSFIGQYSGKKEKEPAEGNESSEAPSPVNAMNSFV.

In some instances, the methods described herein may employ a BTTS that specifically binds NRCAM, including e.g., human NRCAM Isoform 1, human NRCAM Isoform 2, human NRCAM Isoform 3, human NRCAM Isoform 4, human NRCAM Isoform 5, human NRCAM Isoform 6, or any combination thereof.

In some instances, useful priming antigens may include Cadherin-10 (CDH10). CDH10 is a calcium-dependent cell adhesion protein predominantly expressed in brain and a type II classical cadherin of the cadherin superfamily encoded by the cadherin 10 gene, located in humans at 5p14.2-p14.1. CDH10 protein may be found in multiple transcript variants due to alternative splicing and at least one isoform is found in humans, including the CDH10 protein having the following amino acid sequence:

(SEQ ID NO: 29)
MTIHQFLLLLFLFWVCLPHFCSPEIMFRRTPVPQQRILSSRVPRSDGKILH

RQKRGWMWNQFFLLEEYTGSDYQYVGKLHSDQDKGDGSLKYILSGDGAGT

LFIIDEKTGDIHATRRIDREEKAFYTLRAQAINRRTLRPVEPESEFVIKI

HDINDNEPTFPEEIYTASVPEMSVVGTSVVQVTATDADDPSYGNSARVIY

SILQGQPYFSVEPETGIIRTALPNMNRENREQYQVVIQAKDMGGQMGGLS

GTTTVNITLTDVNDNPPRFPQNTIHLRVLESSPVGTAIGSVKATDADTGK

NAEVEYRIIDGDGTDMFDIVTEKDTQEGIITVKKPLDYESRRLYTLKVEA

ENTHVDPRFYYLGPFKDTTIVKISIEDVDEPPVFSRSSYLFEVHEDIEVG

TIIGTVMARDPDSISSPIRFSLDRHTDLDRIFNIHSGNGSLYTSKPLDRE

LSQWHNLTVIAAEINNPKETTRVAVFVRILDVNDNAPQFAVFYDTFVCEN

ARPGQLIQTISAVDKDDPLGGQKFFFSLAAVNPNFTVQDNEDNTARILTR

KNGFNRHEISTYLLPVVISDNDYPIQSSTGTLTIRVCACDSQGNMQSCSA

EALLLPAGLSTGALIAILLCIIILLVIVVLFAALKRQRKKEPLILSKEDI

RDNIVSYNDEGGGEEDTQAFDIGTLRNPAAIEEKKLRRDIIPETLFIPRR

-continued
TPTAPDNTDVRDFINERLKEHDLDPTAPPYDSLATYAYEGNDSIAESLSS

LESGTTEGDQNYDYLREWGPRFNKLAEMYGGGESDKDS.

In some instances, the methods described herein may employ a BTTS that specifically binds CDH10, including e.g., human CDH10 and the CDH10 amino acid sequence provided above.

In some instances, useful priming antigens may include Protocadherin gamma-C5 (PCDHGC5; also known as PCDH-gamma-05). PCDHGC5 is a member of the protocadherin gamma gene cluster, has an immunoglobulin-like organization and is a neural cadherin-like cell adhesion protein encoded by the protocadherin gamma subfamily C, 5 gene, located in humans at 5q31.3. PCDHGC5 protein may be found in at least one isoform in humans, including PCDHGC5 Isoform 1 having the following amino acid sequence:

(SEQ ID NO: 30)
MGPKTLPQLAGKWQVLCMLSLCCWGWVSGQLRYSVVEESEPGTLVGNVAQ

DLGLKMTDLLSRRLQLGSEENGRYFSLSLMSGALAVNQKIDRESLCGAST

SCLLPVQVVTEHPLELIRVEVEILDLNDNSPSFATPEREMRISESAASGA

RFPPLDSAQDPDVGTNTVSFYTLSPNSHFSLNVKTLKDGKPFPELVLEQQL

DREAQARHQLVLTAVDGGTPARSGTTLISVIVLDINDNAPTFQSSVLRVG

IPENAPIGTLLLRLNATDPDEGTNGQLDYSFGDHTSEAVRNLFGLDPSSG

AIHVLGPIDFEESRFYEIHARARDQGQPAMEGHCVIQVDVGDVNDNAPEV

LLASLANPVLESTPVGTVVGLFNVRDRDSGRNGEVSLDISPDLPFQIKPS

ENHYSLLTSQPLDREATSHYIIELLASDAGSPSLHKHLTIRLNISDVNDN

APRFNQQLYTAYILENRPPGSLLCTVAASDPDTGDNARLTYSIVGNQVQG

APASFVYVNPEDGRIFAQRTFDYELLQMLQIVVGVRDSGSPPLHANTSLH

VFVLDENDNAPAVLHPRPDWEHSAPQRLPRSAPPGSLVTKVTAVDADAGH

NAWLSYSLLPQSTAPGLFLVSTHTGEVRTARALLEDDSDTQQVVVLVRDN

GDPSLSSTATVLLVLEDEDPEEMPKSSDFLIHPPERSDLTLYLIVALATV

SLLSLVTFTFLSAKCLQGNADGDGGGQCCRRQDSPSPDFYKQSSPNLQV

SSDGTLKYMEVTLRPTDSQSHCYRTCFSPASDGSDFTFLRPLSVQQPTAL

ALEPDAIRSRSNTLRERSQQAPPNTDWRFSQAQRPGTSGSQNGDDTGTWP

NNQFDTEMLQAMILASASEAADGSSTLGGGAGTMGLSARYGPQFTLQHVP

DYRQNVYIPGSNATLTNAAGKRDGKAPAGGNGNKKKSGKKEKK, and PCDHGC5 Isoform 2 having the following amino acid sequence:

(SEQ ID NO: 31)
MGPKTLPQLAGKWQVLCMLSLCCWGWVSGQLRYSVVEESEPGTLVGNVAQ

DLGLKMTDLLSRRLQLGSEENGRYFSLSLMSGALAVNQKIDRESLCGAST

SCLLPVQVVTEHPLELIRVEVEILDLNDNSPSFATPEREMRISESAASGA

RFPPLDSAQDPDVGTNTVSFYTLSPNSHFSLNVKTLKDGKPFPELVLEQQL

DREAQARHQLVLTAVDGGTPARSGTTLISVIVLDINDNAPTFQSSVLRVG

IPENAPIGTLLLRLNATDPDEGTNGQLDYSFGDHTSEAVRNLFGLDPSSG

AIHVLGPIDFEESRFYEIHARARDQGQPAMEGHCVIQVDVGDVNDNAPEV

LLASLANPVLESTPVGTVVGLFNVRDRDSGRNGEVSLDISPDLPFQIKPS

ENHYSLLTSQPLDREATSHYIIELLASDAGSPSLHKHLTIRLNISDVNDN

APRFNQQLYTAYILENRPPGSLLCTVAASDPDTGDNARLTYSIVGNQVQG

APASSFVYVNPEDGRIFAQRTFDYELLQMLQIVVGVRDSGSPPLHANTSL

HVFVLDENDNAPAVLHPRPDWEHSAPQRLPRSAPPGSLVTKVTAVDADAG

HNAWLSYSLLPQSTAPGLFLVSTHTGEVRTARALLEDDSDTQQVVVLVRD

NGDPSLSSTATVLLVLEDEDPEEMPKSSDFLIHPPERSDLTLYLIVALAT

VSLLSLVTFTFLSAKCLQGNADGDGGGQCCRRQDSPSPDFYKQSSPNLQ

VSSDGTLKYMEVTLRPTDSQSHCYRTCFSPASDGSDFTFLRPLSVQQPTA

LALEPDAIRSRSNTLRERSQVRGSAPPRATPGGGTGEAARPHKGLNLHPL

LSGRLGRWLRSTRFSGSLDRLRETRVAD.

In some instances, the methods described herein may employ a BTTS that specifically binds PCDHGC5, including e.g., human PCDHGC5 Isoform 1, human PCDHGC5 Isoform 2, or both.

In some instances, useful priming antigens may include CD70 (Also known as CD27L; LPFS3; CD27-L; CD27LG; TNFSF7; TNLG8A). CD70 is a cytokine that belongs to the tumor necrosis factor (TNF) ligand family and is encoded by the CD70 gene, located in humans at 19p13.3. CD70 is a ligand for TNFRSF27/CD2 and is a surface antigen on activated, but not on resting, T and B lymphocytes. CD70 protein may be found in at least two isoforms in humans, including CD70 isoform 1 having the following amino acid sequence:

(SEQ ID NO: 32)
MPEEGSGCSVRRRPYGCVLRAALVPLVAGLVICLVVCIQRFAQAQQQLPL

ESLGWDVAELQLNHTGPQQDPRLYWQGGPALGRSFLHGPELDKGQLRIHR

DGIYMVHIQVTLAICSSTTASRHHPTTLAVGICSPASRSISLLRLSFHQG

CTIASQRLTPLARGDTLCTNLTGTLLPSRNTDETFFGVQWVRP, and isoform 2 having the following sequence:

(SEQ ID NO: 33)
MPEEGSGCSVRRRPYGCVLRAALVPLVAGLVICLVVCIQRFAQAQQQLPL

ESLGWDVAELQLNHTGPQQDPRLYWQGGPALGRSFLHGPELDKGQLRIHR

DGIYMVHIQVTLAICSSTTASRHHPTTLAVGICSPASRSISLLRLSFHQG

LFGFWNWGLKVKCFLRHLIWTAHCHPLTQLVFMQALQSWRNHHCSHFTDE

ENRGVNR.

In some instances, the methods described herein may employ a BTTS that specifically binds CD70, including e.g., human CD70.

In some instances, useful priming antigens may include chondroitin sulfate proteoglycan 5 (CSPG5; also known as NGC, Acidic leucine-rich EGF-like domain-containing brain protein and Neuroglycan C). CSPG5 is a proteoglycan that may function as a neural growth and differentiation factor and is encoded by the CSPG5 gene, located in humans at 3p21.31. CSPG5 may function as a growth and differentiation factor involved in neuritogenesis. CSPG5 protein may be found in at least three isoforms in humans, including CSPG5 isoform 1 having the following amino acid sequence:

(SEQ ID NO: 34)
MGRAGGGGPGRGPPPLLLFLGAALVLASGAVPAREAGSAVEAEELVKGSP

AWEPPANDTREEAGPPAAGEDEASWTAPGGELAGPEEVLQESAAVTGTAW

LEADSPGLGGVTAEAGSGDAQALPATLQAPHEVLGQSIMPPAIPEATEAS

GPPSPTPGDKLSPASELPKESPLEVWLNLGGSTPDPQGPELTYPFQGTLE

PQPASDIIDIDYFEGLDGEGRGADLGSFPGSPGTSENHPDTEGETPSWSL

LDLYDDFTPFDESDFYPTTSFYDDLDEEEEEEEDDKDAVGGGDLEDENEL

LVPTGKPGLGPGTGQPTSRWHAVPPQHTLGSVPGSSIALRPRPGEPGRDL

ASSENGTECRSGFVRHNGSCRSVCDLFPSYCHNGGQCYLVENIGAFCRCN

TQDYIWHKGMRCESIITDFQVMCVAVGSAALVLLLLFMMTVFFAKKLYLL

KTENTKLRRTNKFRTPSELHNDNFSLSTIAEGSHPNVRKLCNTPRTSSPH

ARALAHYDNVICQDDPSAPHKIQEVLKSCLKEEESFNIQNSMSPKLEGGK

GDQADLDVNCLQNNLT;

CSPG5 isoform 2 having the following amino acid sequence:

(SEQ ID NO: 35)
MGRAGGGGPGRGPPPLLLFLGAALVLASGAVPAREAGSAVEAEELVKGSP

AWEPPANDTREEAGPPAAGEDEASWTAPGGELAGPEEVLQESAAVTGTAW

LEADSPGLGGVTAEAGSGDAQALPATLQAPHEVLGQSIMPPAIPEATEAS

GPPSPTPGDKLSPASELPKESPLEVWLNLGGSTPDPQGPELTYPFQGTLE

PQPASDIIDIDYFEGLDGEGRGADLGSFPGSPGTSENHPDTEGETPSWSL

LDLYDDFTPFDESDFYPTTSFYDDLDEEEEEEEDDKDAVGGGDLEDENEL

LVPTGKPGLGPGTGQPTSRWHAVPPQHTLGSVPGSSIALRPRPGEPGRDL

ASSENGTECRSGFVRHNGSCRSVCDLFPSYCHNGGQCYLVENIGAFCRCN

TQDYIWHKGMRCESIITDFQVMCVAVGSAALVLLLLFMMTVFFAKKLYLL

KTENTKLRRTNKFRTPSELHNDNFSLSTIAEGSHPNDDPSAPHKIQEVLK

SCLKEEESFNIQNSMSPKLEGGKGDQADLDVNCLQNNLT;

and CSPG5 isoform 3 having the following amino acid sequence:

(SEQ ID NO : 36)
MPPAIPEATEASGPPSPTPGDKLSPASELPKESPLEVWLNLGGSTPDPQG

PELTYPFQGTLEPQPASDIIDIDYFEGLDGEGRGADLGSFPGSPGTSENH

PDTEGETPSWSLLDLYDDFTPFDESDFYPTTSFYDDLDEEEEEEEDDKDA

VGGGDLEDENELLVPTGKPGLGPGTGQPTSRWHAVPPQHTLGSVPGSSIA

LRPRPGEPGRDLASSENGTECRSGFVRHNGSCRSVCDLFPSYCHNGGQCY

LVENIGAFCRCNTQDYIWHKGMRCESIITDFQVMCVAVGSAALVLLLLFM

MTVFFAKKLYLLKTENTKLRRTNKFRTPSELHNDNFSLSTIAEGSHPNDD

PSAPHKIQEVLKSCLKEEESFNIQNSMSPKLEGGKGDQADLDVNCLQNNL

T.

In some instances, the methods described herein may employ a BTTS that specifically binds CSPG5, including e.g., human CSPG5.

In some instances, useful priming antigens may include brevican (BCAN; Also known as Brevican core protein; Chondroitin sulfate proteoglycan 7 (CSPG7); Brain-enriched hyaluronan-binding protein (BEHAB)). BCAN is a member of the lectican family of chondroitin sulfate proteoglycans that is specifically expressed in the central nervous system and is encoded by the BCAN gene, located in humans at 1q23.1. BCAN may play a role in the terminally differentiating and the adult nervous system during postnatal development. BCAN protein may be found in at least two isoforms in humans, including BCAN isoform 1 having the following amino acid sequence:

(SEQ ID NO: 37)
MAQLFLPLLAALVLAQAPAALADVLEGDSSEDRAFRVRIAGDAPLQGVLG

GALTIPCHVHYLRPPPSRRAVLGSPRVKWTFLSRGREAEVLVARGVRVKV

NEAYRFRVALPAYPASLTDVSLALSELRPNDSGIYRCEVQHGIDDSSDAV

EVKVKGVVFLYREGSARYAFSFSGAQEACARIGAHIATPEQLYAAYLGGY

EQCDAGWLSDQTVRYPIQTPREACYGDMDGFPGVRNYGVVDPDDLYDVYC

YAEDLNGELFLGDPPEKLTLEEARAYCQERGAEIATTGQLYAAWDGGLDH

CSPGWLADGSVRYPIVTPSQRCGGGLPGVKTLFLFPNQTGFPNKHSRFNV

YCFRDSAQPSAIPEASNPASNPASDGLEAIVTVTETLEELQLPQEATESE

SRGAIYSIPIMEDGGGGSSTPEDPAEAPRTLLEFETQSMVPPTGFSEEEG

KALEEEEKYEDEEEKEEEEEEEVEDEALWAWPSELSSPGPEASLPTEPA

AQEESLSQAPARAVLQPGASPLPDGESEASRPPRVHGPPTETLPTPRERN

LASPSPSTLVEAREVGEATGGPELSGVPRGESEETGSSEGAPSLLPATRA

PEGTRELEAPSEDNSGRTAPAGTSVQAQPVLPTDSASRGGVAVVPASGDC

VPSPCHNGGTCLEEEEGVRCLCLPGYGGDLCDVGLRFCNPGWDAFQGACY

KHFSTRRSWEEAETQCRMYGAHLASISTPEEQDFINNRYREYQWIGLNDR

TIEGDFLWSDGVPLLYENWNPGQPDSYFLSGENCVVMVWHDQGQWSDVPC

NYHLSYTCKMGLVSCGPPPELPLAQVFGRPRLRYEVDTVLRYRCREGLAQ

RNLPLIRCQENGRWEAPQISCVPRRPARALHPEEDPEGRQGRLLGRWKAL

LIPPSSPMPGP;

and BCAN isoform 2 having the following amino acid sequence:

(SEQ ID NO: 38)
MAQLFLPLLAALVLAQAPAALADVLEGDSEDRAFRVRIAGDAPLQGVLGG

ALTIPCHVHYLRPPPSRRAVLGSPRVKWTFLSRGREAEVLVARGVRVKVN

EAYRFRVALPAYPASLTDVSLALSELRPNDSGIYRCEVQHGIDDSSDAVE

VKVKGVVFLYREGSARYAFSFSGAQEACARIGAHIATPEQLYAAYLGGYE

-continued
QCDAGWLSDQTVRYPIQTPREACYGDMDGFPGVRNYGVVDPDDLYDVYCY

AEDLNGELFLGDPPEKLTLEEARAYCQERGAEIATTGQLYAAWDGGLDHC

SPGWLADGSVRYPIVTPSQRCGGGLPGVKTLFLFPNQTGFPNKHSRFNVY

CFRDSAQPSAIPEASNPASNPASDGLEAIVTVTETLEELQLPQEATESES

RGAIYSIPIMEDGGGGSSTPEDPAEAPRTLLEFETQSMVPPTGFSEEEGK

ALEEEEKYEDEEEKEEEEEEEVEDEALWAWPSELSSPGPEASLPTEPAA

QEESLSQAPARAVLQPGASPLPDGESEASRPPRVHGPPTETLPTPRERNL

ASPSPSTLVEAREVGEATGGPELSGVPRGESEETGSSEGAPSLLPATRAP

EGTRELEAPSEDNSGRTAPAGTSVQAQPVLPTDSASRGGVAVVPASGNSA

QGSTALSILLLFFPLQLWVT.

In some instances, the methods described herein may employ a BTTS that specifically binds BCAN, including e.g., human BCAN.

In some instances, useful priming antigens may include glutamate metabotropic receptor 3 (GRM3; Also known as GLUR3; mGlu3; GPRC1C; MGLUR3; Metabotropic glutamate receptor 3). GRM3 is a G-protein coupled receptor for glutamate that is encoded by the GRM3 gene, located in humans at 7q21.11-q21.12. GRM3 ligand binding causes a conformation change that triggers signaling via guanine nucleotide-binding proteins (G proteins) and modulates the activity of down-stream effectors. Signaling inhibits adenylate cyclase activity. GRM3 protein may be found in at least two isoforms in humans, including GRM3 isoform 1 having the following amino acid sequence:

(SEQ ID NO: 39)
MKMLTRLQVLTLALFSKGFLLSLGDHNFLRREIKIEGDLVLGGLFPINEK

GTGTEECGRINEDRGIQRLEAMLFAIDEINKDDYLLPGVKLGVHILDTCS

RDTYALEQSLEFVRASLTKVDEAEYMCPDGSYAIQEMPLLIAGVIGGSYS

SVSIQVANLLRLFQIPQISYASTSAKLSDKSRYDYFARTVPPDFYQAKAM

AEILRFFNWTYVSTVASEGDYGETGIEAFEQEARLRNICIATAEKVGRSN

IRKSYDSVIRELLQKPNARVVVLFMRSDDSRELIAAASRANASFTWVASD

GWGAQESIIKGSEHVAYGAITLELASQPVRQFDRYFQSLNPYNNHRNPWF

RDFWEQKFQCSLQNKRNHRRVCDKHLAIDSSNYEQESKIMFVVNAVYAMA

HALHKMQRTLCPNTTKLCDAMKILDGKKLYKDYLLKINFTAPFNPNKDAD

SIVKFDTFGDGMGRYNVFNFQNVGGKYSYLKVGHWAETLSLDVNSIHWSR

NSVPTSQCSDPCAPNEMKNMQPGDVCCWICIPCEPYEYLADEFTCMDCGS

GQWPTADLTGCYDLPEDYIRWEDAWAIGPVTIACLGFMCTCMVVTVFIKH

NNTPLVKASGRELCYILLFGVGLSYCMTFFFIAKPSPVICALRRLGLGSS

FAICYSALLTKTNCIARIFDGVKNGAQRPKFISPSSQVFICLGLILVQIV

MVSVWLILEAPGTRRYTLAEKRETVILKCNVKDSMLISLTYDVILVILCT

VYAFKTRKCPENFNEAKFIGFTMYTTCIIWLAFLPIFYVTSSDYRVQTTT

MCISVSLSGFVVLGCLFAPKVHIILFQPQKNVVTHRLHLNRFSVSGTTT

YSQSSASTYVPTVCNGREVLDSTTSSL;

and GRM3 isoform 2 having the following amino acid sequence:

(SEQ ID NO: 40)
MKMLTRLQVLTLALFSKGFLLSLGDHNFLRREIKIEGDLVLGGLFPINEK

GTGTEECGRINEDRGIQRLEAMLFAIDEINKDDYLLPGVKLGVHILDTCS

RDTYALEQSLEFVRASLTKVDEAEYMCPDGSYAIQEMPLLIAGVIGGSYS

SVSIQVANLLRLFQIPQISYASTSAKLSDKSRYDYFARTVPPDFYQAKAM

AEILRFFNWTYVSTVASEGDYGETGIEAFEQEARLRNICIATAEKVGRSN

IRKSYDSVIRELLQKPNARVVVLFMRSDDSRELIAAASRANASFTWVASD

GWGAQESIIKGSEHVAYGAITLELASQPVRQFDRYFQSLNPYNNHRNPWF

RDFWEQKFQCSLQNKRNHRRVCDKHLAIDSNYEQESKIMFVVNAVYAMAH

ALHKMQRTLCPNTTKLCDAMKILDGKKLYKDYLLKINFTGADDNHVHLCQ

PEWLCGLGLFVCTQGSHHPVSTPEECCHTQTAPQQVQCQWNWDHILSVLC

KHVCANGVQWAGSPRLHHLISVIVNCSSVLVFLDC.

In some instances, the methods described herein may employ a BTTS that specifically binds GRM3, including e.g., human GRM3.

In some instances, useful priming antigens may include Protein crumbs homolog 1 (CRB1; LCA8; RP12). CRB1 is similar to the *Drosophila* crumbs protein and localizes to the inner segment of mammalian photoreceptors and is encoded by the crumbs cell polarity complex component 1 gene, located in humans at 1q31.3. CRB1 may maintain cell polarization and adhesion. CRB1 protein may be found in at least five isoforms in humans, including CRB1 isoform 1 having the following amino acid sequence:

(SEQ ID NO: 41)
MALKNINYLLIFYLSFSLLIYIKNSFCNKNNTRCLSNSCQNNSTCKDFSK

DNDCSCSDTANNLDKDCDNMKDPCFSNPCQGSATCVNTPGERSFLCKCPP

GYSGTICETTIGSCGKNSCQHGGICHQDPIYPVCICPAGYAGRFCEIDHD

ECASSPCQNGAVCQDGIDGYSCFCVPGYQGRHCDLEVDECASDPCKNEAT

CLNEIGRYTCICPHNYSGVNCELEIDECWSQPCLNGATCQDALGAYFCDC

APGFLGDHCELNTDECASQPCLHGGLCVDGENRYSCNCTGSGFTGTHCET

LMPLCWSKPCHNNATCEDSVDNYTCHCWPGYTGAQCEIDLNECNSNPCQS

NGECVELSSEKQYGRITGLPSSFSYHEASGYVCICQPGFTGIHCEEDVNE

CSSNPCQNGGTCENLPGNYTCHCPFDNLSRTFYGGRDCSDILLGCTHQQC

LNNGTCIPHFQDGQHGFSCLCPSGYTGSLCEIATTLSFEGDGFLWVKSGS

VTTKGSVCNIALRFQTVQPMALLLFRSNRDVFVKLELLSGYIHLSIQVNN

QSKVLLFISHNTSDGEWHFVEVIFAEAVTLTLIDDSCKEKCIAKAPTPLE

SDQSICAFQNSFLGGLPVGMTSNGVALLNFYNMPSTPSFVGCLQDIKIDW

NHITLENISSGSSLNVKAGCVRKDWCESQPCQSRGRCINLWLSYQCDCHR

PYEGPNCLREYVAGRFGQDDSTGYVIFTLDESYGDTISLSMFVRTLQPSG

LLLALENSTYQYIRVWLERGRLAMLTPNSPKLVVKFVLNDGNVHLISLKI

KPYKIELYQSSQNLGFISASTWKIEKGDVIYIGGLPDKQETELNGGFFKG

CIQDVRLNNQNLEFFPNPTNNASLNPVLVNVTQGCAGDNSCKSNPCHNGG

```
VCHSRWDDFSCSCPALTSGKACEEVQWCGFSPCPHGAQCQPVLQGFECIA

NAVFNGQSGQILFRSNGNITRELTNITFGFRTRDANVIILHAEKEPEFLN

ISIQDSRLFFQLQSGNSFYMLSLTSLQSVNDGTWHEVTLSMTDPLSQTSR

WQMEVDNETPFVTSTIATGSLNFLKDNTDIYVGDRAIDNIKGLQGCLSTI

EIGGIYLSYFENVHGFINKPQEEQFLKISTNSVVTGCLQLNVCNSNPCLH

GGNCEDIYSSYHCSCPLGWSGKHCELNIDECFSNPCIFIGNCSDRVAAYH

CTCEPGYTGVNCEVDIDNCQSHQCANGATCISHTNGYSCLCFGNFTGKFC

RQSRLPSTVCGNEKTNLTCYNGGNCTEFQTELKCMCRPGFTGEWCEKDID

ECASDPCVNGGLCQDLLNKFQCLCDVAFAGERCEVDLADDLISDIFTTIG

SVTVALLLILLLAIVASVVTSNKRATQGTYSPSRQEKEGSRVEMWNLMPP

PAMERLI;
```

CRB 1 isoform 2 having the following amino acid sequence:

```
                                        (SEQ ID NO: 42)
MALKNINYLLIFYLSFSLLIYIKNSFCNKNNTRCLSNSCQNNSTCKDFSK

DNDCSCSDTANNLDKDCDNMKDPCFSNPCQGSATCVNTPGERSFLCKCPP

GYSGTICETTIGSCGKNSCQHGGICHQDPIYPVCICPAGYAGRFCEIDHD

ECASSPCQNGAVCQDGIDGYSCFCVPGYQGRHCDLEVDECASDPCKNEAT

CLNEIGRYTCICPHNYSGVNCELEIDECWSQPCLNGATCQDALGAYFCDC

APGFLGDHCELNTDECASQPCLHGGLCVDGENRYSCNCTGSGFTGTHCET

LMPLCWSKPCHNNATCEDSVDNYTCHCWPGYTGAQCEIDLNECNSNPCQS

NGECVELSSEKQYGRITGLPSSFSYHEASGYVCICQPGFTGIHCEEDVNE

CSSNPCQNGGTCENLPGNYTCHCPFDNLSRTFYGGRDCSDILLGCTHQQC

LNNGTCIPHFQDGQHGFSCLCPSGYTGSLCEIATTLSFEGDGFLWVKSGS

VTTKGSVCNIALRFQTVQPMALLLFRSNRDVFVKLELLSGYIHLSIQVNN

QSKVLLFISHNTSDGEWHFVEVIFAEAVTLTLIDDSCKEKCIAKAPTPLE

SDQSICAFQNSFLGGLPVGMTSNGVALLNFYNMPSTPSFVGCLQDIKIDW

NHITLENISSGSSLNVKAGCVRKDWCESQPCQSRGRCINLWLSYQCDCHR

PYEGPNCLREYVAGRFGQDDSTGYVIFTLDESYGDTISLSMFVRTLQPSG

LLLALENSTYQYIRVWLERGRLAMLTPNSPKLVVKFVLNDGNVHLISLKI

KPYKIELYQSSQNLGFISASTWKIEKGDVIYIGGLPDKQETELNGGFFKG

CIQDVRLNNQNLEFFPNPTNNASLNPVLVNVTQGCAGDNSCKSNPCHNGG

VCHSRWDDFSCSCPALTSGKACEEVQWCGFSPCPHGAQCQPVLQGFECIA

NAVFNGQSGQILFRSNGNITRELTNITFGFRTRDANVIILHAEKEPEFLN

ISIQDSRLFFQLQSGNSFYMLSLTSLQSVNDGTWHEVTLSMTDPLSQTSR

WQMEVDNETPFVTSTIATGSLNFLKDNTDIYVGDRAIDNIKGLQGCLSTI

EIGGIYLSYFENVHGFINKPQEEQFLKISTNSVVTGCLQLNVCNSNPCLH

GGNCEDIYSSYHCSCPLGWSGKHCELNIDECFSNPCIFIGNCSDRVAAYH

CTCEPGYTGVNCEVDIDNCQSHQCANGATCISHTNGYSCLCFGNFTGKFC

RQSRLPSTVCGNEKTNLTCYNGGNCTEFQTELKCMCRPGFTGEWCEKDID

ECASDPCVNGGLCQDLLNKFQCLCDVAFAGERCEVDVSSLSFYVSLLFWQ

NLFQLLSYLILRMNDEPVVEWGEQEDY;
```

CRB1 isoform 3 having the following amino acid sequence:

```
                                        (SEQ ID NO: 43)
MALKNINYLLIFYLSFSLLIYIKNSFCNKNNTRCLSNSCQNNSTCKDFSK

DNDCSCSDTANNLDKDCDNMKDPCFSNPCQGSATCVNTPGERSFLCKCPP

GYSGTICETTIGSCGKNSCQHGGICHQDPIYPVCICPAGYAGRFCEIDHD

ECASSPCQNGAVCQDGIDGYSCFCVPGYQGRHCDLEVDECASDPCKNEAT

CLNEIGRYTCICPHNYSGYTGAQCEIDLNECNSNPCQSNGECVELSSEKQ

YGRITGLPSSFSYHEASGYVCICQPGFTGIHCEEDVNECSSNPCQNGGTC

ENLPGNYTCHCPFDNLSRTFYGGRDCSDILLGCTHQQCLNNGTCIPHFQD

GQHGFSCLCPSGYTGSLCEIATTLSFEGDGFLWVKSGSVTTKGSVCNIAL

RFQTVQPMALLLFRSNRDVFVKLELLSGYIHLSIQVNNQSKVLLFISHNT

SDGEWHFVEVIFAEAVTLTLIDDSCKEKCIAKAPTPLESDQSICAFQNSF

LGGLPVGMTSNGVALLNFYNMPSTPSFVGCLQDIKIDWNHITLENISSGS

SLNVKAGCVRKDWCESQPCQSRGRCINLWLSYQCDCHRPYEGPNCLREYV

AGRFGQDDSTGYVIFTLDESYGDTISLSMFVRTLQPSGLLLALENSTYQY

IRVWLERGRLAMLTPNSPKLVVKFVLNDGNVHLISLKIKPYKIELYQSSQ

NLGFISASTWKIEKGDVIYIGGLPDKQETELNGGFFKGCIQDVRLNNQNL

EFFPNPTNNASLNPVLVNVTQGCAGDNSCKSNPCHNGGVCHSRWDDFSCS

CPALTSGKACEEVQWCGFSPCPHGAQCQPVLQGFECIANAVFNGQSGQIL

FRSNGNITRELTNITFGFRTRDANVIILHAEKEPEFLNISIQDSRLFFQL

QSGNSFYMLSLTSLQSVNDGTWHEVTLSMTDPLSQTSRWQMEVDNETPFV

TSTIATGSLNFLKDNTDIYVGDRAIDNIKGLQGCLSTIEIGGIYLSYFEN

VHGFINKPQEEQFLKISTNSVVTGCLQLNVCNSNPCLHGGNCEDIYSSYH

CSCPLGWSGKHCELNIDECFSNPCIHGNCSDRVAAYHCTCEPGYTGVNCE

VDIDNCQSHQCANGATCISHTNGYSCLCFGNFTGKFCRQSRLPSTVCGNE

KTNLTCYNGGNCTEFQTELKCMCRPGFTGEWCEKDIDECASDPCVNGGLC

QDLLNKFQCLCDVAFAGERCEVDLADDLISDIFTTIGSVTVALLLILLLA

IVASVVTSNKRATQGTYSPSRQEKEGSRVEMWNLMPPPAMERLI;
```

CRB1 isoform 4 having the following amino acid sequence: and

```
                                        (SEQ ID NO: 44)
MIRNSLCQPSRCLDEYLFFNRKMFGARTHGFHILMAMLIGIHCEEDVNEC

SSNPCQNGGTCENLPGNYTCHCPFDNLSRTFYGGRDCSDILLGCTHQQCL

NNGTCIPHFQDGQHGFSCLCPSGYTGSLCEIATTLSFEGDGFLWVKSGSV

TTKGSVCNIALRFQTVQPMALLLFRSNRDVFVKLELLSGYIHLSIQVNNQ

SKVLLFISHNTSDGEWHFVEVIFAEAVTLTLIDDSCKEKCIAKAPTPLES

DQSICAFQNSFLGGLPVGMTSNGVALLNFYNMPSTPSFVGCLQDIKIDWN

HITLENISSGSSLNVKAGCVRKDWCESQPCQSRGRCINLWLSYQCDCHRP
```

-continued

YEGPNCLREYVAGRFGQDDSTGYVIFTLDESYGDTISLSMFVRTLQPSGL

LLALENSTYQYIRVWLERGRLAMLTPNSPKLVVKFVLNDGNVHLISLKIK

PYKIELYQSSQNLGFISASTWKIEKGDVIYIGGLPDKQETELNGGFFKGC

IQDVRLNNQNLEFFPNPTNNASLNPVLVNVTQGCAGDNSCKSNPCHNGGV

CHSRWDDFSCSCPALTSGKACEEVQWCGFSPCPHGAQCQPVLQGFECIAN

AVFNGQSGQILFRSNGNITRELTNITFGFRTRDANVIILHAEKEPEFLNI

SIQDSRLFFQLQSGNSFYMLSLTSLQSVNDGTWHEVTLSMTDPLSQTSRW

QMEVDNETPFVTSTIATGSLNFLKDNTDIYVGDRAIDNIKGLQGCLSTIE

IGGIYLSYFENVHGFINKPQEEQFLKISTNSVVTGCLQLNVCNSNPCLHG

GNCEDIYSSYHCSCPLGWSGKHCELNIDECFSNPCIFIGNCSDRVAAYHC

TCEPGYTGVNCEVDIDNCQSHQCANGATCISHTNGYSCLCFGNFTGKFCR

QSRLPSTVCGNEKTNLTCYNGGNCTEFQTELKCMCRPGFTGEW;

and CRB1 isoform 5 having the following amino acid sequence:

(SEQ ID NO: 45)
MALKNINYLLIFYLSFSLLIYIKNSFCNKNNTRCLSNSCQNNSTCKDFSK

DNDCSCSDTANNLDKDCDNMKDPCFSNPCQGSATCVNTPGERSFLCKCPP

GYSGTICETTIGSCGKNSCQHGGICHQDPIYPVCICPAGYAGRFCEIDHD

ECASSPCQNGAVCQDGIDGYSCFCVPGYQGRHCDLEVDECASDPCKNEAT

CLNEIGRYTCICPHNYSGVNCELEIDECWSQPCLNGATCQDALGAYFCDC

APGFLGDHCELNTDECASQPCLHGGLCVDGENRYSCNCTGSGFTGTHCET

LMPLCWSKPCHNNATCEDSVDNYTCHCWPGYTGAQCEIDLNECNSNPCQS

NGECVELSSEKQYGRITGLPSSFSYHEASGYVCICQPGFTGIHCEEDVNE

CSSNPCQNGGTCENLPGNYTCHCPFDNLSRTFYGGRDCSDILLGCTHQQC

LNNGTCIPHFQDGQHGFSCLCPSGYTGSLCEIATTLSFEGDGFLWVKSGS

VTTKGSVCNIALRFQTVQPMALLLFRSNRDVFVKLELLSGYIHLSIQVNN

QSKVLLFISHNTSDGEWHFVEVIFAEAVTLTLIDDSCKEKCIAKAPTPLE

SDQSICAFQNSFLGGLPVGMTSNGVALLNFYNMPSTPSFVGCLQDIKIDW

NHITLENISSGSSLNVKAGCVRKDWCESQPCQSRGRCINLWLSYQCDCHR

PYEGPNCLRGKFCRQSRLPSTVCGNEKTNLTCYNGGNCTEFQTELKCMCR

PGFTGEWCEKDIDECASDPCVNGGLCQDLLNKFQCLCDVAFAGERCEVDL

ADDLISDIFTTIGSVTVALLLILLLAIVASVVTSNKRATQGTYSPSRQEK

EGSRVEMWNLMPPPAMERLI.

In some instances, the methods described herein may employ a BTTS that specifically binds CRB1, including e.g., human CRB1.

In some instances, useful priming antigens may include Neuromodulin (GAP43; Also known as B-50; PP46; Axonal membrane protein GAP-43; Neural phosphoprotein B-50; pp46). GAP43 has been termed a 'growth' or 'plasticity' protein because it is expressed at high levels in neuronal growth cones during development and axonal regeneration and is encoded by the growth associated protein 43 gene, located in humans at 3q13.31. GAP43 is a major component of the motile "growth cones" that form the tips of elongating axons. GAP43 protein may be found in at least two isoforms in humans, including GAP43 isoform 1 having the following amino acid sequence:

(SEQ ID NO: 46)
MLCCMRRTKQVEKNDDDQKIEQDGIKPEDKAHKAATKIQASFRGHITRKK

LKGEKKDDVQAAEAEANKKDEAPVADGVEKKGEGTTTAEAAPATGSKPDE

PGKAGETPSEEKKGEGDAATEQAAPQAPASSEEKAGSAETESATKASTDN

SPSSKAEDAPAKEEPKQADVPAAVTAAAATTPAAEDAAAKATAQPPTETG

ESSQAEENIEAVDETKPKESARQDEGKEEEPEADQEHA;

and GAP43 isoform 2 having the following amino acid sequence:

(SEQ ID NO: 47)
MTKSCSELCHPALHFLPCLGGLRKNLQRAVRPSPYSLGFLTFWISRVEKN

DDDQKIEQDGIKPEDKAHKAATKIQASFRGHITRKKLKGEKKDDVQAAEA

EANKKDEAPVADGVEKKGEGTTTAEAAPATGSKPDEPGKAGETPSEEKKG

EGDAATEQAAPQAPASSEEKAGSAETESATKASTDNSPSSKAEDAPAKEE

PKQADVPAAVTAAAATTPAAEDAAAKATAQPPTETGESSQAEENIEAVDE

TKPKESARQDEGKEEEPEADQEHA.

In some instances, the methods described herein may employ a BTTS that specifically binds GAP43, including e.g., human GAP43.

In some instances, useful priming antigens may include Sodium/potassium-transporting ATPase subunit beta-2 (ATP1B2; also known as Adhesion molecule in glia, AMOG; Sodium/potassium-dependent ATPase subunit beta-2). ATP1B2 is the non-catalytic component of the active enzyme, which catalyzes the hydrolysis of ATP coupled with the exchange of Na+ and K+ ions across the plasma membrane and is encoded by the ATPase Na+/K+ transporting subunit beta 2 gene, located in humans at 17p13.1. ATP1B2 belongs to the family of Na+/K+ and H+/K+ ATPases beta chain proteins, and to the subfamily of Na+/K+-ATPases. ATP1B2 protein may be found in at least one isoform in humans, including ATP1B2 having the following amino acid sequence:

(SEQ ID NO: 48)
MVIQKEKKSCGQVVEEWKEFVWNPRTHQFMGRTGTSWAFILLFYLVFGF

LTAMFTLTMWVMLQTVSDHTPKYQDRLATPGLMIRPKTENLDVIVNVSDT

ESWDQHVQKLNKFLEPYNDSIQAQKNDVCRPGRYYEQPDNGVLNYPKRAC

QFNRTQLGNCSGIGDSTHYGYSTGQPCVFIKMNRVINFYAGANQSMNVTC

AGKRDEDAENLGNFVMFPANGNIDLMYFPYYGKKFHVNYTQPLVAVKFLN

VTPNVEVNVECRINAANIATDDERDKFAGRVAFKLRINKT.

In some instances, the methods described herein may employ a BTTS that specifically binds ATP1B2, including e.g., human ATP1B2.

In some instances, useful priming antigens may include Ran guanine nucleotide release factor MOG1 (MOG1; also known as RANGRF, Ran guanine nucleotide release factor, RanGNRF, Ran-binding protein MOG1, HSPC165; HSPC236). MOG1 is a protein that has been shown to function as a guanine nucleotide release factor in mouse and to regulate the expression and function of the Nav1.5 cardiac sodium channel in humans and is encoded by the RAN guanine nucleotide release factor gene, located in humans at 7p13.1. MOG1 may regulate the intracellular trafficking of RAN, promote guanine nucleotide release from RAN, inhibit binding of new GTP by preventing the binding of the RAN guanine nucleotide exchange factor RCC1, regulate the levels of GTP-bound RAN in the nucleus, and/or enhance the expression of SCN5A at the cell membrane in cardiomyocytes. MOG1 protein may be found in at least four isoforms in humans, including MOG1 isoform 1 having the following amino acid sequence:

(SEQ ID NO: 70)
MEPTRDCPLFGGAFSAILPMGAIDVSDLRPVPDNQEVFCHPVTDQSLIVE

LLELQAHVRGEAAARYHFEDVGGVQGARAVHVESVQPLSLENLALRGRCQ

EAWVLSGKQQIAKENQQVAKDVTLHQALLRLPQYQTDLLLTFNQPPPDNR

SSLGPENLSPAPWSLGDFEQLVTSLTLHDPNIFGPQ;

MOG1 isoform 2 having the following amino acid sequence:

(SEQ ID NO: 71)
MEPTRDCPLFGGAFSAILPMGAIDVSDLRPVPDNQEVFCHPVTDQSLIVE

LLELQAHVRGEAAARYHFEDVGGVQGARAVHVESVQPLSLENLALRGRCQ

EAWVLSGKQQIAKENQQVAKDVTLHQALLRLPQYQTDLLLTFNQPP;

MOG1 isoform 3 having the following amino acid sequence:

(SEQ ID NO: 72)
MEPTRDCPLFGGAFSAILPMGAIDVSDLRPVPDNQEVFCHPVTDQSLIVE

LLELQAHVRGEAAARYHFEDVGGVQGARAVHVESVQPLSLENLALRGRCQ

EAWVLSGKQQIAKENQQVRARECVMSWKGGSGDAEIQVSILTLIPLGSKG

RDTSSGLAEAAPVPD;

and MOG1 isoform 4 having the following amino acid sequence:

(SEQ ID NO: 73)
MEPTRDCPLFGGAFSAILPMGAIDVSDLRPVPDNQEVFCHPVTDQSLIVE

LLELQAHVRGEAAARYHFEDVGGVQGARAVHVESVQPLSLENLALRGRCQ

EAWVLSGKQQIAKENQQP.

In some instances, the methods described herein may employ a BTTS that specifically binds MOG1, including e.g., human MOG1.

In some instances, useful priming antigens may include PTPRZ1-MET. PTPRZ1-MET is a fusion of PTPRZ1, described herein, and Hepatocyte growth factor receptor (MET; also known as HGF receptor; HGFR; AUTS9; RCCP2; c-Met; DFNB97; Proto-oncogene c-Met), which is encoded by the MET proto-oncogene, receptor tyrosine kinase gene, located in humans at 7q31.2. MET is a member of the receptor tyrosine kinase family of proteins and the product of the proto-oncogene MET. MET protein may be found in at least three isoforms in humans, including MET isoform 1 having the following amino acid sequence:

(SEQ ID NO: 49)
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGMAGGTLLTLTGNYLNSGNSRHISIGGKTCTLK

SVSNSILECYTPAQTISTEFAVKLKIDLANRETSIFSYREDPIVYEIHPT

KSFISGGSTITGVGKNLNSVSVPRMVINVHEAGRNFTVACQHRSNSEIIC

CTTPSLQQLNLQLPLKTKAFFMLDGILSKYFDLIYVHNPVFKPFEKPVMI

SMGNENVLEIKGNDIDPEAVKGEVLKVGNKSCENIHLHSEAVLCTVPNDL

LKLNSELNIEWKQAISSTVLGKVIVQPDQNFTGLIAGVVSISTALLLLLG

FFLWLKKRKQIKDLGSELVRYDARVHTPHLDRLVSARSVSPTTEMVSNES

VDYRATFPEDQFPNSSQNGSCRQVQYPLTDMSPILTSGDSDISSPLLQNT

VHIDLSALNPELVQAVQHVVIGPSSLIVHFNEVIGRGHFGCVYHGTLLDN

DGKKIHCAVKSLNRITDIGEVSQFLTEGIIMKDFSHPNVLSLLGICLRSE

GSPLVVLPYMKHGDLRNFIRNETHNPTVKDLIGFGLQVAKGMKYLASKKF

VHRDLAARNCMLDEKFTVKVADFGLARDMYDKEYYSVHNKTGAKLPVKWM

ALESLQTQKFTTKSDVWSFGVLLWELMTRGAPPYPDVNTFDITVYLLQGR

RLLQPEYCPDPLYEVMLKCWHPKAEMRPSFSELVSRISAIFSTFIGEHYV

HVNATYVNVKCVAPYPSLLSSEDNADDEVDTRPASFWETS;

MET isoform 2 having the following amino acid sequence:

(SEQ ID NO: 50)
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

-continued

```
YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFISTWWKEPLNIVSFLFCFASGGSTITGVGKNLNSVSVPRMVINVHEA

GRNFTVACQHRSNSEIICCTTPSLQQLNLQLPLKTKAFFMLDGILSKYFD

LIYVHNPVFKPFEKPVMISMGNENVLEIKGNDIDPEAVKGEVLKVGNKSC

ENIHLHSEAVLCTVPNDLLKLNSELNIEWKQAISSTVLGKVIVQPDQNFT

GLIAGVVSISTALLLLLGFFLWLKKRKQIKDLGSELVRYDARVHTPHLDR

LVSARSVSPTTEMVSNESVDYRATFPEDQFPNSSQNGSCRQVQYPLTDMS

PILTSGDSDISSPLLQNTVHIDLSALNPELVQAVQHVVIGPSSLIVHFNE

VIGRGHFGCVYHGTLLDNDGKKIHCAVKSLNRITDIGEVSQFLTEGIIMK

DFSHPNVLSLLGICLRSEGSPLVVLPYMKHGDLRNFIRNETHNPTVKDLI

GFGLQVAKGMKYLASKKFVHRDLAARNCMLDEKFTVKVADFGLARDMYDK

EYYSVHNKTGAKLPVKWMALESLQTQKFTTKSDVWSFGVLLWELMTRGAP

PYPDVNTFDITVYLLQGRRLLQPEYCPDPLYEVMLKCWHPKAEMRPSFSE

LVSRISAIFSTFIGEHYVHVNATYVNVKCVAPYPSLLSSEDNADDEVDTR

PASFWETS;
``` and MET isoform 3 having the following amino acid sequence:

```
                                        (SEQ ID NO: 51)
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFIRHVNIALIQR.
```

In some instances, the methods described herein may employ a BTTS that specifically binds a PTPRZ1-MET, including e.g., a human PTPRZ1-MET fusion. PTPRZ1-MET fusions are described in Hu et al. Cell. 2018 Nov. 29; 175(6):1665-1678; Bao et al. Genome Res. 2014 November; 24(11):1765-73; and Zeng et al. Oncogene. 2017 Sep. 21; 36(38):5369-5381; the disclosures of which are incorporated herein by reference in their entirety.

In some instances, combinations of two or more priming antigens may be employed, including but not limited to e.g., where such combinations include but are not limited to one or more of the above described examples of suitable priming antigens. In some instances, such combinations may find use in an OR gate as described herein. In some instances, a two-headed BTTS may be employed, including but not limited to e.g., where the two-headed BTTS binds to two priming antigens, including but not limited to two of the above described examples of suitable priming antigens.

In some instances, all cells of a heterogeneous GBM may express an employed killing antigen. Such heterogeneous GBMs may be said to be homogeneous for killing antigen expression. In some instances, a heterogeneous GBM may be heterogeneous for priming antigen expression but homogeneous for killing antigen expression. Accordingly, in certain embodiments, certain cells of the heterogeneous GBM may express both the priming antigen and the killing antigen. In such instances, the methods of the present disclosure may be employed where the heterogeneous GBM still includes cells that express the killing antigen but not the priming antigen.

In some instances, a heterogeneous GBM may be heterogeneous for both priming antigen expression and targeting/killing antigen expression, including where the targeting/killing antigen is expressed by less than 100% of the cells of the heterogeneous GBM. In some instances, the targeting/killing antigen may be expressed in a majority of the cells of the heterogeneous GBM but less than 100% of the cells, including but not limited to e.g., where more than 95%, more than 90%, more than 85%, more than 80%, more than 75%, more than 70%, more than 65%, more than 60%, more than 55%, or more than 50% of the cells of the heterogeneous GBM.

In some instances, multiple antigen-specific therapeutics targeting different targeting/killing antigens may be employed. In some instances, antigen-specific therapeutics targeting multiple different targeting/killing antigens may be employed. In some instances, multiple targeting/killing antigens may be targeted in cases where targeting/killing antigen expression is heterogeneous, including where e.g., one or more of the subject targeting/killing antigens is expressed by a majority of the cells of the GBM, where one or more of the subject targeting/killing antigens is expressed by a minority of the cells of the GBM, and the like. In some instances, the targeting of two or more different targeting/killing antigens results in combination of antigens employed targeting 100% or nearly 100% (e.g., 99% or greater, 98% or greater, 95% or greater, 90% or greater, etc.) of the cells of the GBM.

In some instances, a targeting/killing antigen may be expressed by non-GBM cells in the subject. Put another way, a subject having a EGFRvIII(−) GBM having heterogeneous or homogeneous expression of a targeting/killing antigen may, in some instances, also express the targeting/killing antigen in cells other than the GBM, e.g., away from the GBM. Such cells may, in some instances, be referred to as bystander cells. In some instances, through the use of a circuit described herein, bystander cells at a site other than GBM or outside of the relative proximity of the GBM may not be substantially or unduly affected by immune cells employed in the methods described herein.

Useful antigens that may be employed as targeting antigens include but are not limited to e.g., Ephrin type-A receptor 2 (EphA2), Ephrin type-A receptor 3 (EphA3), Interleukin-13 receptor (IL13R) (e.g., IL13RA1 or IL13RA2), Epidermal growth factor receptor (EGFR), erb-b2 receptor tyrosine kinase 2 (ERBB2) and the like. In some instances, an employed priming antigen may find use as a targeting antigen. For example, in some instances, a priming antigen may be employed as both a priming antigen and a killing antigen, including but not limited to e.g., as in a AND-OR gate where the priming antigen functions as a priming antigen to induce expression of one or more antigen-specific therapeutics specific for the priming antigen as a first targeting/killing antigen and a second targeting/killing antigen. In such instances, the second targeting/killing antigen may, but need not necessarily, be selected from EphA2, EphA3, IL13R (e.g., IL13RA1 or IL13RA2), EGFR, and ERBB2.

In some instances, useful targeting/killing antigens include Ephrin type-A receptor 2 (EphA2). EphA2 is a receptor tyrosine kinase encoded by the EPH receptor A2 gene located at 1p36.13 in humans. EphA2 protein may be found in at least one isoform in humans, including EphA2 Isoform 1 having the following amino acid sequence:

(SEQ ID NO: 52)
MELQAARACFALLWGCALAAAAAAQGKEVVLLDFAAAGGELGWLTHPYGK

GWDLMQNIMNDMPIYMYSVCVMSGDQDNWLRTNWVYRGEAERIFIELKFT

VRDCNSFPGGASSCKETFNLYYAESDLDYGTNFQKRLFTKIDTIAPDEIT

VSSDFEARHVKLNVEERSVGPLTRKGFYLAFQDIGACVALLSVRVYYKKC

PELLQGLAHFPETIAGSDAPSLATVAGTCVDHAVVPPGGEEPRMHCAVDG

EWLVPIGQCLCQAGYEKVEDACQACSPGFFKFEASESPCLECPEHTLPSP

EGATSCECEEGFFRAPQDPASMPCTRPPSAPHYLTAVGMGAKVELRWTPP

QDSGGREDIVYSVTCEQCWPESGECGPCEASVRYSEPPHGLTRTSVTVSD

LEPHMNYTFTVEARNGVSGLVTSRSFRTASVSINQTEPPKVRLEGRSTTS

LSVSWSIPPPQQSRVWKYEVTYRKKGDSNSYNVRRTEGFSVTLDDLAPDT

TYLVQVQALTQEGQGAGSKVHEFQTLSPEGSGNLAVIGGVAVGVVLLLVL

AGVGFFIHRRRKNQRARQSPEDVYFSKSEQLKPLKTYVDPHTYEDPNQAV

LKFTTEIHPSCVTRQKVIGAGEFGEVYKGMLKTSSGKKEVPVAIKTLKAG

YTEKQRVDFLGEAGIMGQFSHHNIIRLEGVISKYKPMMIITEYMENGALD

KFLREKDGEFSVLQLVGMLRGIAAGMKYLANMNYVHRDLAARNILVNSNL

VCKVSDFGLSRVLEDDPEATYTTSGGKIPIRWTAPEAISYRKFTSASDVW

SFGIVMWEVMTYGERPYWELSNHEVMKAINDGFRLPTPMDCPSAIYQLMM

QCWQQERARRPKFADIVSILDKLIRAPDSLKTLADFDPRVSIRLPSTSGS

EGVPFRTVSEWLESIKMQQYTEHFMAAGYTAIEKVVQMTNDDIKRIGVRL

PGHQKRIAYSLLGLKDQVNTVGIPI;

and EphA2 Isoform 2 having the following amino acid sequence:

(SEQ ID NO: 53)
MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD

GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKVTPRGAGLALAGPTAGDRLVT.

In some instances, the methods described herein may employ an antigen-specific therapeutic that specifically binds EphA2, including e.g., human EphA2 Isoform 1, human EphA2 Isoform 2, or both human EphA2 Isoform 1 and human EphA2 Isoform 2.

In some instances, useful EphA2 binding domains may include antibody based EphA2 binding domains, including but not limited to an EphA2 scFv. In some instances, a useful EphA2 scFv may have the following amino acid sequence or a variant thereof:

(SEQ ID NO: 54)
EIVLTQSPGTLSLSPGERATLSCRASQSVSSSNLAWYQQKPGQAPRLLIY

GASSRATGVPDRFSGSGSGTDFTLTISRLEPEDFAVYYCQQSSSYPWTFG

QGTKVEIKRTGGGGSGAGGSGGGGTGGGGSEVDLLESGGGLVQPGGSLRL

SCAASGFTFSRYWMHWVRQAPGKGLEWVSSISPYDGETNYADSVKGRFTI

SRDNSKNTLYLQMNSLRAEDTAVYYCARISEWYNWAVDVFDYWGQGTLVT

VSS;

including e.g., where the useful EphA2 has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, a useful EphA2 scFv may have the following amino acid sequence or a variant thereof:

(SEQ ID NO: 55)
QVQLLESGGGLVQPGGSLRLSCAASGFTFSSYTMSWVRQAPGQALEWMGT

ISSGGTYTYYPDSVKGRFTISRDNAKNSLYLQMNSLRAEDTAVYYCAREA

IFTYWGRGTLVTSSGGGGSGGGGSGGGGSDIQLTQSPSSLSASVGDRVTI

TCKASQDINNYLSWYQQKPGQAPRLLIYRANRLVDGVPDRFSGSGYGTDF

TLTINNIESEDAAYYFCLKYDVFPYTFGQGTKVEIKS;

including e.g., where the useful EphA2 has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, useful EphA2 binding domains include those described in Goldgur et al., Growth Factors. (2014) 32(6):214-22 and Damschroder et al., Mol Immunol. (2007) 44(11):3049-60; the disclosures of which are incorporated herein by reference in their entirety.

In some instances, useful targeting/killing antigens include Ephrin type-A receptor 3 (EphA3). EphA3 is a receptor tyrosine kinase encoded by the EPH receptor A3 gene located at 3p11.1 in humans. EphA3 protein may be found in at least two isoforms in humans, including EphA3 Isoform 1 having the following amino acid sequence:

(SEQ ID NO: 56)
MDCQLSILLLLSCSVLDSFGELIPQPSNEVNLLDSKTIQGELGWISYPSH

GWEEISGVDEHYTPIRTYQVCNVMDHSQNNWLRTNWVPRNSAQKIYVELK

FTLRDCNSIPLVLGTCKETFNLYYMESDDDHGVKFREHQFTKIDTIAADE

SFTQMDLGDRILKLNTEIREVGPVNKKGFYLAFQDVGACVALVSVRVYFK

KCPFTVKNLAMFPDTVPMDSQSLVEVRGSCVNNSKEEDPPRMYCSTEGEW

LVPIGKCSCNAGYEERGFMCQACRPGFYKALDGNMKCAKCPPHSSTQEDG

SMNCRCENNYFRADKDPPSMACTRPPSSPRNVISNINETSVILDWSWPLD

TGGRKDVTFNIICKKCGWNIKQCEPCSPNVRFLPRQFGLTNTTVTVTDLL

AHTNYTFEIDAVNGVSELSSPPRQFAAVSITTNQAAPSPVLTIKKDRTSR

NSISLSWQEPEHPNGIILDYEVKYYEKQEQETSYTILRARGTNVTISSLK

PDTIYVFQIRARTAAGYGTNSRKFEFETSPDSFSISGESSQVVMIAISAA

VAIILLTVVIYVLIGRFCGYKSKHGADEKRLHFGNGHLKLPGLRTYVDPH

TYEDPTQAVHEFAKELDATNISIDKVVGAGEFGEVCSGRLKLPSKKEISV

AIKTLKVGYTEKQRRDFLGEASIMGQFDHPNIIRLEGVVTKSKPVMIVTE

YMENGSLDSFLRKHDAQFTVIQLVGMLRGIASGMKYLSDMGYVHRDLAAR

NILINSNLVCKVSDFGLSRVLEDDPEAAYTTRGGKIPIRWTSPEAIAYRK

FTSASDVWSYGIVLWEVMSYGERPYWEMSNQDVIKAVDEGYRLPPPMDCP

AALYQLMLDCWQKDRNNRPKFEQIVSILDKLIRNPGSLKIITSAAARPSN

LLLDQSNVDITTFRTTGDWLNGVWTAHCKEIFTGVEYSSCDTIAKISTDD

MKKVGVTVVGPQKKIISSIKALETQSKNGPVPV;

and EphA3 Isoform 2 having the following amino acid sequence:

(SEQ ID NO: 57)
MDCQLSILLLLSCSVLDSFGELIPQPSNEVNLLDSKTIQGELGWISYPSH

GWEEISGVDEHYTP1RTYQVCNVMDHSQNNWLRTNWVPRNSAQKIYVELK

FTLRDCNSIPLVLGTCKETFNLYYMESDDDHGVKFREHQFTKIDTIAADE

SFTQMDLGDRILKLNTEIREVGPVNKKGFYLAFQDVGACVALVSVRVYFK

KCPFTVKNLAMFPDTVPMDSQSLVEVRGSCVNNSKEEDPPRMYCSTEGEW

LVPIGKCSCNAGYEERGFMCQACRPGFYKALDGNMKCAKCPPHSSTQEDG

SMNCRCENNYFRADKDPPSMACTRPPSSPRNVISNINETSVILDWSWPLD

TGGRKDVTFNIICKKCGWNIKQCEPCSPNVRFLPRQFGLTNTTVTVTDLL

AHTNYTFEIDAVNGVSELSSPPRQFAAVSITTNQAAPSPVLTIKKDRTSR

NSISLSWQEPEHPNGIILDYEVKYYEKQEQETSYTILRARGTNVTISSLK

PDTIYVFQIRARTAAGYGTNSRKFEFETSPDCMYYFNAV.

In some instances, the methods described herein may employ an antigen-specific therapeutic that specifically binds EphA3, including e.g., human EphA3 Isoform 1, human EphA3 Isoform 2, or both human EphA3 Isoform 1 and human EphA3 Isoform 2.

In some instances, useful targeting/killing antigens include receptors for Interleukin-13 (IL13). IL13 is an immunoregulatory cytokine encoded by the interleukin 13 gene located at 5q31.1 in humans, which is a ligand for IL13R proteins: interleukin 13 receptor subunit alpha 1 (IL13RA1) and interleukin 13 receptor subunit alpha 2 (IL13RA2). An exemplary amino acid sequence of human IL13 is as follows:

(SEQ ID NO: 58)
MHPLLNPLLLALGLMALLLTTVIALTCLGGFASPGPVPPSTALRELIEEL

VNITQNQKAPLCNGSMVWSINLTAGMYCAALESLINVSGCSAIEKTQRML

SGFCPHKVSAGQFSSLHVRDTKIEVAQFVKDLLLHLKKLFREGRFN.

In some instances, the methods described herein may employ an antigen-specific therapeutic that specifically binds an IL13R, including IL13RA1 and/or IL13RA2, including e.g., human IL13RA1 Isoform 1, human IL13RA1 Isoform 2, human IL13RA2, or any combination thereof. Representative human amino acid sequences of IL13RA1 and IL13RA2 and isoforms thereof are provided above.

In some instances, useful IL13R binding domains may be derived from IL13, including but not limited to IL13 conjugation products (e.g., wild-type or mutated IL13 conjugated to one or more moieties), derivatives or mutants of IL13, e.g., IL13 muteins, and the like. Useful muteins include but are not limited to e.g., IL13 muteins including one or more amino acid substitutions including E13K and/or K105R.

In some instances, as summarized above, useful IL13R binding domains may include a ligand-based binding domain derived from IL13, including but not limited to an IL13 mutein-based binding domain. In some instances, a useful IL13 mutein-based binding domain may have the following amino acid sequence or a variant thereof:

(SEQ ID NO: 59)
LTCLGGFASPGPVPPSTALRKLIEELVNITQNQKAPLCNGSMVWSINLTA

GMYCAALESLINVSGCSAIEKTQRMLSGFCPHKVSAGQFSSLHVRDTKIE

VAQFVKDLLLHLRKLFREGRFN;

including e.g., where the useful IL13 mutein-based binding domain has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, useful IL13R (e.g., IL13RA1 or IL13RA2) binding domains include those described in Krebs et al., Cytotherapy. (2014) 16(8):1121-31; the disclosure of which is incorporated herein by reference in its entirety.

In some instances, useful targeting/killing antigens include epidermal growth factor receptor (EGFR, also known as Proto-oncogene c-ErbB-1, Receptor tyrosine-protein kinase erbB-1, ERBB, HER1, mENA, ERBB1, PIG61, and NISBD2). EGFR is a receptor tyrosine kinase encoded by the epidermal growth factor receptor gene, present at 7p11.2 in humans. Known ligands of EGFR include EGF, TGFA/TGF-alpha, amphiregulin, epigen/ EPGN, BTC/betacellulin, epiregulin/EREG and HBEGF/ heparin-binding EGF. EGFR protein may be found in at least one isoform in humans, including EGFR Isoform 1 having the following amino acid sequence:

(SEQ ID NO: 60)
MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFV
ENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGM
VGALLLLLVVALGIGLFMRRRHIVRKRTLRRLLQERELVEPLTPSGEAPN
QALLRILKETEFKKIKVLGSGAFGTVYKGLW1PEGEKVKIPVAIKELREA
TSPKANKEILDEAYVMASVDNPHVCRLLGICLTSTVQLITQLMPFGCLLD
YVREHKDNIGSQYLLNWCVQIAKGMNYLEDRRLVHRDLAARNVLVKTPQH
VKITDFGLAKLLGAEEKEYHAEGGKVPIKWMALESILHRIYTHQSDVWSY
GVTVWELMTFGSKPYDG1PASEISSILEKGERLPQPPICTIDVYMIMVKC
WMIDADSRPKFRELIIEFSKMARDPQRYLVIQGDERMHLPSPTDSNFYRA
LMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKR
PAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRV
APQSSEFIGA,

EGFR Isoform 2 having the following amino acid sequence:

(SEQ ID NO: 61)
MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGLS,

EGFR Isoform 3 having the following amino acid sequence:

(SEQ ID NO: 62)
MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCK
ATGQVCHALCSPEGCWGPEPRDCVSCRNVSRGRECVDKCNLLEGEPREFV
ENSECIQCHPECLPQAMNITCTGRGPDNCIQCAHYIDGPHCVKTCPAGVM
GENNTLVWKYADAGHVCHLCHPNCTYGPGNESLKAMLFCLFKLSSCNQSN
DGSVSHQSGSPAAQESCLGWIPSLLPSEFQLGWGGCSHLHAWPSASVIIT
ASSCH, and EGFR Isoform 4 having the following amino acid sequence:

(SEQ ID NO: 63)
MRPSGTAGAALLALLAALCPASRALEEKKVCQGTSNKLTQLGTFEDHFLS
LQRMFNNCEVVLGNLEITYVQRNYDLSFLKTIQEVAGYVLIALNTVERIP
LENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCW
GAGEENCQKLTKIICAQQCSGRCRGKSPSDCCHNQCAAGCTGPRESDCLV
CRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLS
INATNIKHFKNCTSISGDLHILPVAFRGDSFTHTPPLDPQELDILKTVKE
ITGFLLIQAWPENRTDLHAFENLEIIRGRTKQHGQFSLAVVSLNITSLGL
RSLKEISDGDVIISGNKNLCYANTINWKKLFGTSGOKTKIISNRGENSCK
ATGQVCHALCSPEGCWGPEPRDCVSCRNVSRGRECVDKCNLLEGEPREFV
ENSECIQCHPECLPQAMNITCTGRGPDNCIQCAHYIDGPHCVKTCPAGVM
GENNTLVWKYADAGHVCHLCHPNCTYGS.

In some instances, the methods described herein may employ an antigen-specific therapeutic that specifically binds an EGFR, including human EGFR, including e.g., human EGFR Isoform 1, human EGFR Isoform 2, human EGFR Isoform 3, EGFR Isoform 4, or any combination thereof.

In some instances, useful targeting/killing antigens include Erb-b2 receptor tyrosine kinase 2 (ERBB2; also known as Metastatic lymph node gene 19 protein, Proto-oncogene Neu, Proto-oncogene c-ErbB-2, Tyrosine kinase-type cell surface receptor HER2, NEU, NGL, HER2, TKR1, CD340, HER-2, MLN 19, and HER-2/neu). ERBB2 is a protein tyrosine kinase that is encoded by the erb-b2 receptor tyrosine kinase 2 gene, located at 17q12 in humans. ERBB2 protein may be found in at least one isoform in humans, including ERBB2 Isoform 1 having the following amino acid sequence:

(SEQ ID NO: 64)
MELAALCRWGLLLALLPPGAASTQVCTGTDMKLRLPASPETHLDMLRHLY
QGCQVVQGNLELTYLPTNASLSFLQDIQEVQGYVLIAHNQVRQVPLQRLR
IVRGTQLFEDNYALAVLDNGDPLNNTTPVTGASPGGLRELQLRSLTEILK
GGVLIQRNPQLCYQDTILWKDIFHKNNQLALTLIDTNRSRACHPCSPMCK
GSRCWGESSEDCQSLTRTVCAGGCARCKGPLPTDCCHEQCAAGCTGPKHS
DCLACLHFNHSGICELHCPALVTYNTDTFESMPNPEGRYTFGASCVTACP
YNYLSTDVGSCTLVCPLHNQEVTAEDGTQRCEKCSKPCARVCYGLGMEHL
REVRAVTSANIQEFAGCKKIFGSLAFLPESFDGDPASNTAPLQPEQLQVF
ETLEEITGYLYISAWPDSLPDLSVFQNLQVIRGRILHNGAYSLTLQGLGI
SWLGLRSLRELGSGLALIHHNTHLCFVHTVPWDQLFRNPHQALLHTANRP
EDECVGEGLACHQLCARGHCWGPGPTQCVNCSQFLRGQECVEECRVLQGL
PREYVNARHCLPCHPECQPQNGSVTCFGPEADQCVACAHYKDPPFCVARC
PSGVKPDLSYMPIWKFPDEEGACQPCPINCTHSCVDLDDKGCPAEQRASP
LTSIISAVVGILLVVVLGVVFGILIKRRQQKIRKYTMRRLLQETELVEPL
TPSGAMPNQAQMRILKETELRKVKVLGSGAFGTVYKGIWIPDGENVKIPV
AIKVLRENTSPKANKEILDEAYVMAGVGSPYVSRLLGICLTSTVQLVTQL
MPYGCLLDHVRENRGRLGSQDLLNWCMQIAKGMSYLEDVRLVHRDLAARN
VLVKSPNHVKITDFGLARLLDIDETEYHADGGKVPIKWMALESILRRRFT
HQSDVWSYGVTVWELMTFGAKPYDGIPAREIPDLLEKGERLPQPPICTID
VYMIMVKCWMIDSECRPRFRELVSEFSRMARDPQRFVVIQNEDLGPASPL
DSTFYRSLLEDDDMGDLVDAEEYLVPQQGFFCPDPAPGAGGMVHHRHRSS
STRSGGGDLTLGLEPSEEEAPRSPLAPSEGAGSDVFDGDLGMGAAKGLQS
LPTHDPSPLQRYSEDPTVPLPSETDGYVAPLTCSPQPEYVNQPDVRPQPP
SPREGPLPAARPAGATLERPKTLSPGKNGVVKDVFAFGGAVENPEYLTPQ
GGAAPQPHPPPAFSPAFDNLYYWDQDPPERGAPPSTFKGTPTAENPEYLG
LDVPV,

ERBB2 Isoform 2 having the following amino acid sequence:

(SEQ ID NO: 65)
MPIWKFPDEEGACQPCPINCTHSCVDLDDKGCPAEQRASPLTSIISAVVG
ILLVVVLGVVFGILIKRRQQKIRKYTMRRLLQETELVEPLTPSGAMPNQA
QMRILKETELRKVKVLGSGAFGTVYKGIWIPDGENVKIPVAIKVLRENTS
PKANKEILDEAYVMAGVGSPYVSRLLGICLTSTVQLVTQLMPYGCLLDHV
RENRGRLGSQDLLNWCMQIAKGMSYLEDVRLVHRDLAARNVLVKSPNHVK
ITDFGLARLLDIDETEYHADGGKVPIKWMALESILRRRFTHQSDVWSYGV
TVWELMTFGAKPYDGIPAREIPDLLEKGERLPQPPICTIDVYMIMVKCWM
IDSECRPRFRELVSEFSRMARDPQRFVVIQNEDLGPASPLDSTFYRSLLE
DDDMGDLVDAEEYLVPQQGFFCPDPAPGAGGMVHHRHRSSSTRSGGGDLT
LGLEPSEEEAPRSPLAPSEGAGSDVFDGDLGMGAAKGLQSLPTHDPSPLQ
RYSEDPTVPLPSETDGYVAPLTCSPQPEYVNQPDVRPQPPSPREGPLPAA
RPAGATLERPKTLSPGKNGVVKDVFAFGGAVENPEYLTPQGGAAPQPHPP
PAFSPAFDNLYYWDQDPPERGAPPSTFKGTPTAENPEYLGLDVPV,

ERBB2 Isoform 3 having the following amino acid sequence:

(SEQ ID NO: 66)
MRRLLQETELVEPLTPSGAMPNQAQMRILKETELRKVKVLGSGAFGTVYK
GIWIPDGENVKIPVAIKVLRENTSPKANKEILDEAYVMAGVGSPYVSRLL
GICLTSTVQLVTQLMPYGCLLDHVRENRGRLGSQDLLNWCMQIAKGMSYL
EDVRLVHRDLAARNVLVKSPNHVKITDFGLARLLDIDETEYHADGGKVPI
KWMALESILRRRFTHQSDVWSYGVTVWELMTFGAKPYDGIPAREIPDLLE
KGERLPQPPICTIDVYMIMVKCWMIDSECRPRFRELVSEFSRMARDPQRF
VVIQNEDLGPASPLDSTFYRSLLEDDDMGDLVDAEEYLVPQQGFFCPDPA
PGAGGMVHHRHRSSSTRSGGGDLTLGLEPSEEEAPRSPLAPSEGAGSDVF
DGDLGMGAAKGLQSLPTHDPSPLQRYSEDPTVPLPSETDGYVAPLTCSPQ
PEYVNQPDVRPQPPSPREGPLPAARPAGATLERPKTLSPGKNGVVKDVFA
FGGAVENPEYLTPQGGAAPQPHPPPAFSPAFDNLYYWDQDPPERGAPPST
FKGTPTAENPEYLGLDVPV,

ERBB2 Isoform 4 having the following amino acid sequence:

(SEQ ID NO: 67)
MPRGSWKPQVCTGTDMKLRLPASPETHLDMLRHLYQGCQVVQGNLELTYL
PTNASLSFLQDIQEVQGYVLIAHNQVRQVPLQRLRIVRGTQLFEDNYALA
VLDNGDPLNNTTPVTGASPGGLRELQLRSLTEILKGGVLIQRNPQLCYQD
TILWKDIFHKNNQLALTLIDTNRSRACHPCSPMCKGSRCWGESSEDCQSL
TRTVCAGGCARCKGPLPTDCCHEQCAAGCTGPKHSDCLACLHFNHSGICE
LHCPALVTYNTDTFESMPNPEGRYTFGASCVTACPYNYLSTDVGSCTLVC
PLHNQEVTAEDGTQRCEKCSKPCARVCYGLGMEHLREVRAVTSANIQEFA
GCKKIFGSLAFLPESFDGDPASNTAPLQPEQLQVFETLEEITGYLYISAW
PDSLPDLSVFQNLQVIRGRILHNGAYSLTLQGLGISWLGLRSLRELGSGL
ALIHHNTHLCFVHTVPWDQLFRNPHQALLHTANRPEDECVGEGLACHQLC
ARGHCWGPGPTQCVNCSQFLRGQECVEECRVLQGLPREYVNARHCLPCHP
ECQPQNGSVTCFGPEADQCVACAHYKDPPFCVARCPSGVKPDLSYMPIWK
FPDEEGACQPCPINCTHSCVDLDDKGCPAEQRASPLTSIISAVVGILLVV
VLGVVFGILIKRRQQKIRKYTMRRLLQETELVEPLTPSGAMPNQAQMRIL
KETELRKVKVLGSGAFGTVYKGIWIPDGENVKIPVAIKVLRENTSPKANK
EILDEAYVMAGVGSPYVSRLLGICLTSTVQLVTQLMPYGCLLDHVRENRG
RLGSQDLLNWCMQIAKGMSYLEDVRLVHRDLAARNVLVKSPNHVKITDFG
LARLLDIDETEYHADGGKVPIKWMALESILRRRFTHQSDVWSYGVTVWEL
MTFGAKPYDGIPAREIPDLLEKGERLPQPPICTIDVYMIMVKCWMIDSEC
RPRFRELVSEFSRMARDPQRFVVIQNEDLGPASPLDSTFYRSLLEDDDMG
DLVDAEEYLVPQQGFFCPDPAPGAGGMVHHRHRSSSTRSGGGDLTLGLEP

ERBB2 Isoform 5 having the following amino acid sequence:

(SEQ ID NO: 68)
```
MKLRLPASPETHLDMLRHLYQGCQVVQGNLELTYLPTNASLSFLQDIQEV
QGYVLIAHNQVRQVPLQRLRIVRGTQLFEDNYALAVLDNGDPLNNTTPVT
GASPGGLRELQLRSLTEILKGGVLIQRNPQLCYQDTILWKDIFHKNNQLA
LTLIDTNRSRACHPCSPMCKGSRCWGESSEDCQSLTRTVCAGGCARCKGP
LPTDCCHEQCAAGCTGPKHSDCLACLHFNHSGICELHCPALVTYNTDTFE
SMPNPEGRYTFGASCVTACPYNYLSTDVGSCTLVCPLHNQEVTAEDGTQR
CEKCSKPCARVCYGLGMEHLREVRAVTSANIQEFAGCKKIFGSLAFLPES
FDGDPASNTAPLQPEQLQVFETLEEITGYLYISAWPDSLPDLSVFQNLQV
IRGRILHNGAYSLTLQGLGISWLGLRSLRELGSGLALIHHNTHLCFVHTV
PWDQLFRNPHQALLHTANRPEDECVGEGLACHQLCARGHCWGPGPTQCVN
CSQFLRGQECVEECRVLQGLPREYVNARHCLPCHPECQPQNGSVTCFGPE
ADQCVACAHYKDPPFCVARCPSGVKPDLSYMPIWKFPDEEGACQPCPINC
THSCVDLDDKGCPAEQRASPLTSIISAVVGILLVVVLGVVFGILIKRRQQ
KIRKYTMRRLLQETELVEPLTPSGAMPNQAQMRILKETELRKVKVLGSGA
FGTVYKGIWIPDGENVKIPVAIKVLRENTSPKANKEILDEAYVMAGVGSP
YVSRLLGICLTSTVQLVTQLMPYGCLLDHVRENRGRLGSQDLLNWCMQIA
KGMSYLEDVRLVHRDLAARNVLVKSPNHVKITDFGLARLLDIDETEYHAD
GGKVPIKWMALESILRRRFTHQSDVWSYGVTVWELMTFGAKPYDGIPARE
IPDLLEKGERLPQPPICTIDVYMIMVKCWMIDSECRPRFRELVSEFSRMA
RDPQRFVVIQNEDLGPASPLDSTFYRSLLEDDDMGDLVDAEEYLVPQQGF
FCPDPAPGAGGMVHHRHRSSSTRSGGGDLTLGLEPSEEEAPRSPLAPSEG
AGSDVFDGDLGMGAAKGLQSLPTHDPSPLQRYSEDPTVPLPSETDGYVAP
LTCSPQPEYVNQPDVRPQPPSPREGPLPAARPAGATLERPKTLSPGKNGV
VKDVFAFGGAVENPEYLTPQGGAAPQPHPPPAFSPAFDNLYYWDQDPPER
GAPPSTFKGTPTAENPEYLGLDVPV,
``` and ERBB2 Isoform 6 having the following amino acid sequence:

(SEQ ID NO: 69)
```
MELAALCRWGLLLALLPPGAASTQVCTGTDMKLRLPASPETHLDMLRHLY
QGCQVVQGNLELTYLPTNASLSFLQDIQEVQGYVLIAHNQVRQVPLQRLR
IVRGTQLFEDNYALAVLDNGDPLNNTTPVTGASPGGLRELQLRSLTEILK
GGVLIQRNPQLCYQDTILWKDIFHKNNQLALTLIDTNRSRACHPCSPMCK
GSRCWGESSEDCQSLTRTVCAGGCARCKGPLPTDCCHEQCAAGCTGPKHS
DCLACLHFNHSGICELHCPALVTYNTDTFESMPNPEGRYTFGASCVTACP
YNYLSTDVGSCTLVCPLHNQEVTAEDGTQRCEKCSKPCARVCYGLGMEHL
REVRAVTSANIQEFAGCKKIFGSLAFLPESFDGDPASNTAPLQPEQLQVF
ETLEEITGYLYISAWPDSLPDLSVFQNLQVIRGRILHNGAYSLTLQGLGI
SWLGLRSLRELGSGLALIHHNTHLCFVHTVPWDQLFRNPHQALLHTANRP
EDECVGEGLACHQLCARGHCWGPGPTQCVNCSQFLRGQECVEECRVLQGL
PREYVNARHCLPCHPECQPQNGSVTCFGPEADQCVACAHYKDPPFCVARC
PSGVKPDLSYMPIWKFPDEEGACQPCPINCTHSPLTSIISAVVGILLVVV
LGVVFGILIKRROOKIRKYTMRRLLOETELVEPLTPSGAMPNQAQMRILK
ETELRKVKVLGSGAFGTVYKGIWIPDGENVKIPVAIKVLRENTSPKANKE
ILDETISNLFSNFAPRGPSACCEPTCWCHSGKGQDSLPREEWGRQRRFCL
WGCRGEPRVLDTPGRSCPSAPPSSCLQPSLRQPLLLGPGPTRAGGSTQHL
QRDTYGREPRVPGSGRASVNQKAKSAEALMCPQGAGKA.
```

In some instances, the methods described herein may employ an antigen-specific therapeutic that specifically binds an ERBB2, including human ERBB2, including e.g., human ERBB2 Isoform 1, human ERBB2 Isoform 2, human ERBB2 Isoform 3, human ERBB2 Isoform 4, human ERBB2 Isoform 5, human ERBB2 Isoform 6, or any combination thereof.

In some instances, combinations of two or more targeting antigens may be employed, including but not limited to e.g., where such combinations include EphA2 and EphA3, EphA2 and IL13R (e.g., IL13RA1 or IL13RA2), EphA2 and EGFR, EphA2 and ERBB2, EphA3 and IL13R (e.g., IL13RA1 or IL13RA2), EphA3 and EGFR, EphA3 and ERBB2, IL13R (e.g., IL13RA1 or IL13RA2) and EGFR, IL13R (e.g., IL13RA1 or IL13RA2) and ERBB2, or EGFR and ERBB2. In some instances, such combinations may find use in an OR gate as described herein. In some instances, a two-headed antigen-specific therapeutic may be employed, including but not limited to e.g., where the two-headed antigen-specific therapeutic binds to EphA2 and EphA3, EphA2 and IL13R (e.g., IL13RA1 or IL13RA2), EphA2 and EGFR, EphA2 and ERBB2, EphA3 and IL13R (e.g., IL13RA1 or IL13RA2), EphA3 and EGFR, EphA3 and ERBB2, IL13R (e.g., IL13RA1 or IL13RA2) and EGFR, IL13R (e.g., IL13RA1 or IL13RA2) and ERBB2, or EGFR and ERBB2.

Antigen-Specific Therapeutics

As summarized above, in the present methods a BTTS responsive to a priming antigen may induce the expression of an antigen-specific therapeutic responsive to one or more targeting antigens. Useful antigen-specific therapeutics will vary and may include surfaced expressed and secreted antigen-specific therapeutics. For example, in some instances, an antigen-specific therapeutic used in the methods of the present disclosure may be expressed, in response to the activation of a BTTS, on the surface of an immune cell, i.e., the immune cell genetically modified to encode a priming/targeting circuit as described herein. In some instances, an antigen-specific therapeutic used in the methods of the present disclosure may be secreted, in response to the activation of a BTTS, from an immune cell, i.e., the immune cell genetically modified to encode a priming/targeting circuit as described herein.

In general, except where described otherwise, the antigen-specific therapeutic of a herein described circuit will not be expressed in the absence of the activation of the BTTS that induces its expression. Also, except where described otherwise, an antigen-specific therapeutic of a herein described circuit will not be active in the absence of the antigen to which it binds, i.e., without binding the antigen to which the antigen-specific therapeutic is specific. Binding of its respective antigen, or antigens in the case of multi- or bispecific agents, results in activation of the antigen-specific therapeutic. When expressed by, or otherwise engaged with, an immune cell and bound to antigen(s) the antigen-specific therapeutic may activate the immune cell. Activated immune cells may mediate one or more beneficial effects with respect to a heterogeneous GBM of a subject, including those described herein such as but not limited to e.g., cancer cell killing, cytokine release, and the like.

The term "antigen", with respect to the herein described antigen-specific binding domains, is used in a broad sense to refer to essentially any specific binding partner to which the antigen-specific therapeutic binds. As such, any convenient specific binding pair, i.e., specific binding member and specific binding partner pair, may find use in the antigen-specific therapeutics of the instant methods including but not limited to e.g., antigen-antibody pairs, ligand receptor pairs, scaffold protein pairs, etc. In some instances, the specific binding member may be an antibody and its binding partner may be an antigen to which the antibody specifically binds. In some instances, the specific binding member may be a receptor and its binding partner may be a ligand to which the receptor specifically binds. In some instances, the specific binding member may be a ligand and its binding partner may be a receptor to which the ligand specifically binds.

In some instances, useful ligand-receptor specific binding pairs may include where the specific binding member is a mutein of a ligand having at least one mutation relative to the wild-type ligand, including but not limited to e.g., one or more mutations, two or more mutations, three or more mutations, four or more mutations, five or more mutations, etc. In some instances, useful muteins will have at least 90% sequence identity with the relevant wild-type amino acid sequence, including but not limited to e.g., at least 95%, at least 96%, at least 97%, at least 98%, at least 99%, etc., sequence identity with the relevant wild-type amino acid sequence. In some instances, a mutein employed in the subject polypeptide may have higher affinity for the receptor as compared to the affinity between the receptor and the wild-type ligand.

Antigen-specific therapeutics useful in the methods of the present disclosure will vary and may include but are not limited to e.g., chimeric antigen receptors (CARs), T cell receptors (TCRs), chimeric bispecific binding members, and the like.

Useful CARs include essentially any CAR useful in the treatment of cancer, including single-chain and multi-chain CARs, directed to one or more targeting antigens. A CAR used in the instant methods will generally include, at a minimum, an antigen binding domain, a transmembrane domain and an intracellular signaling domain. An employed CAR may further include one or more costimulatory domains.

Non-limiting examples of CARs that may be employed include those used in commercialized CAR T cell (CART) therapies that are directed to one or more appropriate targeting antigens or have been modified to be directed to one or more appropriate targeting antigens. For example, in some instances, one or more CARs may be employed that target one or more targeting antigens, including but not limited to e.g., EphA2, EphA3, IL13R (e.g., IL13RA1 or IL13RA2), EGFR, and ERBB2.

Useful CARs that may be modified to be directed to one or more appropriate targeting antigens include but are not limited to those CARs directed to CD19 and BCMA, including e.g., the anti-CD19-4-1BB-CD3ζ CAR expressed by lentivirus loaded CTL019 (Tisagenlecleucel-T) CAR-T cells, also referred to as Kymriah™ (tisagenlecleucel) as commercialized by Novartis (Basel, Switzerland) and the anti-BCMA-4-1BB-CD3ζ CAR expressed by lentivirus loaded CAR-T cells called "bb2121" as commercialized by bluebird bio, Inc. (Cambridge, MA) and Celgene Corporation (Summit, NJ).

Useful CARs, e.g., that may be modified to be directed to an appropriate targeting antigen, or useful domains thereof, e.g., that may be employed in a CAR directed to an appropriate targeting antigens, in some instances may include those described in U.S. Pat. Nos. 9,914,909; 9,821,012; 9,815,901; 9,777,061; 9,662,405; 9,657,105; 9,629,877; 9,624,276; 9,598,489; 9,587,020; 9,574,014; 9,573,988; 9,499,629; 9,446,105; 9,394,368; 9,328,156; 9,233,125; 9,175,308 and 8,822,647; the disclosures of which are incorporated herein by reference in their entirety. In some instances, useful CARs may include or exclude heterodimeric, also referred to as dimerizable or switchable, CARs and/or include or exclude one or more of the domains thereof. Useful heterodimeric CARs and/or useful domains thereof may, in some instances, include those described in U.S. Pat. Nos. 9,587,020 and 9,821,012 as well as U.S. Pub. Nos. US20170081411A1, US20160311901A1, US20160311907A1, US20150266973A1 and PCT Pub. Nos. WO2014127261A1, WO2015142661A1, WO2015090229A1 and WO2015017214A1; the disclosures of which are incorporated herein by reference in their entirety.

As summarized above, in some instances, the antigen binding domain of a CAR, such but not limited to e.g., those described in any one of the documents referenced above, may be substituted or amended with an alternative or additional antigen binding domain directed to a different antigen, such as but not limited to one or more of the antigens described herein, for use in the herein described methods. In such instances, the intracellular portions (i.e., the intracellular signaling domain or the one or more costimulatory domains) of the antigen-domain-substituted CAR may or may not be modified.

Useful CARs and/or useful domains thereof may, in some instances, include those that have been or are currently being investigated in one or more clinical trials, including but not limited to the CARs directed to the following antigens (listed with an exemplary corresponding clinical trial number, further information pertaining to which may be retrieved by visiting www(dot)clinicaltrials(dot)gov): AFP, e.g., in NCT03349255; BCMA, e.g., in NCT03288493; CD10, e.g., in NCT03291444; CD117, e.g., in NCT03291444; CD123, e.g., in NCT03114670; CD133, e.g., in NCT02541370; CD138, e.g., in NCT01886976; CD171, e.g., in NCT02311621; CD19, e.g., in NCT02813252; CD20, e.g., in NCT03277729; CD22, e.g., in NCT03244306; CD30, e.g., in NCT02917083; CD33, e.g., in NCT03126864; CD34, e.g., in NCT03291444; CD38, e.g., in NCT03291444; CD5, e.g., in NCT03081910; CD56, e.g., in NCT03291444; CD7, e.g., in NCT02742727; CD70, e.g., in NCT02830724; CD80, e.g., in NCT03356808; CD86, e.g., in NCT03356808; CEA, e.g., in NCT02850536; CLD18, e.g., in NCT03159819; CLL-1, e.g., in NCT03312205; cMet, e.g., in NCT01837602;

EGFR, e.g., in NCT03182816; EGFRvIII, e.g., in NCT02664363; EpCAM, e.g., in NCT03013712; EphA2, e.g., in NCT02575261; GD-2, e.g., in NCT01822652; Glypican 3, e.g., in NCT02905188; GPC3, e.g., in NCT02723942; HER-2, e.g., in NCT02547961; kappa immunoglobulin, e.g., in NCT00881920; LeY, e.g., in NCT02958384; LMP1, e.g., in NCT02980315; mesothelin, e.g., in NCT02930993; MG7, e.g., in NCT02862704; MUC1, e.g., in NCT02587689; NKG2D-ligands, e.g., in NCT02203825; PD-L1, e.g., in NCT03330834; PSCA, e.g., in NCT02744287; PSMA, e.g., in NCT03356795; ROR1, e.g., in NCT02706392; ROR1R, e.g., in NCT02194374; TACI, e.g., in NCT03287804; and VEGFR2, e.g., in NCT01218867.

Useful TCRs include essentially any TCR useful in the treatment of cancer, including single-chain and multi-chain TCRs, directed to a targeting antigen. A TCR used in the instant methods will generally include, at a minimum, an antigen binding domain and a modified or unmodified TCR chain, or portion thereof, including but not limited to e.g., a modified or unmodified α-chain, a modified or unmodified β-chain, etc. An employed TCR may further include one or more costimulatory domains. In some instances, a TCR employed herein will include an alpha chain and a beta chain and recognize antigen when presented by a major histocompatibility complex.

Essentially any TCR can be induced by a BTTS using a method of the present disclosure including e.g., TCRs that are specific for any of a variety of epitopes, including, e.g., an epitope expressed on the surface of a cancer cell, a peptide-MHC complex on the surface of cancer cell, and the like. In some cases, the TCR is an engineered TCR.

Non-limiting examples of engineered TCRs, including those having immune cell activation function and that may be modified to include an antigen-binding domain specific for a suitable targeting antigen, useful in the methods described herein include, e.g., antigen-specific TCRs, Monoclonal TCRs (MTCRs), Single chain MTCRs, High Affinity CDR2 Mutant TCRs, CD1-binding MTCRs, High Affinity NY-ESO TCRs, VYG HLA-A24 Telomerase TCRs, including e.g., those described in PCT Pub Nos. WO 2003/020763, WO 2004/033685, WO 2004/044004, WO 2005/114215, WO 2006/000830, WO 2008/038002, WO 2008/039818, WO 2004/074322, WO 2005/113595, WO 2006/125962; Strommes et al. Immunol Rev. 2014; 257(1):145-64; Schmitt et al. Blood. 2013; 122(3):348-56; Chapuls et al. Sci Transl Med. 2013; 5(174):174ra27; Thaxton et al. Hum Vaccin Immunother. 2014; 10(11):3313-21 (PMID: 25483644); Gschweng et al. Immunol Rev. 2014; 257(1): 237-49 (PMID:24329801); Hinrichs et al. Immunol Rev. 2014; 257(1):56-71 (PMID:24329789); Zoete et al. Front Immunol. 2013; 4:268 (PMID:24062738); Man et al. Clin Exp Immunol. 2012; 167(2):216-25 (PMID:22235997); Zhang et al. Adv Drug Deliv Rev. 2012; 64(8):756-62 (PMID:22178904); Chhabra et al. Scientific World Journal. 2011; 11:121-9 (PMID:21218269); Boulter et al. Clin Exp Immunol. 2005; 142(3):454-60 (PMID:16297157); Sami et al. Protein Eng Des Sel. 2007; 20(8):397-403; Boulter et al. Protein Eng. 2003; 16(9):707-11; Ashfield et al. IDrugs. 2006; 9(8):554-9; Li et al. Nat Biotechnol. 2005; 23(3):349-54; Dunn et al. Protein Sci. 2006; 15(4):710-21; Liddy et al. Mol Biotechnol. 2010; 45(2); Liddy et al. Nat Med. 2012; 18(6):980-7; Oates, et al. Oncoimmunology. 2013; 2(2): e22891; McCormack, et al. Cancer Immunol Immunother. 2013 April; 62(4):773-85; Bossi et al. Cancer Immunol Immunother. 2014; 63(5):437-48 and Oates, et al. Mol Immunol. 2015 October; 67(2 Pt A):67-74; the disclosures of which are incorporated herein by reference in their entirety.

Useful TCRs include those having wild-type affinity for their respective antigen as well as those having enhanced affinity for their respective antigen. TCRs having enhanced affinity for their respective antigen may be referred to as "affinity enhanced" or "enhanced affinity" TCRs. The affinity of a TCR may be enhanced by any convenient means, including but not limited to binding-site engineering (i.e., rational design), screening (e.g., TCR display), or the like. Non-limiting examples of affinity enhanced TCRs and methods of generating enhanced affinity TCRs include but are not limited to e.g., those described in PCT Pub. Nos. 20150118208, 2013256159, 20160083449; 20140349855, 20100113300, 20140371085, 20060127377, 20080292549, 20160280756, 20140065111, 20130058908, 20110038842, 20110014169, 2003276403 and the like; the disclosures of which are incorporated herein by reference in their entirety. Further engineered TCRs, modified to be directed to an appropriate targeting antigen, that may be expressed in response to release of an intracellular domain of a BTTS of the present disclosure include e.g., those described in PCT Application No. US2017/048040; the disclosure of which is incorporated herein by reference in its entirety.

Useful TCRs, which may be modified to be directed to an appropriate targeting antigen, may, in some instances, also include those described in U.S. Pat. Nos. 9,889,161; 9,889,160; 9,868,765; 9,862,755; 9,717,758; 9,676,867; 9,409,969; 9,115,372; 8,951,510; 8,906,383; 8,889,141; 8,722,048; 8,697,854; 8,603,810; 8,383,401; 8,361,794; 8,283,446; 8,143,376; 8,003,770; 7,998,926; 7,666,604; 7,456,263; 7,446,191; 7,446,179; 7,329,731; 7,265,209; and 6,770,749; the disclosures of which are incorporated herein by reference in their entirety.

As described above, in some instances, the antigen binding domain of a TCR, such as but not limited to e.g., those described or referenced above, may be substituted or amended with an alternative or additional antigen binding domain directed to a different antigen, such as but not limited to one or more of the antigens described herein, for use in the herein described methods. In such instances, the other portions (i.e., the transmembrane domain, any intracellular signaling domains, etc.) of the antigen-domain-substituted TCR may or may not be modified.

As summarized above, in some instances, useful antigen-specific therapeutics may include those that, upon induction by an activated BTTS, are expressed and secreted from the producing cell, including e.g., where the secreting cell is an immune cell. For example, upon binding of a BTTS expressed by an immune cell, the BTTS may induce expression and secretion of an encoded antigen-specific therapeutic specific for a targeting antigen. The secreted antigen-specific therapeutic may target a target antigen expressing cancer cell in trans, thereby mediating killing of the target cell. As described herein, in some instances, a secreted antigen-specific therapeutic may increase the zone of targeting or the zone of killing of a subject circuit as compared to a similar circuit encoding a non-secreted (e.g., membrane expressed) antigen-specific therapeutic.

Useful secreted antigen-specific therapeutics will vary and in some instances may include but are not limited to e.g., chimeric bispecific binding members. In some instances, useful chimeric bispecific binding members may include those that target a protein expressed on the surface of an immune cell, including but not limited to e.g., a component of the T cell receptor (TCR), e.g., one or more T cell co-receptors. Chimeric bispecific binding members that bind to a component of the TCR may be referred to herein as a TCR-targeted bispecific binding agent. Chimeric bispecific binding members useful in the instant methods will generally be specific for a targeting antigen and may, in some instances, be specific for a targeting antigen and a protein expressed on the surface of an immune cell (e.g., a component of a TCR such as e.g., a CD3 co-receptor).

Non-limiting examples of useful chimeric bispecific binding members include those that bind Ephrin type-A receptor 2 (EphA2), Ephrin type-A receptor 3 (EphA3), Interleukin-13 receptor (IL13R) (e.g., IL13RA1 or IL13RA2), Epidermal growth factor receptor (EGFR) or erb-b2 receptor tyrosine kinase 2 (ERBB2). Non-limiting examples of useful chimeric bispecific binding members also include those that have been modified to bind EphA2, EphA3, IL13R (e.g., IL13RA1 or IL13RA2), EGFR or ERBB2.

In some instances, useful chimeric bispecific binding members may include a bispecific T cell engager (BiTE). A BiTE is generally made by fusing a specific binding member (e.g., a scFv) that binds an immune cell antigen to a specific binding member (e.g., a scFv) that binds a cancer antigen (e.g., a tumor associated antigen, a tumor specific antigen, etc.). For example, an exemplary BiTE includes an anti-CD3 scFv fused to an anti-tumor associated antigen (e.g., EpCAM, CD19, etc.) scFv via a short peptide linker (e.g., a five amino acid linker, e.g., GGGGS).

In some instances, a BiTE, suitable for use in the herein described methods may include e.g., an anti-CD3×anti-CD19 BiTE (e.g., Blinatumomab) that has been modified to bind a suitable targeting antigen (including but not limited to e.g., EphA2, EphA3, IL13R (e.g., IL13RA1 or IL13RA2), EGFR or ERBB2), an anti-EpCAM×anti-CD3 BiTE (e.g., MT110) that has been modified to bind a suitable targeting antigen (including but not limited to e.g., EphA2, EphA3, IL13R (e.g., IL13RA1 or IL13RA2), EGFR or ERBB2), an anti-CEA×anti-CD3 BiTE (e.g., MT111/MEDI-565) that has been modified to bind a suitable targeting antigen (including but not limited to e.g., EphA2, EphA3, IL13R (e.g., IL13RA1 or IL13RA2), EGFR or ERBB2), an anti-CD33×anti-CD3 BiTE that has been modified to bind a suitable targeting antigen (including but not limited to e.g., EphA2, EphA3, IL13R (e.g., IL13RA1 or IL13RA2), EGFR or ERBB2), an anti-HER2 BiTE that has been modified to bind a suitable targeting antigen (including but not limited to e.g., EphA2, EphA3, IL13R (e.g., IL13RA1 or IL13RA2), EGFR or ERBB2), an anti-EGFR BiTE, an anti-IgE BiTE that has been modified to bind a suitable targeting antigen (including but not limited to e.g., EphA2, EphA3, IL13R (e.g., IL13RA1 or IL13RA2), EGFR or ERBB2), and the like.

As summarized above, in some instances, the antigen binding domain of a chimeric bispecific binding member, such as but not limited to e.g., those described or referenced above, may be substituted or amended with an alternative or additional antigen binding domain directed to a different antigen, such as but not limited to one or more of the antigens described herein, for use in the herein described methods. In such instances, the other portions (i.e., linker domain, any immune cell targeting domains, etc.) of the antigen-domain-substituted chimeric bispecific binding member may or may not be modified.

In some instances, a payload induced by binding of a BTTS to its respective priming antigen in a herein described method may include a secreted bio-orthogonal adapter molecule. Such bio-orthogonal adapter molecules may, in some instances, be configured to target and bind a targeting antigen and also bind or be bound by a heterologous polypeptide expressed by an immune cell.

For example, in some instances, a subject circuit employed in the herein described methods may encode, within an immune cell: a BTTS responsive to a priming antigen; a bio-orthogonal adapter molecule specific for a targeting antigen; and a therapeutic, or portion thereof, which binds the bio-orthogonal adapter molecule. In such a circuit, expression and secretion of the bio-orthogonal adapter molecule is induced upon binding of the BTTS to the priming antigen (including but not limited to e.g., IL13RA2, IL13RA1, Neuroligin, NRXN1, PTPRZ1, NRCAM, CDH10, PCDHGC5, CD70, CSPG5, BCAN, GRM3, CRB1, GAP43, ATP1B2, MOG1, and PTPRZ1-MET). Then, in the presence of both (1) a cancer cell expressing the targeting antigen and (2) the therapeutic that binds the bio-orthogonal adapter molecule, the therapeutic binds the bio-orthogonal adapter molecule which then binds the targeting antigen, thereby activating the therapeutic. The activated therapeutic may then mediate a therapeutic effect (e.g., a cytotoxic effect) on the cancer cell expressing the targeting antigen, including where the targeting antigen is expressed in trans with respect to the priming antigen. As described herein, in some instances, a secreted bio-orthogonal adapter molecule may increase the zone of targeting or the zone of killing of a subject circuit as compared to a similar circuit encoding a non-secreted (e.g., membrane expressed) antigen-specific therapeutic.

Bio-orthogonal adapter molecules may be employed in various contexts within the herein described methods. For example, in some instances, a bio-orthogonal adapter molecule may be employed that includes a diffusible antigen binding portion of an antigen-specific therapeutic, such as e.g., a diffusible antigen binding portion of a CAR, a diffusible antigen binding portion of a TCR, or the like. In some instances, such diffusible antigen binding portion of antigen-specific therapeutics may be referred to a "diffusible head", including e.g., a "diffusible CAR head", a "diffusible TCR head", and the like. In some instances, a diffusible antigen binding portion may be specific for one or more of EphA2, EphA3, IL13R (e.g., IL13RA1 or IL13RA2), EGFR and/or ERBB2.

In some instances, the therapeutic may bind directly to the bio-orthogonal adapter molecule. Strategies for direct binding of the therapeutic to the bio-orthogonal adapter molecule may vary. For example, in some instances, the therapeutic may include a binding domain (e.g., such as an orthogonal antibody or fragment thereof) that binds a binding moiety (e.g., an orthogonal epitope to which an antibody may be directed) covalently attached to the bio-orthogonal adapter. As a non-limiting example, a therapeutic may include a binding domain to a non-naturally occurring epitope, e.g., an anti-fluorescein antibody or a fragment thereof, and the bio-orthogonal adapter molecule may include the epitope, e.g., a fluorescein, covalently attached thereto. In some instances, the configuration of the bio-orthogonal adapter molecule and therapeutic interaction may be reversed as compared to that previously described, including e.g., where the therapeutic includes a covalently attached epitope and the bio-orthogonal adapter molecule includes a binding domain to the epitope. Useful epitopes will vary and may include but are not limited to e.g., small molecule-based epitopes, peptide-based epitopes (e.g., peptide neo-epitopes), oligonucleotide-based epitopes, and the like. The epitope-binding domains will vary correspondingly and may include but are not limited to e.g., small molecule binding domains, peptide binding domains, oligonucleotide binding domains, and the like.

Non-limiting examples of useful bio-orthogonal adapter molecules, and the domains that bind thereto, include but are not limited to e.g., the peptide neo-epitopes and the antibody binding domains that bind thereto as used in switchable CAR (sCAR) T cells, including but not limited to e.g., those described in Rodgers et al. Proc Natl Acad Sci USA. (2016) 113(4):E459-68 and Cao et al., Angew Chem Int Ed Engl. 2016 Jun. 20; 55(26):7520-4 as well as PCT Pub. No. WO2016168773; the disclosures of which are incorporated herein by reference in their entirety.

In some instances, the therapeutic may bind indirectly to the bio-orthogonal adapter molecule, including e.g., where binding is mediated by a diffusible dimerizing agent. Non-limiting examples of suitable dimerizing agents, and the dimerizing domains that bind thereto, include protein dimerizers.

Protein dimerizers generally include polypeptide pairs that dimerize, e.g., in the presence of or when exposed to a dimerizing agent. The dimerizing polypeptide pairs of a protein dimerizer may homo-dimerize or hetero-dimerize (i.e., the dimerizing polypeptide pairs may include two of the same polypeptide that form a homodimer or two different polypeptides that form a heterodimer). Non-limiting pairs of protein dimerizers (with the relevant dimerizing agent in parentheses) include but are not limited to e.g., FK506 binding protein (FKBP) and FKBP (rapamycin); FKBP and calcineurin catalytic subunit A (CnA) (rapamycin); FKBP and cyclophilin (rapamycin); FKBP and FKBP-rapamycin associated protein (FRB) (rapamycin); gyrase B (GyrB) and GyrB (coumermycin); dihydrofolate reductase (DHFR) and DHFR (methotrexate); DmrB and DmrB (AP20187); PYL and ABI (abscisic acid); Cry2 and CIB1 (blue light); GAI and GID1 (gibberellin); and the like. Further description, including the amino acid sequences, of such protein dimerizers is provided in U.S. Patent Application Publication No. US 2015-0368342 A1; the disclosure of which is incorporated herein by reference in its entirety.

Useful protein dimerizers also include those nuclear hormone receptor derived protein dimerizers that dimerize in the presence of a dimerizing agent described in PCT Pub. No. WO 2017/120546 and U.S. Patent Pub. No. US 2017/0306303 A1; the disclosures of which are incorporated by reference herein in their entirety, and the like. Such nuclear hormone receptor derived dimerizers will generally include a first member of the dimerization pair that is a co-regulator of a nuclear hormone receptor and a second member of the dimerization pair comprises an LBD of the nuclear hormone receptor.

Where a bio-orthogonal adapter molecule is employed in a subject circuit, the expression of the therapeutic, which binds the bio-orthogonal adapter molecule to mediate targeting antigen recognition, may or may not be controlled by the circuit. Put another way, the expression of the therapeutic may or may not be tied to the activation of the BTTS (e.g., the binding of the BTTS to priming antigen or another antigen) of the circuit. In some instances, the circuit may be configured such that binding of a BTTS to its antigen induces expression of a therapeutic which binds a bio-orthogonal adapter molecule. In some instances, the BTTS that induces expression of the therapeutic is the same BTTS that induces expression of the bio-orthogonal adapter molecule. In some instance, the therapeutic is induced by a BTTS that is different (i.e., separate) from the BTTS that induces expression of the bio-orthogonal adapter molecule.

In some instances, expression of a therapeutic which binds a bio-orthogonal adapter molecule may not be induced by a BTTS. For example, in some instances, rather than being induced by a BTTS, such a therapeutic is expressed under the control of a separate regulatory element or sequence, including but not limited to e.g., where the expression of the therapeutic is constitutive, inducible, conditional, tissue specific, cell type specific, or the like. In some instances, for example, independent expression (e.g., constitutive expression, inducible expression, etc.) of the therapeutic by introduced immune cells allows for a diffusible bio-orthogonal adapter molecule to mediate the activation of the therapeutic in immune cells that are distant from the site of priming.

In some instances, expression of a bio-orthogonal adapter molecule, bound by a therapeutic, may not be induced by a BTTS, including where the corresponding therapeutic is induced by a BTTS. For example, in some instances, rather than being induced by a BTTS, such a bio-orthogonal adapter molecule is expressed under the control of a separate regulatory element or sequence, including but not limited to e.g., where the expression of the bio-orthogonal adapter molecule is constitutive, inducible, conditional, tissue specific, cell type specific, or the like. In some instances, the bio-orthogonal adapter molecule may be externally provided.

In some instances, an antigen-specific therapeutic may have an extracellular domain that includes a first member of a specific binding pair that binds a second member of the specific binding pair, wherein the extracellular domain does not include any additional first or second member of a second specific binding pair. For example, in some instances, an antigen-specific therapeutic may have an extracellular domain that includes a first antigen-binding domain that binds an antigen, wherein the extracellular domain does not include any additional antigen-binding domains and does not bind any other antigens. A subject antigen-specific therapeutic may, in some instances, include only a single extracellular domain. Accordingly, an employed antigen-specific therapeutic may be specific for a single antigen and only specific for the single antigen. Such, antigen-specific therapeutics may be referred to as a "single antigen antigen-specific therapeutic".

In some instances, an antigen-specific therapeutic may have an extracellular domain that includes the first or second members of two or more specific binding pairs. For example, in some instances, an antigen-specific therapeutic may have an extracellular domain that includes a first antigen-binding domain and a second antigen-binding domain that are different such that the extracellular domain is specific for two different antigens. In some instances, an antigen-specific therapeutic may have two or more extracellular domains that each includes the first or second members of two different specific binding pairs. For example, in some instances, an antigen-specific therapeutic may have a first extracellular domain that includes a first antigen-binding domain and a second extracellular domain that includes a second antigen-binding domain where the two different antigen binding domains are each specific for a different antigen. As such, the antigen-specific therapeutic may be specific for two different antigens.

An antigen-specific therapeutic specific for two or more different antigens, containing either two extracellular domains or one extracellular domain specific for two different antigens, may be configured such that the binding of either antigen to the antigen-specific therapeutic is sufficient to active the antigen-specific therapeutic. Such an antigen-specific therapeutic, capable of being activated by any of two or more antigens, may find use in the described circuits as a component of a logic gate containing OR functionality. In some instances, an antigen-specific therapeutic specific for two different antigens may be referred to as a "two-headed antigen-specific therapeutic". Antigen-specific therapeutics specific for multiple antigens will not be limited to only two antigens and may, e.g., be specific for and/or activated by more than two antigens, including e.g., three or more, four or more, five or more, etc.

For example, an antigen-specific therapeutic specific for two or more different antigens may bind, and/or be activated by, EphA2 or EphA3, EphA2 or IL13RA1, EphA2 or IL13RA2, EphA2 or EGFR, EphA2 or ERBB2, EphA3 or IL13RA1, EphA3 or IL13RA2, EphA3 or EGFR, EphA3 or ERBB2, IL13RA1 or IL13RA2, IL13RA1 or EGFR, IL13RA1 or ERBB2, IL13RA2 or EGFR, IL13RA2 or ERBB2, or EGFR or ERBB2.

An example of an antigen-specific therapeutic specific for two or more different antigens is a tandem CAR (also referred to as "tan CAR" or "tanCAR"). A "tandem CAR" is a bispecific CAR that includes two or more non-identical antigen recognition domains. Non-limiting examples of tandem CARs include those described in U.S. Pat. Nos. 9,447,194; 10,155,038; 10,189,903; and 10,239,948; U.S. Patent Application Pub. No. 20130280220 and PCT Application Pub. No. WO/2013/123061; the disclosures of which are incorporated herein by reference in their entirety. Tandem CARs may be configured to bind a variety of different antigens, including but not limited to e.g., two or more or the antigens described herein and/or two or more of the antigens described in U.S. Pat. Nos. 9,447,194; 10,155,038; 10,189,903; and 10,239,948; U.S. Patent Application Pub. No. 20130280220 and PCT Application Pub. No. WO/2013/123061.

Binding Triggered Transcriptional Switches (BTTS)

The methods of the instant disclosure include the use of circuits employing a BTTS to induce expression of an encoded antigen-specific therapeutic. As used herein, a "binding-triggered transcriptional switch" or BTTS generally refers to a synthetic modular polypeptide or system of interacting polypeptides having an extracellular domain that includes a first member of a specific binding pair, a binding-transducer and an intracellular domain. Upon binding of the second member of the specific binding pair to the BTTS the binding signal is transduced to the intracellular domain such that the intracellular domain becomes activated and performs some function within the cell that it does not perform in the absence of the binding signal. Binding triggered transcriptional switches are described in e.g., PCT Pub. No. WO 2016/138034 as well as U.S. Pat. Nos. 9,670,281 and 9,834,608; the disclosures of which are incorporated herein by reference in their entirety.

The specific binding member of the extracellular domain generally determines the specificity of the BTTS. In some instances, a BTTS may be referred according to its specificity as determined based on its specific binding member. For example, a specific binding member having binding partner "X" may be referred to as an X-BTTS or an anti-X BTTS.

Any convenient specific binding pair, i.e., specific binding member and specific binding partner pair, may find use in the BTTS of the instant methods including but not limited to e.g., antigen-antibody pairs, ligand receptor pairs, scaffold protein pairs, etc. In some instances, the specific binding member may be an antibody and its binding partner may be an antigen to which the antibody specifically binds. In some instances, the specific binding member may be a receptor and its binding partner may be a ligand to which the receptor specifically binds. In some instances, the specific binding member may be a scaffold protein and its binding partner may be a protein to which the scaffold protein specifically binds. Useful specific binding pairs include those specific for priming antigen and/or one or more targeting/killing antigens, including those described herein.

In some cases, the specific binding member is an antibody. The antibody can be any antigen-binding antibody-based polypeptide, a wide variety of which are known in the art. In some instances, the specific binding member is or includes a monoclonal antibody, a single chain Fv (scFv), a Fab, etc. Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing V$\alpha$V$\beta$) are also suitable for use.

Where the specific binding member of a BTTS is an antibody-based binding member, the BTTS can be activated in the presence of a binding partner to the antibody-based binding member, including e.g., an antigen specifically bound by the antibody-based binding member. In some instances, antibody-based binding member may be defined, as is commonly done in the relevant art, based on the antigen bound by the antibody-based binding member, including e.g., where the antibody-based binding member is described as an "anti-" antigen antibody, e.g., an anti-priming antigen antibody (e.g., an anti-IL13RA2 antibody, anti-IL13RA1 antibody, anti-Neuroligin antibody, anti-NRXN1 antibody, anti-PTPRZ1 antibody, anti-NRCAM antibody, anti-CDH10 antibody, anti-PCDHGC5 antibody, anti-CD70 antibody anti-CSPG5 antibody, anti-BCAN antibody, anti-GRM3 antibody, anti-CRB1 antibody, anti-GAP43 antibody, anti-ATP1B2 antibody, anti-PTPRZ1-MET fusion antibody, etc.). Accordingly, antibody-based binding members suitable for inclusion in a BTTS or an antigen-specific therapeutic of the present methods can have a variety of antigen-binding specificities.

The components of BTTSs, employed in the described methods, and the arrangement of the components of the switch relative to one another will vary depending on many factors including but not limited to e.g., the desired binding trigger, the activity of the intracellular domain, the overall function of the BTTS, the broader arrangement of a molecular circuit comprising the BTTS, etc. The first binding member may include but is not limited to e.g., those agents that bind an antigen described herein. The intracellular domain may include but is not limited e.g., those intracellular domains that activate or repress transcription at a regulatory sequence, e.g., to induce or inhibit expression of a downstream component of a particular circuit.

The binding transducer of BTTSs will also vary depending on the desired method of transduction of the binding signal. Generally, binding transducers may include those polypeptides and/or domains of polypeptides that transduce an extracellular signal to intracellular signaling e.g., as performed by the receptors of various signal transduction pathways. Transduction of a binding signal may be achieved through various mechanisms including but not limited to e.g., binding-induced proteolytic cleavage, binding-induced phosphorylation, binding-induced conformational change, etc. In some instances, a binding-transducer may contain a ligand-inducible proteolytic cleavage site such that upon binding the binding-signal is transduced by cleavage of the BTTS, e.g., to liberate an intracellular domain. For example, in some instances, a BTTS may include a Notch derived cleavable binding transducer, such as, e.g., a chimeric notch receptor polypeptide as described herein.

In other instances, the binding signal may be transduced in the absence of inducible proteolytic cleavage. Any signal transduction component or components of a signaling transduction pathway may find use in a BTTS whether or not proteolytic cleavage is necessary for signal propagation. For example, in some instances, a phosphorylation-based binding transducer, including but not limited to e.g., one or more signal transduction components of the Jak-Stat pathway, may find use in a non-proteolytic BTTS.

For simplicity, BTTSs, including but not limited to chimeric notch receptor polypeptides, are described primarily as single polypeptide chains. However, BTTSs, including chimeric notch receptor polypeptides, may be divided or split across two or more separate polypeptide chains where the joining of the two or more polypeptide chains to form a functional BTTS, e.g., a chimeric notch receptor polypeptide, may be constitutive or conditionally controlled. For example, constitutive joining of two portions of a split BTTS may be achieved by inserting a constitutive heterodimerization domain between the first and second portions of the split polypeptide such that upon heterodimerization the split portions are functionally joined.

Useful BTTSs that may be employed in the subject methods include, but are not limited to modular extracellular sensor architecture (MESA) polypeptides. A MESA polypeptide comprises: a) a ligand binding domain; b) a transmembrane domain; c) a protease cleavage site; and d) a functional domain. The functional domain can be a transcription regulator (e.g., a transcription activator, a transcription repressor). In some cases, a MESA receptor comprises two polypeptide chains. In some cases, a MESA receptor comprises a single polypeptide chain. Non-limiting examples of MESA polypeptides are described in, e.g., U.S. Patent Publication No. 2014/0234851; the disclosure of which is incorporated herein by reference in its entirety.

Useful BTTSs that may be employed in the subject methods include, but are not limited to polypeptides employed in the TANGO assay. The subject TANGO assay employs a TANGO polypeptide that is a heterodimer in which a first polypeptide comprises a tobacco etch virus (Tev) protease and a second polypeptide comprises a Tev proteolytic cleavage site (PCS) fused to a transcription factor. When the two polypeptides are in proximity to one another, which proximity is mediated by a native protein-protein interaction, Tev cleaves the PCS to release the transcription factor. Non-limiting examples of TANGO polypeptides are described in, e.g., Barnea et al. (Proc Natl Acad Sci USA. 2008 Jan. 8; 105(1):64-9); the disclosure of which is incorporated herein by reference in its entirety.

Useful BTTSs that may be employed in the subject methods include, but are not limited to von Willebrand Factor (vWF) cleavage domain-based BTTSs, such as but not limited to e.g., those containing a unmodified or modified vWF A2 domain. A subject vWF cleavage domain-based BTTS will generally include: an extracellular domain comprising a first member of a binding pair; a von Willebrand Factor (vWF) cleavage domain comprising a proteolytic cleavage site; a cleavable transmembrane domain and an intracellular domain. Non-limiting examples of vWF cleavage domains and vWF cleavage domain-based BTTSs are described in Langridge & Struhl (Cell (2017) 171(6): 1383-1396); the disclosure of which is incorporated herein by reference in its entirety.

Useful BTTSs that may be employed in the subject methods include, but are not limited to chimeric Notch receptor polypeptides, such as but not limited to e.g., synNotch polypeptides, non-limiting examples of which are described in PCT Pub. No. WO 2016/138034, U.S. Pat. Nos. 9,670,281, 9,834,608, Roybal et al. Cell (2016) 167(2):419-432, Roybal et al. Cell (2016) 164(4):770-9, and Morsut et al. Cell (2016) 164(4):780-91; the disclosures of which are incorporated herein by reference in their entirety.

SynNotch polypeptides are generally proteolytically cleavable chimeric polypeptides that generally include: a) an extracellular domain comprising a specific binding member; b) a proteolytically cleavable Notch receptor polypeptide comprising one or more proteolytic cleavage sites; and c) an intracellular domain. Binding of the specific binding member by its binding partner generally induces cleavage of the synNotch at the one or more proteolytic cleavage sites, thereby releasing the intracellular domain. In some instances, the instant methods may include where release of the intracellular domain triggers (i.e., induces) the production of an encoded payload, the encoding nucleic acid sequence of which is contained within the cell. Depending on the particular context, the produced payload is then generally expressed on the cell surface or secreted. SynNotch polypeptides generally include at least one sequence that is heterologous to the Notch receptor polypeptide (i.e., is not derived from a Notch receptor), including e.g., where the extracellular domain is heterologous, where the intracellular domain is heterologous, where both the extracellular domain and the intracellular domain are heterologous to the Notch receptor, etc.

Useful synNotch BTTSs will vary in the domains employed and the architecture of such domains. SynNotch polypeptides will generally include a Notch receptor polypeptide that includes one or more ligand-inducible proteolytic cleavage sites. The length of Notch receptor polypeptides will vary and may range in length from about 50 amino acids or less to about 1000 amino acids or more.

In some cases, the Notch receptor polypeptide present in a synNotch polypeptide has a length of from 50 amino acids (aa) to 1000 aa, e.g., from 50 aa to 75 aa, from 75 aa to 100 aa, from 100 aa to 150 aa, from 150 aa to 200 aa, from 200 aa to 250 aa, from 250 a to 300 aa, from 300 aa to 350 aa, from 350 aa to 400 aa, from 400 aa to 450 aa, from 450 aa to 500 aa, from 500 aa to 550 aa, from 550 aa to 600 aa, from 600 aa to 650 aa, from 650 aa to 700 aa, from 700 aa to 750 aa, from 750 aa to 800 aa, from 800 aa to 850 aa, from 850 aa to 900 aa, from 900 aa to 950 aa, or from 950 aa to 1000 aa. In some cases, the Notch receptor polypeptide present in a synNotch polypeptide has a length of from 300 aa to 400 aa, from 300 aa to 350 aa, from 300 aa to 325 aa, from 350 aa to 400 aa, from 750 aa to 850 aa, from 50 aa to 75 aa. In some cases, the Notch receptor polypeptide has a length of from 310 aa to 320 aa, e.g., 310 aa, 311 aa, 312 aa, 313 aa, 314 aa, 315 aa, 316 aa, 317 aa, 318 aa, 319 aa, or 320 aa. In some cases, the Notch receptor polypeptide has a length of 315 aa. In some cases, the Notch receptor polypeptide has a length of from 360 aa to 370 aa, e.g., 360 aa, 361 aa, 362 aa, 363 aa 364 aa, 365 aa, 366 aa, 367 aa, 368 aa, 369 aa, or 370 aa. In some cases, the Notch receptor polypeptide has a length of 367 aa.

In some cases, a Notch receptor polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a Notch receptor. In some instances, the Notch regulatory region of a Notch receptor polypeptide is a mammalian Notch regulatory region, including but not limited to e.g., a mouse Notch (e.g., mouse Notch1, mouse Notch2, mouse Notch3 or mouse Notch4) regulatory region, a rat Notch regulatory region (e.g., rat Notch1, rat Notch2 or rat Notch3), a human Notch regulatory region (e.g., human Notch1, human Notch2, human Notch3 or human Notch4), and the like or a Notch regulatory region derived from a mammalian Notch regulatory region and having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a mammalian Notch regulatory region of a mammalian Notch receptor amino acid sequence.

Subject Notch regulatory regions may include or exclude various components (e.g., domains, cleavage sites, etc.) thereof. Examples of such components of Notch regulatory regions that may be present or absent in whole or in part, as appropriate, include e.g., one or more EGF-like repeat domains, one or more Lin12/Notch repeat domains, one or more heterodimerization domains (e.g., HD-N or HD-C), a transmembrane domain, one or more proteolytic cleavage sites (e.g., a furin-like protease site (e.g., an 51 site), an ADAM-family protease site (e.g., an S2 site) and/or a gamma-secretase protease site (e.g., an S3 site)), and the like. Notch receptor polypeptides may, in some instances, exclude all or a portion of one or more Notch extracellular domains, including e.g., Notch-ligand binding domains such as Delta-binding domains. Notch receptor polypeptides may, in some instances, include one or more non-functional versions of one or more Notch extracellular domains, including e.g., Notch-ligand binding domains such as Delta-binding domains. Notch receptor polypeptides may, in some instances, exclude all or a portion of one or more Notch intracellular domains, including e.g., Notch Rbp-associated molecule domains (i.e., RAM domains), Notch Ankyrin repeat domains, Notch transactivation domains, Notch PEST domains, and the like. Notch receptor polypeptides may, in some instances, include one or more non-functional versions of one or more Notch intracellular domains, including e.g., non-functional Notch Rbp-associated molecule domains (i.e., RAM domains), non-functional Notch Ankyrin repeat domains, non-functional Notch transactivation domains, non-functional Notch PEST domains, and the like.

Non-limiting examples of particular synNotch BTTSs, the domains thereof, and suitable domain arrangements are described in PCT Pub. Nos. WO 2016/138034, WO 2017/193059, WO 2018/039247 and U.S. Pat. Nos. 9,670,281 and 9,834,608; the disclosures of which are incorporated herein by reference in their entirety.

Domains of a useful BTTS, e.g., the extracellular domain, the binding-transducer domain, the intracellular domain, etc., may be joined directly, i.e., with no intervening amino acid residues or may include a peptide linker that joins two domains. Peptide linkers may be synthetic or naturally derived including e.g., a fragment of a naturally occurring polypeptide.

A peptide linker can vary in length of from about 3 amino acids (aa) or less to about 200 aa or more, including but not limited to e.g., from 3 aa to 10 aa, from 5 aa to 15 aa, from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A peptide linker can have a length of from 3 aa to 30 aa, e.g., 3, 4, 5, 6, 7, 8, 9, 10, 11, 12, 13, 14, 15, 16, 17, 18, 19, 20, 21, 22, 23, 24, 25, 26, 27, 28, 29, or 30 aa. A peptide linker can have a length of from 5 aa to 50 aa, e.g., from 5 aa to 40 aa, from 5 aa to 35 aa, from 5 aa to 30 aa, from 5 aa to 25 aa, from 5 aa to 20 aa, from 5 aa to 15 aa or from 5 aa to 10 aa.

In some instances, a BTTS may have an extracellular domain that includes a first member of a specific binding pair that binds a second member of the specific binding pair, wherein the extracellular domain does not include any additional first or second member of a second specific binding pair. For example, in some instances, a BTTS may have an extracellular domain that includes a first antigen-binding domain that binds an antigen, wherein the extracellular domain does not include any additional antigen-binding domains and does not bind any other antigens. A subject BTTS may, in some instances, include only a single extracellular domain. Accordingly, an employed BTTS may be specific for a single antigen and only specific for the single antigen. Such, BTTSs may be referred to as a "single antigen BTTS". In some instances, a "dual antigen BTTS" may be employed.

In some instances, a BTTS may have an extracellular domain that includes the first or second members of two or more specific binding pairs. For example, in some instances, a BTTS may have an extracellular domain that includes a first antigen-binding domain and a second antigen-binding domain that are different such that the extracellular domain is specific for two different antigens. In some instances, a BTTS may have two or more extracellular domains that each includes the first or second members of two different specific binding pairs. For example, in some instances, a BTTS may have a first extracellular domain that includes a first antigen-binding domain and a second extracellular domain that includes a second antigen-binding domain where the two different antigen binding domains are each specific for a different antigen. As such, the BTTS may be specific for two different antigens.

For example, a BTTS that is specific for two or more different antigens may bind, and/or be activated by, IL13RA2 or IL13RA1, IL13RA2 or Neuroligin, IL13RA2 or NRXN1, IL13RA2 or PTPRZ1, IL13RA2 or NRCAM, IL13RA2 or CDH10, IL13RA2 or PCDHGC5, IL13RA2 or CD70, IL13RA2 or CSPG5, IL13RA2 or BCAN, IL13RA2 or GRM3, IL13RA2 or CRB1, IL13RA2 or GAP43, IL13RA2 or ATP1B2, IL13RA2 or MOG1, IL13RA2 or PTPRZ1-MET, IL13RA1 or Neuroligin, IL13RA1 or NRXN1, IL13RA1 or PTPRZ1, IL13RA1 or NRCAM, IL13RA1 or CDH10, IL13RA1 or PCDHGC5, IL13RA1 or CD70, IL13RA1 or CSPG5, IL13RA1 or BCAN, IL13RA1 or GRM3, IL13RA1 or CRB1, IL13RA1 or GAP43, IL13RA1 or ATP1B2, IL13RA1 or MOG1, IL13RA1 or PTPRZ1-MET, Neuroligin or NRXN1, Neuroligin or PTPRZ1, Neuroligin or NRCAM, Neuroligin or CDH10, Neuroligin or PCDHGC5, Neuroligin or CD70, Neuroligin or CSPG5, Neuroligin or BCAN, Neuroligin or GRM3, Neuroligin or CRB1, Neuroligin or GAP43, Neuroligin or ATP1B2, Neuroligin or MOG1, Neuroligin or PTPRZ1-MET, NRXN1 or PTPRZ1, NRXN1 or NRCAM, NRXN1 or CDH10, NRXN1 or PCDHGC5, NRXN1 or CD70, NRXN1 or CSPG5, NRXN1 or BCAN, NRXN1 or GRM3, NRXN1 or CRB1, NRXN1 or GAP43, NRXN1 or ATP1B2, NRXN1 or MOG1, NRXN1 or PTPRZ1-MET, PTPRZ1 or NRCAM, PTPRZ1 or CDH10, PTPRZ1 or PCDHGC5, PTPRZ1 or CD70, PTPRZ1 or CSPG5, PTPRZ1 or BCAN, PTPRZ1 or GRM3, PTPRZ1 or CRB1, PTPRZ1 or GAP43, PTPRZ1 or ATP1B2, PTPRZ1 or MOG1, PTPRZ1 or PTPRZ1-MET, NRCAM or CDH10, NRCAM or PCDHGC5, NRCAM or CD70, NRCAM or CSPG5, NRCAM or BCAN, NRCAM or GRM3, NRCAM or CRB1, NRCAM or GAP43, NRCAM or ATP1B2, NRCAM or MOG1, NRCAM or PTPRZ1-MET, CDH10 or PCDHGC5, CDH10 or CD70, CDH10 or CSPG5, CDH10 or BCAN, CDH10 or GRM3, CDH10 or CRB1, CDH10 or GAP43, CDH10 or ATP1B2, CDH10 or MOG1, CDH10 or PTPRZ1-MET, PCDHGC5 or CD70, PCDHGC5 or CSPG5, PCDHGC5 or BCAN, PCDHGC5 or GRM3, PCDHGC5 or CRB1, PCDHGC5 or GAP43, PCDHGC5 or ATP1B2, PCDHGC5 or MOG1, PCDHGC5 or PTPRZ1-MET, CD70 or CSPG5, CD70 or BCAN, CD70 or GRM3, CD70 or CRB1, CD70 or GAP43, CD70 or ATP1B2, CD70 or MOG1, CD70 or PTPRZ1-MET, CSPG5 or BCAN, CSPG5 or GRM3, CSPG5 or CRB1, CSPG5 or GAP43, CSPG5 or ATP1B2, CSPG5 or MOG1, CSPG5 or PTPRZ1-MET, BCAN or GRM3, BCAN or CRB1, BCAN or GAP43, BCAN or ATP1B2, BCAN or MOG1, BCAN or PTPRZ1-MET, GRM3 or CRB1, GRM3 or GAP43, GRM3 or ATP1B2, GRM3 or MOG1, GRM3 or PTPRZ1-MET, CRB1 or GAP43, CRB1 or ATP1B2, CRB1 or MOG1, CRB1 or PTPRZ1-MET, GAP43 or ATP1B2, GAP43 or MOG1, GAP43 or PTPRZ1-MET, ATP1B2 or MOG1, ATP1B2 or PTPRZ1-MET, or MOG1 or PTPRZ1-MET.

A BTTS specific for two or more different antigens, containing either two extracellular domains or one extracellular domain specific for two different antigens, may be configured such that the binding of either antigen to the BTTS is sufficient to trigger activation of the BTTS, e.g., proteolytic cleavage of a cleavage domain of the BTTS, e.g., releasing an intracellular domain of the BTTS. Such a BTTS, capable of being triggered by any of two or more antigens, may find use in the described circuits as a component of a logic gate containing OR functionality. In some instances, a BTTS specific for two different antigens may be referred to as a "two-headed BTTS" or a tandem BTTS (or tanBTTS). For example, in some instances, a synNotch BTTS configured to bind two or more different antigens may be referred to as a tandem SynNotch or tanSynNotch. BTTS specific for multiple antigens will not be limited to only two antigens and may, e.g., be specific for and/or triggered by more than two antigens, including e.g., three or more, four or more, five or more, etc.

Methods of Making

The present disclosure further includes methods of making the nucleic acids, circuits, and cells employed in the herein described methods. In making the subject nucleic acids and circuits, and components thereof, any convenient methods of nucleic acid manipulation, modification and amplification (e.g., collectively referred to as "cloning") may be employed. In making the subject cells, containing the nucleic acids encoding the described circuits, convenient methods of transfection, transduction, culture, etc., may be employed.

A nucleotide sequence encoding all or a portion of the components of a circuit of the present disclosure can be present in an expression vector and/or a cloning vector. Where a subject circuit or component thereof is split between two or more separate polypeptides, nucleotide sequences encoding the two or more polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid comprising a nucleotide sequence encoding a circuit or component thereof of the present disclosure will in some embodiments be DNA or RNA, e.g., in vitro synthesized DNA, recombinant DNA, in vitro synthesized RNA, recombinant RNA, etc. Methods for in vitro synthesis of DNA/RNA are known in the art; any known method can be used to synthesize DNA/RNA comprising a desired sequence. Methods for introducing DNA/RNA into a host cell are known in the art. Introducing DNA/RNA into a host cell can be carried out in vitro or ex vivo or in vivo. For example, a host cell (e.g., an NK cell, a cytotoxic T lymphocyte, etc.) can be transduced, transfected or electroporated in vitro or ex vivo with DNA/RNA comprising a nucleotide sequence encoding all or a portion of a circuit of the present disclosure.

Methods of the instant disclosure may further include culturing a cell genetically modified to encode a circuit of the instant disclosure including but not limited to e.g., culturing the cell prior to administration, culturing the cell in vitro or ex vivo (e.g., the presence or absence of one or more antigens), etc. Any convenient method of cell culture may be employed whereas such methods will vary based on various factors including but not limited to e.g., the type of cell being cultured, the intended use of the cell (e.g., whether the cell is cultured for research or therapeutic purposes), etc. In some instances, methods of the instant disclosure may further include common processes of cell culture including but not limited to e.g., seeding cell cultures, feeding cell cultures, passaging cell cultures, splitting cell cultures, analyzing cell cultures, treating cell cultures with a drug, harvesting cell cultures, etc.

Methods of the instant disclosure may, in some instances, further include receiving and/or collecting cells that are used in the subject methods. In some instances, cells are collected from a subject. Collecting cells from a subject may include obtaining a tissue sample from the subject and enriching, isolating and/or propagating the cells from the tissue sample. Isolation and/or enrichment of cells may be performed using any convenient method including e.g., isolation/enrichment by culture (e.g., adherent culture, suspension culture, etc.), cell sorting (e.g., FACS, microfluidics, etc.), and the like. Cells may be collected from any convenient cellular tissue sample including but not limited to e.g., blood (including e.g., peripheral blood, cord blood, etc.), bone marrow, a biopsy, a skin sample, a cheek swab, etc. In some instances, cells are received from a source including e.g., a blood bank, tissue bank, etc. Received cells may have been previously isolated or may be received as part of a tissue sample thus isolation/enrichment may be performed after receiving the cells and prior to use. In certain instances, received cells may be non-primary cells including e.g., cells of a cultured cell line. Suitable cells for use in the herein described methods are further detailed herein.

Nucleic Acids

As summarized above, the present disclosure provides nucleic acids encoding a circuit for treating a subject for a heterogeneous EGFRvIII(−) GBM and components thereof. The subject nucleic acids may include, e.g., a sequence encoding a BTTS specific for a priming antigen, including e.g., a priming antigen specific-BTTS specific for one or more of IL13RA2, IL13RA1, Neuroligin, NRXN1, PTPRZ1, NRCAM, CDH10, PCDHGC5, CD70, CSPG5, BCAN, GRM3, CRB1, GAP43, ATP1B2, MOG1, and/or PTPRZ1-MET, and a sequence encoding a targeting antigen-specific therapeutic, including e.g., a targeting antigen-specific therapeutic specific for one or more of EphA2, EphA3, IL13R (e.g., IL13RA1 or IL13RA2), EGFR and/or ERBB2.

Such nucleic acids may be configured such that the sequence encoding the targeting antigen-specific therapeutic is operably linked to a regulatory sequence responsive to activation of the BTTS. Provided are nucleic acids encoding essentially any circuit employing trans-targeting utilizing recognition of a priming antigen expressed on a first EGFRvIII(−) GBM cell to target a second EGFRvIII(−) GBM cell expressing a targeting antigen, including but not limited to those circuits specifically described herein. Encompassed are isolated nucleic acids encoding the subject circuits as well as various configurations containing such nucleic acids, such as vectors, e.g., expression cassettes, recombinant expression vectors, viral vectors, and the like.

Recombinant expression vectors of the present disclosure include those comprising one or more of the described nucleic acids. A nucleic acid comprising a nucleotide sequence encoding all or a portion of the components of a circuit of the present disclosure will in some embodiments be DNA, including, e.g., a recombinant expression vector. A nucleic acid comprising a nucleotide sequence encoding all or a portion of the components of a circuit of the present disclosure will in some embodiments be RNA, e.g., in vitro synthesized RNA.

As summarized above, in some instances, the subject circuits may make use of an encoding nucleic acid (e.g., a nucleic acid encoding a BTTS or an antigen-specific therapeutic) that is operably linked to a regulatory sequence such as a transcriptional control element (e.g., a promoter; an enhancer; etc.). In some cases, the transcriptional control element is inducible. In some cases, the transcriptional control element is constitutive. In some cases, the promoters are functional in eukaryotic cells. In some cases, the promoters are cell type-specific promoters. In some cases, the promoters are tissue-specific promoters.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some instances, a transcriptional control element of a herein described nucleic acid may include a cis-acting regulatory sequence. Any suitable cis-acting regulatory sequence may find use in the herein described nucleic acids. For example, in some instances a cis-acting regulatory sequence may be or include an upstream activating sequence or upstream activation sequence (UAS). In some instances, a UAS of a herein described nucleic acid may be a Gal4 responsive UAS.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is an immune cell promoter such as a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90: 7739; and Marodon et al. (2003) *Blood* 101:3416. As another example, a CD8 gene promoter can be used. NK cell-specific expression can be achieved by use of an Ncr1 (p46) promoter; see, e.g., Eckelhart et al. (2011) *Blood* 117:1565.

In some instances, an immune cell specific promoter of a nucleic acid of the present disclosure may be a promoter of a B29 gene promoter, a CD14 gene promoter, a CD43 gene promoter, a CD45 gene promoter, a CD68 gene promoter, a IFN-β gene promoter, a WASP gene promoter, a T-cell receptor β-chain gene promoter, a V9 γ (TRGV9) gene promoter, a V2 6 (TRDV2) gene promoter, and the like.

In some cases, a nucleic acid comprising a nucleotide sequence encoding a circuit of the present disclosure, or one or more components thereof, is a recombinant expression vector or is included in a recombinant expression vector. In some embodiments, the recombinant expression vector is a viral construct, e.g., a recombinant adeno-associated virus (AAV) construct, a recombinant adenoviral construct, a recombinant lentiviral construct, a recombinant retroviral construct, etc. In some cases, a nucleic acid comprising a nucleotide sequence encoding a circuit of the present disclosure, or one or more components thereof, is a recombinant lentivirus vector. In some cases, a nucleic acid comprising a nucleotide sequence encoding a circuit of the present disclosure, or one or more components thereof, is a recombinant AAV vector.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

In some instances, nucleic acids of the present disclosure may have a single sequence encoding two or more polypeptides where expression of the two or more polypeptides is made possible by the presence of a sequence element between the individual coding regions that facilitates separate expression of the individual polypeptides. Such sequence elements, may be referred to herein as bicistronic-facilitating sequences, where the presence of a bicistronic-facilitating sequence between two coding regions makes possible the expression of a separate polypeptide from each coding region present in a single nucleic acid sequence. In some instances, a nucleic acid may contain two coding regions encoding two polypeptides present in a single nucleic acid with a bicistronic-facilitating sequence between the coding regions. Any suitable method for separate expression of multiple individual polypeptides from a single nucleic acid sequence may be employed and, similarly, any suitable method of bicistronic expression may be employed.

In some instances, a bicistronic-facilitating sequence may allow for the expression of two polypeptides from a single nucleic acid sequence that are temporarily joined by a cleavable linking polypeptide. In such instances, a bicistronic-facilitating sequence may include one or more encoded peptide cleavage sites. Suitable peptide cleavage sites include those of self-cleaving peptides as well as those cleaved by a separate enzyme. In some instances, a peptide cleavage site of a bicistronic-facilitating sequence may include a furin cleavage site (i.e., the bicistronic-facilitating sequence may encode a furin cleavage site).

In some instances, the bicistronic-facilitating sequence may encode a self-cleaving peptide sequence. Useful self-cleaving peptide sequences include but are not limited to e.g., peptide 2A sequences, including but not limited to e.g., the T2A sequence.

In some instances, a bicistronic-facilitating sequence may include one or more spacer encoding sequences. Spacer encoding sequences generally encode an amino acid spacer, also referred to in some instances as a peptide tag. Useful spacer encoding sequences include but are not limited to e.g., V5 peptide encoding sequences, including those sequences encoding a V5 peptide tag.

Multi- or bicistronic expression of multiple coding sequences from a single nucleic acid sequence may make use of but is not limited to those methods employing furin cleavage, T2A, and V5 peptide tag sequences. For example, in some instances, an internal ribosome entry site (IRES) based system may be employed. Any suitable method of bicistronic expression may be employed including but not limited to e.g., those described in Yang et al. (2008) Gene Therapy. 15(21):1411-1423; Martin et al. (2006) BMC Biotechnology. 6:4; the disclosures of which are incorporated herein by reference in their entirety.

Cells

As summarized above, the present disclosure also provides immune cells. Immune cells of the present disclosure include those that contain one or more of the described nucleic acids, expression vectors, etc., encoding a described circuit. Immune cells of the present disclosure include mammalian immune cells including e.g., those that are genetically modified to produce the components of a circuit of the present disclosure or to which a nucleic acid, as described above, has been otherwise introduced. In some instances, the subject immune cells have been transduced with one or more nucleic acids and/or expression vectors to express one or more components of a circuit of the present disclosure.

Suitable mammalian immune cells include primary cells and immortalized cell lines. Suitable mammalian cell lines include human cell lines, non-human primate cell lines, rodent (e.g., mouse, rat) cell lines, and the like. In some instances, the cell is not an immortalized cell line, but is instead a cell (e.g., a primary cell) obtained from an individual. For example, in some cases, the cell is an immune cell, immune cell progenitor or immune stem cell obtained from an individual. As an example, the cell is a lymphoid cell, e.g., a lymphocyte, or progenitor thereof, obtained from an individual. As another example, the cell is a cytotoxic cell, or progenitor thereof, obtained from an individual. As another example, the cell is a stem cell or progenitor cell obtained from an individual.

As used herein, the term "immune cells" generally includes white blood cells (leukocytes) which are derived from hematopoietic stem cells (HSC) produced in the bone marrow. "Immune cells" includes, e.g., lymphoid cells, i.e., lymphocytes (T cells, B cells, natural killer (NK) cells), and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses. "B cell" includes mature and immature cells of the B cell lineage including e.g., cells that express CD19 such as Pre B cells, Immature B cells, Mature B cells, Memory B cells and plasmablasts. Immune cells also include B cell progenitors such as Pro B cells and B cell lineage derivatives such as plasma cells.

Immune cells encoding a circuit of the present disclosure may be generated by any convenient method. Nucleic acids encoding one or more components of a subject circuit may be stably or transiently introduced into the subject immune cell, including where the subject nucleic acids are present only temporarily, maintained extrachromosomally, or integrated into the host genome. Introduction of the subject nucleic acids and/or genetic modification of the subject immune cell can be carried out in vivo, in vitro, or ex vivo.

In some cases, the introduction of the subject nucleic acids and/or genetic modification is carried out ex vivo. For example, a T lymphocyte, a stem cell, or an NK cell is obtained from an individual; and the cell obtained from the individual is modified to express components of a circuit of the present disclosure. The modified cell can thus be redirected to one or more antigens of choice, as defined by the one or more antigen binding domains present on the introduced components of the circuit. In some cases, the modified cell is modulated ex vivo. In other cases, the cell is introduced into (e.g., the individual from whom the cell was obtained) and/or already present in an individual; and the cell is modulated in vivo, e.g., by administering a nucleic acid or vector to the individual in vivo.

Circuits

As summarized above, the present disclosure also provides circuits encoded by nucleic acid sequences, also referred to in some instances as molecular circuits. Such circuits may, in some instances, be present and/or configured in expression vectors and/or expression cassettes. The subject nucleic acids of the present circuits may, in some instances, be contained within a vector, including e.g., viral and non-viral vectors. Such circuits may, in some instances, be present in cells, such as immune cells, or may be introduced into cells by various means, including e.g., through the use of a viral vector. Cells may, in some instances, be genetically modified to encode a subject circuit, where such modification may be effectively permanent (e.g., integrated) or transient as desired.

Encoded components of the circuits of the present disclosure will generally include at a minimum at least one encoded BTTS and at least one encoded antigen-specific therapeutic. Circuits of the present disclosure integrate multiple inputs, where such inputs include antigens, such as one or more priming antigens (e.g., IL13RA2, IL13RA1, Neuroligin, NRXN1, PTPRZ1, NRCAM, CDH10, PCDHGC5, CD70, CSPG5, BCAN, GRM3, CRB1, GAP43, ATP1B2, MOG1, PTPRZ1-MET and/or combinations thereof), one or more targeting antigens (e.g., EphA2, EphA3, IL13R (e.g., IL13RA1 or IL13RA2), EGFR, ERBB2 and/or combinations thereof) and the like. The expression of a component of a circuit of the present disclosure may be dependent upon the state (i.e., active/inactive state) of another component of the circuit. For example, the expression of an antigen-specific therapeutic may be dependent upon the activation of a BTTS, where the BTTS is activated by binding to an antigen for which the BTTS is specific. In some instances, dependency of one component of the circuit on another may be mediated by a regulatory sequence. For example, a sequence encoding a second component of a circuit may be operably linked to a regulatory sequence that is responsive to the activation of a first component of the circuit, thus linking the expression of the second component to the activation of the first.

The use of a BTTS in a circuit of the present disclosure facilitates the linking of expression and/or activity to molecular binding events. Systems involving binding-triggered transcriptional switches, and components thereof, have been described in PCT Publication No. WO 2016/138034, US Patent Application Pub. No. US 2016-0264665 A1 and issued U.S. Pat. Nos. 9,670,281 and 9,834,608; the disclosures of which are incorporated by reference herein in their entirety.

Circuits of the present disclosure may be configured in various ways. In some instances, the independent activities and/or induced expression of two or more polypeptides or domains of a single polypeptide may generate a logic gated circuit. Such logic gated circuits may include but are not limited to e.g., "AND gates", "OR gates", "NOT gates" and combinations thereof including e.g., higher order gates including e.g., higher order AND gates, higher order OR gates, higher order NOT gates, higher order combined gates (i.e., gates using some combination of AND, OR and/or NOT gates). In some instances, useful circuits may further include IF/THEN gates.

"AND" gates include where two or more inputs are required for propagation of a signal. For example, in some instances, an AND gate allows signaling through a first input of a first polypeptide or a first polypeptide domain and a second input dependent upon the output of the first input. In an AND gate two inputs, e.g., two antigens, are required for signaling through the circuit.

"OR" gates include where either of two or more inputs may allow for the propagation of a signal. For example, in some instances, an OR gate allows signaling through binding of either of two different antigens. In an OR gate any one input, e.g., either of two antigens, may induce the signaling output of the circuit. In one embodiment, an OR gate may be achieved through the use of two separate molecules or constructs. In another embodiment, an OR gate may be achieved through the use of a single construct that recognizes two antigens, including e.g., a BTTS or an antigen-specific therapeutic (e.g., a CAR or TCR) having two different antigen binding domains that each bind a different antigen and each binding event can independently propagate the signal (e.g., induce expression of a downstream component of the circuit, activate an immune cell, etc.).

"NOT" gates include where an input is capable of preventing the propagation of a signal. For example, in some instances, a NOT gate inhibits signaling through a circuit of the instant disclosure. In one embodiment, a NOT gate may prevent the expression of a component of a circuit, or activation of a particular component of the circuit, e.g., a CAR or a TCR.

"IF/THEN" gates include where the output of the gate depends upon a first input. For example, in some instances, IF a first input is present THEN signaling may proceed through a second input, and where the first input is absent signaling may not proceed. A non-limiting example of a circuit that includes an IF/THEN gate is a circuit having at least two receptors where the first receptor, in response to an input, induces expression of the second receptor, which has some output in response to a second input. As such, IF the first input of the first receptor is present, THEN the second receptor is expressed and signaling can proceed through the second receptor via the second input to produce the output. IF/THEN gates may or may not include an OR component (e.g., a receptor with OR functionality).

Figure 4:
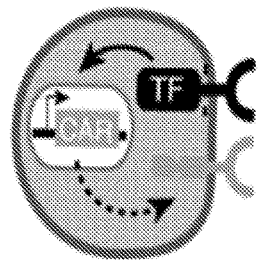
FIG. 4 depicts cells that contain IF/THEN circuits with and without OR gate functionality at the relevant binding triggered transcriptional switch, the antigen-specific therapeutic, or both.
Figure 4:
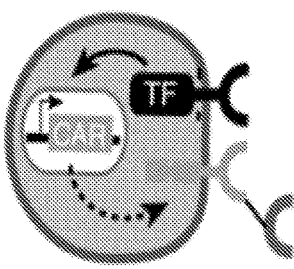
Figure 4:
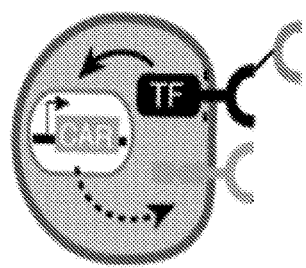
Figure 4:
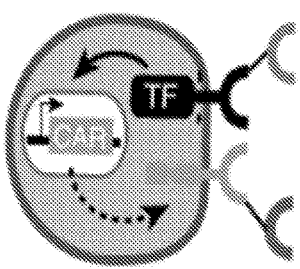

Non-limiting examples of IF/THEN gates, including examples with OR functionality, are depicted in FIG. 4. The circuit depicted in the first (top) cell of FIG. 4 includes a BTTS responsive to antigen "A" and an antigen-specific therapeutic that binds antigen "C". Note that although the antigen-specific therapeutic is depicted as a CAR, the disclosure is not so limited and other antigen-specific therapeutics may be readily substituted. In the first (top) circuit, IF antigen A is present THEN cell killing is induced based on the presence of antigen C.

In various embodiments, OR functionality may be employed, including where one or more components of a subject circuit include an OR functionality. As shown in the second, third and fourth cells depicted in FIG. 4, OR functionality may be provided by a BTTS, an antigen-specific therapeutic, or both having specificity for, and being triggered or activated by, two or more antigens.

For example, in the second (from the top) cell depicted in FIG. 4, a circuit is employed that includes a BTTS responsive to antigen "A" and an antigen-specific therapeutic that binds to, and is activated by, antigen "C" or antigen "D". In such a circuit, IF antigen A is present THEN cell killing is induced based on the presence of antigen C OR antigen D. Note that killing of cells expressing antigen C and antigen D may also be induced, as well as killing of cells that express antigen C alone or antigen D alone.

In the third (from the top) cell depicted in FIG. 4, a circuit is employed that includes a BTTS responsive to antigen "A" or antigen "B" and an antigen-specific therapeutic that binds to, and is activated by, antigen "C". In such a circuit, IF antigen A OR antigen B is present THEN cell killing is induced based on the presence of antigen C. Note that the immune cells encoding the subject circuit may be primed to kill by a cell expressing only antigen A, only antigen B, or both antigens A and B.

In the fourth (bottom) cell depicted in FIG. 4, a circuit is employed that includes a BTTS responsive to antigen "A" or antigen "B" and an antigen-specific therapeutic that binds to, and is activated by, antigen "C" or antigen "D". In such a circuit, IF antigen A OR antigen B is present THEN cell killing is induced based on the presence of antigen C or antigen D. Note that the immune cells encoding the subject circuit may be primed to kill by a cell expressing only antigen A, only antigen B, or both antigens A and B. Also note that killing of cells expressing antigen C and antigen D may also be induced, as well as killing of cells that express antigen C alone or antigen D alone.

In some instances, the use of OR functionality may have certain advantages. For example, the above described circuits having OR gate functionality (i.e., the second, third and fourth cells of FIG. 4) and variations thereof provide resistance to escape and improved efficacy for heterogeneous cancers because, without being bound by theory, to escape a cancer (or tumor) would need to contain, or evolve/produce, a cell that does not express either of the two priming and/or killing antigens.

In some instances, multiple antigen binding domains present on a BTTS or antigen-specific therapeutic may provide an OR gate capability to the herein described molecular circuits. For example, in some instances, a BTTS having two different antigen binding domains may be responsive to a first antigen (e.g., a first priming antigen) OR a second antigen (e.g., a second priming antigen). In some instances, an antigen-specific therapeutic (e.g., a CAR, a TCR, etc.) having two different antigen binding domains may be responsive to a first antigen (e.g., a first targeting antigen) OR a second antigen (e.g., a second targeting antigen).

In some instances, such OR gates may be combined with other gates, including an AND gate. For example, a nucleic acid encoding an OR-gate antigen-specific therapeutic having two different antigen binding domains may be operably linked to a promoter that is responsive to a BTTS which is responsive to a priming antigen. As such, upon binding the priming antigen, the BTTS drives expression of the antigen-specific therapeutic which is responsive to two different antigens, resulting in an AND-OR gate.

In some instances, OR gates may find use in the circuits of the present disclosure to produce an OR gate for two or more targeting antigens (or two or more killing antigens). For example, in some instances, the circuit may be configured such that the cell genetically modified with the circuit contains a nucleic acid sequence encoding an antigen-specific therapeutic that binds to a first targeting/killing antigen or a second targeting/killing antigen expressed by a targeted cancer cell (or expressed by two different targeted cancer cells), thereby producing a cell that is activated, e.g., activated for cell killing, by either the first targeting/killing antigen or the second targeting/killing antigen. In some instances, a circuit of the present disclosure may include nucleic acid sequence encoding a first antigen-specific therapeutic and second antigen-specific therapeutic that each bind to a different targeting/killing antigen. Useful antigens in such dual antigen-specific therapeutic OR gates include but are not limited to e.g., EphA2, EphA3, IL13R (e.g., IL13RA1 or IL13RA2), EGFR and ERBB2.

In some instances, an OR gate may be employed to allow for simultaneous targeting of cells both in trans and in cis. For example, in some instances, a second killing antigen to which an OR gate is directed may be expressed by the priming cell. In some instances, an OR gate for targeting may be employed to target two antigens that that are not mutually exclusively expressed within cells of the EGFRvIII (−) GBM (i.e., GBM cells with overlapping, but not completely coincident, expression of two antigens). For example, in some instances, the second killing antigen to which an OR gate is targeted may be expressed by a subpopulation of GBM cells that also expresses the first killing antigen. However, the cancer may further include a subpopulation of cells that express the second killing antigen but not the first killing antigen. In some instances, the first and second killing antigens employed in an OR gate will not have overlapping expression in the cells of the heterogeneous cancer. As such, in some instances, the second killing antigen may be expressed by a cell of the heterogeneous EGFRvIII(−) GBM other than the priming cell and/or the GBM cell that expresses the first killing antigen.

Kits

The present disclosure provides a kit for carrying out a method as described herein and/or constructing one or more circuits, components thereof, nucleic acids encoding a circuit or a component thereof, etc. In some cases, a subject kit comprises a vector, e.g., an expression vector or a delivery vector, comprising a nucleotide sequence encoding a circuit of the present disclosure or one or more portions thereof. Delivery vectors may be provided in a delivery device or may be provided separately, e.g., as a kit that includes the delivery vector and the delivery device as separate components of the kit.

In some cases, a subject kit comprises a cell, e.g., a host cell or host cell line, that is or is to be genetically modified with a nucleic acid comprising nucleotide sequence encoding a circuit of the present disclosure or a portion thereof. In some cases, a subject kit comprises a cell, e.g., a host cell, that is or is to be genetically modified with a recombinant expression vector comprising a nucleotide sequence encoding a circuit of the present disclosure. Kit components can be in the same container, or in separate containers.

Any of the above-described kits can further include one or more additional reagents, where such additional reagents can be selected from: a dilution buffer; a reconstitution solution; a wash buffer; a control reagent; a control expression vector; a nucleic acid encoding a negative control (e.g., a circuit that lacks the one or more critical elements); a nucleic acid encoding a positive control polypeptide; and the like.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of treating a subject for an epidermal growth factor receptor variant III (EGFRvIII) negative glioblastoma, the method comprising:
   administering to the subject an immune cell genetically modified with:
   (a) a nucleic acid sequence encoding a binding triggered transcriptional switch (BTTS) that binds to a priming antigen expressed by the EGFRvIII negative glioblastoma;
   (b) a nucleic acid sequence encoding an antigen-specific therapeutic that binds to a killing antigen expressed by the EGFRvIII negative glioblastoma; and
   (c) a regulatory sequence operably linked to (b) that is responsive to the BTTS; wherein binding of the BTTS to the priming antigen activates expression of the antigen-specific therapeutic which binds the killing antigen thereby inducing killing of glioblastoma cells expressing the killing antigen.

2a. The method according to aspect 1, wherein the priming antigen is selected from the group consisting of: Interleukin-13 receptor subunit alpha-2 (IL13RA2), Interleukin-13 receptor subunit alpha-1 (IL13RA1), Neuroligin, Neurexin-1-beta (NRXN1), Receptor-type tyrosine-protein phosphatase zeta (PTPRZ1), Neuronal cell adhesion molecule (NRCAM), Cadherin-10 (CDH10) and Protocadherin gamma-05 (PCDHGC5).

2b. The method according to aspect 1, wherein the priming antigen is selected from the group consisting of: CD70 antigen (CD70), Chondroitin sulfate proteoglycan 5 (CSPG5), Brevican core protein (BCAN), Metabotropic glutamate receptor 3 (GRM3), Protein crumbs homolog 1 (CRB1), Neuromodulin (GAP43), Sodium/potassium-transporting ATPase subunit beta-2 (ATP1B2), Ran-binding protein MOG1 (MOG1), and a Receptor-type tyrosine-protein phosphatase zeta-Hepatocyte growth factor receptor fusion (PTPRZ1-MET).

3a. The method according to any of the preceding aspects, wherein less than 95% of the cells of the EGFRvIII negative glioblastoma express the priming antigen.

3b. The method according to any of the preceding aspects, wherein less than 90% of the cells of the EGFRvIII negative glioblastoma express the priming antigen.
4. The method according to any of the preceding aspects, wherein less than 50% of the cells of the EGFRvIII negative glioblastoma express the priming antigen.
5. The method according to any of the preceding aspects, wherein the killing antigen is expressed by all cells of the glioblastoma.
6. The method according to any of the preceding aspects, wherein the killing antigen is expressed by non-glioblastoma cells in the subject.
7. The method according to any of the preceding aspects, wherein the killing antigen is selected from the group consisting of: Ephrin type-A receptor 2 (EphA2), Ephrin type-A receptor 3 (EphA3), Interleukin-13 receptor subunit alpha-1 (IL13RA1), Interleukin-13 receptor subunit alpha-2 (IL13RA2), Epidermal growth factor receptor (EGFR) and erb-b2 receptor tyrosine kinase 2 (ERBB2).
8. The method according to any of the preceding aspects, wherein the antigen-specific therapeutic, when expressed, is expressed on the surface of the immune cell.
9. The method according to aspect 8, wherein the antigen-specific therapeutic is a chimeric antigen receptor (CAR) or a T cell receptor (TCR).
10. The method according to any of aspects 1 to 7, wherein the antigen-specific therapeutic, when expressed, is secreted by the immune cell.
11. The method according to aspect 10, wherein the antigen-specific therapeutic is a chimeric bispecific binding member.
12. The method according to aspect 11, wherein the chimeric bispecific binding member is a TCR-targeted bispecific binding agent.
13. The method according to aspect 11 or aspect 12, wherein the chimeric bispecific binding member is specific for the killing antigen and a protein expressed on the surface of an immune cell.
14. The method according to any of the preceding aspects, wherein the antigen-specific therapeutic comprises a bio-orthogonal adapter molecule.
15. The method according to aspect 14, wherein the bio-orthogonal adapter molecule is bound by an extracellular domain of a switchable CAR.
16. The method according to aspect 14 or aspect 15, wherein the bio-orthogonal adapter molecule binds an antigen selected from the group consisting of: EphA2, EphA3, IL13RA1, IL12RA2, EGFR and ERBB2.
17. The method according to any of the preceding aspects, wherein the antigen-specific therapeutic binds two different killing antigens expressed by the glioblastoma.
18. The method according to aspect 17, wherein the two different killing antigens are expressed by glioblastoma cells expressing the priming antigen.
19. The method according to aspect 17, wherein the two different killing antigens are expressed by glioblastoma cells not expressing the priming antigen.
20. The method according to aspect 17, wherein the two different killing antigens are expressed in the same glioblastoma cells.
21. The method according to aspect 17, wherein the two different killing antigens are expressed in different glioblastoma cells.
22. The method according to any of aspects 17 to 21, wherein the two different killing antigens are selected from the group consisting of: EphA2, EphA3, IL13RA1, IL12RA2, EGFR and ERBB2.
23. The method according to any of the preceding aspects, wherein the BTTS binds two different priming antigens.
24. The method according to aspect 23, wherein the two different priming antigens are selected from the group consisting of: IL13RA2, IL13RA1, Neuroligin, NRXN1, PTPRZ1, NRCAM, CDH10, PCDHGC5, CD70, CSPG5, BCAN, GRM3, CRB1, GAP43, ATP1B2, MOG1, and PTPRZ1-MET.
25. The method according to any of the preceding aspects, wherein the immune cell is further genetically modified with a nucleic acid sequence encoding a second antigen-specific therapeutic that binds to a second killing antigen expressed by the glioblastoma.
26. The method according to aspect 25, wherein the second killing antigen is expressed by glioblastoma cells expressing the priming antigen.
27. The method according to aspect 25, wherein the second killing antigen is expressed by glioblastoma cells not expressing the priming antigen.
28. The method according to any of aspects 25 to 27, wherein the second killing antigen is expressed by glioblastoma cells expressing the first killing antigen.
29. The method according to any of aspects 25 to 28, wherein the second killing antigen is selected from the group consisting of: EphA2, EphA3, IL13R, EGFR and ERBB2.
30. The method according to any of aspects 25 to 29, wherein the second killing antigen is expressed by all cells of the glioblastoma.
31. The method according to any of aspects 25 to 30, wherein the second killing antigen is expressed by non-glioblastoma cells in the subject.
32. The method according to any of the preceding aspects, wherein the BTTS is a SynNotch polypeptide.
33. The method according to any of the preceding aspects, wherein the immune cell is a myeloid cell.
34. The method according to any of aspects 1 to 32, wherein the immune cell is a lymphoid cell.
35. The method according to aspect 34, wherein the lymphoid cell is selected from the group consisting of: a T lymphocyte, a B lymphocyte and a Natural Killer cell.
36. The method according to any of the preceding aspects, wherein the method further comprises identifying that the glioblastoma is EGFRvIII negative.
37. The method according to any of the preceding aspects, wherein the method further comprises identifying that the glioblastoma comprises cells that express the killing antigen.
38. The method according to aspect 36 or aspect 37, wherein the identifying comprises assaying cellular expression of EGFRvIII, the killing antigen or both in a sample of the glioblastoma obtained from the subject.
39. The method according to aspect 38, wherein the sample is a biopsy.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Treatment of EGFRvIII(−) Glioblastoma Using Prime/Kill Circuit

Amplification of the epidermal growth factor receptor (EGFR) gene is the most frequent genetic change associated with glioblastoma (GBM), which results in overexpression of the transmembrane tyrosine kinase receptor, EGFR. GBM showing amplified EGFR frequently overexpresses the receptor variant III (EGFRvIII). Certain forms of GBM, however, do not display EGFRvIII expression. Despite a lack of EGFRvIII expression, at the cellular level EGFRvIII(−) GBM tumors are nonetheless frequently heterogeneous.

No known single antigen, which could potentially be targeted in GBM, is absolutely specific and homogeneously present in all GBM tumor cells. Also, many antigens that could potentially be targeted in GBM are also expressed in other normal tissues. Thus, even combining two or more independently targeted antigens in EGFRvIII(−) GBM would either still not be expected to be completely effective (i.e., not all cells of the GBM would be targeted) or be expected to yield toxic cross-reactivity (i.e., non-cancerous bystander cells/tissues would also be targeted).

In this example, a novel approach to use the targeting specificity of two or more antigens in EGFRvIII(−) tumors was developed. The method employs a priming antigen expressed by the GBM to prime the expression of a second molecule that targets and kills tumor cells based on a second antigen (or combination of antigens). This approach is effective even if the second antigen(s) are not perfectly tumor-specific. Without being bound by theory, in essence this approach harnesses two or more imperfect antigens to develop a combinatorial T cell that shows both high selectivity and is insensitive to antigen expression heterogeneity.

Figure 1B:
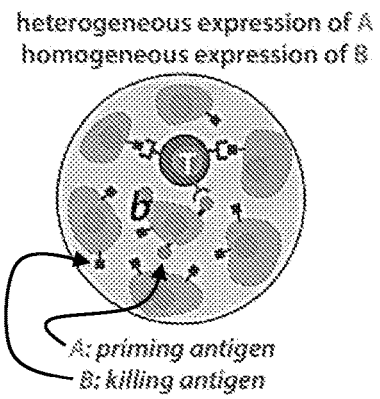

Circuits were designed in which a therapeutic cell is primed based on a priming antigen, inducing expression of killing agent (e.g., a CAR, a BiTE, etc.) that then kills based on a homogenous antigen (see FIG. 1A). In other words, in this example, the circuit is primed based on a cancer-specific but heterogeneous antigen, but is then activated to kill in a "killing zone" around the priming antigen cells by targeting a homogeneously expressed antigen (see FIG. 1B). The killing zone size is tunable based on a variety of factors such as, but not limited to, killing receptor (e.g., CAR) stability or the use of extracellular diffusible agents as killing payload (e.g. bispecific adapters) (see FIG. 1C and FIG. 1D).

As depicted in FIG. 1A-1D, priming of therapeutic cells, such as a cell engineered with a circuit as depicted in FIG. 1A, creates a killing zone around the therapeutic cell such that tumor cells expressing the killing antigen are targeted even when such tumor cells do not express the priming antigen. An example of this scenario is schematized in FIG. 1B, which shows a therapeutic cell, shown as a T cell, primed by a tumor heterogeneously expressing the priming antigen. The primed therapeutic cell targets and kills tumor cells in its proximity, including those expressing the killing antigen but not the priming antigen. In this way, cells in the proximity of the tumor prime the therapeutic cells to create a killing zone around the primed cell, leading to effective clearance of all tumor cells.

Figure 1C:
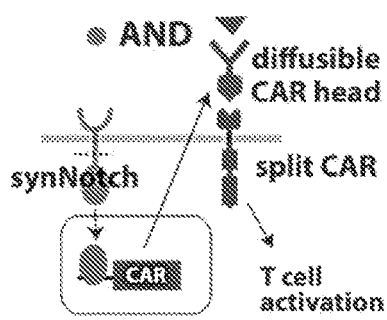

The size of the killing zone may be widened or tuned as desired, e.g., through the use of a diffusible payload, stability of the therapeutic employed (e.g., CAR stability). For example, FIG. 1C depicts a circuit that includes a synNotch binding-triggered transcriptional switch configured to bind a priming antigen (circle) which induces expression of a diffusible CAR head. The diffusible CAR head is specific for a killing antigen (triangle) and is bound by a portion of a CAR, referred to in FIG. 1C as a "split CAR", that includes the intracellular signaling components necessary for T cell activation upon antigen binding. Accordingly, by diffusing away from the primed cell, the diffusible CAR head serves to mediate antigen recognition and target cell killing in more distant T cells that express the split CAR, but do not necessarily express the diffusible CAR head.

Figure 1D:
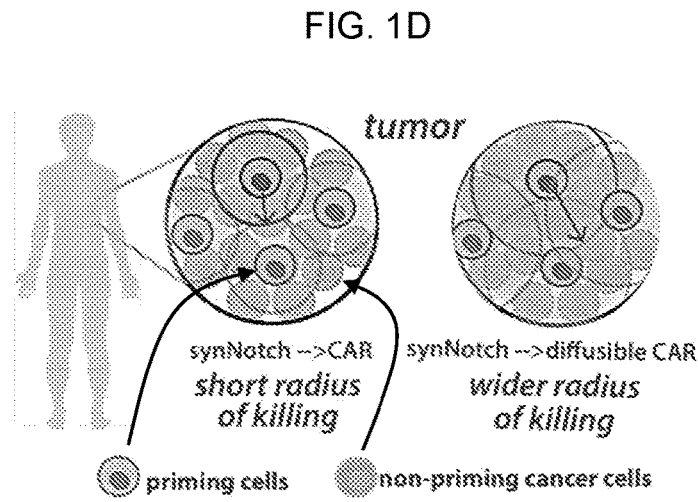

As depicted in the left panel of FIG. 1D, by using a circuit that includes a synNotch driving expression of a traditional CAR (i.e., a single continuous chain having an antigen recognition domain and the intracellular signaling components), the killing radius of non-priming cancer cells that express the killing antigen is kept relatively short. In comparison, as depicted in the right panel of FIG. 1D, by using a circuit that includes a diffusible orthogonal bispecific adapter, such as a diffusible CAR head, the killing radius of non-priming cancer cells that express the killing antigen is widened. Accordingly, the desired killing radius may be controlled as desired. In some instances, e.g., a short killing radius may be desired where a killing antigen is expressed in non-cancerous tissues (i.e., bystander tissues). In other instances, a wide killing radius may be desired where, e.g., relatively few cells expressing the priming antigen are present diffusely throughout a cancerous area of a subject.

Example 2: Testing SynNotch Receptor Antigen Targets for Glioblastoma

Figure 2A:
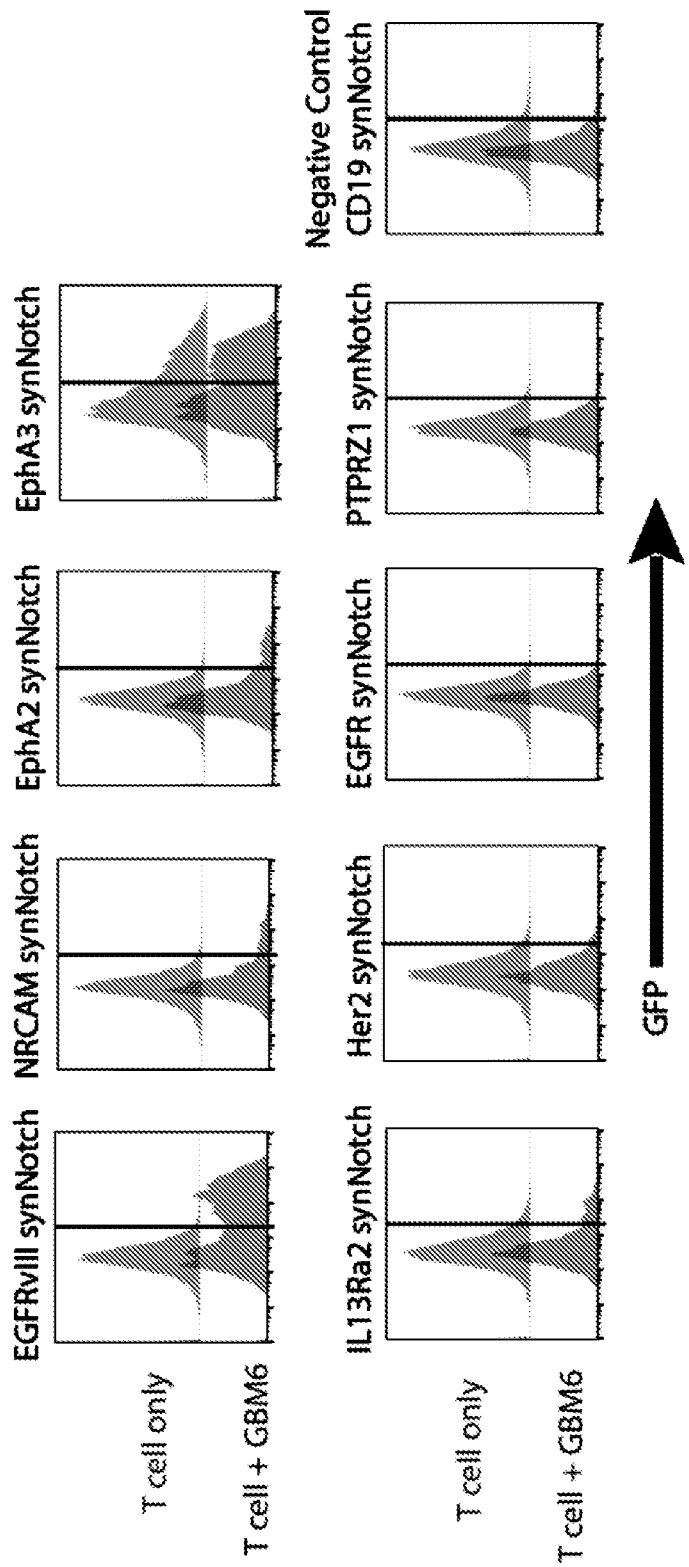
FIG. 2A-2B demonstrate the activation, selectively in the presence of targeted GBM cells, of synNotch receptors targeted to various antigens in synNotch→CAR T cell GBM circuits as described herein.

In this example, circuits employing synNotch receptors to various target antigens were tested in T cells for targeting of GBM. Specifically, human primary CD8+ T cells were engineered with a selection of synNotch receptor antigen targets for Glioblastoma, namely EGFRvIII, NRCAM, EphA2, EphA3, IL13Ra2, Her2, EGFR, and PTRZ1, and the corresponding response elements controlling expression of a reporter (eGFP). These CD8+ synNotch AND-gate T cells are configured to first sense the respective surface GBM antigen via the synNotch receptor, and then, if detected, express the eGFP reporter. Primary CD8+ synNotch AND-gate T cells were cultured alone ("T cell only") or co-cultured with GBM cells ("T cell+GBM6). The GMB cells employed were GBM6 cells, a human patient-derived xenograft (PDX) adult glioblastoma cell line. FIG. 2A provides histograms of reporter (eGFP) expression levels, showing synNotch receptor activation for the various antigens.

Figure 2B:
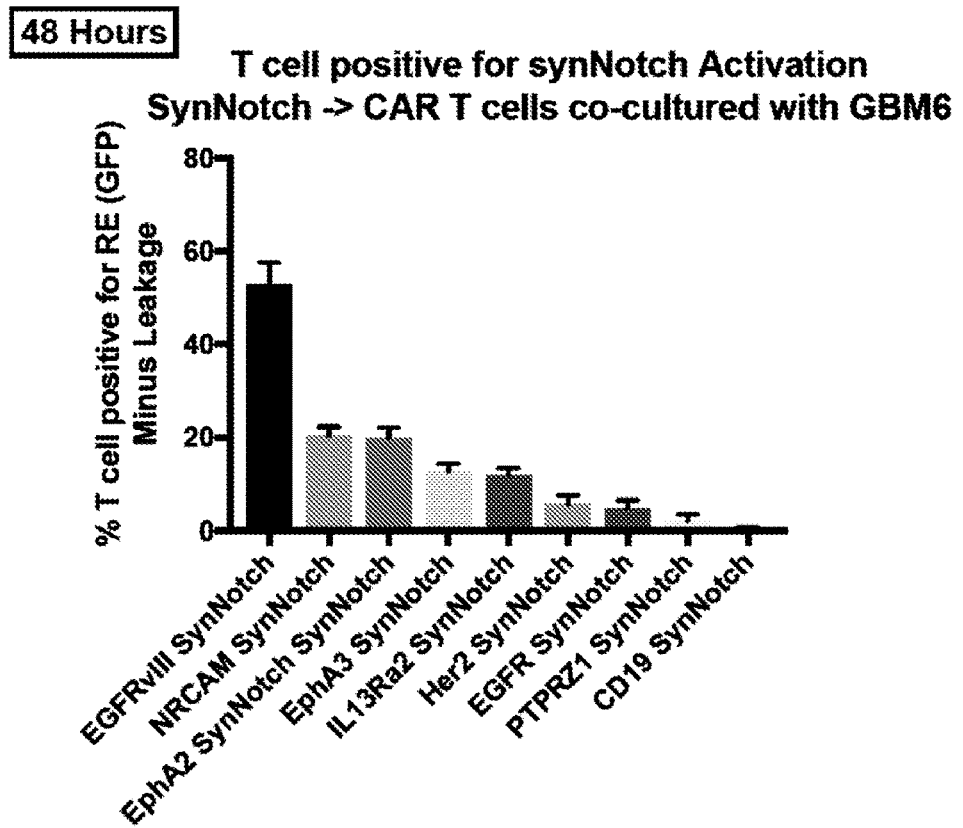

FIG. 2B provides quantification related to FIG. 2A. Specifically, quantification of CD8+ synNotch AND-gate primary T cell activation minus the basal leakage of GFP expression that is independent of synNotch receptor binding to its target antigen. These data show the various levels of activation of the construct tested with the particular GBM6 cell line, demonstrating that various antigens may be targeted, e.g., depending on the desired level of activation sensitivity and/or the presence and/or level of the particular antigen in target cell populations.

Figure 3A:
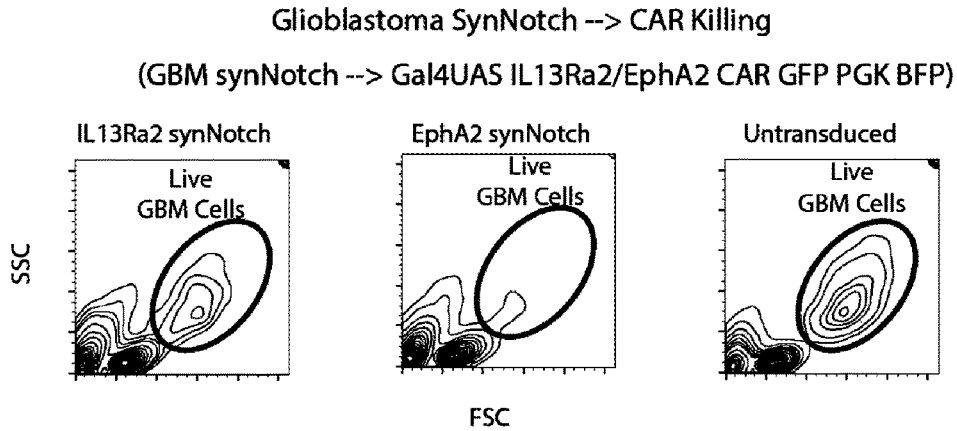
FIG. 3A-3D demonstrate selective synNotch activation and cell killing in the presence of targeted GBM cells with synNotch→CAR T circuits as described herein.

Circuits employing IL13Ra2 and EphA2 antigen targeting were further evaluated. Specifically, human primary CD8+ T cells were engineered with the anti-IL13Ra2 synNotch receptor or anti-EphA2 synNotch receptor with the corresponding response elements controlling expression of the anti-IL13Ra2/EphA2-4-1BBz CAR GFP receptor. These CD8+ synNotch AND-gate T cells first sense surface EphA2 or IL13Ra2, respectively, via the synNotch receptor, and then the cells express the anti-IL13Ra2/EphA2 CAR and are primed for activation in response to CAR antigen binding. FIG. 3A provides forward (FSC) and side scatter (SSC) flow cytometry plots after 24 hr co-culture of CD8+ synNotch AND-gate primary T cells with a primary GBM cell line (SF11411). The target SF11411 are indicated in the circular gates. As shown by a reduction of cells in the SF11411 gate in the IL13Ra2 synNotch and EphA2 synNotch panels as compared to the untransduced controls, the synNotch AND-gate T cells targeting either antigen resulted in killing of the targeted SF11411 GBM cells.

Figure 3B:
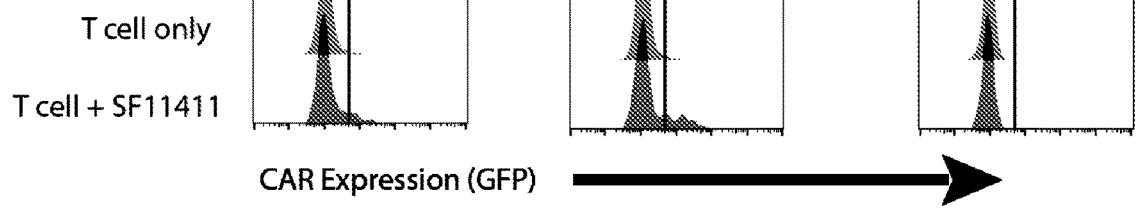

Expression of the CAR, as measured via the GFP reporter, was assessed in the presence ("T cell+SF11411") and absence ("T cell only") of target SF11411 GBM cells. FIG. 3B provides histograms of a-IL13Ra2/EphA2 CAR GFP receptor expression level in these contexts, showing that the CAR is expressed, and/or expression is increased, when the engineered T cells are co-cultured with SF11411 as compared to when the engineered T cells are cultured alone.

Figure 3C:
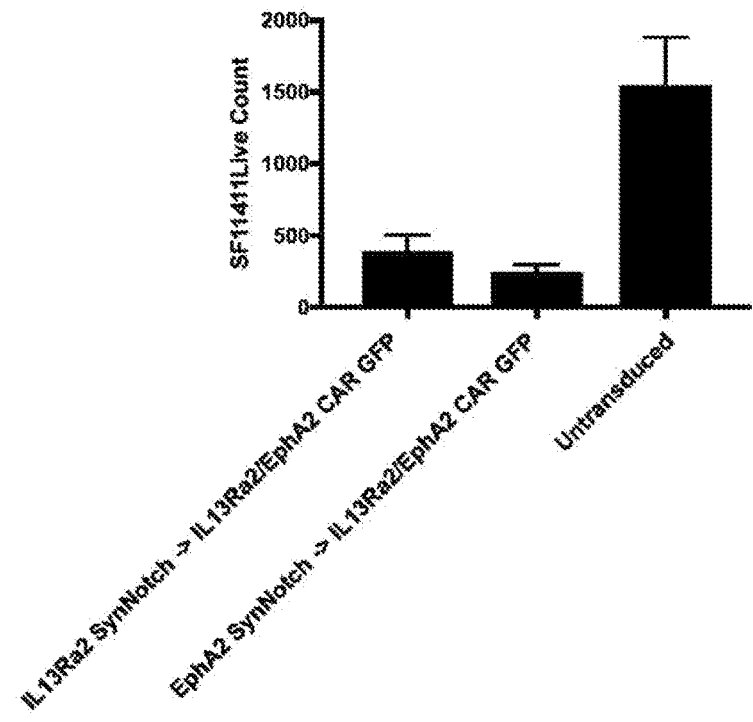
Figure 3D:
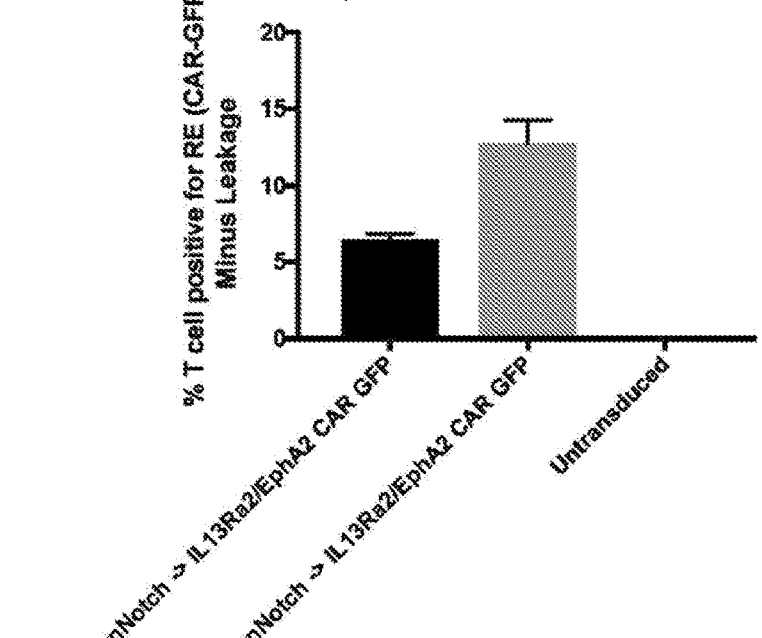

FIG. 3C provides quantification related to FIG. 3A, specifically showing quantification of replicate CD8+ synNotch AND-gate primary T cell cytotoxicity induced by the IL13Ra2 synNotch and EphA2 synNotch circuits. FIG. 3D provides quantification related to FIG. 3B, specifically showing quantification of CD8+ synNotch AND-gate primary T cell activation minus the basal leakage of GFP expression that is independent of synNotch receptor binding to its target antigen. As can be seen in the data, expression of the encoded CAR is induced in the presence of GBM target cells (SF11411).

Collectively, these data demonstrate that various antigens may be employed in the subject circuits to drive expression of an antigen-specific therapeutic, such as a CAR, in the presence of target GBM cells. In addition, the target therapeutic is essentially not expressed in the absence of the target GBM cells due to the absence of the antigen which induces expression of the therapeutic. Correspondingly, these data demonstrate targeted and effective killing of GBM cells the circuits described herein.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a subject for a glioblastoma, the method comprising:
   administering to the subject an immune cell genetically modified with:
   (a) a nucleic acid sequence encoding a binding triggered transcriptional switch (BTTS) that binds to a Brevican core protein (BCAN;
   (b) a nucleic acid sequence encoding a tandem chimeric antigen receptor (CAR) or T cell receptor (TCR) that has a first binding domain that recognizes Ephrin type-A receptor 2 (EphA2) and a second binding domain that recognizes Interleukin-13 receptor subunit alpha-2 (IL13RA2); and
   (c) a regulatory sequence operably linked to (b) that is responsive to the BTTS;
   wherein binding of the BTTS to BCAN activates expression of the tandem CAR or TCR, which binds EphA2 or IL13A2 in the glioblastoma and induces killing of glioblastoma cells.

2. The method according to claim 1, wherein less than 95% of the cells of the glioblastoma express BCAN.

3. The method according to claim 1, wherein less than 90% of the cells of the glioblastoma express BCAN.

4. The method according to claim 1, wherein less than 50% of the cells of the glioblastoma express BCAN.

5. The method according to claim 1, wherein EphA2 and IL13RA2 are expressed by all cells of the glioblastoma.

6. The method according to claim 1, wherein EphA2 and IL13RA2 are expressed by non-glioblastoma cells in the subject.

7. The method according to claim 1, wherein the tandem CAR or TCR, when expressed, is expressed on the surface of the immune cell.

8. The method of claim 1, wherein the subject is a human subject.

9. The method of claim 1, wherein the immune cell is a cytotoxic T cell.

10. The method of claim 1, wherein the BTTS comprises:
    an extracellular domain that comprises a binding domain that recognizes BCAN;
    a transmembrane domain;
    one or more protease cleavage domains;
    and a transcriptional activator,
    wherein binding of the extracellular domain to BCAN results in cleavage of the BTTS at the one or more protease cleavage domains to release the transcriptional activator, and wherein the released transcriptional activator binds to the regulatory sequence of (c) and activates expression of the tandem chimeric antigen receptor (CAR) or T cell receptor (TCR).

11. The method of claim 1, wherein the nucleic acid sequence of (b) encodes the tandem CAR.

12. The method of claim 1, wherein the glioblastoma is an epidermal growth factor receptor variant III (EGFRvIII) negative glioblastoma.

13. The method of claim 1, wherein the glioblastoma is an epidermal growth factor receptor variant III (EGFRvIII) positive glioblastoma.

* * * * *

UNITED STATES PATENT AND TRADEMARK OFFICE
CERTIFICATE OF CORRECTION

Page 1 of 1

PATENT NO.        : 12,090,170 B2
APPLICATION NO.   : 17/042032
DATED             : September 17, 2024
INVENTOR(S)       : Lim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 978 days.

Signed and Sealed this
Twenty-sixth Day of August, 2025

Coke Morgan Stewart
*Acting Director of the United States Patent and Trademark Office*

SEQUENCE LISTING

```
<160> NUMBER OF SEQ ID NOS: 73

<210> SEQ ID NO 1
<211> LENGTH: 943
<212> TYPE: PRT
<213> ORGANISM: Homo sapiens

<400> SEQUENCE: 1

Met Arg Pro Ser Gly Thr Ala Gly Ala Ala Phe Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
```

```
                165                 170                 175
Asn Ile Thr Ser Leu Gly Leu Arg Ser Leu Lys Glu Ile Ser Asp Gly
                180                 185                 190

Asp Val Ile Ile Ser Gly Asn Lys Asn Leu Cys Tyr Ala Asn Thr Ile
                195                 200                 205

Asn Trp Lys Lys Leu Phe Gly Thr Ser Gly Gln Lys Thr Lys Ile Ile
            210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
                260                 265                 270

Asn Leu Leu Glu Gly Glu Pro Arg Glu Phe Val Glu Asn Ser Glu Cys
                275                 280                 285

Ile Gln Cys His Pro Glu Cys Leu Pro Gln Ala Met Asn Ile Thr Cys
                290                 295                 300

Thr Gly Arg Gly Pro Asp Asn Tyr Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
                340                 345                 350

Cys His Pro Asn Cys Thr Tyr Gly Cys Thr Gly Pro Gly Leu Glu Gly
                355                 360                 365

Cys Pro Thr Asn Gly Pro Lys Ile Pro Ser Ile Ala Thr Gly Met Val
            370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
                420                 425                 430

Asn Gln Ala Leu Leu Arg Ile Leu Lys Glu Thr Glu Phe Lys Lys Ile
            435                 440                 445

Lys Val Leu Gly Ser Gly Ala Phe Gly Thr Val Tyr Lys Gly Leu Trp
            450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
                500                 505                 510

Ile Cys Leu Thr Ser Thr Val Gln Leu Ile Thr Gln Leu Met Pro Phe
            515                 520                 525

Gly Cys Leu Leu Asp Tyr Val Arg Glu His Lys Asp Asn Ile Gly Ser
            530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
                565                 570                 575

Leu Val Lys Thr Pro Gln His Val Lys Ile Thr Asp Phe Gly Leu Ala
            580                 585                 590
```

```
Lys Leu Leu Gly Ala Glu Glu Lys Glu Tyr His Ala Glu Gly Gly Lys
            595                 600                 605

Val Pro Ile Lys Trp Met Ala Leu Glu Ser Ile Leu His Arg Ile Tyr
        610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
            660                 665                 670

Thr Ile Asp Val Tyr Met Ile Met Val Lys Cys Trp Met Ile Asp Ala
        675                 680                 685

Asp Ser Arg Pro Lys Phe Arg Glu Leu Ile Ile Glu Phe Ser Lys Met
690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
            740                 745                 750

Gln Gln Gly Phe Phe Ser Ser Pro Ser Thr Ser Arg Thr Pro Leu Leu
        755                 760                 765

Ser Ser Leu Ser Ala Thr Ser Asn Asn Ser Thr Val Ala Cys Ile Asp
770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
            820                 825                 830

Arg Pro Ala Gly Ser Val Gln Asn Pro Val Tyr His Asn Gln Pro Leu
        835                 840                 845

Asn Pro Ala Pro Ser Arg Asp Pro His Tyr Gln Asp Pro His Ser Thr
850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
                885                 890                 895

Gln Ile Ser Leu Asp Asn Pro Asp Tyr Gln Gln Asp Phe Phe Pro Lys
            900                 905                 910

Glu Ala Lys Pro Asn Gly Ile Phe Lys Gly Ser Thr Ala Glu Asn Ala
        915                 920                 925

Glu Tyr Leu Arg Val Ala Pro Gln Ser Ser Glu Phe Ile Gly Ala
930                 935                 940

<210> SEQ ID NO 2
<211> LENGTH: 380
<212> TYPE: PRT
<213> ORGANISM: Homo sapiens

<400> SEQUENCE: 2

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
```

```
            20                  25                  30
Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
                100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
            130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
                180                 185                 190

Gln Asn Ile Gly Cys Arg Phe Pro Tyr Leu Glu Ala Ser Asp Tyr Lys
                195                 200                 205

Asp Phe Tyr Ile Cys Val Asn Gly Ser Ser Glu Asn Lys Pro Ile Arg
            210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
                260                 265                 270

Glu Ile Glu Ile Arg Glu Asp Asp Thr Thr Leu Val Thr Ala Thr Val
            275                 280                 285

Glu Asn Glu Thr Tyr Thr Leu Lys Thr Thr Asn Glu Thr Arg Gln Leu
            290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
            355                 360                 365

Tyr Pro Lys Met Ile Pro Glu Phe Phe Cys Asp Thr
    370                 375                 380

<210> SEQ ID NO 3
<211> LENGTH: 427
<212> TYPE: PRT
<213> ORGANISM: Homo sapiens

<400> SEQUENCE: 3

Met Glu Trp Pro Ala Arg Leu Cys Gly Leu Trp Ala Leu Leu Leu Cys
1               5                   10                  15
```

```
Ala Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val
            35                  40                  45

Ile Trp Thr Trp Asn Pro Pro Glu Gly Ala Ser Ser Asn Cys Ser Leu
50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
            85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
            115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
            195                 200                 205

Asn Ala Gly Lys Ile Lys Pro Ser Phe Asn Ile Val Pro Leu Thr Ser
210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
            275                 280                 285

Arg Asn Val Glu Asn Thr Ser Cys Phe Met Val Pro Gly Val Leu Pro
290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Leu Tyr Ile Thr Met Leu Leu Ile Val
            340                 345                 350

Pro Val Ile Val Ala Gly Ala Ile Ile Val Leu Leu Leu Tyr Leu Lys
            355                 360                 365

Arg Leu Lys Ile Ile Phe Pro Pro Ile Pro Asp Pro Gly Lys Ile
370                 375                 380

Phe Lys Glu Met Phe Gly Asp Gln Asn Asp Asp Thr Leu His Trp Lys
385                 390                 395                 400

Lys Tyr Asp Ile Tyr Glu Lys Gln Thr Lys Glu Thr Asp Ser Val
                405                 410                 415

Val Leu Ile Glu Asn Leu Lys Lys Ala Ser Gln
            420                 425
```

```
<210> SEQ ID NO 4
<211> LENGTH: 279
<212> TYPE: PRT
<213> ORGANISM: Homo sapiens

<400> SEQUENCE: 4

Met Glu Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val
            35                  40                  45

Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Arg Phe
        275

<210> SEQ ID NO 5
<211> LENGTH: 816
<212> TYPE: PRT
<213> ORGANISM: Homo sapiens

<400> SEQUENCE: 5

Met Ser Arg Pro Gln Gly Leu Leu Trp Leu Pro Leu Leu Phe Thr Pro
1               5                   10                  15

Val Cys Val Met Leu Asn Ser Asn Val Leu Leu Trp Leu Thr Ala Leu
            20                  25                  30

Ala Ile Lys Phe Thr Leu Ile Asp Ser Gln Ala Gln Tyr Pro Val Val
            35                  40                  45

Asn Thr Asn Tyr Gly Lys Ile Arg Gly Leu Arg Thr Pro Leu Pro Asn
```

```
            50                  55                  60
Glu Ile Leu Gly Pro Val Gln Tyr Leu Gly Val Pro Tyr Ala Ser
 65                  70                  75                  80

Pro Pro Thr Gly Glu Arg Arg Phe Gln Pro Pro Glu Pro Pro Ser Ser
                     85                  90                  95

Trp Thr Gly Ile Arg Asn Thr Thr Gln Phe Ala Ala Val Cys Pro Gln
                100                 105                 110

His Leu Asp Glu Arg Ser Leu Leu His Asp Met Leu Pro Ile Trp Phe
                115                 120                 125

Thr Ala Asn Leu Asp Thr Leu Met Thr Tyr Val Gln Asp Gln Asn Glu
            130                 135                 140

Asp Cys Leu Tyr Leu Asn Ile Tyr Val Pro Thr Glu Asp Asp Ile His
145                 150                 155                 160

Asp Gln Asn Ser Lys Lys Pro Val Met Val Tyr Ile His Gly Gly Ser
                165                 170                 175

Tyr Met Glu Gly Thr Gly Asn Met Ile Asp Gly Ser Ile Leu Ala Ser
                180                 185                 190

Tyr Gly Asn Val Ile Val Ile Thr Ile Asn Tyr Arg Leu Gly Ile Leu
                195                 200                 205

Gly Phe Leu Ser Thr Gly Asp Gln Ala Ala Lys Gly Asn Tyr Gly Leu
                210                 215                 220

Leu Asp Gln Ile Gln Ala Leu Arg Trp Ile Glu Glu Asn Val Gly Ala
225                 230                 235                 240

Phe Gly Gly Asp Pro Lys Arg Val Thr Ile Phe Gly Ser Gly Ala Gly
                245                 250                 255

Ala Ser Cys Val Ser Leu Leu Thr Leu Ser His Tyr Ser Glu Gly Leu
                260                 265                 270

Phe Gln Lys Ala Ile Ile Gln Ser Gly Thr Ala Leu Ser Ser Trp Ala
                275                 280                 285

Val Asn Tyr Gln Pro Ala Lys Tyr Thr Arg Ile Leu Ala Asp Lys Val
                290                 295                 300

Gly Cys Asn Met Leu Asp Thr Thr Asp Met Val Glu Cys Leu Arg Asn
305                 310                 315                 320

Lys Asn Tyr Lys Glu Leu Ile Gln Gln Thr Ile Thr Pro Ala Thr Tyr
                325                 330                 335

His Ile Ala Phe Gly Pro Val Ile Asp Gly Asp Val Ile Pro Asp Asp
                340                 345                 350

Pro Gln Ile Leu Met Glu Gln Gly Glu Phe Leu Asn Tyr Asp Ile Met
                355                 360                 365

Leu Gly Val Asn Gln Gly Glu Gly Leu Lys Phe Val Asp Gly Ile Val
                370                 375                 380

Asp Asn Glu Asp Gly Val Thr Pro Asn Asp Phe Asp Phe Ser Val Ser
385                 390                 395                 400

Asn Phe Val Asp Asn Leu Tyr Gly Tyr Pro Glu Gly Lys Asp Thr Leu
                405                 410                 415

Arg Glu Thr Ile Lys Phe Met Tyr Thr Asp Trp Ala Asp Lys Glu Asn
                420                 425                 430

Pro Glu Thr Arg Arg Lys Thr Leu Val Ala Leu Phe Thr Asp His Gln
                435                 440                 445

Trp Val Ala Pro Ala Val Ala Thr Ala Asp Leu His Ala Gln Tyr Gly
                450                 455                 460

Ser Pro Thr Tyr Phe Tyr Ala Phe Tyr His His Cys Gln Ser Glu Met
465                 470                 475                 480
```

-continued

```
Lys Pro Ser Trp Ala Asp Ser Ala His Gly Asp Glu Val Pro Tyr Val
                485                 490                 495
Phe Gly Ile Pro Met Ile Gly Pro Thr Glu Leu Phe Ser Cys Asn Phe
            500                 505                 510
Ser Lys Asn Asp Val Met Leu Ser Ala Val Val Met Thr Tyr Trp Thr
        515                 520                 525
Asn Phe Ala Lys Thr Gly Asp Pro Asn Gln Pro Val Pro Gln Asp Thr
    530                 535                 540
Lys Phe Ile His Thr Lys Pro Asn Arg Phe Glu Glu Val Ala Trp Ser
545                 550                 555                 560
Lys Tyr Asn Pro Lys Asp Gln Leu Tyr Leu His Ile Gly Leu Lys Pro
                565                 570                 575
Arg Val Arg Asp His Tyr Arg Ala Thr Lys Val Ala Phe Trp Leu Glu
            580                 585                 590
Leu Val Pro His Leu His Asn Leu Asn Glu Ile Phe Gln Tyr Val Ser
        595                 600                 605
Thr Thr Thr Lys Val Pro Pro Pro Asp Met Thr Ser Phe Pro Tyr Gly
    610                 615                 620
Thr Arg Arg Ser Pro Ala Lys Ile Trp Pro Thr Thr Lys Arg Pro Ala
625                 630                 635                 640
Ile Thr Pro Ala Asn Asn Pro Lys His Ser Lys Asp Pro His Lys Thr
                645                 650                 655
Gly Pro Glu Asp Thr Thr Val Leu Ile Glu Thr Lys Arg Asp Tyr Ser
            660                 665                 670
Thr Glu Leu Ser Val Thr Ile Ala Val Gly Ala Ser Leu Leu Phe Leu
        675                 680                 685
Asn Ile Leu Ala Phe Ala Ala Leu Tyr Tyr Lys Lys Asp Lys Arg Arg
    690                 695                 700
His Glu Thr His Arg Arg Pro Ser Pro Gln Arg Asn Thr Thr Asn Asp
705                 710                 715                 720
Ile Ala His Ile Gln Asn Glu Glu Ile Met Ser Leu Gln Met Lys Gln
                725                 730                 735
Leu Glu His Asp His Glu Cys Glu Ser Leu Gln Ala His Asp Thr Leu
            740                 745                 750
Arg Leu Thr Cys Pro Pro Asp Tyr Thr Leu Thr Leu Arg Arg Ser Pro
        755                 760                 765
Asp Asp Ile Pro Leu Met Thr Pro Asn Thr Ile Thr Met Ile Pro Asn
    770                 775                 780
Thr Leu Thr Gly Met Gln Pro Leu His Thr Phe Asn Thr Phe Ser Gly
785                 790                 795                 800
Gly Gln Asn Ser Thr Asn Leu Pro His Gly His Ser Thr Thr Arg Val
                805                 810                 815

<210> SEQ ID NO 6
<211> LENGTH: 836
<212> TYPE: PRT
<213> ORGANISM: Homo sapiens

<400> SEQUENCE: 6

Met Ser Arg Pro Gln Gly Leu Leu Trp Leu Pro Leu Leu Phe Thr Pro
1               5                   10                  15
Val Cys Val Met Leu Asn Ser Asn Val Leu Leu Trp Leu Thr Ala Leu
                20                  25                  30
Ala Ile Lys Phe Thr Leu Ile Asp Ser Gln Ala Gln Tyr Pro Val Val
```

```
            35                  40                  45
Asn Thr Asn Tyr Gly Lys Ile Arg Gly Leu Arg Thr Pro Leu Pro Asn
 50                  55                  60

Glu Ile Leu Gly Pro Val Gln Tyr Leu Gly Val Pro Tyr Ala Ser
 65                  70                  75                  80

Pro Pro Thr Gly Glu Arg Arg Phe Gln Pro Glu Pro Pro Ser Ser
                 85                  90                  95

Trp Thr Gly Ile Arg Asn Thr Thr Gln Phe Ala Ala Val Cys Pro Gln
                100                 105                 110

His Leu Asp Glu Arg Ser Leu Leu His Asp Met Leu Pro Ile Trp Phe
                115                 120                 125

Thr Ala Asn Leu Asp Thr Leu Met Thr Tyr Val Gln Asp Gln Asn Glu
130                 135                 140

Asp Cys Leu Tyr Leu Asn Ile Tyr Val Pro Thr Glu Asp Gly Ala Asn
145                 150                 155                 160

Thr Lys Lys Asn Ala Asp Asp Ile Thr Ser Asn Asp Arg Gly Glu Asp
                165                 170                 175

Glu Asp Ile His Asp Gln Asn Ser Lys Lys Pro Val Met Val Tyr Ile
                180                 185                 190

His Gly Gly Ser Tyr Met Glu Gly Thr Gly Asn Met Ile Asp Gly Ser
                195                 200                 205

Ile Leu Ala Ser Tyr Gly Asn Val Ile Val Thr Ile Asn Tyr Arg
210                 215                 220

Leu Gly Ile Leu Gly Phe Leu Ser Thr Gly Asp Gln Ala Ala Lys Gly
225                 230                 235                 240

Asn Tyr Gly Leu Leu Asp Gln Ile Gln Ala Leu Arg Trp Ile Glu Glu
                245                 250                 255

Asn Val Gly Ala Phe Gly Gly Asp Pro Lys Arg Val Thr Ile Phe Gly
                260                 265                 270

Ser Gly Ala Gly Ala Ser Cys Val Ser Leu Leu Thr Leu Ser His Tyr
                275                 280                 285

Ser Glu Gly Leu Phe Gln Lys Ala Ile Ile Gln Ser Gly Thr Ala Leu
290                 295                 300

Ser Ser Trp Ala Val Asn Tyr Gln Pro Ala Lys Tyr Thr Arg Ile Leu
305                 310                 315                 320

Ala Asp Lys Val Gly Cys Asn Met Leu Asp Thr Thr Asp Met Val Glu
                325                 330                 335

Cys Leu Arg Asn Lys Asn Tyr Lys Glu Leu Ile Gln Gln Thr Ile Thr
                340                 345                 350

Pro Ala Thr Tyr His Ile Ala Phe Gly Pro Val Ile Asp Gly Asp Val
                355                 360                 365

Ile Pro Asp Asp Pro Gln Ile Leu Met Glu Gln Gly Glu Phe Leu Asn
                370                 375                 380

Tyr Asp Ile Met Leu Gly Val Asn Gln Gly Glu Gly Leu Lys Phe Val
385                 390                 395                 400

Asp Gly Ile Val Asp Asn Glu Asp Gly Val Thr Pro Asn Asp Phe Asp
                405                 410                 415

Phe Ser Val Ser Asn Phe Val Asp Asn Leu Tyr Gly Tyr Pro Glu Gly
                420                 425                 430

Lys Asp Thr Leu Arg Glu Thr Ile Lys Phe Met Tyr Thr Asp Trp Ala
                435                 440                 445

Asp Lys Glu Asn Pro Glu Thr Arg Arg Lys Thr Leu Val Ala Leu Phe
                450                 455                 460
```

```
Thr Asp His Gln Trp Val Ala Pro Ala Val Thr Ala Asp Leu His
465                 470                 475                 480

Ala Gln Tyr Gly Ser Pro Thr Tyr Phe Tyr Ala Phe Tyr His His Cys
                485                 490                 495

Gln Ser Glu Met Lys Pro Ser Trp Ala Asp Ser Ala His Gly Asp Glu
            500                 505                 510

Val Pro Tyr Val Phe Gly Ile Pro Met Ile Gly Pro Thr Glu Leu Phe
            515                 520                 525

Ser Cys Asn Phe Ser Lys Asn Asp Val Met Leu Ser Ala Val Val Met
530                 535                 540

Thr Tyr Trp Thr Asn Phe Ala Lys Thr Gly Asp Pro Asn Gln Pro Val
545                 550                 555                 560

Pro Gln Asp Thr Lys Phe Ile His Thr Lys Pro Asn Arg Phe Glu Glu
                565                 570                 575

Val Ala Trp Ser Lys Tyr Asn Pro Lys Asp Gln Leu Tyr Leu His Ile
                580                 585                 590

Gly Leu Lys Pro Arg Val Arg Asp His Tyr Arg Ala Thr Lys Val Ala
            595                 600                 605

Phe Trp Leu Glu Leu Val Pro His Leu His Asn Leu Asn Glu Ile Phe
610                 615                 620

Gln Tyr Val Ser Thr Thr Thr Lys Val Pro Pro Asp Met Thr Ser
625                 630                 635                 640

Phe Pro Tyr Gly Thr Arg Arg Ser Pro Ala Lys Ile Trp Pro Thr Thr
                645                 650                 655

Lys Arg Pro Ala Ile Thr Pro Ala Asn Asn Pro Lys His Ser Lys Asp
                660                 665                 670

Pro His Lys Thr Gly Pro Glu Asp Thr Thr Val Leu Ile Glu Thr Lys
            675                 680                 685

Arg Asp Tyr Ser Thr Glu Leu Ser Val Thr Ile Ala Val Gly Ala Ser
    690                 695                 700

Leu Leu Phe Leu Asn Ile Leu Ala Phe Ala Ala Leu Tyr Tyr Lys Lys
705                 710                 715                 720

Asp Lys Arg Arg His Glu Thr His Arg Arg Pro Ser Pro Gln Arg Asn
                725                 730                 735

Thr Thr Asn Asp Ile Ala His Ile Gln Asn Glu Glu Ile Met Ser Leu
                740                 745                 750

Gln Met Lys Gln Leu Glu His Asp His Glu Cys Glu Ser Leu Gln Ala
            755                 760                 765

His Asp Thr Leu Arg Leu Thr Cys Pro Pro Asp Tyr Thr Leu Thr Leu
770                 775                 780

Arg Arg Ser Pro Asp Asp Ile Pro Leu Met Thr Pro Asn Thr Ile Thr
785                 790                 795                 800

Met Ile Pro Asn Thr Leu Thr Gly Met Gln Pro Leu His Thr Phe Asn
                805                 810                 815

Thr Phe Ser Gly Gly Gln Asn Ser Thr Asn Leu Pro His Gly His Ser
                820                 825                 830

Thr Thr Arg Val
        835

<210> SEQ ID NO 7
<211> LENGTH: 816
<212> TYPE: PRT
<213> ORGANISM: Homo sapiens
```

```
<400> SEQUENCE: 7

Met Leu Arg Pro Gln Gly Leu Leu Trp Leu Pro Leu Leu Phe Thr Ser
1               5                   10                  15

Val Cys Val Met Leu Asn Ser Asn Val Leu Leu Trp Ile Thr Ala Leu
                20                  25                  30

Ala Ile Lys Phe Thr Leu Ile Asp Ser Gln Ala Gln Tyr Pro Val Val
            35                  40                  45

Asn Thr Asn Tyr Gly Lys Ile Gln Gly Leu Arg Thr Pro Leu Pro Ser
        50                  55                  60

Glu Ile Leu Gly Pro Val Glu Gln Tyr Leu Gly Val Pro Tyr Ala Ser
65                  70                  75                  80

Pro Pro Thr Gly Glu Arg Arg Phe Gln Pro Pro Glu Ser Pro Ser Ser
                85                  90                  95

Trp Thr Gly Ile Arg Asn Ala Thr Gln Phe Ser Ala Val Cys Pro Gln
            100                 105                 110

His Leu Asp Glu Arg Phe Leu Leu His Asp Met Leu Pro Ile Trp Phe
        115                 120                 125

Thr Thr Ser Leu Asp Thr Leu Met Thr Tyr Val Gln Asp Gln Asn Glu
130                 135                 140

Asp Cys Leu Tyr Leu Asn Ile Tyr Val Pro Met Glu Asp Asp Ile His
145                 150                 155                 160

Glu Gln Asn Ser Lys Lys Pro Val Met Val Tyr Ile His Gly Gly Ser
                165                 170                 175

Tyr Met Glu Gly Thr Gly Asn Met Ile Asp Gly Ser Ile Leu Ala Ser
            180                 185                 190

Tyr Gly Asn Val Ile Val Ile Thr Ile Asn Tyr Arg Leu Gly Ile Leu
        195                 200                 205

Gly Phe Leu Ser Thr Gly Asp Gln Ala Ala Lys Gly Asn Tyr Gly Leu
210                 215                 220

Leu Asp Gln Ile Gln Ala Leu Arg Trp Ile Glu Glu Asn Val Gly Ala
225                 230                 235                 240

Phe Gly Gly Asp Pro Lys Arg Val Thr Ile Phe Gly Ser Gly Ala Gly
                245                 250                 255

Ala Ser Cys Val Ser Leu Leu Thr Leu Ser His Tyr Ser Glu Gly Leu
            260                 265                 270

Phe Gln Lys Ala Ile Ile Gln Ser Gly Thr Ala Leu Ser Ser Trp Ala
        275                 280                 285

Val Asn Tyr Gln Pro Ala Lys Tyr Thr Arg Ile Leu Ala Asp Lys Val
290                 295                 300

Gly Cys Asn Met Leu Asp Thr Thr Asp Met Val Glu Cys Leu Lys Asn
305                 310                 315                 320

Lys Asn Tyr Lys Glu Leu Ile Gln Gln Thr Ile Thr Pro Ala Thr Tyr
                325                 330                 335

His Ile Ala Phe Gly Pro Val Ile Asp Gly Asp Val Ile Pro Asp Asp
            340                 345                 350

Pro Gln Ile Leu Met Glu Gln Gly Glu Phe Leu Asn Tyr Asp Ile Met
        355                 360                 365

Leu Gly Val Asn Gln Gly Glu Gly Leu Lys Phe Val Asp Gly Ile Val
370                 375                 380

Asp Asn Glu Asp Gly Val Thr Pro Asn Asp Phe Asp Phe Ser Val Ser
385                 390                 395                 400

Asn Phe Val Asp Asn Leu Tyr Gly Tyr Pro Glu Gly Lys Asp Thr Leu
                405                 410                 415
```

Arg Glu Thr Ile Lys Phe Met Tyr Thr Asp Trp Ala Asp Lys Glu Asn
                420                 425                 430

Pro Glu Thr Arg Arg Lys Thr Leu Val Ala Leu Phe Thr Asp His Gln
            435                 440                 445

Trp Val Ala Pro Ala Val Ala Thr Ala Asp Leu His Ala Gln Tyr Gly
450                 455                 460

Ser Pro Thr Tyr Phe Tyr Ala Phe Tyr His His Cys Gln Ser Glu Met
465                 470                 475                 480

Lys Pro Ser Trp Ala Asp Ser Ala His Gly Asp Glu Val Pro Tyr Val
                485                 490                 495

Phe Gly Ile Pro Met Ile Gly Pro Thr Glu Leu Phe Ser Cys Asn Phe
                500                 505                 510

Ser Lys Asn Asp Val Met Leu Ser Ala Val Val Met Thr Tyr Trp Thr
            515                 520                 525

Asn Phe Ala Lys Thr Gly Asp Pro Asn Gln Pro Val Pro Gln Asp Thr
530                 535                 540

Lys Phe Ile His Thr Lys Pro Asn Arg Phe Glu Glu Val Ala Trp Ser
545                 550                 555                 560

Lys Tyr Asn Pro Lys Asp Gln Leu Tyr Leu His Ile Gly Leu Lys Pro
                565                 570                 575

Arg Val Arg Asp His Tyr Arg Ala Thr Lys Val Ala Phe Trp Leu Glu
                580                 585                 590

Leu Val Pro His Leu His Asn Leu Asn Glu Ile Phe Gln Tyr Val Ser
            595                 600                 605

Thr Thr Thr Lys Val Pro Pro Asp Met Thr Ser Phe Pro Tyr Gly
610                 615                 620

Thr Arg Arg Ser Pro Ala Lys Ile Trp Pro Thr Thr Lys Arg Pro Ala
625                 630                 635                 640

Ile Thr Pro Ala Asn Asn Pro Lys His Ser Lys Asp Pro His Lys Thr
                645                 650                 655

Gly Pro Glu Asp Thr Thr Val Leu Ile Glu Thr Lys Arg Asp Tyr Ser
                660                 665                 670

Thr Glu Leu Ser Val Thr Ile Ala Val Gly Ala Ser Leu Leu Phe Leu
            675                 680                 685

Asn Ile Leu Ala Phe Ala Ala Leu Tyr Tyr Lys Lys Asp Lys Arg Arg
690                 695                 700

His Glu Thr His Arg His Pro Ser Pro Gln Arg Asn Thr Thr Asn Asp
705                 710                 715                 720

Ile Thr His Ile Gln Asn Glu Glu Ile Met Ser Leu Gln Met Lys Gln
                725                 730                 735

Leu Glu His Asp His Glu Cys Glu Ser Leu Gln Ala His Asp Thr Leu
            740                 745                 750

Arg Leu Thr Cys Pro Pro Asp Tyr Thr Leu Thr Leu Arg Arg Ser Pro
            755                 760                 765

Asp Asp Ile Pro Phe Met Thr Pro Asn Thr Ile Thr Met Ile Pro Asn
770                 775                 780

Thr Leu Met Gly Met Gln Pro Leu His Thr Phe Lys Thr Phe Ser Gly
785                 790                 795                 800

Gly Gln Asn Ser Thr Asn Leu Pro His Gly His Ser Thr Thr Arg Val
                805                 810                 815

<210> SEQ ID NO 8
<211> LENGTH: 648

<212> TYPE: PRT
<213> ORGANISM: Homo sapiens

<400> SEQUENCE: 8

Met Val Tyr Ile His Gly Gly Ser Tyr Met Glu Thr Gly Asn Met
1               5                   10                  15

Ile Asp Gly Ser Ile Leu Ala Ser Tyr Gly Asn Val Ile Val Ile Thr
            20                  25                  30

Ile Asn Tyr Arg Leu Gly Ile Leu Gly Phe Leu Ser Thr Gly Asp Gln
            35                  40                  45

Ala Ala Lys Gly Asn Tyr Gly Leu Leu Asp Gln Ile Gln Ala Leu Arg
        50                  55                  60

Trp Ile Glu Glu Asn Val Gly Ala Phe Gly Gly Asp Pro Lys Arg Val
65                  70                  75                  80

Thr Ile Phe Gly Ser Gly Ala Gly Ala Ser Cys Val Ser Leu Leu Thr
                85                  90                  95

Leu Ser His Tyr Ser Glu Gly Leu Phe Gln Lys Ala Ile Ile Gln Ser
            100                 105                 110

Gly Thr Ala Leu Ser Ser Trp Ala Val Asn Tyr Gln Pro Ala Lys Tyr
        115                 120                 125

Thr Arg Ile Leu Ala Asp Lys Val Gly Cys Asn Met Leu Asp Thr Thr
    130                 135                 140

Asp Met Val Glu Cys Leu Lys Asn Lys Asn Tyr Lys Glu Leu Ile Gln
145                 150                 155                 160

Gln Thr Ile Thr Pro Ala Thr Tyr His Ile Ala Phe Gly Pro Val Ile
                165                 170                 175

Asp Gly Asp Val Ile Pro Asp Pro Gln Ile Leu Met Glu Gln Gly
            180                 185                 190

Glu Phe Leu Asn Tyr Asp Ile Met Leu Gly Val Asn Gln Gly Glu Gly
        195                 200                 205

Leu Lys Phe Val Asp Gly Ile Val Asp Asn Glu Asp Gly Val Thr Pro
    210                 215                 220

Asn Asp Phe Asp Phe Ser Val Ser Asn Phe Val Asp Asn Leu Tyr Gly
225                 230                 235                 240

Tyr Pro Glu Gly Lys Asp Thr Leu Arg Glu Thr Ile Lys Phe Met Tyr
                245                 250                 255

Thr Asp Trp Ala Asp Lys Glu Asn Pro Glu Thr Arg Arg Lys Thr Leu
            260                 265                 270

Val Ala Leu Phe Thr Asp His Gln Trp Val Ala Pro Ala Val Ala Thr
        275                 280                 285

Ala Asp Leu His Ala Gln Tyr Gly Ser Pro Thr Tyr Phe Tyr Ala Phe
    290                 295                 300

Tyr His His Cys Gln Ser Glu Met Lys Pro Ser Trp Ala Asp Ser Ala
305                 310                 315                 320

His Gly Asp Glu Val Pro Tyr Val Phe Gly Ile Pro Met Ile Gly Pro
                325                 330                 335

Thr Glu Leu Phe Ser Cys Asn Phe Ser Lys Asn Asp Val Met Leu Ser
            340                 345                 350

Ala Val Val Met Thr Tyr Trp Thr Asn Phe Ala Lys Thr Gly Asp Pro
        355                 360                 365

Asn Gln Pro Val Pro Gln Asp Thr Lys Phe Ile His Thr Lys Pro Asn
    370                 375                 380

Arg Phe Glu Glu Val Ala Trp Ser Lys Tyr Asn Pro Lys Asp Gln Leu
385                 390                 395                 400

```
Tyr Leu His Ile Gly Leu Lys Pro Arg Val Arg Asp His Tyr Arg Ala
                405                 410                 415

Thr Lys Val Ala Phe Trp Leu Glu Leu Val Pro His Leu His Asn Leu
            420                 425                 430

Asn Glu Ile Phe Gln Tyr Val Ser Thr Thr Lys Val Pro Pro
        435                 440                 445

Asp Met Thr Ser Phe Pro Tyr Gly Thr Arg Arg Ser Pro Ala Lys Ile
    450                 455                 460

Trp Pro Thr Thr Lys Arg Pro Ala Ile Thr Pro Ala Asn Asn Pro Lys
465                 470                 475                 480

His Ser Lys Asp Pro His Lys Thr Gly Pro Glu Asp Thr Thr Val Leu
                485                 490                 495

Ile Glu Thr Lys Arg Asp Tyr Ser Thr Glu Leu Ser Val Thr Ile Ala
                500                 505                 510

Val Gly Ala Ser Leu Leu Phe Leu Asn Ile Leu Ala Phe Ala Ala Leu
            515                 520                 525

Tyr Tyr Lys Lys Asp Lys Arg Arg His Glu Thr His Arg His Pro Ser
        530                 535                 540

Pro Gln Arg Asn Thr Thr Asn Asp Ile Thr His Ile Gln Asn Glu Glu
545                 550                 555                 560

Ile Met Ser Leu Gln Met Lys Gln Leu Glu His Asp His Glu Cys Glu
                565                 570                 575

Ser Leu Gln Ala His Asp Thr Leu Arg Leu Thr Cys Pro Pro Asp Tyr
            580                 585                 590

Thr Leu Thr Leu Arg Arg Ser Pro Asp Asp Ile Pro Phe Met Thr Pro
        595                 600                 605

Asn Thr Ile Thr Met Ile Pro Asn Thr Leu Met Gly Met Gln Pro Leu
    610                 615                 620

His Thr Phe Lys Thr Phe Ser Gly Gly Gln Asn Ser Thr Asn Leu Pro
625                 630                 635                 640

His Gly His Ser Thr Thr Arg Val
                645

<210> SEQ ID NO 9
<211> LENGTH: 134
<212> TYPE: PRT
<213> ORGANISM: Homo sapiens

<400> SEQUENCE: 9

Met Leu Pro Ile Trp Phe Thr Thr Ser Leu Asp Thr Leu Met Thr Tyr
1               5                   10                  15

Val Gln Asp Gln Asn Glu Asp Cys Leu Tyr Leu Asn Ile Tyr Val Pro
                20                  25                  30

Met Glu Asp Gly Thr Asn Ile Lys Arg Asn Ala Asp Asp Ile Thr Ser
            35                  40                  45

Asn Asp His Gly Glu Asp Lys Asp Ile His Glu Gln Asn Ser Lys Lys
        50                  55                  60

Pro Val Met Val Tyr Ile His Gly Gly Ser Tyr Met Glu Gly Thr Gly
65                  70                  75                  80

Asn Met Ile Asp Gly Ser Ile Leu Ala Ser Tyr Gly Asn Val Ile Val
                85                  90                  95

Ile Thr Ile Asn Tyr Arg Leu Gly Ile Leu Gly Met Gln Glu Ala Arg
                100                 105                 110

Leu Cys Gly Ser Ser Lys Met Phe Asn Tyr Phe Lys Ser Pro Phe Thr
```

```
                  115                 120                 125

Asn Leu Ile Asn Phe Phe
            130

<210> SEQ ID NO 10
<211> LENGTH: 256
<212> TYPE: PRT
<213> ORGANISM: Homo sapiens

<400> SEQUENCE: 10

Met Leu Arg Pro Gln Gly Leu Leu Trp Leu Pro Leu Phe Thr Ser
1               5                   10                  15

Val Cys Val Met Leu Asn Ser Asn Val Leu Leu Trp Ile Thr Ala Leu
                20                  25                  30

Ala Ile Lys Phe Thr Leu Ile Asp Ser Gln Ala Gln Tyr Pro Val Val
            35                  40                  45

Asn Thr Asn Tyr Gly Lys Ile Gln Gly Leu Arg Thr Pro Leu Pro Ser
        50                  55                  60

Glu Ile Leu Gly Pro Val Glu Gln Tyr Leu Gly Val Pro Tyr Ala Ser
65                  70                  75                  80

Pro Pro Thr Gly Glu Arg Arg Phe Gln Pro Pro Glu Ser Pro Ser Ser
                    85                  90                  95

Trp Thr Gly Ile Arg Asn Ala Thr Gln Phe Ser Ala Val Cys Pro Gln
                100                 105                 110

His Leu Asp Glu Arg Phe Leu Leu His Asp Met Leu Pro Ile Trp Phe
            115                 120                 125

Thr Thr Ser Leu Asp Thr Leu Met Thr Tyr Val Gln Asp Gln Asn Glu
        130                 135                 140

Asp Cys Leu Tyr Leu Asn Ile Tyr Val Pro Met Glu Asp Gly Thr Asn
145                 150                 155                 160

Ile Lys Arg Asn Ala Asp Asp Ile Thr Ser Asn Asp His Gly Glu Asp
                165                 170                 175

Lys Asp Ile His Glu Gln Asn Ser Lys Lys Pro Val Met Val Tyr Ile
            180                 185                 190

His Gly Gly Ser Tyr Met Glu Gly Thr Gly Asn Met Ile Asp Gly Ser
        195                 200                 205

Ile Leu Ala Ser Tyr Gly Asn Val Ile Val Thr Ile Asn Tyr Arg
        210                 215                 220

Leu Gly Ile Leu Gly Met Gln Glu Ala Arg Leu Cys Gly Ser Ser Lys
225                 230                 235                 240

Met Phe Asn Tyr Phe Lys Ser Pro Phe Thr Asn Leu Ile Asn Phe Phe
                245                 250                 255

<210> SEQ ID NO 11
<211> LENGTH: 848
<212> TYPE: PRT
<213> ORGANISM: Homo sapiens

<400> SEQUENCE: 11

Met Trp Leu Arg Leu Gly Pro Pro Ser Leu Ser Leu Ser Pro Lys Pro
1               5                   10                  15

Thr Val Gly Arg Ser Leu Cys Leu Thr Leu Trp Phe Leu Ser Leu Ala
                20                  25                  30

Leu Arg Ala Ser Thr Gln Ala Pro Ala Pro Thr Val Asn Thr His Phe
            35                  40                  45

Gly Lys Leu Arg Gly Ala Arg Val Pro Leu Pro Ser Glu Ile Leu Gly
```

```
                50                  55                  60
Pro Val Asp Gln Tyr Leu Gly Val Pro Tyr Ala Ala Pro Pro Ile Gly
 65                  70                  75                  80

Glu Lys Arg Phe Leu Pro Pro Glu Pro Pro Ser Trp Ser Gly Ile
                     85                  90                  95

Arg Asn Ala Thr His Phe Pro Pro Val Cys Pro Gln Asn Ile His Thr
                    100                 105                 110

Ala Val Pro Glu Val Met Leu Pro Val Trp Phe Thr Ala Asn Leu Asp
                115                 120                 125

Ile Val Ala Thr Tyr Ile Gln Glu Pro Asn Glu Asp Cys Leu Tyr Leu
130                 135                 140

Asn Val Tyr Val Pro Thr Glu Asp Val Lys Arg Ile Ser Lys Glu Cys
145                 150                 155                 160

Ala Arg Lys Pro Asn Lys Lys Ile Cys Arg Lys Gly Ser Gly Ala
                    165                 170                 175

Lys Lys Gln Gly Glu Asp Leu Ala Asp Asn Asp Gly Asp Glu Asp Glu
                180                 185                 190

Asp Ile Arg Asp Ser Gly Ala Lys Pro Val Met Val Tyr Ile His Gly
                195                 200                 205

Gly Ser Tyr Met Glu Gly Thr Gly Asn Met Ile Asp Gly Ser Ile Leu
                210                 215                 220

Ala Ser Tyr Gly Asn Val Ile Val Ile Thr Leu Asn Tyr Arg Val Gly
225                 230                 235                 240

Val Leu Gly Phe Leu Ser Thr Gly Asp Gln Ala Ala Lys Gly Asn Tyr
                    245                 250                 255

Gly Leu Leu Asp Gln Ile Gln Ala Leu Arg Trp Val Ser Glu Asn Ile
                260                 265                 270

Ala Phe Phe Gly Gly Asp Pro Arg Arg Ile Thr Val Phe Gly Ser Gly
                275                 280                 285

Ile Gly Ala Ser Cys Val Ser Leu Leu Thr Leu Ser His His Ser Glu
                290                 295                 300

Gly Leu Phe Gln Arg Ala Ile Ile Gln Ser Gly Ser Ala Leu Ser Ser
305                 310                 315                 320

Trp Ala Val Asn Tyr Gln Pro Val Lys Tyr Thr Ser Leu Leu Ala Asp
                    325                 330                 335

Lys Val Gly Cys Asn Val Leu Asp Thr Val Asp Met Val Asp Cys Leu
                340                 345                 350

Arg Gln Lys Ser Ala Lys Glu Leu Val Glu Gln Asp Ile Gln Pro Ala
                355                 360                 365

Arg Tyr His Val Ala Phe Gly Pro Val Ile Asp Gly Asp Val Ile Pro
370                 375                 380

Asp Asp Pro Glu Ile Leu Met Glu Gln Gly Glu Phe Leu Asn Tyr Asp
385                 390                 395                 400

Ile Met Leu Gly Val Asn Gln Gly Glu Gly Leu Lys Phe Val Glu Gly
                    405                 410                 415

Val Val Asp Pro Glu Asp Gly Val Ser Gly Thr Asp Phe Asp Tyr Ser
                420                 425                 430

Val Ser Asn Phe Val Asp Asn Leu Tyr Gly Tyr Pro Glu Gly Lys Asp
                435                 440                 445

Thr Leu Arg Glu Thr Ile Lys Phe Met Tyr Thr Asp Trp Ala Asp Arg
                450                 455                 460

Asp Asn Pro Glu Thr Arg Arg Lys Thr Leu Val Ala Leu Phe Thr Asp
465                 470                 475                 480
```

His Gln Trp Val Glu Pro Ser Val Val Thr Ala Asp Leu His Ala Arg
                485                 490                 495

Tyr Gly Ser Pro Thr Tyr Phe Tyr Ala Phe Tyr His His Cys Gln Ser
            500                 505                 510

Leu Met Lys Pro Ala Trp Ser Asp Ala Ala His Gly Asp Glu Val Pro
        515                 520                 525

Tyr Val Phe Gly Val Pro Met Val Gly Pro Thr Asp Leu Phe Pro Cys
    530                 535                 540

Asn Phe Ser Lys Asn Asp Val Met Leu Ser Ala Val Val Met Thr Tyr
545                 550                 555                 560

Trp Thr Asn Phe Ala Lys Thr Gly Asp Pro Asn Lys Pro Val Pro Gln
                565                 570                 575

Asp Thr Lys Phe Ile His Thr Lys Ala Asn Arg Phe Glu Glu Val Ala
            580                 585                 590

Trp Ser Lys Tyr Asn Pro Arg Asp Gln Leu Tyr Leu His Ile Gly Leu
        595                 600                 605

Lys Pro Arg Val Arg Asp His Tyr Arg Ala Thr Lys Val Ala Phe Trp
    610                 615                 620

Lys His Leu Val Pro His Leu Tyr Asn Leu His Asp Met Phe His Tyr
625                 630                 635                 640

Thr Ser Thr Thr Thr Lys Val Pro Pro Asp Thr Thr His Ser Ser
                645                 650                 655

His Ile Thr Arg Arg Pro Asn Gly Lys Thr Trp Ser Thr Lys Arg Pro
            660                 665                 670

Ala Ile Ser Pro Ala Tyr Ser Asn Glu Asn Ala Gln Gly Ser Trp Asn
        675                 680                 685

Gly Asp Gln Asp Ala Gly Pro Leu Leu Val Glu Asn Pro Arg Asp Tyr
690                 695                 700

Ser Thr Glu Leu Ser Val Thr Ile Ala Val Gly Ala Ser Leu Leu Phe
705                 710                 715                 720

Leu Asn Val Leu Ala Phe Ala Ala Leu Tyr Tyr Arg Lys Asp Lys Arg
                725                 730                 735

Arg Gln Glu Pro Leu Arg Gln Pro Ser Pro Gln Arg Gly Ala Gly Ala
            740                 745                 750

Pro Glu Leu Gly Ala Ala Pro Glu Glu Leu Ala Ala Leu Gln Leu
        755                 760                 765

Gly Pro Thr His His Glu Cys Glu Ala Gly Pro Pro His Asp Thr Leu
    770                 775                 780

Arg Leu Thr Ala Leu Pro Asp Tyr Thr Leu Thr Leu Arg Arg Ser Pro
785                 790                 795                 800

Asp Asp Ile Pro Leu Met Thr Pro Asn Thr Ile Thr Met Ile Pro Asn
                805                 810                 815

Ser Leu Val Gly Leu Gln Thr Leu His Pro Tyr Asn Thr Phe Ala Ala
            820                 825                 830

Gly Phe Asn Ser Thr Gly Leu Pro His Ser His Ser Thr Thr Arg Val
        835                 840                 845

<210> SEQ ID NO 12
<211> LENGTH: 828
<212> TYPE: PRT
<213> ORGANISM: Homo sapiens

<400> SEQUENCE: 12

Met Trp Leu Arg Leu Gly Pro Pro Ser Leu Ser Leu Ser Pro Lys Pro

-continued

```
1               5                   10                  15
Thr Val Gly Arg Ser Leu Cys Leu Thr Leu Trp Phe Leu Ser Leu Ala
                20                  25                  30
Leu Arg Ala Ser Thr Gln Ala Pro Ala Pro Thr Val Asn Thr His Phe
                35                  40                  45
Gly Lys Leu Arg Gly Ala Arg Val Pro Leu Pro Ser Glu Ile Leu Gly
                50                  55                  60
Pro Val Asp Gln Tyr Leu Gly Val Pro Tyr Ala Ala Pro Pro Ile Gly
65                  70                  75                  80
Glu Lys Arg Phe Leu Pro Pro Glu Pro Pro Ser Trp Ser Gly Ile
                85                  90                  95
Arg Asn Ala Thr His Phe Pro Pro Val Cys Pro Gln Asn Ile His Thr
                100                 105                 110
Ala Val Pro Glu Val Met Leu Pro Val Trp Phe Thr Ala Asn Leu Asp
                115                 120                 125
Ile Val Ala Thr Tyr Ile Gln Glu Pro Asn Glu Asp Cys Leu Tyr Leu
                130                 135                 140
Asn Val Tyr Val Pro Thr Glu Asp Gly Ser Gly Ala Lys Lys Gln Gly
145                 150                 155                 160
Glu Asp Leu Ala Asp Asn Asp Gly Asp Glu Asp Ile Arg Asp
                165                 170                 175
Ser Gly Ala Lys Pro Val Met Val Tyr Ile His Gly Gly Ser Tyr Met
                180                 185                 190
Glu Gly Thr Gly Asn Met Ile Asp Gly Ser Ile Leu Ala Ser Tyr Gly
                195                 200                 205
Asn Val Ile Val Ile Thr Leu Asn Tyr Arg Val Gly Val Leu Gly Phe
210                 215                 220
Leu Ser Thr Gly Asp Gln Ala Ala Lys Gly Asn Tyr Gly Leu Leu Asp
225                 230                 235                 240
Gln Ile Gln Ala Leu Arg Trp Val Ser Glu Asn Ile Ala Phe Phe Gly
                245                 250                 255
Gly Asp Pro Arg Arg Ile Thr Val Phe Gly Ser Gly Ile Gly Ala Ser
                260                 265                 270
Cys Val Ser Leu Leu Thr Leu Ser His His Ser Glu Gly Leu Phe Gln
                275                 280                 285
Arg Ala Ile Ile Gln Ser Gly Ser Ala Leu Ser Ser Trp Ala Val Asn
                290                 295                 300
Tyr Gln Pro Val Lys Tyr Thr Ser Leu Leu Ala Asp Lys Val Gly Cys
305                 310                 315                 320
Asn Val Leu Asp Thr Val Asp Met Val Asp Cys Leu Arg Gln Lys Ser
                325                 330                 335
Ala Lys Glu Leu Val Glu Gln Asp Ile Gln Pro Ala Arg Tyr His Val
                340                 345                 350
Ala Phe Gly Pro Val Ile Asp Gly Asp Val Ile Pro Asp Asp Pro Glu
                355                 360                 365
Ile Leu Met Glu Gln Gly Glu Phe Leu Asn Tyr Asp Ile Met Leu Gly
                370                 375                 380
Val Asn Gln Gly Glu Gly Leu Lys Phe Val Glu Gly Val Val Asp Pro
385                 390                 395                 400
Glu Asp Gly Val Ser Gly Thr Asp Phe Asp Tyr Ser Val Ser Asn Phe
                405                 410                 415
Val Asp Asn Leu Tyr Gly Tyr Pro Glu Gly Lys Asp Thr Leu Arg Glu
                420                 425                 430
```

Thr Ile Lys Phe Met Tyr Thr Asp Trp Ala Asp Arg Asp Asn Pro Glu
            435                 440                 445

Thr Arg Arg Lys Thr Leu Val Ala Leu Phe Thr Asp His Gln Trp Val
    450                 455                 460

Glu Pro Ser Val Val Thr Ala Asp Leu His Ala Arg Tyr Gly Ser Pro
465                 470                 475                 480

Thr Tyr Phe Tyr Ala Phe Tyr His His Cys Gln Ser Leu Met Lys Pro
                485                 490                 495

Ala Trp Ser Asp Ala Ala His Gly Asp Glu Val Pro Tyr Val Phe Gly
            500                 505                 510

Val Pro Met Val Gly Pro Thr Asp Leu Phe Pro Cys Asn Phe Ser Lys
        515                 520                 525

Asn Asp Val Met Leu Ser Ala Val Val Met Thr Tyr Trp Thr Asn Phe
    530                 535                 540

Ala Lys Thr Gly Asp Pro Asn Lys Pro Val Pro Gln Asp Thr Lys Phe
545                 550                 555                 560

Ile His Thr Lys Ala Asn Arg Phe Glu Glu Val Ala Trp Ser Lys Tyr
                565                 570                 575

Asn Pro Arg Asp Gln Leu Tyr Leu His Ile Gly Leu Lys Pro Arg Val
            580                 585                 590

Arg Asp His Tyr Arg Ala Thr Lys Val Ala Phe Trp Lys His Leu Val
        595                 600                 605

Pro His Leu Tyr Asn Leu His Asp Met Phe His Tyr Thr Ser Thr Thr
    610                 615                 620

Thr Lys Val Pro Pro Asp Thr Thr His Ser Ser His Ile Thr Arg
625                 630                 635                 640

Arg Pro Asn Gly Lys Thr Trp Ser Thr Lys Arg Pro Ala Ile Ser Pro
                645                 650                 655

Ala Tyr Ser Asn Glu Asn Ala Gln Gly Ser Trp Asn Gly Asp Gln Asp
            660                 665                 670

Ala Gly Pro Leu Leu Val Glu Asn Pro Arg Asp Tyr Ser Thr Glu Leu
        675                 680                 685

Ser Val Thr Ile Ala Val Gly Ala Ser Leu Leu Phe Leu Asn Val Leu
    690                 695                 700

Ala Phe Ala Ala Leu Tyr Tyr Arg Lys Asp Lys Arg Arg Gln Glu Pro
705                 710                 715                 720

Leu Arg Gln Pro Ser Pro Gln Arg Gly Ala Gly Ala Pro Glu Leu Gly
                725                 730                 735

Ala Ala Pro Glu Glu Leu Ala Ala Leu Gln Leu Gly Pro Thr His
            740                 745                 750

His Glu Cys Glu Ala Gly Pro Pro His Asp Thr Leu Arg Leu Thr Ala
        755                 760                 765

Leu Pro Asp Tyr Thr Leu Thr Leu Arg Arg Ser Pro Asp Asp Ile Pro
    770                 775                 780

Leu Met Thr Pro Asn Thr Ile Thr Met Ile Pro Asn Ser Leu Val Gly
785                 790                 795                 800

Leu Gln Thr Leu His Pro Tyr Asn Thr Phe Ala Ala Gly Phe Asn Ser
                805                 810                 815

Thr Gly Leu Pro His Ser His Ser Thr Thr Arg Val
            820                 825

<210> SEQ ID NO 13
<211> LENGTH: 808

```
<212> TYPE: PRT
<213> ORGANISM: Homo sapiens

<400> SEQUENCE: 13

Met Trp Leu Arg Leu Gly Pro Pro Ser Leu Ser Leu Ser Pro Lys Pro
1               5                   10                  15

Thr Val Gly Arg Ser Leu Cys Leu Thr Leu Trp Phe Leu Ser Leu Ala
            20                  25                  30

Leu Arg Ala Ser Thr Gln Ala Pro Ala Pro Thr Val Asn Thr His Phe
        35                  40                  45

Gly Lys Leu Arg Gly Ala Arg Val Pro Leu Pro Ser Glu Ile Leu Gly
    50                  55                  60

Pro Val Asp Gln Tyr Leu Gly Val Pro Tyr Ala Ala Pro Pro Ile Gly
65                  70                  75                  80

Glu Lys Arg Phe Leu Pro Pro Glu Pro Pro Ser Trp Ser Gly Ile
            85                  90                  95

Arg Asn Ala Thr His Phe Pro Pro Val Cys Pro Gln Asn Ile His Thr
            100                 105                 110

Ala Val Pro Glu Val Met Leu Pro Val Trp Phe Thr Ala Asn Leu Asp
            115                 120                 125

Ile Val Ala Thr Tyr Ile Gln Glu Pro Asn Glu Asp Cys Leu Tyr Leu
            130                 135                 140

Asn Val Tyr Val Pro Thr Glu Asp Asp Ile Arg Asp Ser Gly Ala Lys
145                 150                 155                 160

Pro Val Met Val Tyr Ile His Gly Gly Ser Tyr Met Glu Gly Thr Gly
                165                 170                 175

Asn Met Ile Asp Gly Ser Ile Leu Ala Ser Tyr Gly Asn Val Ile Val
            180                 185                 190

Ile Thr Leu Asn Tyr Arg Val Gly Val Leu Gly Phe Leu Ser Thr Gly
            195                 200                 205

Asp Gln Ala Ala Lys Gly Asn Tyr Gly Leu Leu Asp Gln Ile Gln Ala
            210                 215                 220

Leu Arg Trp Val Ser Glu Asn Ile Ala Phe Phe Gly Gly Asp Pro Arg
225                 230                 235                 240

Arg Ile Thr Val Phe Gly Ser Gly Ile Gly Ala Ser Cys Val Ser Leu
                245                 250                 255

Leu Thr Leu Ser His His Ser Glu Gly Leu Phe Gln Arg Ala Ile Ile
            260                 265                 270

Gln Ser Gly Ser Ala Leu Ser Ser Trp Ala Val Asn Tyr Gln Pro Val
            275                 280                 285

Lys Tyr Thr Ser Leu Leu Ala Asp Lys Val Gly Cys Asn Val Leu Asp
            290                 295                 300

Thr Val Asp Met Val Asp Cys Leu Arg Gln Lys Ser Ala Lys Glu Leu
305                 310                 315                 320

Val Glu Gln Asp Ile Gln Pro Ala Arg Tyr His Val Ala Phe Gly Pro
                325                 330                 335

Val Ile Asp Gly Asp Val Ile Pro Asp Asp Pro Glu Ile Leu Met Glu
            340                 345                 350

Gln Gly Glu Phe Leu Asn Tyr Asp Ile Met Leu Gly Val Asn Gln Gly
            355                 360                 365

Glu Gly Leu Lys Phe Val Glu Gly Val Val Asp Pro Glu Asp Gly Val
            370                 375                 380

Ser Gly Thr Asp Phe Asp Tyr Ser Val Ser Asn Phe Val Asp Asn Leu
385                 390                 395                 400
```

```
Tyr Gly Tyr Pro Glu Gly Lys Asp Thr Leu Arg Glu Thr Ile Lys Phe
                405                 410                 415
Met Tyr Thr Asp Trp Ala Asp Arg Asp Asn Pro Glu Thr Arg Arg Lys
            420                 425                 430
Thr Leu Val Ala Leu Phe Thr Asp His Gln Trp Val Glu Pro Ser Val
        435                 440                 445
Val Thr Ala Asp Leu His Ala Arg Tyr Gly Ser Pro Thr Tyr Phe Tyr
    450                 455                 460
Ala Phe Tyr His His Cys Gln Ser Leu Met Lys Pro Ala Trp Ser Asp
465                 470                 475                 480
Ala Ala His Gly Asp Glu Val Pro Tyr Val Phe Gly Val Pro Met Val
                485                 490                 495
Gly Pro Thr Asp Leu Phe Pro Cys Asn Phe Ser Lys Asn Asp Val Met
            500                 505                 510
Leu Ser Ala Val Val Met Thr Tyr Trp Thr Asn Phe Ala Lys Thr Gly
        515                 520                 525
Asp Pro Asn Lys Pro Val Pro Gln Asp Thr Lys Phe Ile His Thr Lys
    530                 535                 540
Ala Asn Arg Phe Glu Glu Val Ala Trp Ser Lys Tyr Asn Pro Arg Asp
545                 550                 555                 560
Gln Leu Tyr Leu His Ile Gly Leu Lys Pro Arg Val Arg Asp His Tyr
                565                 570                 575
Arg Ala Thr Lys Val Ala Phe Trp Lys His Leu Val Pro His Leu Tyr
            580                 585                 590
Asn Leu His Asp Met Phe His Tyr Thr Ser Thr Thr Lys Val Pro
        595                 600                 605
Pro Pro Asp Thr Thr His Ser Ser His Ile Thr Arg Arg Pro Asn Gly
    610                 615                 620
Lys Thr Trp Ser Thr Lys Arg Pro Ala Ile Ser Pro Ala Tyr Ser Asn
625                 630                 635                 640
Glu Asn Ala Gln Gly Ser Trp Asn Gly Asp Gln Asp Ala Gly Pro Leu
                645                 650                 655
Leu Val Glu Asn Pro Arg Asp Tyr Ser Thr Glu Leu Ser Val Thr Ile
            660                 665                 670
Ala Val Gly Ala Ser Leu Leu Phe Leu Asn Val Leu Ala Phe Ala Ala
        675                 680                 685
Leu Tyr Tyr Arg Lys Asp Lys Arg Arg Gln Glu Pro Leu Arg Gln Pro
    690                 695                 700
Ser Pro Gln Arg Gly Ala Gly Ala Pro Glu Leu Gly Ala Ala Pro Glu
705                 710                 715                 720
Glu Glu Leu Ala Ala Leu Gln Leu Gly Pro Thr His His Glu Cys Glu
                725                 730                 735
Ala Gly Pro Pro His Asp Thr Leu Arg Leu Thr Ala Leu Pro Asp Tyr
            740                 745                 750
Thr Leu Thr Leu Arg Arg Ser Pro Asp Asp Ile Pro Leu Met Thr Pro
        755                 760                 765
Asn Thr Ile Thr Met Ile Pro Asn Ser Leu Val Gly Leu Gln Thr Leu
    770                 775                 780
His Pro Tyr Asn Thr Phe Ala Ala Gly Phe Asn Ser Thr Gly Leu Pro
785                 790                 795                 800
His Ser His Ser Thr Thr Arg Val
                805
```

<210> SEQ ID NO 14
<211> LENGTH: 472
<212> TYPE: PRT
<213> ORGANISM: Homo sapiens

<400> SEQUENCE: 14

Met Tyr Gln Arg Met Leu Arg Cys Gly Ala Glu Leu Gly Ser Pro Gly
1               5                   10                  15

Gly Gly Gly Gly Gly Gly Gly Gly Gly Ala Gly Gly Arg Leu Ala
            20                  25                  30

Leu Leu Trp Ile Val Pro Leu Thr Leu Ser Gly Leu Leu Gly Val Ala
            35                  40                  45

Trp Gly Ala Ser Ser Leu Gly Ala His His Ile His His Phe His Gly
        50                  55                  60

Ser Ser Lys His His Ser Val Pro Ile Ala Ile Tyr Arg Ser Pro Ala
65                  70                  75                  80

Ser Leu Arg Gly Gly His Ala Gly Thr Thr Tyr Ile Phe Ser Lys Gly
                85                  90                  95

Gly Gly Gln Ile Thr Tyr Lys Trp Pro Pro Asn Asp Arg Pro Ser Thr
            100                 105                 110

Arg Ala Asp Arg Leu Ala Ile Gly Phe Ser Thr Val Gln Lys Glu Ala
            115                 120                 125

Val Leu Val Arg Val Asp Ser Ser Ser Gly Leu Gly Asp Tyr Leu Glu
        130                 135                 140

Leu His Ile His Gln Gly Lys Ile Gly Val Lys Phe Asn Val Gly Thr
145                 150                 155                 160

Asp Asp Ile Ala Ile Glu Glu Ser Asn Ala Ile Ile Asn Asp Gly Lys
                165                 170                 175

Tyr His Val Val Arg Phe Thr Arg Ser Gly Gly Asn Ala Thr Leu Gln
            180                 185                 190

Val Asp Ser Trp Pro Val Ile Glu Arg Tyr Pro Ala Gly Asn Asn Asp
        195                 200                 205

Asn Glu Arg Leu Ala Ile Ala Arg Gln Arg Ile Pro Tyr Arg Leu Gly
    210                 215                 220

Arg Val Val Asp Glu Trp Leu Leu Asp Lys Gly Arg Gln Leu Thr Ile
225                 230                 235                 240

Phe Asn Ser Gln Ala Thr Ile Ile Gly Gly Lys Glu Gln Gly Gln
                245                 250                 255

Pro Phe Gln Gly Gln Leu Ser Gly Leu Tyr Tyr Asn Gly Leu Lys Val
            260                 265                 270

Leu Asn Met Ala Ala Glu Asn Asp Ala Asn Ile Ala Ile Val Gly Asn
        275                 280                 285

Val Arg Leu Val Gly Glu Val Pro Ser Ser Met Thr Thr Glu Ser Thr
    290                 295                 300

Ala Thr Ala Met Gln Ser Glu Met Ser Thr Ser Ile Met Glu Thr Thr
305                 310                 315                 320

Thr Thr Leu Ala Thr Ser Thr Ala Arg Arg Gly Lys Pro Pro Thr Lys
                325                 330                 335

Glu Pro Ile Ser Gln Thr Thr Asp Ile Leu Val Ala Ser Ala Glu
            340                 345                 350

Cys Pro Ser Asp Asp Glu Asp Ile Asp Pro Cys Glu Pro Ser Ser Gly
        355                 360                 365

Gly Leu Ala Asn Pro Thr Arg Ala Gly Gly Arg Glu Pro Tyr Pro Gly
    370                 375                 380

Ser Ala Glu Val Ile Arg Glu Ser Ser Thr Thr Gly Met Val Val
385                 390                 395                 400

Gly Ile Val Ala Ala Ala Leu Cys Ile Leu Ile Leu Leu Tyr Ala
            405                 410                 415

Met Tyr Lys Tyr Arg Asn Arg Asp Glu Gly Ser Tyr His Val Asp Glu
        420                 425                 430

Ser Arg Asn Tyr Ile Ser Asn Ser Ala Gln Ser Asn Gly Ala Val Val
        435                 440                 445

Lys Glu Lys Gln Pro Ser Ser Ala Lys Ser Ser Asn Lys Asn Lys Lys
        450                 455                 460

Asn Lys Asp Lys Glu Tyr Tyr Val
465                 470

<210> SEQ ID NO 15
<211> LENGTH: 442
<212> TYPE: PRT
<213> ORGANISM: Homo sapiens

<400> SEQUENCE: 15

Met Tyr Gln Arg Met Leu Arg Cys Gly Ala Glu Leu Gly Ser Pro Gly
1               5                   10                  15

Gly Gly Gly Gly Gly Gly Gly Gly Ala Gly Gly Arg Leu Ala
            20                  25                  30

Leu Leu Trp Ile Val Pro Leu Thr Leu Ser Gly Leu Leu Gly Val Ala
            35                  40                  45

Trp Gly Ala Ser Ser Leu Gly Ala His His Ile His His Phe His Gly
    50                  55                  60

Ser Ser Lys His His Ser Val Pro Ile Ala Ile Tyr Arg Ser Pro Ala
65                  70                  75                  80

Ser Leu Arg Gly Gly His Ala Gly Thr Thr Tyr Ile Phe Ser Lys Gly
                85                  90                  95

Gly Gly Gln Ile Thr Tyr Lys Trp Pro Pro Asn Asp Arg Pro Ser Thr
            100                 105                 110

Arg Ala Asp Arg Leu Ala Ile Gly Phe Ser Thr Val Gln Lys Glu Ala
        115                 120                 125

Val Leu Val Arg Val Asp Ser Ser Ser Gly Leu Gly Asp Tyr Leu Glu
    130                 135                 140

Leu His Ile His Gln Gly Lys Ile Gly Val Lys Phe Asn Val Gly Thr
145                 150                 155                 160

Asp Asp Ile Ala Ile Glu Glu Ser Asn Ala Ile Ile Asn Asp Gly Lys
                165                 170                 175

Tyr His Val Val Arg Phe Thr Arg Ser Gly Gly Asn Ala Thr Leu Gln
            180                 185                 190

Val Asp Ser Trp Pro Val Ile Glu Arg Tyr Pro Ala Gly Arg Gln Leu
        195                 200                 205

Thr Ile Phe Asn Ser Gln Ala Thr Ile Ile Gly Gly Lys Glu Gln Gln
    210                 215                 220

Gly Gln Pro Phe Gln Gly Gln Leu Ser Gly Leu Tyr Tyr Asn Gly Leu
225                 230                 235                 240

Lys Val Leu Asn Met Ala Ala Glu Asn Asp Ala Asn Ile Ala Ile Val
                245                 250                 255

Gly Asn Val Arg Leu Val Gly Glu Val Pro Ser Ser Met Thr Thr Glu
            260                 265                 270

Ser Thr Ala Thr Ala Met Gln Ser Glu Met Ser Thr Ser Ile Met Glu

```
              275                 280                 285
Thr Thr Thr Thr Leu Ala Thr Ser Thr Ala Arg Arg Gly Lys Pro Pro
        290                 295                 300

Thr Lys Glu Pro Ile Ser Gln Thr Thr Asp Asp Ile Leu Val Ala Ser
305                 310                 315                 320

Ala Glu Cys Pro Ser Asp Asp Glu Asp Ile Asp Pro Cys Glu Pro Ser
                    325                 330                 335

Ser Gly Gly Leu Ala Asn Pro Thr Arg Ala Gly Gly Arg Glu Pro Tyr
                340                 345                 350

Pro Gly Ser Ala Glu Val Ile Arg Glu Ser Ser Thr Thr Gly Met
            355                 360                 365

Val Val Gly Ile Val Ala Ala Ala Leu Cys Ile Leu Ile Leu Leu
        370                 375                 380

Tyr Ala Met Tyr Lys Tyr Arg Asn Arg Asp Glu Gly Ser Tyr His Val
385                 390                 395                 400

Asp Glu Ser Arg Asn Tyr Ile Ser Asn Ser Ala Gln Ser Asn Gly Ala
                405                 410                 415

Val Val Lys Glu Lys Gln Pro Ser Ser Ala Lys Ser Ser Asn Lys Asn
                420                 425                 430

Lys Lys Asn Lys Asp Lys Glu Tyr Tyr Val
            435                 440
```

<210> SEQ ID NO 16
<211> LENGTH: 1477
<212> TYPE: PRT
<213> ORGANISM: Homo sapiens

<400> SEQUENCE: 16

```
Met Gly Thr Ala Leu Leu Gln Arg Gly Gly Cys Phe Leu Leu Cys Leu
1               5                   10                  15

Ser Leu Leu Leu Leu Gly Cys Trp Ala Glu Leu Gly Ser Gly Leu Glu
                20                  25                  30

Phe Pro Gly Ala Glu Gly Gln Trp Thr Arg Phe Pro Lys Trp Asn Ala
            35                  40                  45

Cys Cys Glu Ser Glu Met Ser Phe Gln Leu Lys Thr Arg Ser Ala Arg
        50                  55                  60

Gly Leu Val Leu Tyr Phe Asp Asp Glu Gly Phe Cys Asp Phe Leu Glu
65                  70                  75                  80

Leu Ile Leu Thr Arg Gly Gly Arg Leu Gln Leu Ser Phe Ser Ile Phe
                85                  90                  95

Cys Ala Glu Pro Ala Thr Leu Leu Ala Asp Thr Pro Val Asn Asp Gly
                100                 105                 110

Ala Trp His Ser Val Arg Ile Arg Arg Gln Phe Arg Asn Thr Thr Leu
            115                 120                 125

Phe Ile Asp Gln Val Glu Ala Lys Trp Val Glu Val Lys Ser Lys Arg
130                 135                 140

Arg Asp Met Thr Val Phe Ser Gly Leu Phe Val Gly Gly Leu Pro Pro
145                 150                 155                 160

Glu Leu Arg Ala Ala Ala Leu Lys Leu Thr Leu Ala Ser Val Arg Glu
                165                 170                 175

Arg Glu Pro Phe Lys Gly Trp Ile Arg Asp Val Arg Val Asn Ser Ser
                180                 185                 190

Gln Val Leu Pro Val Asp Ser Gly Glu Val Lys Leu Asp Asp Glu Pro
            195                 200                 205
```

-continued

Pro Asn Ser Gly Gly Ser Pro Cys Glu Ala Gly Glu Gly Glu
210                 215                 220

Gly Gly Val Cys Leu Asn Gly Val Cys Ser Val Val Asp Asp Gln
225                 230                 235                 240

Ala Val Cys Asp Cys Ser Arg Thr Gly Phe Arg Gly Lys Asp Cys Ser
                245                 250                 255

Gln Glu Asp Asn Asn Val Glu Gly Leu Ala His Leu Met Met Gly Asp
            260                 265                 270

Gln Gly Lys Ser Lys Gly Lys Glu Glu Tyr Ile Ala Thr Phe Lys Gly
        275                 280                 285

Ser Glu Tyr Phe Cys Tyr Asp Leu Ser Gln Asn Pro Ile Gln Ser Ser
290                 295                 300

Ser Asp Glu Ile Thr Leu Ser Phe Lys Thr Leu Gln Arg Asn Gly Leu
305                 310                 315                 320

Met Leu His Thr Gly Lys Ser Ala Asp Tyr Val Asn Leu Ala Leu Lys
                325                 330                 335

Asn Gly Ala Val Ser Leu Val Ile Asn Leu Gly Ser Gly Ala Phe Glu
            340                 345                 350

Ala Leu Val Glu Pro Val Asn Gly Lys Phe Asn Asp Asn Ala Trp His
        355                 360                 365

Asp Val Lys Val Thr Arg Asn Leu Arg Gln His Ser Gly Ile Gly His
370                 375                 380

Ala Met Val Thr Ile Ser Val Asp Gly Ile Leu Thr Thr Thr Gly Tyr
385                 390                 395                 400

Thr Gln Glu Asp Tyr Thr Met Leu Gly Ser Asp Asp Phe Phe Tyr Val
                405                 410                 415

Gly Gly Ser Pro Ser Thr Ala Asp Leu Pro Gly Ser Pro Val Ser Asn
            420                 425                 430

Asn Phe Met Gly Cys Leu Lys Glu Val Val Tyr Lys Asn Asn Asp Val
        435                 440                 445

Arg Leu Glu Leu Ser Arg Leu Ala Lys Gln Gly Asp Pro Lys Met Lys
450                 455                 460

Ile His Gly Val Val Ala Phe Lys Cys Glu Asn Val Ala Thr Leu Asp
465                 470                 475                 480

Pro Ile Thr Phe Glu Thr Pro Glu Ser Phe Ile Ser Leu Pro Lys Trp
                485                 490                 495

Asn Ala Lys Lys Thr Gly Ser Ile Ser Phe Asp Phe Arg Thr Thr Glu
            500                 505                 510

Pro Asn Gly Leu Ile Leu Phe Ser His Gly Lys Pro Arg His Gln Lys
        515                 520                 525

Asp Ala Lys His Pro Gln Met Ile Lys Val Asp Phe Phe Ala Ile Glu
530                 535                 540

Met Leu Asp Gly His Leu Tyr Leu Leu Leu Asp Met Gly Ser Gly Thr
545                 550                 555                 560

Ile Lys Ile Lys Ala Leu Leu Lys Lys Val Asn Asp Gly Glu Trp Tyr
                565                 570                 575

His Val Asp Phe Gln Arg Asp Gly Arg Ser Gly Thr Ile Ser Val Asn
            580                 585                 590

Thr Leu Arg Thr Pro Tyr Thr Ala Pro Gly Glu Ser Glu Ile Leu Asp
        595                 600                 605

Leu Asp Asp Glu Leu Tyr Leu Gly Gly Leu Pro Glu Asn Lys Ala Gly
610                 615                 620

Leu Val Phe Pro Thr Glu Val Trp Thr Ala Leu Leu Asn Tyr Gly Tyr

```
                625                 630                 635                 640
        Val Gly Cys Ile Arg Asp Leu Phe Ile Asp Gly Gln Ser Lys Asp Ile
                        645                 650                 655

Arg Gln Met Ala Glu Val Gln Ser Thr Ala Gly Val Lys Pro Ser Cys
                        660                 665                 670

Ser Lys Glu Thr Ala Lys Pro Cys Leu Ser Asn Pro Cys Lys Asn Asn
                        675                 680                 685

Gly Met Cys Arg Asp Gly Trp Asn Arg Tyr Val Cys Asp Cys Ser Gly
                        690                 695                 700

Thr Gly Tyr Leu Gly Arg Ser Cys Glu Arg Glu Ala Thr Val Leu Ser
        705                 710                 715                 720

Tyr Asp Gly Ser Met Phe Met Lys Ile Gln Leu Pro Val Val Met His
                        725                 730                 735

Thr Glu Ala Glu Asp Val Ser Leu Arg Phe Arg Ser Gln Arg Ala Tyr
                        740                 745                 750

Gly Ile Leu Met Ala Thr Thr Ser Arg Asp Ser Ala Asp Thr Leu Arg
                        755                 760                 765

Leu Glu Leu Asp Ala Gly Arg Val Lys Leu Thr Val Asn Leu Asp Cys
                        770                 775                 780

Ile Arg Ile Asn Cys Asn Ser Ser Lys Gly Pro Glu Thr Leu Phe Ala
        785                 790                 795                 800

Gly Tyr Asn Leu Asn Asp Asn Glu Trp His Thr Val Arg Val Val Arg
                        805                 810                 815

Arg Gly Lys Ser Leu Lys Leu Thr Val Asp Asp Gln Gln Ala Met Thr
                        820                 825                 830

Gly Gln Met Ala Gly Asp His Thr Arg Leu Glu Phe His Asn Ile Glu
                        835                 840                 845

Thr Gly Ile Ile Thr Glu Arg Arg Tyr Leu Ser Ser Val Pro Ser Asn
                        850                 855                 860

Phe Ile Gly His Leu Gln Ser Leu Thr Phe Asn Gly Met Ala Tyr Ile
        865                 870                 875                 880

Asp Leu Cys Lys Asn Gly Asp Ile Asp Tyr Cys Glu Leu Asn Ala Arg
                        885                 890                 895

Phe Gly Phe Arg Asn Ile Ile Ala Asp Pro Val Thr Phe Lys Thr Lys
                        900                 905                 910

Ser Ser Tyr Val Ala Leu Ala Thr Leu Gln Ala Tyr Thr Ser Met His
                        915                 920                 925

Leu Phe Phe Gln Phe Lys Thr Thr Ser Leu Asp Gly Leu Ile Leu Tyr
                        930                 935                 940

Asn Ser Gly Asp Gly Asn Asp Phe Ile Val Val Glu Leu Val Lys Gly
        945                 950                 955                 960

Tyr Leu His Tyr Val Phe Asp Leu Gly Asn Gly Ala Asn Leu Ile Lys
                        965                 970                 975

Gly Ser Ser Asn Lys Pro Leu Asn Asp Asn Gln Trp His Asn Val Met
                        980                 985                 990

Ile Ser Arg Asp Thr Ser Asn Leu His Thr Val Lys Ile Asp Thr Lys
                        995                 1000                1005

Ile Thr Thr Gln Ile Thr Ala Gly Ala Arg Asn Leu Asp Leu Lys
                        1010                1015                1020

Ser Asp Leu Tyr Ile Gly Gly Val Ala Lys Glu Thr Tyr Lys Ser
                        1025                1030                1035

Leu Pro Lys Leu Val His Ala Lys Glu Gly Phe Gln Gly Cys Leu
                        1040                1045                1050
```

```
Ala Ser Val Asp Leu Asn Gly Arg Leu Pro Asp Leu Ile Ser Asp
    1055                1060                1065

Ala Leu Phe Cys Asn Gly Gln Ile Glu Arg Gly Cys Glu Gly Pro
    1070                1075                1080

Ser Thr Thr Cys Gln Glu Asp Ser Cys Ser Asn Gln Gly Val Cys
    1085                1090                1095

Leu Gln Gln Trp Asp Gly Phe Ser Cys Asp Cys Ser Met Thr Ser
    1100                1105                1110

Phe Ser Gly Pro Leu Cys Asn Asp Pro Gly Thr Thr Tyr Ile Phe
    1115                1120                1125

Ser Lys Gly Gly Gln Ile Thr Tyr Lys Trp Pro Pro Asn Asp
    1130                1135                1140

Arg Pro Ser Thr Arg Ala Asp Arg Leu Ala Ile Gly Phe Ser Thr
    1145                1150                1155

Val Gln Lys Glu Ala Val Leu Val Arg Val Asp Ser Ser Ser Gly
    1160                1165                1170

Leu Gly Asp Tyr Leu Glu Leu His Ile His Gln Gly Lys Ile Gly
    1175                1180                1185

Val Lys Phe Asn Val Gly Thr Asp Asp Ile Ala Ile Glu Glu Ser
    1190                1195                1200

Asn Ala Ile Ile Asn Asp Gly Lys Tyr His Val Val Arg Phe Thr
    1205                1210                1215

Arg Ser Gly Gly Asn Ala Thr Leu Gln Val Asp Ser Trp Pro Val
    1220                1225                1230

Ile Glu Arg Tyr Pro Ala Gly Arg Gln Leu Thr Ile Phe Asn Ser
    1235                1240                1245

Gln Ala Thr Ile Ile Ile Gly Gly Lys Glu Gln Gly Gln Pro Phe
    1250                1255                1260

Gln Gly Gln Leu Ser Gly Leu Tyr Tyr Asn Gly Leu Lys Val Leu
    1265                1270                1275

Asn Met Ala Ala Glu Asn Asp Ala Asn Ile Ala Ile Val Gly Asn
    1280                1285                1290

Val Arg Leu Val Gly Glu Val Pro Ser Ser Met Thr Thr Glu Ser
    1295                1300                1305

Thr Ala Thr Ala Met Gln Ser Glu Met Ser Thr Ser Ile Met Glu
    1310                1315                1320

Thr Thr Thr Thr Leu Ala Thr Ser Thr Ala Arg Arg Gly Lys Pro
    1325                1330                1335

Pro Thr Lys Glu Pro Ile Ser Gln Thr Thr Asp Asp Ile Leu Val
    1340                1345                1350

Ala Ser Ala Glu Cys Pro Ser Asp Asp Glu Asp Ile Asp Pro Cys
    1355                1360                1365

Glu Pro Ser Ser Gly Gly Leu Ala Asn Pro Thr Arg Ala Gly Gly
    1370                1375                1380

Arg Glu Pro Tyr Pro Gly Ser Ala Glu Val Ile Arg Glu Ser Ser
    1385                1390                1395

Ser Thr Thr Gly Met Val Val Gly Ile Val Ala Ala Ala Ala Leu
    1400                1405                1410

Cys Ile Leu Ile Leu Leu Tyr Ala Met Tyr Lys Tyr Arg Asn Arg
    1415                1420                1425

Asp Glu Gly Ser Tyr His Val Asp Glu Ser Arg Asn Tyr Ile Ser
    1430                1435                1440
```

-continued

Asn Ser Ala Gln Ser Asn Gly Ala Val Val Lys Glu Lys Gln Pro
    1445                1450                1455

Ser Ser Ala Lys Ser Ser Asn Lys Asn Lys Lys Asn Lys Asp Lys
    1460                1465                1470

Glu Tyr Tyr Val
    1475

<210> SEQ ID NO 17
<211> LENGTH: 1496
<212> TYPE: PRT
<213> ORGANISM: Homo sapiens

<400> SEQUENCE: 17

Met Gly Thr Ala Leu Leu Gln Arg Gly Gly Cys Phe Leu Leu Cys Leu
1               5                   10                  15

Ser Leu Leu Leu Leu Gly Cys Trp Ala Glu Leu Gly Ser Gly Leu Glu
                20                  25                  30

Phe Pro Gly Ala Glu Gly Gln Trp Thr Arg Phe Pro Lys Trp Asn Ala
            35                  40                  45

Cys Cys Glu Ser Glu Met Ser Phe Gln Leu Lys Thr Arg Ser Ala Arg
        50                  55                  60

Gly Leu Val Leu Tyr Phe Asp Asp Glu Gly Phe Cys Asp Phe Leu Glu
65                  70                  75                  80

Leu Ile Leu Thr Arg Gly Gly Arg Leu Gln Leu Ser Phe Ser Ile Phe
                85                  90                  95

Cys Ala Glu Pro Ala Thr Leu Leu Ala Asp Thr Pro Val Asn Asp Gly
            100                 105                 110

Ala Trp His Ser Val Arg Ile Arg Arg Gln Phe Arg Asn Thr Thr Leu
        115                 120                 125

Phe Ile Asp Gln Val Glu Ala Lys Trp Val Glu Val Lys Ser Lys Arg
    130                 135                 140

Arg Asp Met Thr Val Phe Ser Gly Leu Phe Val Gly Gly Leu Pro Pro
145                 150                 155                 160

Glu Leu Arg Ala Ala Ala Leu Lys Leu Thr Leu Ala Ser Val Arg Glu
                165                 170                 175

Arg Glu Pro Phe Lys Gly Trp Ile Arg Asp Val Arg Val Asn Ser Ser
            180                 185                 190

Gln Val Leu Pro Val Asp Ser Gly Glu Val Lys Leu Asp Asp Glu Pro
        195                 200                 205

Pro Asn Ser Gly Gly Gly Ser Pro Cys Glu Ala Gly Glu Glu Gly Glu
    210                 215                 220

Gly Gly Val Cys Leu Asn Gly Gly Val Cys Ser Val Val Asp Asp Gln
225                 230                 235                 240

Ala Val Cys Asp Cys Ser Arg Thr Gly Phe Arg Gly Lys Asp Cys Ser
                245                 250                 255

Gln Glu Asp Asn Asn Val Glu Gly Leu Ala His Leu Met Met Gly Asp
            260                 265                 270

Gln Gly Lys Ser Lys Gly Lys Glu Glu Tyr Ile Ala Thr Phe Lys Gly
        275                 280                 285

Ser Glu Tyr Phe Cys Tyr Asp Leu Ser Gln Asn Pro Ile Gln Ser Ser
    290                 295                 300

Ser Asp Glu Ile Thr Leu Ser Phe Lys Thr Leu Gln Arg Asn Gly Leu
305                 310                 315                 320

Met Leu His Thr Gly Lys Ser Ala Asp Tyr Val Asn Leu Ala Leu Lys
                325                 330                 335

```
Asn Gly Ala Val Ser Leu Val Ile Asn Leu Gly Ser Gly Ala Phe Glu
                340                 345                 350

Ala Leu Val Glu Pro Val Asn Gly Lys Phe Asn Asp Asn Ala Trp His
                355                 360                 365

Asp Val Lys Val Thr Arg Asn Leu Arg Gln Val Thr Ile Ser Val Asp
            370                 375                 380

Gly Ile Leu Thr Thr Thr Gly Tyr Thr Gln Glu Asp Tyr Thr Met Leu
385                 390                 395                 400

Gly Ser Asp Asp Phe Phe Tyr Val Gly Gly Ser Pro Ser Thr Ala Asp
                    405                 410                 415

Leu Pro Gly Ser Pro Val Ser Asn Asn Phe Met Gly Cys Leu Lys Glu
                420                 425                 430

Val Val Tyr Lys Asn Asn Asp Val Arg Leu Glu Leu Ser Arg Leu Ala
                435                 440                 445

Lys Gln Gly Asp Pro Lys Met Lys Ile His Gly Val Val Ala Phe Lys
                450                 455                 460

Cys Glu Asn Val Ala Thr Leu Asp Pro Ile Thr Phe Glu Thr Pro Glu
465                 470                 475                 480

Ser Phe Ile Ser Leu Pro Lys Trp Asn Ala Lys Lys Thr Gly Ser Ile
                485                 490                 495

Ser Phe Asp Phe Arg Thr Thr Glu Pro Asn Gly Leu Ile Leu Phe Ser
                500                 505                 510

His Gly Lys Pro Arg His Gln Lys Asp Ala Lys His Pro Gln Met Ile
                515                 520                 525

Lys Val Asp Phe Phe Ala Ile Glu Met Leu Asp Gly His Leu Tyr Leu
                530                 535                 540

Leu Leu Asp Met Gly Ser Gly Thr Ile Lys Ile Lys Ala Leu Leu Lys
545                 550                 555                 560

Lys Val Asn Asp Gly Glu Trp Tyr His Val Asp Phe Gln Arg Asp Gly
                565                 570                 575

Arg Ser Gly Thr Ile Ser Val Asn Thr Leu Arg Thr Pro Tyr Thr Ala
                580                 585                 590

Pro Gly Glu Ser Glu Ile Leu Asp Leu Asp Asp Glu Leu Tyr Leu Gly
                595                 600                 605

Gly Leu Pro Glu Asn Lys Ala Gly Leu Val Phe Pro Thr Glu Val Trp
                610                 615                 620

Thr Ala Leu Leu Asn Tyr Gly Tyr Val Gly Cys Ile Arg Asp Leu Phe
625                 630                 635                 640

Ile Asp Gly Gln Ser Lys Asp Ile Arg Gln Met Ala Glu Val Gln Ser
                    645                 650                 655

Thr Ala Gly Val Lys Pro Ser Cys Ser Lys Glu Thr Ala Lys Pro Cys
                660                 665                 670

Leu Ser Asn Pro Cys Lys Asn Asn Gly Met Cys Arg Asp Gly Trp Asn
                675                 680                 685

Arg Tyr Val Cys Asp Cys Ser Gly Thr Gly Tyr Leu Gly Arg Ser Cys
                690                 695                 700

Glu Arg Glu Ala Thr Val Leu Ser Tyr Asp Gly Ser Met Phe Met Lys
705                 710                 715                 720

Ile Gln Leu Pro Val Val Met His Thr Glu Ala Glu Asp Val Ser Leu
                725                 730                 735

Arg Phe Arg Ser Gln Arg Ala Tyr Gly Ile Leu Met Ala Thr Thr Ser
                740                 745                 750
```

-continued

Arg Asp Ser Ala Asp Thr Leu Arg Leu Glu Leu Asp Ala Gly Arg Val
            755                 760                 765

Lys Leu Thr Val Asn Leu Asp Cys Ile Arg Ile Asn Cys Asn Ser Ser
770                 775                 780

Lys Gly Pro Glu Thr Leu Phe Ala Gly Tyr Asn Leu Asn Asp Asn Glu
785                 790                 795                 800

Trp His Thr Val Arg Val Arg Arg Gly Lys Ser Leu Lys Leu Thr
                805                 810                 815

Val Asp Asp Gln Gln Ala Met Thr Gly Gln Met Ala Gly Asp His Thr
            820                 825                 830

Arg Leu Glu Phe His Asn Ile Glu Thr Gly Ile Ile Thr Glu Arg Arg
        835                 840                 845

Tyr Leu Ser Ser Val Pro Ser Asn Phe Ile Gly His Leu Gln Ser Leu
    850                 855                 860

Thr Phe Asn Gly Met Ala Tyr Ile Asp Leu Cys Lys Asn Gly Asp Ile
865                 870                 875                 880

Asp Tyr Cys Glu Leu Asn Ala Arg Phe Gly Phe Arg Asn Ile Ile Ala
                885                 890                 895

Asp Pro Val Thr Phe Lys Thr Lys Ser Ser Tyr Val Ala Leu Ala Thr
            900                 905                 910

Leu Gln Ala Tyr Thr Ser Met His Leu Phe Phe Gln Phe Lys Thr Thr
        915                 920                 925

Ser Leu Asp Gly Leu Ile Leu Tyr Asn Ser Gly Asp Gly Asn Asp Phe
930                 935                 940

Ile Val Val Glu Leu Val Lys Gly Tyr Leu His Tyr Val Phe Asp Leu
945                 950                 955                 960

Gly Asn Gly Ala Asn Leu Ile Lys Gly Ser Ser Asn Lys Pro Leu Asn
                965                 970                 975

Asp Asn Gln Trp His Asn Val Met Ile Ser Arg Asp Thr Ser Asn Leu
            980                 985                 990

His Thr Val Lys Ile Asp Thr Lys Ile Thr Thr Gln Ile Thr Ala Gly
        995                 1000                1005

Ala Arg Asn Leu Asp Leu Lys Ser Asp Leu Tyr Ile Gly Gly Val
    1010                1015                1020

Ala Lys Glu Thr Tyr Lys Ser Leu Pro Lys Leu Val His Ala Lys
    1025                1030                1035

Glu Gly Phe Gln Gly Cys Leu Ala Ser Val Asp Leu Asn Gly Arg
    1040                1045                1050

Leu Pro Asp Leu Ile Ser Asp Ala Leu Phe Cys Asn Gly Gln Ile
    1055                1060                1065

Glu Arg Gly Cys Glu Gly Pro Ser Thr Thr Cys Gln Glu Asp Ser
    1070                1075                1080

Cys Ser Asn Gln Gly Val Cys Leu Gln Gln Trp Asp Gly Phe Ser
    1085                1090                1095

Cys Asp Cys Ser Met Thr Ser Phe Ser Gly Pro Leu Cys Asn Asp
    1100                1105                1110

Pro Gly Thr Thr Tyr Ile Phe Ser Lys Gly Gly Gly Gln Ile Thr
    1115                1120                1125

Tyr Lys Trp Pro Pro Asn Asp Arg Pro Ser Thr Arg Ala Asp Arg
    1130                1135                1140

Leu Ala Ile Gly Phe Ser Thr Val Gln Lys Glu Ala Val Leu Val
    1145                1150                1155

Arg Val Asp Ser Ser Ser Gly Leu Gly Asp Tyr Leu Glu Leu His

```
                1160                1165                1170

Ile His Gln Gly Lys Ile Gly Val Lys Phe Asn Val Gly Thr Asp
    1175                1180                1185

Asp Ile Ala Ile Glu Glu Ser Asn Ala Ile Ile Asn Asp Gly Lys
    1190                1195                1200

Tyr His Val Val Arg Phe Thr Arg Ser Gly Gly Asn Ala Thr Leu
    1205                1210                1215

Gln Val Asp Ser Trp Pro Val Ile Glu Arg Tyr Pro Ala Gly Asn
    1220                1225                1230

Asn Asp Asn Glu Arg Leu Ala Ile Ala Arg Gln Arg Ile Pro Tyr
    1235                1240                1245

Arg Leu Gly Arg Val Val Asp Glu Trp Leu Leu Asp Lys Gly Arg
    1250                1255                1260

Gln Leu Thr Ile Phe Asn Ser Gln Ala Thr Ile Ile Ile Gly Gly
    1265                1270                1275

Lys Glu Gln Gly Gln Pro Phe Gln Gly Gln Leu Ser Gly Leu Tyr
    1280                1285                1290

Tyr Asn Gly Leu Lys Val Leu Asn Met Ala Ala Glu Asn Asp Ala
    1295                1300                1305

Asn Ile Ala Ile Val Gly Asn Val Arg Leu Val Gly Glu Val Pro
    1310                1315                1320

Ser Ser Met Thr Thr Glu Ser Thr Ala Thr Ala Met Gln Ser Glu
    1325                1330                1335

Met Ser Thr Ser Ile Met Glu Thr Thr Thr Thr Leu Ala Thr Ser
    1340                1345                1350

Thr Ala Arg Arg Gly Lys Pro Pro Thr Lys Glu Pro Ile Ser Gln
    1355                1360                1365

Thr Thr Asp Asp Ile Leu Val Ala Ser Ala Glu Cys Pro Ser Asp
    1370                1375                1380

Asp Glu Asp Ile Asp Pro Cys Glu Pro Ser Ser Ala Asn Pro Thr
    1385                1390                1395

Arg Ala Gly Gly Arg Glu Pro Tyr Pro Gly Ser Ala Glu Val Ile
    1400                1405                1410

Arg Glu Ser Ser Ser Thr Thr Gly Met Val Val Gly Ile Val Ala
    1415                1420                1425

Ala Ala Ala Leu Cys Ile Leu Ile Leu Leu Tyr Ala Met Tyr Lys
    1430                1435                1440

Tyr Arg Asn Arg Asp Glu Gly Ser Tyr His Val Asp Glu Ser Arg
    1445                1450                1455

Asn Tyr Ile Ser Asn Ser Ala Gln Ser Asn Gly Ala Val Val Lys
    1460                1465                1470

Glu Lys Gln Pro Ser Ser Ala Lys Ser Ser Asn Lys Asn Lys Lys
    1475                1480                1485

Asn Lys Asp Lys Glu Tyr Tyr Val
    1490                1495

<210> SEQ ID NO 18
<211> LENGTH: 1547
<212> TYPE: PRT
<213> ORGANISM: Homo sapiens

<400> SEQUENCE: 18

Met Gly Thr Ala Leu Leu Gln Arg Gly Gly Cys Phe Leu Leu Cys Leu
1               5                   10                  15
```

Ser Leu Leu Leu Leu Gly Cys Trp Ala Glu Leu Gly Ser Gly Leu Glu
                20                  25                  30

Phe Pro Gly Ala Glu Gly Gln Trp Thr Arg Phe Pro Lys Trp Asn Ala
            35                  40                  45

Cys Cys Glu Ser Glu Met Ser Phe Gln Leu Lys Thr Arg Ser Ala Arg
        50                  55                  60

Gly Leu Val Leu Tyr Phe Asp Asp Glu Gly Phe Cys Asp Phe Leu Glu
65                  70                  75                  80

Leu Ile Leu Thr Arg Gly Gly Arg Leu Gln Leu Ser Phe Ser Ile Phe
                85                  90                  95

Cys Ala Glu Pro Ala Thr Leu Leu Ala Asp Thr Pro Val Asn Asp Gly
            100                 105                 110

Ala Trp His Ser Val Arg Ile Arg Arg Gln Phe Arg Asn Thr Thr Leu
        115                 120                 125

Phe Ile Asp Gln Val Glu Ala Lys Trp Val Glu Val Lys Ser Lys Arg
    130                 135                 140

Arg Asp Met Thr Val Phe Ser Gly Leu Phe Val Gly Gly Leu Pro Pro
145                 150                 155                 160

Glu Leu Arg Ala Ala Ala Leu Lys Leu Thr Leu Ala Ser Val Arg Glu
                165                 170                 175

Arg Glu Pro Phe Lys Gly Trp Ile Arg Asp Val Arg Val Asn Ser Ser
            180                 185                 190

Gln Val Leu Pro Val Asp Ser Gly Glu Val Lys Leu Asp Asp Glu Pro
        195                 200                 205

Pro Asn Ser Gly Gly Gly Ser Pro Cys Glu Ala Gly Glu Glu Gly Glu
210                 215                 220

Gly Gly Val Cys Leu Asn Gly Gly Val Cys Ser Val Val Asp Asp Gln
225                 230                 235                 240

Ala Val Cys Asp Cys Ser Arg Thr Gly Phe Arg Gly Lys Asp Cys Ser
                245                 250                 255

Gln Glu Ile Lys Phe Gly Leu Gln Cys Val Leu Pro Val Leu Leu His
            260                 265                 270

Asp Asn Asp Gln Gly Lys Tyr Cys Cys Ile Asn Thr Ala Lys Pro Leu
        275                 280                 285

Thr Glu Lys Asp Asn Asn Val Glu Gly Leu Ala His Leu Met Met Gly
    290                 295                 300

Asp Gln Gly Lys Ser Lys Gly Lys Glu Glu Tyr Ile Ala Thr Phe Lys
305                 310                 315                 320

Gly Ser Glu Tyr Phe Cys Tyr Asp Leu Ser Gln Asn Pro Ile Gln Ser
                325                 330                 335

Ser Ser Asp Glu Ile Thr Leu Ser Phe Lys Thr Leu Gln Arg Asn Gly
            340                 345                 350

Leu Met Leu His Thr Gly Lys Ser Ala Asp Tyr Val Asn Leu Ala Leu
        355                 360                 365

Lys Asn Gly Ala Val Ser Leu Val Ile Asn Leu Gly Ser Gly Ala Phe
    370                 375                 380

Glu Ala Leu Val Glu Pro Val Asn Gly Lys Phe Asn Asp Asn Ala Trp
385                 390                 395                 400

His Asp Val Lys Val Thr Arg Asn Leu Arg Gln His Ser Gly Ile Gly
                405                 410                 415

His Ala Met Val Asn Lys Leu His Cys Ser Val Thr Ile Ser Val Asp
            420                 425                 430

Gly Ile Leu Thr Thr Thr Gly Tyr Thr Gln Glu Asp Tyr Thr Met Leu 435                 440                 445
Gly Ser Asp Asp Phe Phe Tyr Val Gly Gly Ser Pro Ser Thr Ala Asp
450                     455                 460

Leu Pro Gly Ser Pro Val Ser Asn Asn Phe Met Gly Cys Leu Lys Glu
465                     470                 475                 480

Val Val Tyr Lys Asn Asn Asp Val Arg Leu Glu Leu Ser Arg Leu Ala
                    485                 490                 495

Lys Gln Gly Asp Pro Lys Met Lys Ile His Gly Val Val Ala Phe Lys
                500                 505                 510

Cys Glu Asn Val Ala Thr Leu Asp Pro Ile Thr Phe Glu Thr Pro Glu
                515                 520                 525

Ser Phe Ile Ser Leu Pro Lys Trp Asn Ala Lys Lys Thr Gly Ser Ile
530                 535                 540

Ser Phe Asp Phe Arg Thr Thr Glu Pro Asn Gly Leu Ile Leu Phe Ser
545                 550                 555                 560

His Gly Lys Pro Arg His Gln Lys Asp Ala Lys His Pro Gln Met Ile
                565                 570                 575

Lys Val Asp Phe Phe Ala Ile Glu Met Leu Asp Gly His Leu Tyr Leu
                580                 585                 590

Leu Leu Asp Met Gly Ser Gly Thr Ile Lys Ile Lys Ala Leu Leu Lys
                595                 600                 605

Lys Val Asn Asp Gly Glu Trp Tyr His Val Asp Phe Gln Arg Asp Gly
610                 615                 620

Arg Ser Gly Thr Ile Ser Val Asn Thr Leu Arg Thr Pro Tyr Thr Ala
625                 630                 635                 640

Pro Gly Glu Ser Glu Ile Leu Asp Leu Asp Asp Glu Leu Tyr Leu Gly
                    645                 650                 655

Gly Leu Pro Glu Asn Lys Ala Gly Leu Val Phe Pro Thr Glu Val Trp
                660                 665                 670

Thr Ala Leu Leu Asn Tyr Gly Tyr Val Gly Cys Ile Arg Asp Leu Phe
                675                 680                 685

Ile Asp Gly Gln Ser Lys Asp Ile Arg Gln Met Ala Glu Val Gln Ser
            690                 695                 700

Thr Ala Gly Val Lys Pro Ser Cys Ser Lys Glu Thr Ala Lys Pro Cys
705                 710                 715                 720

Leu Ser Asn Pro Cys Lys Asn Asn Gly Met Cys Arg Asp Gly Trp Asn
                725                 730                 735

Arg Tyr Val Cys Asp Cys Ser Gly Thr Gly Tyr Leu Gly Arg Ser Cys
                740                 745                 750

Glu Arg Glu Ala Thr Val Leu Ser Tyr Asp Gly Ser Met Phe Met Lys
            755                 760                 765

Ile Gln Leu Pro Val Val Met His Thr Glu Ala Glu Asp Val Ser Leu
            770                 775                 780

Arg Phe Arg Ser Gln Arg Ala Tyr Gly Ile Leu Met Ala Thr Thr Ser
785                 790                 795                 800

Arg Asp Ser Ala Asp Thr Leu Arg Leu Glu Leu Asp Ala Gly Arg Val
                    805                 810                 815

Lys Leu Thr Val Asn Leu Asp Cys Ile Arg Ile Asn Cys Asn Ser Ser
                820                 825                 830

Lys Gly Pro Glu Thr Leu Phe Ala Gly Tyr Asn Leu Asn Asp Asn Glu
            835                 840                 845

Trp His Thr Val Arg Val Val Arg Gly Lys Ser Leu Lys Leu Thr
850                 855                 860

-continued

```
Val Asp Asp Gln Gln Ala Met Thr Gly Gln Met Ala Gly Asp His Thr
865                 870                 875                 880

Arg Leu Glu Phe His Asn Ile Glu Thr Gly Ile Ile Thr Glu Arg Arg
            885                 890                 895

Tyr Leu Ser Ser Val Pro Ser Asn Phe Ile Gly His Leu Gln Ser Leu
        900                 905                 910

Thr Phe Asn Gly Met Ala Tyr Ile Asp Leu Cys Lys Asn Gly Asp Ile
    915                 920                 925

Asp Tyr Cys Glu Leu Asn Ala Arg Phe Gly Phe Arg Asn Ile Ile Ala
930                 935                 940

Asp Pro Val Thr Phe Lys Thr Lys Ser Ser Tyr Val Ala Leu Ala Thr
945                 950                 955                 960

Leu Gln Ala Tyr Thr Ser Met His Leu Phe Phe Gln Phe Lys Thr Thr
            965                 970                 975

Ser Leu Asp Gly Leu Ile Leu Tyr Asn Ser Gly Asp Gly Asn Asp Phe
        980                 985                 990

Ile Val Val Glu Leu Val Lys Gly Tyr Leu His Tyr Val Phe Asp Leu
    995                 1000                1005

Gly Asn Gly Ala Asn Leu Ile Lys Gly Ser Ser Asn Lys Pro Leu
    1010                1015                1020

Asn Asp Asn Gln Trp His Asn Val Met Ile Ser Arg Asp Thr Ser
    1025                1030                1035

Asn Leu His Thr Val Lys Ile Asp Thr Lys Ile Thr Thr Gln Ile
    1040                1045                1050

Thr Ala Gly Ala Arg Asn Leu Asp Leu Lys Ser Asp Leu Tyr Ile
    1055                1060                1065

Gly Gly Val Ala Lys Glu Thr Tyr Lys Ser Leu Pro Lys Leu Val
    1070                1075                1080

His Ala Lys Glu Gly Phe Gln Gly Cys Leu Ala Ser Val Asp Leu
    1085                1090                1095

Asn Gly Arg Leu Pro Asp Leu Ile Ser Asp Ala Leu Phe Cys Asn
    1100                1105                1110

Gly Gln Ile Glu Arg Gly Cys Glu Gly Pro Ser Thr Thr Cys Gln
    1115                1120                1125

Glu Asp Ser Cys Ser Asn Gln Gly Val Cys Leu Gln Gln Trp Asp
    1130                1135                1140

Gly Phe Ser Cys Asp Cys Ser Met Thr Ser Phe Ser Gly Pro Leu
    1145                1150                1155

Cys Asn Asp Pro Gly Thr Thr Tyr Ile Phe Ser Lys Gly Gly Gly
    1160                1165                1170

Gln Ile Thr Tyr Lys Trp Pro Pro Asn Asp Arg Pro Ser Thr Arg
    1175                1180                1185

Ala Asp Arg Leu Ala Ile Gly Phe Ser Thr Val Gln Lys Glu Ala
    1190                1195                1200

Val Leu Val Arg Val Asp Ser Ser Ser Gly Leu Gly Asp Tyr Leu
    1205                1210                1215

Glu Leu His Ile His Gln Gly Lys Ile Gly Val Lys Phe Asn Val
    1220                1225                1230

Gly Thr Asp Asp Ile Ala Ile Glu Glu Ser Asn Ala Ile Ile Asn
    1235                1240                1245

Asp Gly Lys Tyr His Val Val Arg Phe Thr Arg Ser Gly Gly Asn
    1250                1255                1260
```

Ala Thr Leu Gln Val Asp Ser Trp Pro Val Ile Glu Arg Tyr Pro
1265                1270                1275

Ala Gly Asn Asn Asp Asn Glu Arg Leu Ala Ile Ala Arg Gln Arg
    1280                1285                1290

Ile Pro Tyr Arg Leu Gly Arg Val Val Asp Glu Trp Leu Leu Asp
    1295                1300                1305

Lys Gly Arg Gln Leu Thr Ile Phe Asn Ser Gln Ala Thr Ile Ile
    1310                1315                1320

Ile Gly Gly Lys Glu Gln Gly Gln Pro Phe Gln Gly Gln Leu Ser
1325                1330                1335

Gly Leu Tyr Tyr Asn Gly Leu Lys Val Leu Asn Met Ala Ala Glu
    1340                1345                1350

Asn Asp Ala Asn Ile Ala Ile Val Gly Asn Val Arg Leu Val Gly
    1355                1360                1365

Glu Val Pro Ser Ser Met Thr Thr Glu Ser Thr Ala Thr Ala Met
    1370                1375                1380

Gln Ser Glu Met Ser Thr Ser Ile Met Glu Thr Thr Thr Thr Leu
1385                1390                1395

Ala Thr Ser Thr Ala Arg Arg Gly Lys Pro Pro Thr Lys Glu Pro
    1400                1405                1410

Ile Ser Gln Thr Thr Asp Asp Ile Leu Val Ala Ser Ala Glu Cys
    1415                1420                1425

Pro Ser Asp Asp Glu Asp Ile Asp Pro Cys Glu Pro Ser Ser Gly
    1430                1435                1440

Gly Leu Ala Asn Pro Thr Arg Ala Gly Gly Arg Glu Pro Tyr Pro
    1445                1450                1455

Gly Ser Ala Glu Val Ile Arg Glu Ser Ser Ser Thr Thr Gly Met
    1460                1465                1470

Val Val Gly Ile Val Ala Ala Ala Ala Leu Cys Ile Leu Ile Leu
1475                1480                1485

Leu Tyr Ala Met Tyr Lys Tyr Arg Asn Arg Asp Glu Gly Ser Tyr
    1490                1495                1500

His Val Asp Glu Ser Arg Asn Tyr Ile Ser Asn Ser Ala Gln Ser
    1505                1510                1515

Asn Gly Ala Val Val Lys Glu Lys Gln Pro Ser Ser Ala Lys Ser
    1520                1525                1530

Ser Asn Lys Asn Lys Lys Asn Lys Asp Lys Glu Tyr Tyr Val
1535                1540                1545

<210> SEQ ID NO 19
<211> LENGTH: 139
<212> TYPE: PRT
<213> ORGANISM: Homo sapiens

<400> SEQUENCE: 19

Met Asp Met Arg Trp His Cys Glu Asn Ser Gln Thr Thr Asp Ile
1               5                   10                  15

Leu Val Ala Ser Ala Glu Cys Pro Ser Asp Asp Glu Asp Ile Asp Pro
                20                  25                  30

Cys Glu Pro Ser Ser Ala Asn Pro Thr Arg Ala Gly Gly Arg Glu Pro
            35                  40                  45

Tyr Pro Gly Ser Ala Glu Val Ile Arg Glu Ser Ser Ser Thr Thr Gly
        50                  55                  60

Met Val Val Gly Ile Val Ala Ala Ala Ala Leu Cys Ile Leu Ile Leu
65                  70                  75                  80

Leu Tyr Ala Met Tyr Lys Tyr Arg Asn Arg Asp Glu Gly Ser Tyr His
            85                  90                  95

Val Asp Glu Ser Arg Asn Tyr Ile Ser Asn Ser Ala Gln Ser Asn Gly
            100                 105                 110

Ala Val Val Lys Glu Lys Gln Pro Ser Ser Ala Lys Ser Ser Asn Lys
            115                 120                 125

Asn Lys Lys Asn Lys Asp Lys Glu Tyr Tyr Val
            130                 135

<210> SEQ ID NO 20
<211> LENGTH: 2315
<212> TYPE: PRT
<213> ORGANISM: Homo sapiens

<400> SEQUENCE: 20

Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Gln Arg Lys Leu
            20                  25                  30

Val Glu Glu Ile Gly Trp Ser Tyr Thr Gly Ala Leu Asn Gln Lys Asn
            35                  40                  45

Trp Gly Lys Lys Tyr Pro Thr Cys Asn Ser Pro Lys Gln Ser Pro Ile
        50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
            85                  90                  95

Asn Thr Gly Lys Thr Val Glu Ile Asn Leu Thr Asn Asp Tyr Arg Val
            100                 105                 110

Ser Gly Gly Val Ser Glu Met Val Phe Lys Ala Ser Lys Ile Thr Phe
            115                 120                 125

His Trp Gly Lys Cys Asn Met Ser Ser Asp Gly Ser Glu His Ser Leu
        130                 135                 140

Glu Gly Gln Lys Phe Pro Leu Glu Met Gln Ile Tyr Cys Phe Asp Ala
145                 150                 155                 160

Asp Arg Phe Ser Ser Phe Glu Glu Ala Val Lys Gly Lys Gly Lys Leu
            165                 170                 175

Arg Ala Leu Ser Ile Leu Phe Glu Val Gly Thr Glu Glu Asn Leu Asp
            180                 185                 190

Phe Lys Ala Ile Ile Asp Gly Val Glu Ser Val Ser Arg Phe Gly Lys
            195                 200                 205

Gln Ala Ala Leu Asp Pro Phe Ile Leu Leu Asn Leu Leu Pro Asn Ser
        210                 215                 220

Thr Asp Lys Tyr Tyr Ile Tyr Asn Gly Ser Leu Thr Ser Pro Pro Cys
225                 230                 235                 240

Thr Asp Thr Val Asp Trp Ile Val Phe Lys Asp Thr Val Ser Ile Ser
            245                 250                 255

Glu Ser Gln Leu Ala Val Phe Cys Glu Val Leu Thr Met Gln Gln Ser
            260                 265                 270

Gly Tyr Val Met Leu Met Asp Tyr Leu Gln Asn Asn Phe Arg Glu Gln
            275                 280                 285

Gln Tyr Lys Phe Ser Arg Gln Val Phe Ser Ser Tyr Thr Gly Lys Glu
        290                 295                 300

Glu Ile His Glu Ala Val Cys Ser Ser Glu Pro Glu Asn Val Gln Ala

```
        305                 310                 315                 320
Asp Pro Glu Asn Tyr Thr Ser Leu Leu Val Thr Trp Glu Arg Pro Arg
                325                 330                 335

Val Val Tyr Asp Thr Met Ile Glu Lys Phe Ala Val Leu Tyr Gln Gln
                340                 345                 350

Leu Asp Gly Glu Asp Gln Thr Lys His Glu Phe Leu Thr Asp Gly Tyr
                355                 360                 365

Gln Asp Leu Gly Ala Ile Leu Asn Asn Leu Leu Pro Asn Met Ser Tyr
        370                 375                 380

Val Leu Gln Ile Val Ala Ile Cys Thr Asn Gly Leu Tyr Gly Lys Tyr
385                 390                 395                 400

Ser Asp Gln Leu Ile Val Asp Met Pro Thr Asp Asn Pro Glu Leu Asp
                405                 410                 415

Leu Phe Pro Glu Leu Ile Gly Thr Glu Ile Ile Lys Glu Glu
                420                 425                 430

Glu Gly Lys Asp Ile Glu Glu Gly Ala Ile Val Asn Pro Gly Arg Asp
                435                 440                 445

Ser Ala Thr Asn Gln Ile Arg Lys Lys Glu Pro Gln Ile Ser Thr Thr
        450                 455                 460

Thr His Tyr Asn Arg Ile Gly Thr Lys Tyr Asn Glu Ala Lys Thr Asn
465                 470                 475                 480

Arg Ser Pro Thr Arg Gly Ser Glu Phe Ser Gly Lys Gly Asp Val Pro
                485                 490                 495

Asn Thr Ser Leu Asn Ser Thr Ser Gln Pro Val Thr Lys Leu Ala Thr
                500                 505                 510

Glu Lys Asp Ile Ser Leu Thr Ser Gln Thr Val Thr Glu Leu Pro Pro
        515                 520                 525

His Thr Val Glu Gly Thr Ser Ala Ser Leu Asn Asp Gly Ser Lys Thr
                530                 535                 540

Val Leu Arg Ser Pro His Met Asn Leu Ser Gly Thr Ala Glu Ser Leu
545                 550                 555                 560

Asn Thr Val Ser Ile Thr Glu Tyr Glu Glu Glu Ser Leu Leu Thr Ser
                565                 570                 575

Phe Lys Leu Asp Thr Gly Ala Glu Asp Ser Ser Gly Ser Ser Pro Ala
                580                 585                 590

Thr Ser Ala Ile Pro Phe Ile Ser Glu Asn Ile Ser Gln Gly Tyr Ile
        595                 600                 605

Phe Ser Ser Glu Asn Pro Glu Thr Ile Thr Tyr Asp Val Leu Ile Pro
610                 615                 620

Glu Ser Ala Arg Asn Ala Ser Glu Asp Ser Thr Ser Ser Gly Ser Glu
625                 630                 635                 640

Glu Ser Leu Lys Asp Pro Ser Met Glu Gly Asn Val Trp Phe Pro Ser
                645                 650                 655

Ser Thr Asp Ile Thr Ala Gln Pro Asp Val Gly Ser Gly Arg Glu Ser
                660                 665                 670

Phe Leu Gln Thr Asn Tyr Thr Glu Ile Arg Val Asp Glu Ser Glu Lys
        675                 680                 685

Thr Thr Lys Ser Phe Ser Ala Gly Pro Val Met Ser Gln Gly Pro Ser
        690                 695                 700

Val Thr Asp Leu Glu Met Pro His Tyr Ser Thr Phe Ala Tyr Phe Pro
705                 710                 715                 720

Thr Glu Val Thr Pro His Ala Phe Thr Pro Ser Ser Arg Gln Gln Asp
                725                 730                 735
```

-continued

```
Leu Val Ser Thr Val Asn Val Val Tyr Ser Gln Thr Thr Gln Pro Val
                740                 745                 750

Tyr Asn Gly Glu Thr Pro Leu Gln Pro Ser Tyr Ser Ser Glu Val Phe
                755                 760                 765

Pro Leu Val Thr Pro Leu Leu Leu Asp Asn Gln Ile Leu Asn Thr Thr
770                 775                 780

Pro Ala Ala Ser Ser Ser Asp Ser Ala Leu His Ala Thr Pro Val Phe
785                 790                 795                 800

Pro Ser Val Asp Val Ser Phe Glu Ser Ile Leu Ser Ser Tyr Asp Gly
                805                 810                 815

Ala Pro Leu Leu Pro Phe Ser Ser Ala Ser Phe Ser Ser Glu Leu Phe
                820                 825                 830

Arg His Leu His Thr Val Ser Gln Ile Leu Pro Gln Val Thr Ser Ala
                835                 840                 845

Thr Glu Ser Asp Lys Val Pro Leu His Ala Ser Leu Pro Val Ala Gly
850                 855                 860

Gly Asp Leu Leu Leu Glu Pro Ser Leu Ala Gln Tyr Ser Asp Val Leu
865                 870                 875                 880

Ser Thr Thr His Ala Ala Ser Glu Thr Leu Glu Phe Gly Ser Glu Ser
                885                 890                 895

Gly Val Leu Tyr Lys Thr Leu Met Phe Ser Gln Val Glu Pro Pro Ser
                900                 905                 910

Ser Asp Ala Met Met His Ala Arg Ser Ser Gly Pro Glu Pro Ser Tyr
                915                 920                 925

Ala Leu Ser Asp Asn Glu Gly Ser Gln His Ile Phe Thr Val Ser Tyr
                930                 935                 940

Ser Ser Ala Ile Pro Val His Asp Ser Val Gly Val Thr Tyr Gln Gly
945                 950                 955                 960

Ser Leu Phe Ser Gly Pro Ser His Ile Pro Ile Pro Lys Ser Ser Leu
                965                 970                 975

Ile Thr Pro Thr Ala Ser Leu Leu Gln Pro Thr His Ala Leu Ser Gly
                980                 985                 990

Asp Gly Glu Trp Ser Gly Ala Ser  Ser Asp Ser Gly Phe  Leu Leu Pro
                995                 1000                1005

Asp Thr Asp Gly Leu Thr Ala  Leu Asn Ile Ser Ser  Pro Val Ser
        1010                1015                1020

Val Ala Glu Phe Thr Tyr Thr  Thr Ser Val Phe Gly  Asp Asp Asn
        1025                1030                1035

Lys Ala Leu Ser Lys Ser Glu  Ile Ile Tyr Gly Asn  Glu Thr Glu
        1040                1045                1050

Leu Gln Ile Pro Ser Phe Asn  Glu Met Val Tyr Pro  Ser Glu Ser
        1055                1060                1065

Thr Val Met Pro Asn Met Tyr  Asp Asn Val Asn Lys  Leu Asn Ala
        1070                1075                1080

Ser Leu Gln Glu Thr Ser Val  Ser Ile Ser Ser Thr  Lys Gly Met
        1085                1090                1095

Phe Pro Gly Ser Leu Ala His  Thr Thr Thr Lys Val  Phe Asp His
        1100                1105                1110

Glu Ile Ser Gln Val Pro Glu  Asn Asn Phe Ser Val  Gln Pro Thr
        1115                1120                1125

His Thr Val Ser Gln Ala Ser  Gly Asp Thr Ser Leu  Lys Pro Val
        1130                1135                1140
```

-continued

Leu Ser Ala Asn Ser Glu Pro Ala Ser Ser Asp Pro Ala Ser Ser
    1145                1150                1155

Glu Met Leu Ser Pro Ser Thr Gln Leu Leu Phe Tyr Glu Thr Ser
    1160                1165                1170

Ala Ser Phe Ser Thr Glu Val Leu Leu Gln Pro Ser Phe Gln Ala
    1175                1180                1185

Ser Asp Val Asp Thr Leu Leu Lys Thr Val Leu Pro Ala Val Pro
    1190                1195                1200

Ser Asp Pro Ile Leu Val Glu Thr Pro Lys Val Asp Lys Ile Ser
    1205                1210                1215

Ser Thr Met Leu His Leu Ile Val Ser Asn Ser Ala Ser Ser Glu
    1220                1225                1230

Asn Met Leu His Ser Thr Ser Val Pro Val Phe Asp Val Ser Pro
    1235                1240                1245

Thr Ser His Met His Ser Ala Ser Leu Gln Gly Leu Thr Ile Ser
    1250                1255                1260

Tyr Ala Ser Glu Lys Tyr Glu Pro Val Leu Leu Lys Ser Glu Ser
    1265                1270                1275

Ser His Gln Val Val Pro Ser Leu Tyr Ser Asn Asp Glu Leu Phe
    1280                1285                1290

Gln Thr Ala Asn Leu Glu Ile Asn Gln Ala His Pro Pro Lys Gly
    1295                1300                1305

Arg His Val Phe Ala Thr Pro Val Leu Ser Ile Asp Glu Pro Leu
    1310                1315                1320

Asn Thr Leu Ile Asn Lys Leu Ile His Ser Asp Glu Ile Leu Thr
    1325                1330                1335

Ser Thr Lys Ser Ser Val Thr Gly Lys Val Phe Ala Gly Ile Pro
    1340                1345                1350

Thr Val Ala Ser Asp Thr Phe Val Ser Thr Asp His Ser Val Pro
    1355                1360                1365

Ile Gly Asn Gly His Val Ala Ile Thr Ala Val Ser Pro His Arg
    1370                1375                1380

Asp Gly Ser Val Thr Ser Thr Lys Leu Leu Phe Pro Ser Lys Ala
    1385                1390                1395

Thr Ser Glu Leu Ser His Ser Ala Lys Ser Asp Ala Gly Leu Val
    1400                1405                1410

Gly Gly Gly Glu Asp Gly Asp Thr Asp Asp Asp Gly Asp Asp Asp
    1415                1420                1425

Asp Asp Asp Arg Gly Ser Asp Gly Leu Ser Ile His Lys Cys Met
    1430                1435                1440

Ser Cys Ser Ser Tyr Arg Glu Ser Gln Glu Lys Val Met Asn Asp
    1445                1450                1455

Ser Asp Thr His Glu Asn Ser Leu Met Asp Gln Asn Asn Pro Ile
    1460                1465                1470

Ser Tyr Ser Leu Ser Glu Asn Ser Glu Glu Asp Asn Arg Val Thr
    1475                1480                1485

Ser Val Ser Ser Asp Ser Gln Thr Gly Met Asp Arg Ser Pro Gly
    1490                1495                1500

Lys Ser Pro Ser Ala Asn Gly Leu Ser Gln Lys His Asn Asp Gly
    1505                1510                1515

Lys Glu Glu Asn Asp Ile Gln Thr Gly Ser Ala Leu Leu Pro Leu
    1520                1525                1530

Ser Pro Glu Ser Lys Ala Trp Ala Val Leu Thr Ser Asp Glu Glu

```
                1535                1540                1545

Ser  Gly  Ser  Gly  Gln  Gly  Thr  Ser  Asp  Ser  Leu  Asn  Glu  Asn  Glu
         1550                1555                1560

Thr  Ser  Thr  Asp  Phe  Ser  Phe  Ala  Asp  Thr  Asn  Glu  Lys  Asp  Ala
         1565                1570                1575

Asp  Gly  Ile  Leu  Ala  Ala  Gly  Asp  Ser  Glu  Ile  Thr  Pro  Gly  Phe
         1580                1585                1590

Pro  Gln  Ser  Pro  Thr  Ser  Ser  Val  Thr  Ser  Glu  Asn  Ser  Glu  Val
         1595                1600                1605

Phe  His  Val  Ser  Glu  Ala  Glu  Ala  Ser  Asn  Ser  Ser  His  Glu  Ser
         1610                1615                1620

Arg  Ile  Gly  Leu  Ala  Glu  Gly  Leu  Glu  Ser  Glu  Lys  Lys  Ala  Val
         1625                1630                1635

Ile  Pro  Leu  Val  Ile  Val  Ser  Ala  Leu  Thr  Phe  Ile  Cys  Leu  Val
         1640                1645                1650

Val  Leu  Val  Gly  Ile  Leu  Ile  Tyr  Trp  Arg  Lys  Cys  Phe  Gln  Thr
         1655                1660                1665

Ala  His  Phe  Tyr  Leu  Glu  Asp  Ser  Thr  Ser  Pro  Arg  Val  Ile  Ser
         1670                1675                1680

Thr  Pro  Pro  Thr  Pro  Ile  Phe  Pro  Ile  Ser  Asp  Asp  Val  Gly  Ala
         1685                1690                1695

Ile  Pro  Ile  Lys  His  Phe  Pro  Lys  His  Val  Ala  Asp  Leu  His  Ala
         1700                1705                1710

Ser  Ser  Gly  Phe  Thr  Glu  Glu  Phe  Glu  Thr  Leu  Lys  Glu  Phe  Tyr
         1715                1720                1725

Gln  Glu  Val  Gln  Ser  Cys  Thr  Val  Asp  Leu  Gly  Ile  Thr  Ala  Asp
         1730                1735                1740

Ser  Ser  Asn  His  Pro  Asp  Asn  Lys  His  Lys  Asn  Arg  Tyr  Ile  Asn
         1745                1750                1755

Ile  Val  Ala  Tyr  Asp  His  Ser  Arg  Val  Lys  Leu  Ala  Gln  Leu  Ala
         1760                1765                1770

Glu  Lys  Asp  Gly  Lys  Leu  Thr  Asp  Tyr  Ile  Asn  Ala  Asn  Tyr  Val
         1775                1780                1785

Asp  Gly  Tyr  Asn  Arg  Pro  Lys  Ala  Tyr  Ile  Ala  Ala  Gln  Gly  Pro
         1790                1795                1800

Leu  Lys  Ser  Thr  Ala  Glu  Asp  Phe  Trp  Arg  Met  Ile  Trp  Glu  His
         1805                1810                1815

Asn  Val  Glu  Val  Ile  Val  Met  Ile  Thr  Asn  Leu  Val  Glu  Lys  Gly
         1820                1825                1830

Arg  Arg  Lys  Cys  Asp  Gln  Tyr  Trp  Pro  Ala  Asp  Gly  Ser  Glu  Glu
         1835                1840                1845

Tyr  Gly  Asn  Phe  Leu  Val  Thr  Gln  Lys  Ser  Val  Gln  Val  Leu  Ala
         1850                1855                1860

Tyr  Tyr  Thr  Val  Arg  Asn  Phe  Thr  Leu  Arg  Asn  Thr  Lys  Ile  Lys
         1865                1870                1875

Lys  Gly  Ser  Gln  Lys  Gly  Arg  Pro  Ser  Gly  Arg  Val  Val  Thr  Gln
         1880                1885                1890

Tyr  His  Tyr  Thr  Gln  Trp  Pro  Asp  Met  Gly  Val  Pro  Glu  Tyr  Ser
         1895                1900                1905

Leu  Pro  Val  Leu  Thr  Phe  Val  Arg  Lys  Ala  Ala  Tyr  Ala  Lys  Arg
         1910                1915                1920

His  Ala  Val  Gly  Pro  Val  Val  Val  His  Cys  Ser  Ala  Gly  Val  Gly
         1925                1930                1935
```

```
Arg Thr Gly Thr Tyr Ile Val Leu Asp Ser Met Leu Gln Gln Ile
    1940            1945            1950

Gln His Glu Gly Thr Val Asn Ile Phe Gly Phe Leu Lys His Ile
    1955            1960            1965

Arg Ser Gln Arg Asn Tyr Leu Val Gln Thr Glu Glu Gln Tyr Val
    1970            1975            1980

Phe Ile His Asp Thr Leu Val Glu Ala Ile Leu Ser Lys Glu Thr
    1985            1990            1995

Glu Val Leu Asp Ser His Ile His Ala Tyr Val Asn Ala Leu Leu
    2000            2005            2010

Ile Pro Gly Pro Ala Gly Lys Thr Lys Leu Glu Lys Gln Phe Gln
    2015            2020            2025

Leu Leu Ser Gln Ser Asn Ile Gln Gln Ser Asp Tyr Ser Ala Ala
    2030            2035            2040

Leu Lys Gln Cys Asn Arg Glu Lys Asn Arg Thr Ser Ser Ile Ile
    2045            2050            2055

Pro Val Glu Arg Ser Arg Val Gly Ile Ser Ser Leu Ser Gly Glu
    2060            2065            2070

Gly Thr Asp Tyr Ile Asn Ala Ser Tyr Ile Met Gly Tyr Tyr Gln
    2075            2080            2085

Ser Asn Glu Phe Ile Ile Thr Gln His Pro Leu Leu His Thr Ile
    2090            2095            2100

Lys Asp Phe Trp Arg Met Ile Trp Asp His Asn Ala Gln Leu Val
    2105            2110            2115

Val Met Ile Pro Asp Gly Gln Asn Met Ala Glu Asp Glu Phe Val
    2120            2125            2130

Tyr Trp Pro Asn Lys Asp Glu Pro Ile Asn Cys Glu Ser Phe Lys
    2135            2140            2145

Val Thr Leu Met Ala Glu Glu His Lys Cys Leu Ser Asn Glu Glu
    2150            2155            2160

Lys Leu Ile Ile Gln Asp Phe Ile Leu Glu Ala Thr Gln Asp Asp
    2165            2170            2175

Tyr Val Leu Glu Val Arg His Phe Gln Cys Pro Lys Trp Pro Asn
    2180            2185            2190

Pro Asp Ser Pro Ile Ser Lys Thr Phe Glu Leu Ile Ser Val Ile
    2195            2200            2205

Lys Glu Glu Ala Ala Asn Arg Asp Gly Pro Met Ile Val His Asp
    2210            2215            2220

Glu His Gly Gly Val Thr Ala Gly Thr Phe Cys Ala Leu Thr Thr
    2225            2230            2235

Leu Met His Gln Leu Glu Lys Glu Asn Ser Val Asp Val Tyr Gln
    2240            2245            2250

Val Ala Lys Met Ile Asn Leu Met Arg Pro Gly Val Phe Ala Asp
    2255            2260            2265

Ile Glu Gln Tyr Gln Phe Leu Tyr Lys Val Ile Leu Ser Leu Val
    2270            2275            2280

Ser Thr Arg Gln Glu Glu Asn Pro Ser Thr Ser Leu Asp Ser Asn
    2285            2290            2295

Gly Ala Ala Leu Pro Asp Gly Asn Ile Ala Glu Ser Leu Glu Ser
    2300            2305            2310

Leu Val
    2315
```

-continued

```
<210> SEQ ID NO 21
<211> LENGTH: 2308
<212> TYPE: PRT
<213> ORGANISM: Homo sapiens

<400> SEQUENCE: 21
```

| | | | | | | | | | | | | | | |
|---|---|---|---|---|---|---|---|---|---|---|---|---|---|---|
| Met | Arg | Ile | Leu | Lys | Arg | Phe | Leu | Ala | Cys | Ile | Gln | Leu | Leu | Cys | Val |
| 1 | | | | 5 | | | | | 10 | | | | | 15 | |
| Cys | Arg | Leu | Asp | Trp | Ala | Asn | Gly | Tyr | Tyr | Arg | Gln | Arg | Lys | Leu | |
| | | | 20 | | | | | 25 | | | | | 30 | | |
| Val | Glu | Glu | Ile | Gly | Trp | Ser | Tyr | Thr | Gly | Ala | Leu | Asn | Gln | Lys | Asn |
| | | 35 | | | | | 40 | | | | | 45 | | | |
| Trp | Gly | Lys | Lys | Tyr | Pro | Thr | Cys | Asn | Ser | Pro | Lys | Gln | Ser | Pro | Ile |
| 50 | | | | | 55 | | | | | 60 | | | | | |
| Asn | Ile | Asp | Glu | Asp | Leu | Thr | Gln | Val | Asn | Val | Asn | Leu | Lys | Lys | Leu |
| 65 | | | | 70 | | | | | 75 | | | | | 80 | |
| Lys | Phe | Gln | Gly | Trp | Asp | Lys | Thr | Ser | Leu | Glu | Asn | Thr | Phe | Ile | His |
| | | | | 85 | | | | | 90 | | | | | 95 | |
| Asn | Thr | Gly | Lys | Thr | Val | Glu | Ile | Asn | Leu | Thr | Asn | Asp | Tyr | Arg | Val |
| | | | 100 | | | | | 105 | | | | | 110 | | |
| Ser | Gly | Gly | Val | Ser | Glu | Met | Val | Phe | Lys | Ala | Ser | Lys | Ile | Thr | Phe |
| | | 115 | | | | | 120 | | | | | 125 | | | |
| His | Trp | Gly | Lys | Cys | Asn | Met | Ser | Ser | Asp | Gly | Ser | Glu | His | Ser | Leu |
| | | 130 | | | | | 135 | | | | | 140 | | | |
| Glu | Gly | Gln | Lys | Phe | Pro | Leu | Glu | Met | Gln | Ile | Tyr | Cys | Phe | Asp | Ala |
| 145 | | | | | 150 | | | | | 155 | | | | | 160 |
| Asp | Arg | Phe | Ser | Ser | Phe | Glu | Glu | Ala | Val | Lys | Gly | Lys | Gly | Lys | Leu |
| | | | | 165 | | | | | 170 | | | | | 175 | |
| Arg | Ala | Leu | Ser | Ile | Leu | Phe | Glu | Val | Gly | Thr | Glu | Glu | Asn | Leu | Asp |
| | | | 180 | | | | | 185 | | | | | 190 | | |
| Phe | Lys | Ala | Ile | Ile | Asp | Gly | Val | Glu | Ser | Val | Ser | Arg | Phe | Gly | Lys |
| | | | 195 | | | | | 200 | | | | | 205 | | |
| Gln | Ala | Ala | Leu | Asp | Pro | Phe | Ile | Leu | Leu | Asn | Leu | Leu | Pro | Asn | Ser |
| | 210 | | | | | 215 | | | | | 220 | | | | |
| Thr | Asp | Lys | Tyr | Tyr | Ile | Tyr | Asn | Gly | Ser | Leu | Thr | Ser | Pro | Pro | Cys |
| 225 | | | | | 230 | | | | | 235 | | | | | 240 |
| Thr | Asp | Thr | Val | Asp | Trp | Ile | Val | Phe | Lys | Asp | Thr | Val | Ser | Ile | Ser |
| | | | | 245 | | | | | 250 | | | | | 255 | |
| Glu | Ser | Gln | Leu | Ala | Val | Phe | Cys | Glu | Val | Leu | Thr | Met | Gln | Gln | Ser |
| | | | 260 | | | | | 265 | | | | | 270 | | |
| Gly | Tyr | Val | Met | Leu | Met | Asp | Tyr | Leu | Gln | Asn | Asn | Phe | Arg | Glu | Gln |
| | | 275 | | | | | 280 | | | | | 285 | | | |
| Gln | Tyr | Lys | Phe | Ser | Arg | Gln | Val | Phe | Ser | Ser | Tyr | Thr | Gly | Lys | Glu |
| | 290 | | | | | 295 | | | | | 300 | | | | |
| Glu | Ile | His | Glu | Ala | Val | Cys | Ser | Ser | Glu | Pro | Glu | Asn | Val | Gln | Ala |
| 305 | | | | | 310 | | | | | 315 | | | | | 320 |
| Asp | Pro | Glu | Asn | Tyr | Thr | Ser | Leu | Leu | Val | Thr | Trp | Glu | Arg | Pro | Arg |
| | | | | 325 | | | | | 330 | | | | | 335 | |
| Val | Val | Tyr | Asp | Thr | Met | Ile | Glu | Lys | Phe | Ala | Val | Leu | Tyr | Gln | Gln |
| | | | 340 | | | | | 345 | | | | | 350 | | |
| Leu | Asp | Gly | Glu | Asp | Gln | Thr | Lys | His | Glu | Phe | Leu | Thr | Asp | Gly | Tyr |
| | | 355 | | | | | 360 | | | | | 365 | | | |
| Gln | Asp | Leu | Gly | Ala | Ile | Leu | Asn | Asn | Leu | Leu | Pro | Asn | Met | Ser | Tyr |
| | 370 | | | | | 375 | | | | | 380 | | | | |

```
Val Leu Gln Ile Val Ala Ile Cys Thr Asn Gly Leu Tyr Gly Lys Tyr
385                 390                 395                 400

Ser Asp Gln Leu Ile Val Asp Met Pro Thr Asp Asn Pro Glu Leu Asp
                405                 410                 415

Leu Phe Pro Glu Leu Ile Gly Thr Glu Glu Ile Ile Lys Glu Glu Glu
            420                 425                 430

Glu Gly Lys Asp Ile Glu Glu Gly Ala Ile Val Asn Pro Gly Arg Asp
        435                 440                 445

Ser Ala Thr Asn Gln Ile Arg Lys Lys Glu Pro Gln Ile Ser Thr Thr
    450                 455                 460

Thr His Tyr Asn Arg Ile Gly Thr Lys Tyr Asn Glu Ala Lys Thr Asn
465                 470                 475                 480

Arg Ser Pro Thr Arg Gly Ser Glu Phe Ser Gly Lys Gly Asp Val Pro
                485                 490                 495

Asn Thr Ser Leu Asn Ser Thr Ser Gln Pro Val Thr Lys Leu Ala Thr
            500                 505                 510

Glu Lys Asp Ile Ser Leu Thr Ser Gln Thr Val Thr Glu Leu Pro Pro
        515                 520                 525

His Thr Val Glu Gly Thr Ser Ala Ser Leu Asn Asp Gly Ser Lys Thr
    530                 535                 540

Val Leu Arg Ser Pro His Met Asn Leu Ser Gly Thr Ala Glu Ser Leu
545                 550                 555                 560

Asn Thr Val Ser Ile Thr Glu Tyr Glu Glu Glu Ser Leu Leu Thr Ser
                565                 570                 575

Phe Lys Leu Asp Thr Gly Ala Glu Asp Ser Ser Gly Ser Ser Pro Ala
            580                 585                 590

Thr Ser Ala Ile Pro Phe Ile Ser Glu Asn Ile Ser Gln Gly Tyr Ile
        595                 600                 605

Phe Ser Ser Glu Asn Pro Glu Thr Ile Thr Tyr Asp Val Leu Ile Pro
    610                 615                 620

Glu Ser Ala Arg Asn Ala Ser Glu Asp Ser Thr Ser Ser Gly Ser Glu
625                 630                 635                 640

Glu Ser Leu Lys Asp Pro Ser Met Glu Gly Asn Val Trp Phe Pro Ser
                645                 650                 655

Ser Thr Asp Ile Thr Ala Gln Pro Asp Val Gly Ser Gly Arg Glu Ser
            660                 665                 670

Phe Leu Gln Thr Asn Tyr Thr Glu Ile Arg Val Asp Glu Ser Glu Lys
        675                 680                 685

Thr Thr Lys Ser Phe Ser Ala Gly Pro Val Met Ser Gln Gly Pro Ser
    690                 695                 700

Val Thr Asp Leu Glu Met Pro His Tyr Ser Thr Phe Ala Tyr Phe Pro
705                 710                 715                 720

Thr Glu Val Thr Pro His Ala Phe Thr Pro Ser Ser Arg Gln Gln Asp
                725                 730                 735

Leu Val Ser Thr Val Asn Val Val Tyr Ser Gln Thr Thr Gln Pro Val
            740                 745                 750

Tyr Asn Gly Glu Thr Pro Leu Gln Pro Ser Tyr Ser Ser Glu Val Phe
        755                 760                 765

Pro Leu Val Thr Pro Leu Leu Asp Asn Gln Ile Leu Asn Thr Thr
    770                 775                 780

Pro Ala Ala Ser Ser Ser Asp Ser Ala Leu His Ala Thr Pro Val Phe
785                 790                 795                 800
```

```
Pro Ser Val Asp Val Ser Phe Glu Ser Ile Leu Ser Ser Tyr Asp Gly
            805                 810                 815

Ala Pro Leu Leu Pro Phe Ser Ser Ala Ser Phe Ser Ser Glu Leu Phe
        820                 825                 830

Arg His Leu His Thr Val Ser Gln Ile Leu Pro Gln Val Thr Ser Ala
            835                 840                 845

Thr Glu Ser Asp Lys Val Pro Leu His Ala Ser Leu Pro Val Ala Gly
850                 855                 860

Gly Asp Leu Leu Leu Glu Pro Ser Leu Ala Gln Tyr Ser Asp Val Leu
865                 870                 875                 880

Ser Thr Thr His Ala Ala Ser Glu Thr Leu Glu Phe Gly Ser Glu Ser
                885                 890                 895

Gly Val Leu Tyr Lys Thr Leu Met Phe Ser Gln Val Glu Pro Pro Ser
            900                 905                 910

Ser Asp Ala Met Met His Ala Arg Ser Ser Gly Pro Glu Pro Ser Tyr
            915                 920                 925

Ala Leu Ser Asp Asn Glu Gly Ser Gln His Ile Phe Thr Val Ser Tyr
        930                 935                 940

Ser Ser Ala Ile Pro Val His Asp Ser Val Gly Val Thr Tyr Gln Gly
945                 950                 955                 960

Ser Leu Phe Ser Gly Pro Ser His Ile Pro Ile Pro Lys Ser Ser Leu
                965                 970                 975

Ile Thr Pro Thr Ala Ser Leu Leu Gln Pro Thr His Ala Leu Ser Gly
            980                 985                 990

Asp Gly Glu Trp Ser Gly Ala Ser Ser Asp Ser Glu Phe Leu Leu Pro
        995                 1000                1005

Asp Thr Asp Gly Leu Thr Ala Leu Asn Ile Ser Ser Pro Val Ser
    1010                1015                1020

Val Ala Glu Phe Thr Tyr Thr Thr Ser Val Phe Gly Asp Asp Asn
    1025                1030                1035

Lys Ala Leu Ser Lys Ser Glu Ile Ile Tyr Gly Asn Glu Thr Glu
    1040                1045                1050

Leu Gln Ile Pro Ser Phe Asn Glu Met Val Tyr Pro Ser Glu Ser
    1055                1060                1065

Thr Val Met Pro Asn Met Tyr Asp Asn Val Asn Lys Leu Asn Ala
    1070                1075                1080

Ser Leu Gln Glu Thr Ser Val Ser Ile Ser Ser Thr Lys Gly Met
    1085                1090                1095

Phe Pro Gly Ser Leu Ala His Thr Thr Thr Lys Val Phe Asp His
    1100                1105                1110

Glu Ile Ser Gln Val Pro Glu Asn Asn Phe Ser Val Gln Pro Thr
    1115                1120                1125

His Thr Val Ser Gln Ala Ser Gly Asp Thr Ser Leu Lys Pro Val
    1130                1135                1140

Leu Ser Ala Asn Ser Glu Pro Ala Ser Ser Asp Pro Ala Ser Ser
    1145                1150                1155

Glu Met Leu Ser Pro Ser Thr Gln Leu Leu Phe Tyr Glu Thr Ser
    1160                1165                1170

Ala Ser Phe Ser Thr Glu Val Leu Leu Gln Pro Ser Phe Gln Ala
    1175                1180                1185

Ser Asp Val Asp Thr Leu Leu Lys Thr Val Leu Pro Ala Val Pro
    1190                1195                1200

Ser Asp Pro Ile Leu Val Glu Thr Pro Lys Val Asp Lys Ile Ser
```

-continued

```
            1205                1210                1215
Ser Thr Met Leu His Leu Ile Val Ser Asn Ser Ala Ser Ser Glu
            1220                1225                1230
Asn Met Leu His Ser Thr Ser Val Pro Val Phe Asp Val Ser Pro
            1235                1240                1245
Thr Ser His Met His Ser Ala Ser Leu Gln Gly Leu Thr Ile Ser
            1250                1255                1260
Tyr Ala Ser Glu Lys Tyr Glu Pro Val Leu Leu Lys Ser Glu Ser
            1265                1270                1275
Ser His Gln Val Val Pro Ser Leu Tyr Ser Asn Asp Glu Leu Phe
            1280                1285                1290
Gln Thr Ala Asn Leu Glu Ile Asn Gln Ala His Pro Pro Lys Gly
            1295                1300                1305
Arg His Val Phe Ala Thr Pro Val Leu Ser Ile Asp Glu Pro Leu
            1310                1315                1320
Asn Thr Leu Ile Asn Lys Leu Ile His Ser Asp Glu Ile Leu Thr
            1325                1330                1335
Ser Thr Lys Ser Ser Val Thr Gly Lys Val Phe Ala Gly Ile Pro
            1340                1345                1350
Thr Val Ala Ser Asp Thr Phe Val Ser Thr Asp His Ser Val Pro
            1355                1360                1365
Ile Gly Asn Gly His Val Ala Ile Thr Ala Val Ser Pro His Arg
            1370                1375                1380
Asp Gly Ser Val Thr Ser Thr Lys Leu Leu Phe Pro Ser Lys Ala
            1385                1390                1395
Thr Ser Glu Leu Ser His Ser Ala Lys Ser Asp Ala Gly Leu Val
            1400                1405                1410
Gly Gly Gly Glu Asp Gly Asp Thr Asp Asp Gly Asp Asp Asp
            1415                1420                1425
Asp Asp Asp Arg Gly Ser Asp Gly Leu Ser Ile His Lys Cys Met
            1430                1435                1440
Ser Cys Ser Ser Tyr Arg Glu Ser Gln Glu Lys Val Met Asn Asp
            1445                1450                1455
Ser Asp Thr His Glu Asn Ser Leu Met Asp Gln Asn Asn Pro Ile
            1460                1465                1470
Ser Tyr Ser Leu Ser Glu Asn Ser Glu Glu Asp Asn Arg Val Thr
            1475                1480                1485
Ser Val Ser Ser Asp Ser Gln Thr Gly Met Asp Arg Ser Pro Gly
            1490                1495                1500
Lys Ser Pro Ser Ala Asn Gly Leu Ser Gln Lys His Asn Asp Gly
            1505                1510                1515
Lys Glu Glu Asn Asp Ile Gln Thr Gly Ser Ala Leu Leu Pro Leu
            1520                1525                1530
Ser Pro Glu Ser Lys Ala Trp Ala Val Leu Thr Ser Asp Glu Glu
            1535                1540                1545
Ser Gly Ser Gly Gln Gly Thr Ser Asp Ser Leu Asn Glu Asn Glu
            1550                1555                1560
Thr Ser Thr Asp Phe Ser Phe Ala Asp Thr Asn Glu Lys Asp Ala
            1565                1570                1575
Asp Gly Ile Leu Ala Ala Gly Asp Ser Glu Ile Thr Pro Gly Phe
            1580                1585                1590
Pro Gln Ser Pro Thr Ser Ser Val Thr Ser Glu Asn Ser Glu Val
            1595                1600                1605
```

Phe His Val Ser Glu Ala Glu  Ala Ser Asn Ser  His Glu Ser
    1610            1615              1620

Arg Ile Gly Leu Ala Glu Gly  Leu Glu Ser Glu Lys  Lys Ala Val
    1625            1630              1635

Ile Pro Leu Val Ile Val Ser  Ala Leu Thr Phe Ile  Cys Leu Val
    1640            1645              1650

Val Leu Val Gly Ile Leu Ile  Tyr Trp Arg Lys Cys  Phe Gln Thr
    1655            1660              1665

Ala His Phe Tyr Leu Glu Asp  Ser Thr Ser Pro Arg  Val Ile Ser
    1670            1675              1680

Thr Pro Pro Thr Pro Ile Phe  Pro Ile Ser Asp Asp  Val Gly Ala
    1685            1690              1695

Ile Pro Ile Lys His Phe Pro  Lys His Val Ala Asp  Leu His Ala
    1700            1705              1710

Ser Ser Gly Phe Thr Glu Glu  Phe Glu Glu Val Gln  Ser Cys Thr
    1715            1720              1725

Val Asp Leu Gly Ile Thr Ala  Asp Ser Ser Asn His  Pro Asp Asn
    1730            1735              1740

Lys His Lys Asn Arg Tyr Ile  Asn Ile Val Ala Tyr  Asp His Ser
    1745            1750              1755

Arg Val Lys Leu Ala Gln Leu  Ala Glu Lys Asp Gly  Lys Leu Thr
    1760            1765              1770

Asp Tyr Ile Asn Ala Asn Tyr  Val Asp Gly Tyr Asn  Arg Pro Lys
    1775            1780              1785

Ala Tyr Ile Ala Ala Gln Gly  Pro Leu Lys Ser Thr  Ala Glu Asp
    1790            1795              1800

Phe Trp Arg Met Ile Trp Glu  His Asn Val Glu Val  Ile Val Met
    1805            1810              1815

Ile Thr Asn Leu Val Glu Lys  Gly Arg Arg Lys Cys  Asp Gln Tyr
    1820            1825              1830

Trp Pro Ala Asp Gly Ser Glu  Glu Tyr Gly Asn Phe  Leu Val Thr
    1835            1840              1845

Gln Lys Ser Val Gln Val Leu  Ala Tyr Tyr Thr Val  Arg Asn Phe
    1850            1855              1860

Thr Leu Arg Asn Thr Lys Ile  Lys Lys Gly Ser Gln  Lys Gly Arg
    1865            1870              1875

Pro Ser Gly Arg Val Val Thr  Gln Tyr His Tyr Thr  Gln Trp Pro
    1880            1885              1890

Asp Met Gly Val Pro Glu Tyr  Ser Leu Pro Val Leu  Thr Phe Val
    1895            1900              1905

Arg Lys Ala Ala Tyr Ala Lys  Arg His Ala Val Gly  Pro Val Val
    1910            1915              1920

Val His Cys Ser Ala Gly Val  Gly Arg Thr Gly Thr  Tyr Ile Val
    1925            1930              1935

Leu Asp Ser Met Leu Gln Gln  Ile Gln His Glu Gly  Thr Val Asn
    1940            1945              1950

Ile Phe Gly Phe Leu Lys His  Ile Arg Ser Gln Arg  Asn Tyr Leu
    1955            1960              1965

Val Gln Thr Glu Glu Gln Tyr  Val Phe Ile His Asp  Thr Leu Val
    1970            1975              1980

Glu Ala Ile Leu Ser Lys Glu  Thr Glu Val Leu Asp  Ser His Ile
    1985            1990              1995

-continued

```
His Ala Tyr Val Asn Ala Leu Leu Ile Pro Gly Pro Ala Gly Lys
    2000                2005                2010

Thr Lys Leu Glu Lys Gln Phe Gln Leu Leu Ser Gln Ser Asn Ile
    2015                2020                2025

Gln Gln Ser Asp Tyr Ser Ala Ala Leu Lys Gln Cys Asn Arg Glu
    2030                2035                2040

Lys Asn Arg Thr Ser Ser Ile Ile Pro Val Glu Arg Ser Arg Val
    2045                2050                2055

Gly Ile Ser Ser Leu Ser Gly Glu Gly Thr Asp Tyr Ile Asn Ala
    2060                2065                2070

Ser Tyr Ile Met Gly Tyr Tyr Gln Ser Asn Glu Phe Ile Ile Thr
    2075                2080                2085

Gln His Pro Leu Leu His Thr Ile Lys Asp Phe Trp Arg Met Ile
    2090                2095                2100

Trp Asp His Asn Ala Gln Leu Val Val Met Ile Pro Asp Gly Gln
    2105                2110                2115

Asn Met Ala Glu Asp Glu Phe Val Tyr Trp Pro Asn Lys Asp Glu
    2120                2125                2130

Pro Ile Asn Cys Glu Ser Phe Lys Val Thr Leu Met Ala Glu Glu
    2135                2140                2145

His Lys Cys Leu Ser Asn Glu Glu Lys Leu Ile Ile Gln Asp Phe
    2150                2155                2160

Ile Leu Glu Ala Thr Gln Asp Asp Tyr Val Leu Glu Val Arg His
    2165                2170                2175

Phe Gln Cys Pro Lys Trp Pro Asn Pro Asp Ser Pro Ile Ser Lys
    2180                2185                2190

Thr Phe Glu Leu Ile Ser Val Ile Lys Glu Glu Ala Ala Asn Arg
    2195                2200                2205

Asp Gly Pro Met Ile Val His Asp Glu His Gly Gly Val Thr Ala
    2210                2215                2220

Gly Thr Phe Cys Ala Leu Thr Thr Leu Met His Gln Leu Glu Lys
    2225                2230                2235

Glu Asn Ser Val Asp Val Tyr Gln Val Ala Lys Met Ile Asn Leu
    2240                2245                2250

Met Arg Pro Gly Val Phe Ala Asp Ile Glu Gln Tyr Gln Phe Leu
    2255                2260                2265

Tyr Lys Val Ile Leu Ser Leu Val Ser Thr Arg Gln Glu Glu Asn
    2270                2275                2280

Pro Ser Thr Ser Leu Asp Ser Asn Gly Ala Ala Leu Pro Asp Gly
    2285                2290                2295

Asn Ile Ala Glu Ser Leu Glu Ser Leu Val
    2300                2305

<210> SEQ ID NO 22
<211> LENGTH: 1448
<212> TYPE: PRT
<213> ORGANISM: Homo sapiens

<400> SEQUENCE: 22

Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Gln Arg Lys Leu
            20                  25                  30

Val Glu Ile Gly Trp Ser Tyr Thr Gly Ala Leu Asn Gln Lys Asn
        35                  40                  45
```

```
Trp Gly Lys Lys Tyr Pro Thr Cys Asn Ser Pro Lys Gln Ser Pro Ile
 50                  55                  60

Asn Ile Asp Glu Asp Leu Thr Gln Val Asn Val Asn Leu Lys Lys Leu
 65                  70                  75                  80

Lys Phe Gln Gly Trp Asp Lys Thr Ser Leu Glu Asn Thr Phe Ile His
                 85                  90                  95

Asn Thr Gly Lys Thr Val Glu Ile Asn Leu Thr Asn Asp Tyr Arg Val
                100                 105                 110

Ser Gly Gly Val Ser Glu Met Val Phe Lys Ala Ser Lys Ile Thr Phe
            115                 120                 125

His Trp Gly Lys Cys Asn Met Ser Ser Asp Gly Ser Glu His Ser Leu
            130                 135                 140

Glu Gly Gln Lys Phe Pro Leu Glu Met Gln Ile Tyr Cys Phe Asp Ala
145                 150                 155                 160

Asp Arg Phe Ser Ser Phe Glu Glu Ala Val Lys Gly Lys Gly Lys Leu
                165                 170                 175

Arg Ala Leu Ser Ile Leu Phe Glu Val Gly Thr Glu Asn Leu Asp
                180                 185                 190

Phe Lys Ala Ile Ile Asp Gly Val Glu Ser Val Ser Arg Phe Gly Lys
            195                 200                 205

Gln Ala Ala Leu Asp Pro Phe Ile Leu Leu Asn Leu Leu Pro Asn Ser
210                 215                 220

Thr Asp Lys Tyr Tyr Ile Tyr Asn Gly Ser Leu Thr Ser Pro Pro Cys
225                 230                 235                 240

Thr Asp Thr Val Asp Trp Ile Val Phe Lys Asp Thr Val Ser Ile Ser
                245                 250                 255

Glu Ser Gln Leu Ala Val Phe Cys Glu Val Leu Thr Met Gln Gln Ser
            260                 265                 270

Gly Tyr Val Met Leu Met Asp Tyr Leu Gln Asn Asn Phe Arg Glu Gln
            275                 280                 285

Gln Tyr Lys Phe Ser Arg Gln Val Phe Ser Ser Tyr Thr Gly Lys Glu
            290                 295                 300

Glu Ile His Glu Ala Val Cys Ser Ser Glu Pro Glu Asn Val Gln Ala
305                 310                 315                 320

Asp Pro Glu Asn Tyr Thr Ser Leu Leu Val Thr Trp Glu Arg Pro Arg
                325                 330                 335

Val Val Tyr Asp Thr Met Ile Glu Lys Phe Ala Val Leu Tyr Gln Gln
                340                 345                 350

Leu Asp Gly Glu Asp Gln Thr Lys His Glu Phe Leu Thr Asp Gly Tyr
            355                 360                 365

Gln Asp Leu Gly Ala Ile Leu Asn Asn Leu Leu Pro Asn Met Ser Tyr
370                 375                 380

Val Leu Gln Ile Val Ala Ile Cys Thr Asn Gly Leu Tyr Gly Lys Tyr
385                 390                 395                 400

Ser Asp Gln Leu Ile Val Asp Met Pro Thr Asp Asn Pro Glu Leu Asp
                405                 410                 415

Leu Phe Pro Glu Leu Ile Gly Thr Glu Glu Ile Lys Glu Glu
                420                 425                 430

Glu Gly Lys Asp Ile Glu Glu Gly Ala Ile Val Asn Pro Gly Arg Asp
            435                 440                 445

Ser Ala Thr Asn Gln Ile Arg Lys Lys Glu Pro Gln Ile Ser Thr Thr
450                 455                 460
```

```
Thr His Tyr Asn Arg Ile Gly Thr Lys Tyr Asn Glu Ala Lys Thr Asn
465                 470                 475                 480

Arg Ser Pro Thr Arg Gly Ser Glu Phe Ser Gly Lys Gly Asp Val Pro
            485                 490                 495

Asn Thr Ser Leu Asn Ser Thr Ser Gln Pro Val Thr Lys Leu Ala Thr
            500                 505                 510

Glu Lys Asp Ile Ser Leu Thr Ser Gln Thr Val Thr Glu Leu Pro Pro
            515                 520                 525

His Thr Val Glu Gly Thr Ser Ala Ser Leu Asn Asp Gly Ser Lys Thr
            530                 535                 540

Val Leu Arg Ser Pro His Met Asn Leu Ser Gly Thr Ala Glu Ser Leu
545                 550                 555                 560

Asn Thr Val Ser Ile Thr Glu Tyr Glu Glu Ser Leu Leu Thr Ser
                565                 570                 575

Phe Lys Leu Asp Thr Gly Ala Glu Asp Ser Ser Gly Ser Ser Pro Ala
                580                 585                 590

Thr Ser Ala Ile Pro Phe Ile Ser Glu Asn Ile Ser Gln Gly Tyr Ile
            595                 600                 605

Phe Ser Ser Glu Asn Pro Glu Thr Ile Thr Tyr Asp Val Leu Ile Pro
            610                 615                 620

Glu Ser Ala Arg Asn Ala Ser Glu Asp Ser Thr Ser Ser Gly Ser Glu
625                 630                 635                 640

Glu Ser Leu Lys Asp Pro Ser Met Glu Gly Asn Val Trp Phe Pro Ser
                645                 650                 655

Ser Thr Asp Ile Thr Ala Gln Pro Asp Val Gly Ser Gly Arg Glu Ser
            660                 665                 670

Phe Leu Gln Thr Asn Tyr Thr Glu Ile Arg Val Asp Glu Ser Glu Lys
            675                 680                 685

Thr Thr Lys Ser Phe Ser Ala Gly Pro Val Met Ser Gln Gly Pro Ser
            690                 695                 700

Val Thr Asp Leu Glu Met Pro His Tyr Ser Thr Phe Ala Tyr Phe Pro
705                 710                 715                 720

Thr Glu Val Thr Pro His Ala Phe Thr Pro Ser Ser Arg Gln Gln Asp
                725                 730                 735

Leu Val Ser Thr Val Asn Val Val Tyr Ser Gln Thr Thr Gln Pro Val
            740                 745                 750

Tyr Asn Glu Ala Ser Asn Ser Ser His Glu Ser Arg Ile Gly Leu Ala
            755                 760                 765

Glu Gly Leu Glu Ser Glu Lys Lys Ala Val Ile Pro Leu Val Ile Val
            770                 775                 780

Ser Ala Leu Thr Phe Ile Cys Leu Val Val Leu Val Gly Ile Leu Ile
785                 790                 795                 800

Tyr Trp Arg Lys Cys Phe Gln Thr Ala His Phe Tyr Leu Glu Asp Ser
                805                 810                 815

Thr Ser Pro Arg Val Ile Ser Thr Pro Pro Thr Pro Ile Phe Pro Ile
            820                 825                 830

Ser Asp Asp Val Gly Ala Ile Pro Ile Lys His Phe Pro Lys His Val
            835                 840                 845

Ala Asp Leu His Ala Ser Ser Gly Phe Thr Glu Glu Phe Glu Glu Val
            850                 855                 860

Gln Ser Cys Thr Val Asp Leu Gly Ile Thr Ala Asp Ser Ser Asn His
865                 870                 875                 880

Pro Asp Asn Lys His Lys Asn Arg Tyr Ile Asn Ile Val Ala Tyr Asp
```

```
                885                 890                 895
His Ser Arg Val Lys Leu Ala Gln Leu Ala Glu Lys Asp Gly Lys Leu
                900                 905                 910
Thr Asp Tyr Ile Asn Ala Asn Tyr Val Asp Gly Tyr Asn Arg Pro Lys
        915                 920                 925
Ala Tyr Ile Ala Ala Gln Gly Pro Leu Lys Ser Thr Ala Glu Asp Phe
    930                 935                 940
Trp Arg Met Ile Trp Glu His Asn Val Glu Val Ile Val Met Ile Thr
945                 950                 955                 960
Asn Leu Val Glu Lys Gly Arg Arg Lys Cys Asp Gln Tyr Trp Pro Ala
            965                 970                 975
Asp Gly Ser Glu Glu Tyr Gly Asn Phe Leu Val Thr Gln Lys Ser Val
        980                 985                 990
Gln Val Leu Ala Tyr Tyr Thr Val Arg Asn Phe Thr Leu Arg Asn Thr
        995                 1000                1005
Lys Ile Lys Lys Gly Ser Gln  Lys Gly Arg Pro Ser  Gly Arg Val
    1010                1015                1020
Val Thr Gln Tyr His Tyr Thr  Gln Trp Pro Asp Met  Gly Val Pro
    1025                1030                1035
Glu Tyr Ser Leu Pro Val Leu  Thr Phe Val Arg Lys  Ala Ala Tyr
    1040                1045                1050
Ala Lys Arg His Ala Val Gly  Pro Val Val His Cys  Ser Ala
    1055                1060                1065
Gly Val Gly Arg Thr Gly Tyr  Ile Val Leu Asp  Ser Met Leu
    1070                1075                1080
Gln Gln Ile Gln His Glu Gly  Thr Val Asn Ile Phe  Gly Phe Leu
    1085                1090                1095
Lys His Ile Arg Ser Gln Arg  Asn Tyr Leu Val Gln  Thr Glu Glu
    1100                1105                1110
Gln Tyr Val Phe Ile His Asp  Thr Leu Val Glu Ala  Ile Leu Ser
    1115                1120                1125
Lys Glu Thr Glu Val Leu Asp  Ser His Ile His Ala  Tyr Val Asn
    1130                1135                1140
Ala Leu Leu Ile Pro Gly Pro  Ala Gly Lys Thr Lys  Leu Glu Lys
    1145                1150                1155
Gln Phe Gln Leu Leu Ser Gln  Ser Asn Ile Gln Gln  Ser Asp Tyr
    1160                1165                1170
Ser Ala Ala Leu Lys Gln Cys  Asn Arg Glu Lys Asn  Arg Thr Ser
    1175                1180                1185
Ser Ile Ile Pro Val Glu Arg  Ser Arg Val Gly Ile  Ser Ser Leu
    1190                1195                1200
Ser Gly Glu Gly Thr Asp Tyr  Ile Asn Ala Ser Tyr  Ile Met Gly
    1205                1210                1215
Tyr Tyr Gln Ser Asn Glu Phe  Ile Ile Thr Gln His  Pro Leu Leu
    1220                1225                1230
His Thr Ile Lys Asp Phe Trp  Arg Met Ile Trp Asp  His Asn Ala
    1235                1240                1245
Gln Leu Val Val Met Ile Pro  Asp Gly Gln Asn Met  Ala Glu Asp
    1250                1255                1260
Glu Phe Val Tyr Trp Pro Asn  Lys Asp Glu Pro Ile  Asn Cys Glu
    1265                1270                1275
Ser Phe Lys Val Thr Leu Met  Ala Glu Glu His Lys  Cys Leu Ser
    1280                1285                1290
```

-continued

```
Asn Glu Glu Lys Leu Ile Ile Gln Asp Phe Ile Leu Glu Ala Thr
1295                1300                1305

Gln Asp Asp Tyr Val Leu Glu Val Arg His Phe Gln Cys Pro Lys
    1310                1315                1320

Trp Pro Asn Pro Asp Ser Pro Ile Ser Lys Thr Phe Glu Leu Ile
1325                1330                1335

Ser Val Ile Lys Glu Glu Ala Ala Asn Arg Asp Gly Pro Met Ile
    1340                1345                1350

Val His Asp Glu His Gly Gly Val Thr Ala Gly Thr Phe Cys Ala
    1355                1360                1365

Leu Thr Thr Leu Met His Gln Leu Glu Lys Glu Asn Ser Val Asp
    1370                1375                1380

Val Tyr Gln Val Ala Lys Met Ile Asn Leu Met Arg Pro Gly Val
    1385                1390                1395

Phe Ala Asp Ile Glu Gln Tyr Gln Phe Leu Tyr Lys Val Ile Leu
1400                1405                1410

Ser Leu Val Ser Thr Arg Gln Glu Glu Asn Pro Ser Thr Ser Leu
    1415                1420                1425

Asp Ser Asn Gly Ala Ala Leu Pro Asp Gly Asn Ile Ala Glu Ser
    1430                1435                1440

Leu Glu Ser Leu Val
    1445

<210> SEQ ID NO 23
<211> LENGTH: 1304
<212> TYPE: PRT
<213> ORGANISM: Homo sapiens

<400> SEQUENCE: 23

Met Gln Leu Lys Ile Met Pro Lys Lys Arg Leu Ser Ala Gly Arg
1               5                   10                  15

Val Pro Leu Ile Leu Phe Leu Cys Gln Met Ile Ser Ala Leu Glu Val
                20                  25                  30

Pro Leu Asp Pro Lys Leu Leu Glu Asp Leu Val Gln Pro Pro Thr Ile
        35                  40                  45

Thr Gln Gln Ser Pro Lys Asp Tyr Ile Ile Asp Pro Arg Glu Asn Ile
    50                  55                  60

Val Ile Gln Cys Glu Ala Lys Gly Lys Pro Pro Ser Phe Ser Trp
65                  70                  75                  80

Thr Arg Asn Gly Thr His Phe Asp Ile Asp Lys Asp Pro Leu Val Thr
                85                  90                  95

Met Lys Pro Gly Thr Gly Thr Leu Ile Ile Asn Ile Met Ser Glu Gly
            100                 105                 110

Lys Ala Glu Thr Tyr Glu Gly Val Tyr Gln Cys Thr Ala Arg Asn Glu
        115                 120                 125

Arg Gly Ala Ala Val Ser Asn Asn Ile Val Val Arg Pro Ser Arg Ser
    130                 135                 140

Pro Leu Trp Thr Lys Glu Lys Leu Glu Pro Ile Thr Leu Gln Ser Gly
145                 150                 155                 160

Gln Ser Leu Val Leu Pro Cys Arg Pro Pro Ile Gly Leu Pro Pro Pro
                165                 170                 175

Ile Ile Phe Trp Met Asp Asn Ser Phe Gln Arg Leu Pro Gln Ser Glu
            180                 185                 190

Arg Val Ser Gln Gly Leu Asn Gly Asp Leu Tyr Phe Ser Asn Val Leu
```

```
              195                 200                 205
Pro Glu Asp Thr Arg Glu Asp Tyr Ile Cys Tyr Ala Arg Phe Asn His
    210                 215                 220
Thr Gln Thr Ile Gln Gln Lys Gln Pro Ile Ser Val Lys Val Ile Ser
225                 230                 235                 240
Val Asp Glu Leu Asn Asp Thr Ile Ala Ala Asn Leu Ser Asp Thr Glu
                245                 250                 255
Phe Tyr Gly Ala Lys Ser Ser Arg Glu Arg Pro Pro Thr Phe Leu Thr
            260                 265                 270
Pro Glu Gly Asn Ala Ser Asn Lys Glu Glu Leu Arg Gly Asn Val Leu
        275                 280                 285
Ser Leu Glu Cys Ile Ala Glu Gly Leu Pro Thr Pro Ile Ile Tyr Trp
    290                 295                 300
Ala Lys Glu Asp Gly Met Leu Pro Lys Asn Arg Thr Val Tyr Lys Asn
305                 310                 315                 320
Phe Glu Lys Thr Leu Gln Ile Ile His Val Ser Glu Ala Asp Ser Gly
                325                 330                 335
Asn Tyr Gln Cys Ile Ala Lys Asn Ala Leu Gly Ala Ile His His Thr
            340                 345                 350
Ile Ser Val Arg Val Lys Ala Ala Pro Tyr Trp Ile Thr Ala Pro Gln
        355                 360                 365
Asn Leu Val Leu Ser Pro Gly Glu Asp Gly Thr Leu Ile Cys Arg Ala
    370                 375                 380
Asn Gly Asn Pro Lys Pro Arg Ile Ser Trp Leu Thr Asn Gly Val Pro
385                 390                 395                 400
Ile Glu Ile Ala Pro Asp Pro Ser Arg Lys Ile Asp Gly Asp Thr
                405                 410                 415
Ile Ile Phe Ser Asn Val Gln Glu Arg Ser Ser Ala Val Tyr Gln Cys
            420                 425                 430
Asn Ala Ser Asn Glu Tyr Gly Tyr Leu Leu Ala Asn Ala Phe Val Asn
        435                 440                 445
Val Leu Ala Glu Pro Pro Arg Ile Leu Thr Pro Ala Asn Thr Leu Tyr
    450                 455                 460
Gln Val Ile Ala Asn Arg Pro Ala Leu Leu Asp Cys Ala Phe Phe Gly
465                 470                 475                 480
Ser Pro Leu Pro Thr Ile Glu Trp Phe Lys Gly Ala Lys Gly Ser Ala
                485                 490                 495
Leu His Glu Asp Ile Tyr Val Leu His Glu Asn Gly Thr Leu Glu Ile
            500                 505                 510
Pro Val Ala Gln Lys Asp Ser Thr Gly Thr Tyr Thr Cys Val Ala Arg
        515                 520                 525
Asn Lys Leu Gly Met Ala Lys Asn Glu Val His Leu Glu Ile Lys Asp
    530                 535                 540
Pro Thr Trp Ile Val Lys Gln Pro Glu Tyr Ala Val Val Gln Arg Gly
545                 550                 555                 560
Ser Met Val Ser Phe Glu Cys Lys Val Lys His Asp His Thr Leu Ser
                565                 570                 575
Leu Thr Val Leu Trp Leu Lys Asp Asn Arg Glu Leu Pro Ser Asp Glu
            580                 585                 590
Arg Phe Thr Val Asp Lys Asp His Leu Val Val Ala Asp Val Ser Asp
        595                 600                 605
Asp Asp Ser Gly Thr Tyr Thr Cys Val Ala Asn Thr Thr Leu Asp Ser
    610                 615                 620
```

```
Val Ser Ala Ser Ala Val Leu Ser Val Ala Pro Thr Pro Thr Pro
625                 630                 635                 640

Ala Pro Val Tyr Asp Val Pro Asn Pro Pro Phe Asp Leu Glu Leu Thr
                645                 650                 655

Asp Gln Leu Asp Lys Ser Val Gln Leu Ser Trp Thr Pro Gly Asp Asp
            660                 665                 670

Asn Asn Ser Pro Ile Thr Lys Phe Ile Ile Glu Tyr Glu Asp Ala Met
            675                 680                 685

His Lys Pro Gly Leu Trp His His Gln Thr Glu Val Ser Gly Thr Gln
690                 695                 700

Thr Thr Ala Gln Leu Lys Leu Ser Pro Tyr Val Asn Tyr Ser Phe Arg
705                 710                 715                 720

Val Met Ala Val Asn Ser Ile Gly Lys Ser Leu Pro Ser Glu Ala Ser
                725                 730                 735

Glu Gln Tyr Leu Thr Lys Ala Ser Glu Pro Asp Lys Asn Pro Thr Ala
                740                 745                 750

Val Glu Gly Leu Gly Ser Glu Pro Asp Asn Leu Val Ile Thr Trp Lys
                755                 760                 765

Pro Leu Asn Gly Phe Glu Ser Asn Gly Pro Gly Leu Gln Tyr Lys Val
770                 775                 780

Ser Trp Arg Gln Lys Asp Gly Asp Glu Trp Thr Ser Val Val Val
785                 790                 795                 800

Ala Asn Val Ser Lys Tyr Ile Val Ser Gly Thr Pro Thr Phe Val Pro
                805                 810                 815

Tyr Leu Ile Lys Val Gln Ala Leu Asn Asp Met Gly Phe Ala Pro Glu
                820                 825                 830

Pro Ala Val Val Met Gly His Ser Gly Glu Asp Leu Pro Met Val Ala
                835                 840                 845

Pro Gly Asn Val Arg Val Asn Val Val Asn Ser Thr Leu Ala Glu Val
850                 855                 860

His Trp Asp Pro Val Pro Leu Lys Ser Ile Arg Gly His Leu Gln Gly
865                 870                 875                 880

Tyr Arg Ile Tyr Tyr Trp Lys Thr Gln Ser Ser Leu Arg Asn Arg
                885                 890                 895

Arg His Ile Glu Lys Lys Ile Leu Thr Phe Gln Gly Ser Lys Thr His
                900                 905                 910

Gly Met Leu Pro Gly Leu Glu Pro Phe Ser His Tyr Thr Leu Asn Val
                915                 920                 925

Arg Val Val Asn Gly Lys Gly Glu Gly Pro Ala Ser Pro Asp Arg Val
930                 935                 940

Phe Asn Thr Pro Glu Gly Val Pro Ser Ala Pro Ser Ser Leu Lys Ile
945                 950                 955                 960

Val Asn Pro Thr Leu Asp Ser Leu Thr Leu Glu Trp Asp Pro Pro Ser
                965                 970                 975

His Pro Asn Gly Ile Leu Thr Glu Tyr Thr Leu Lys Tyr Gln Pro Ile
                980                 985                 990

Asn Ser Thr His Glu Leu Gly Pro  Leu Val Asp Leu Lys  Ile Pro Ala
            995                 1000                1005

Asn Lys  Thr Arg Trp Thr Leu  Lys Asn Leu Asn Phe  Ser Thr Arg
        1010                1015                1020

Tyr Lys  Phe Tyr Phe Tyr Ala  Gln Thr Ser Ala Gly  Ser Gly Ser
        1025                1030                1035
```

-continued

```
Gln Ile Thr Glu Glu Ala Val Thr Thr Val Asp Glu Ala Gly Ile
    1040                1045                1050

Leu Pro Pro Asp Val Gly Ala Gly Lys Val Gln Ala Val Asn Pro
    1055                1060                1065

Arg Ile Ser Asn Leu Thr Ala Ala Ala Ala Glu Thr Tyr Ala Asn
    1070                1075                1080

Ile Ser Trp Glu Tyr Glu Gly Pro Glu His Val Asn Phe Tyr Val
    1085                1090                1095

Glu Tyr Gly Val Ala Gly Ser Lys Glu Glu Trp Arg Lys Glu Ile
    1100                1105                1110

Val Asn Gly Ser Arg Ser Phe Phe Gly Leu Lys Gly Leu Met Pro
    1115                1120                1125

Gly Thr Ala Tyr Lys Val Arg Val Gly Ala Val Gly Asp Ser Gly
    1130                1135                1140

Phe Val Ser Ser Glu Asp Val Phe Glu Thr Gly Pro Ala Met Ala
    1145                1150                1155

Ser Arg Gln Val Asp Ile Ala Thr Gln Gly Trp Phe Ile Gly Leu
    1160                1165                1170

Met Cys Ala Val Ala Leu Leu Ile Leu Ile Leu Leu Ile Val Cys
    1175                1180                1185

Phe Ile Arg Arg Asn Lys Gly Gly Lys Tyr Pro Val Lys Glu Lys
    1190                1195                1200

Glu Asp Ala His Ala Asp Pro Glu Ile Gln Pro Met Lys Glu Asp
    1205                1210                1215

Asp Gly Thr Phe Gly Glu Tyr Ser Asp Ala Glu Asp His Lys Pro
    1220                1225                1230

Leu Lys Lys Gly Ser Arg Thr Pro Ser Asp Arg Thr Val Lys Lys
    1235                1240                1245

Glu Asp Ser Asp Asp Ser Leu Val Asp Tyr Gly Glu Gly Val Asn
    1250                1255                1260

Gly Gln Phe Asn Glu Asp Gly Ser Phe Ile Gly Gln Tyr Ser Gly
    1265                1270                1275

Lys Lys Glu Lys Glu Pro Ala Glu Gly Asn Glu Ser Ser Glu Ala
    1280                1285                1290

Pro Ser Pro Val Asn Ala Met Asn Ser Phe Val
    1295                1300

<210> SEQ ID NO 24
<211> LENGTH: 1236
<212> TYPE: PRT
<213> ORGANISM: Homo sapiens

<400> SEQUENCE: 24

Met Gln Leu Lys Ile Met Pro Lys Lys Lys Arg Leu Ser Ala Gly Arg
1               5                   10                  15

Val Pro Leu Ile Leu Phe Leu Cys Gln Met Ile Ser Ala Leu Glu Val
                20                  25                  30

Pro Leu Asp Pro Lys Leu Leu Glu Asp Leu Val Gln Pro Thr Ile
        35                  40                  45

Thr Gln Gln Ser Pro Lys Asp Tyr Ile Ile Asp Pro Arg Glu Asn Ile
    50                  55                  60

Val Ile Gln Cys Glu Ala Lys Gly Lys Pro Pro Ser Phe Ser Trp
65                  70                  75                  80

Thr Arg Asn Gly Thr His Phe Asp Ile Asp Lys Asp Pro Leu Val Thr
                85                  90                  95
```

```
Met Lys Pro Gly Thr Gly Thr Leu Ile Ile Asn Ile Met Ser Glu Gly
            100                 105                 110

Lys Ala Glu Thr Tyr Glu Gly Val Tyr Gln Cys Thr Ala Arg Asn Glu
            115                 120                 125

Arg Gly Ala Ala Val Ser Asn Asn Ile Val Val Arg Pro Ser Arg Ser
        130                 135                 140

Pro Leu Trp Thr Lys Glu Lys Leu Glu Pro Ile Thr Leu Gln Ser Gly
145                 150                 155                 160

Gln Ser Leu Val Leu Pro Cys Arg Pro Pro Ile Gly Leu Pro Pro Pro
                165                 170                 175

Ile Ile Phe Trp Met Asp Asn Ser Phe Gln Arg Leu Pro Gln Ser Glu
            180                 185                 190

Arg Val Ser Gln Gly Leu Asn Gly Asp Leu Tyr Phe Ser Asn Val Leu
        195                 200                 205

Pro Glu Asp Thr Arg Glu Asp Tyr Ile Cys Tyr Ala Arg Phe Asn His
        210                 215                 220

Thr Gln Thr Ile Gln Gln Lys Gln Pro Ile Ser Val Lys Val Ile Ser
225                 230                 235                 240

Val Asp Glu Leu Asn Asp Thr Ile Ala Ala Asn Leu Ser Asp Thr Glu
            245                 250                 255

Phe Tyr Gly Ala Lys Ser Ser Arg Glu Arg Pro Pro Thr Phe Leu Thr
            260                 265                 270

Pro Glu Gly Asn Ala Ser Asn Lys Glu Glu Leu Arg Gly Asn Val Leu
            275                 280                 285

Ser Leu Glu Cys Ile Ala Glu Gly Leu Pro Thr Pro Ile Ile Tyr Trp
        290                 295                 300

Ala Lys Glu Asp Gly Met Leu Pro Lys Asn Arg Thr Val Tyr Lys Asn
305                 310                 315                 320

Phe Glu Lys Thr Leu Gln Ile Ile His Val Ser Glu Ala Asp Ser Gly
            325                 330                 335

Asn Tyr Gln Cys Ile Ala Lys Asn Ala Leu Gly Ala Ile His His Thr
            340                 345                 350

Ile Ser Val Arg Val Lys Ala Ala Pro Tyr Trp Ile Thr Ala Pro Gln
        355                 360                 365

Asn Leu Val Leu Ser Pro Gly Glu Asp Gly Thr Leu Ile Cys Arg Ala
        370                 375                 380

Asn Gly Asn Pro Lys Pro Arg Ile Ser Trp Leu Thr Asn Gly Val Pro
385                 390                 395                 400

Ile Glu Ile Ala Pro Asp Asp Pro Ser Arg Lys Ile Asp Gly Asp Thr
                405                 410                 415

Ile Ile Phe Ser Asn Val Gln Glu Arg Ser Ser Ala Val Tyr Gln Cys
            420                 425                 430

Asn Ala Ser Asn Glu Tyr Gly Tyr Leu Leu Ala Asn Ala Phe Val Asn
            435                 440                 445

Val Leu Ala Glu Pro Pro Arg Ile Leu Thr Pro Ala Asn Thr Leu Tyr
        450                 455                 460

Gln Val Ile Ala Asn Arg Pro Ala Leu Leu Asp Cys Ala Phe Phe Gly
465                 470                 475                 480

Ser Pro Leu Pro Thr Ile Glu Trp Phe Lys Gly Ala Lys Gly Ser Ala
                485                 490                 495

Leu His Glu Asp Ile Tyr Val Leu His Glu Asn Gly Thr Leu Glu Ile
            500                 505                 510
```

```
Pro Val Ala Gln Lys Asp Ser Thr Gly Thr Tyr Thr Cys Val Ala Arg
            515                 520                 525
Asn Lys Leu Gly Met Ala Lys Asn Glu Val His Leu Glu Ile Lys Asp
530                 535                 540
Pro Thr Trp Ile Val Lys Gln Pro Glu Tyr Ala Val Val Gln Arg Gly
545                 550                 555                 560
Ser Met Val Ser Phe Glu Cys Lys Val Lys His Asp His Thr Leu Ser
                565                 570                 575
Leu Thr Val Leu Trp Leu Lys Asp Asn Arg Glu Leu Pro Ser Asp Glu
            580                 585                 590
Arg Phe Thr Val Asp Lys Asp His Leu Val Val Ala Asp Val Ser Asp
        595                 600                 605
Asp Asp Ser Gly Thr Tyr Thr Cys Val Ala Asn Thr Thr Leu Asp Ser
    610                 615                 620
Val Ser Ala Ser Ala Val Leu Ser Val Val Ala Pro Thr Pro Thr Pro
625                 630                 635                 640
Ala Pro Val Tyr Asp Val Pro Asn Pro Pro Phe Asp Leu Glu Leu Thr
                645                 650                 655
Asp Gln Leu Asp Lys Ser Val Gln Leu Ser Trp Thr Pro Gly Asp Asp
            660                 665                 670
Asn Asn Ser Pro Ile Thr Lys Phe Ile Ile Glu Tyr Glu Asp Ala Met
        675                 680                 685
His Lys Pro Gly Leu Trp His Gln Thr Glu Val Ser Gly Thr Gln
    690                 695                 700
Thr Thr Ala Gln Leu Lys Leu Ser Pro Tyr Val Asn Tyr Ser Phe Arg
705                 710                 715                 720
Val Met Ala Val Asn Ser Ile Gly Lys Ser Leu Pro Ser Glu Ala Ser
                725                 730                 735
Glu Gln Tyr Leu Thr Lys Ala Ser Glu Pro Asp Lys Asn Pro Thr Ala
            740                 745                 750
Val Glu Gly Leu Gly Ser Glu Pro Asp Asn Leu Val Ile Thr Trp Lys
        755                 760                 765
Pro Leu Asn Gly Phe Glu Ser Asn Gly Pro Gly Leu Gln Tyr Lys Val
    770                 775                 780
Ser Trp Arg Gln Lys Asp Gly Asp Glu Trp Thr Ser Val Val Val
785                 790                 795                 800
Ala Asn Val Ser Lys Tyr Ile Val Ser Gly Thr Pro Thr Phe Val Pro
                805                 810                 815
Tyr Leu Ile Lys Val Gln Ala Leu Asn Asp Met Gly Phe Ala Pro Glu
            820                 825                 830
Pro Ala Val Val Met Gly His Ser Gly Glu Asp Leu Pro Met Val Ala
        835                 840                 845
Pro Gly Asn Val Arg Val Asn Val Asn Ser Thr Leu Ala Glu Val
    850                 855                 860
His Trp Asp Pro Val Pro Leu Lys Ser Ile Arg Gly His Leu Gln Gly
865                 870                 875                 880
Tyr Arg Ile Tyr Tyr Trp Lys Thr Gln Ser Ser Ser Lys Arg Asn Arg
                885                 890                 895
Arg His Ile Glu Lys Lys Ile Leu Thr Phe Gln Gly Ser Lys Thr His
            900                 905                 910
Gly Met Leu Pro Gly Leu Glu Pro Phe Ser His Tyr Thr Leu Asn Val
        915                 920                 925
Arg Val Val Asn Gly Lys Gly Glu Gly Pro Ala Ser Pro Asp Arg Val
```

```
                930             935             940
    Phe Asn Thr Pro Glu Gly Val Pro Ser Ala Pro Ser Ser Leu Lys Ile
    945                 950                 955                 960

Val Asn Pro Thr Leu Asp Ser Leu Thr Leu Glu Trp Asp Pro Pro Ser
                    965                 970                 975

His Pro Asn Gly Ile Leu Thr Glu Tyr Thr Leu Lys Tyr Gln Pro Ile
                980                 985                 990

Asn Ser Thr His Glu Leu Gly Pro Leu Val Asp Leu Lys Ile Pro Ala
            995                 1000                1005

Asn Lys Thr Arg Trp Thr Leu Lys Asn Leu Asn Phe Ser Thr Arg
        1010                1015                1020

Tyr Lys Phe Tyr Phe Tyr Ala Gln Thr Ser Ala Gly Ser Gly Ser
        1025                1030                1035

Gln Ile Thr Glu Glu Ala Val Thr Thr Val Asp Glu Ala Gly Ile
        1040                1045                1050

Leu Pro Pro Asp Val Gly Ala Gly Lys Val Gln Ala Val Asn Pro
        1055                1060                1065

Arg Ile Ser Asn Leu Thr Ala Ala Ala Glu Thr Tyr Ala Asn
        1070                1075                1080

Ile Ser Trp Glu Tyr Glu Gly Pro Glu His Val Asn Phe Tyr Val
        1085                1090                1095

Glu Tyr Gly Val Ala Gly Ser Lys Glu Glu Trp Arg Lys Glu Ile
        1100                1105                1110

Val Asn Gly Ser Arg Ser Phe Phe Gly Leu Lys Gly Leu Met Pro
        1115                1120                1125

Gly Thr Ala Tyr Lys Val Arg Val Gly Ala Val Gly Asp Ser Gly
        1130                1135                1140

Phe Val Ser Ser Glu Asp Val Phe Glu Thr Gly Pro Ala Met Ala
        1145                1150                1155

Ser Arg Gln Val Asp Ile Ala Thr Gln Gly Trp Phe Ile Gly Leu
        1160                1165                1170

Met Cys Ala Val Ala Leu Leu Ile Leu Ile Leu Leu Ile Val Cys
        1175                1180                1185

Phe Ile Arg Arg Asn Lys Gly Gly Lys Tyr Pro Val Lys Glu Lys
        1190                1195                1200

Glu Asp Ala His Ala Asp Pro Glu Ile Gln Pro Met Lys Glu Asp
        1205                1210                1215

Asp Gly Thr Phe Gly Glu Tyr Arg Leu Phe Ser Phe Val Ser Ser
        1220                1225                1230

Ala Ser Phe
        1235

<210> SEQ ID NO 25
<211> LENGTH: 1180
<212> TYPE: PRT
<213> ORGANISM: Homo sapiens

<400> SEQUENCE: 25

Met Gln Leu Lys Ile Met Pro Lys Lys Arg Leu Ser Ala Gly Arg
1               5                   10                  15

Val Pro Leu Ile Leu Phe Leu Cys Gln Met Ile Ser Ala Leu Glu Val
                20                  25                  30

Pro Leu Asp Pro Lys Leu Leu Glu Asp Leu Val Gln Pro Pro Thr Ile
            35                  40                  45
```

```
Thr Gln Gln Ser Pro Lys Asp Tyr Ile Ile Asp Pro Arg Glu Asn Ile
    50              55                  60
Val Ile Gln Cys Glu Ala Lys Gly Lys Pro Pro Pro Ser Phe Ser Trp
 65              70              75                  80
Thr Arg Asn Gly Thr His Phe Asp Ile Asp Lys Asp Pro Leu Val Thr
                85                  90                  95
Met Lys Pro Gly Thr Gly Thr Leu Ile Ile Asn Ile Met Ser Glu Gly
            100                 105                 110
Lys Ala Glu Thr Tyr Glu Gly Val Tyr Gln Cys Thr Ala Arg Asn Glu
            115                 120                 125
Arg Gly Ala Ala Val Ser Asn Asn Ile Val Val Arg Pro Ser Arg Ser
    130                 135                 140
Pro Leu Trp Thr Lys Glu Lys Leu Glu Pro Ile Thr Leu Gln Ser Gly
145                 150                 155                 160
Gln Ser Leu Val Leu Pro Cys Arg Pro Pro Ile Gly Leu Pro Pro Pro
                165                 170                 175
Ile Ile Phe Trp Met Asp Asn Ser Phe Gln Arg Leu Pro Gln Ser Glu
            180                 185                 190
Arg Val Ser Gln Gly Leu Asn Gly Asp Leu Tyr Phe Ser Asn Val Leu
    195                 200                 205
Pro Glu Asp Thr Arg Glu Asp Tyr Ile Cys Tyr Ala Arg Phe Asn His
    210                 215                 220
Thr Gln Thr Ile Gln Gln Lys Gln Pro Ile Ser Val Lys Val Ile Ser
225                 230                 235                 240
Ala Lys Ser Ser Arg Glu Arg Pro Pro Thr Phe Leu Thr Pro Glu Gly
                245                 250                 255
Asn Ala Ser Asn Lys Glu Glu Leu Arg Gly Asn Val Leu Ser Leu Glu
            260                 265                 270
Cys Ile Ala Glu Gly Leu Pro Thr Pro Ile Ile Tyr Trp Ala Lys Glu
    275                 280                 285
Asp Gly Met Leu Pro Lys Asn Arg Thr Val Tyr Lys Asn Phe Glu Lys
    290                 295                 300
Thr Leu Gln Ile Ile His Val Ser Glu Ala Asp Ser Gly Asn Tyr Gln
305                 310                 315                 320
Cys Ile Ala Lys Asn Ala Leu Gly Ala Ile His His Thr Ile Ser Val
                325                 330                 335
Arg Val Lys Ala Ala Pro Tyr Trp Ile Thr Ala Pro Gln Asn Leu Val
            340                 345                 350
Leu Ser Pro Gly Glu Asp Gly Thr Leu Ile Cys Arg Ala Asn Gly Asn
    355                 360                 365
Pro Lys Pro Arg Ile Ser Trp Leu Thr Asn Gly Val Pro Ile Glu Ile
    370                 375                 380
Ala Pro Asp Asp Pro Ser Arg Lys Ile Asp Gly Asp Thr Ile Ile Phe
385                 390                 395                 400
Ser Asn Val Gln Glu Arg Ser Ala Val Tyr Gln Cys Asn Ala Ser Asn
                405                 410                 415
Asn Glu Tyr Gly Tyr Leu Leu Ala Asn Ala Phe Val Asn Val Leu Ala
            420                 425                 430
Glu Pro Pro Arg Ile Leu Thr Pro Ala Asn Thr Leu Tyr Gln Val Ile
            435                 440                 445
Ala Asn Arg Pro Ala Leu Leu Asp Cys Ala Phe Phe Gly Ser Pro Leu
450                 455                 460
Pro Thr Ile Glu Trp Phe Lys Gly Ala Lys Gly Ser Ala Leu His Glu
```

```
                465                 470                 475                 480
        Asp Ile Tyr Val Leu His Glu Asn Gly Thr Leu Glu Ile Pro Val Ala
                        485                 490                 495
        Gln Lys Asp Ser Thr Gly Thr Tyr Thr Cys Val Ala Arg Asn Lys Leu
                        500                 505                 510
        Gly Met Ala Lys Asn Glu Val His Leu Glu Ile Lys Asp Pro Thr Trp
                        515                 520                 525
        Ile Val Lys Gln Pro Glu Tyr Ala Val Val Gln Arg Gly Ser Met Val
                        530                 535                 540
        Ser Phe Glu Cys Lys Val Lys His Asp His Thr Leu Ser Leu Thr Val
        545                 550                 555                 560
        Leu Trp Leu Lys Asp Asn Arg Glu Leu Pro Ser Asp Glu Arg Phe Thr
                        565                 570                 575
        Val Asp Lys Asp His Leu Val Val Ala Asp Val Ser Asp Asp Ser
                        580                 585                 590
        Gly Thr Tyr Thr Cys Val Ala Asn Thr Thr Leu Asp Ser Val Ser Ala
                        595                 600                 605
        Ser Ala Val Leu Ser Val Val Ala Pro Thr Pro Thr Pro Ala Pro Val
                610                 615                 620
        Tyr Asp Val Pro Asn Pro Pro Phe Asp Leu Glu Leu Thr Asp Gln Leu
        625                 630                 635                 640
        Asp Lys Ser Val Gln Leu Ser Trp Thr Pro Gly Asp Asp Asn Asn Ser
                        645                 650                 655
        Pro Ile Thr Lys Phe Ile Ile Glu Tyr Glu Asp Ala Met His Lys Pro
                        660                 665                 670
        Gly Leu Trp His His Gln Thr Glu Val Ser Gly Thr Gln Thr Thr Ala
                        675                 680                 685
        Gln Leu Lys Leu Ser Pro Tyr Val Asn Tyr Ser Phe Arg Val Met Ala
                        690                 695                 700
        Val Asn Ser Ile Gly Lys Ser Leu Pro Ser Glu Ala Ser Glu Gln Tyr
        705                 710                 715                 720
        Leu Thr Lys Ala Ser Glu Pro Asp Lys Asn Pro Thr Ala Val Glu Gly
                        725                 730                 735
        Leu Gly Ser Glu Pro Asp Asn Leu Val Ile Thr Trp Lys Pro Leu Asn
                        740                 745                 750
        Gly Phe Glu Ser Asn Gly Pro Gly Leu Gln Tyr Lys Val Ser Trp Arg
                        755                 760                 765
        Gln Lys Asp Gly Asp Asp Glu Trp Thr Ser Val Val Val Ala Asn Val
                        770                 775                 780
        Ser Lys Tyr Ile Val Ser Gly Thr Pro Thr Phe Val Pro Tyr Leu Ile
        785                 790                 795                 800
        Lys Val Gln Ala Leu Asn Asp Met Gly Phe Ala Pro Glu Pro Ala Val
                        805                 810                 815
        Val Met Gly His Ser Gly Glu Asp Leu Pro Met Val Ala Pro Gly Asn
                        820                 825                 830
        Val Arg Val Asn Val Val Asn Ser Thr Leu Ala Glu Val His Trp Asp
                        835                 840                 845
        Pro Val Pro Leu Lys Ser Ile Arg Gly His Leu Gln Gly Tyr Arg Ile
                850                 855                 860
        Tyr Tyr Trp Lys Thr Gln Ser Ser Ser Lys Arg Asn Arg Arg His Ile
        865                 870                 875                 880
        Glu Lys Lys Ile Leu Thr Phe Gln Gly Ser Lys Thr His Gly Met Leu
                        885                 890                 895
```

Pro Gly Leu Glu Pro Phe Ser His Tyr Thr Leu Asn Val Arg Val Val
                900                 905                 910

Asn Gly Lys Gly Glu Gly Pro Ala Ser Pro Asp Arg Val Phe Asn Thr
            915                 920                 925

Pro Glu Gly Val Pro Ser Ala Pro Ser Ser Leu Lys Ile Val Asn Pro
        930                 935                 940

Thr Leu Asp Ser Leu Thr Leu Glu Trp Asp Pro Pro Ser His Pro Asn
945                 950                 955                 960

Gly Ile Leu Thr Glu Tyr Thr Leu Lys Tyr Gln Pro Ile Asn Ser Thr
                965                 970                 975

His Glu Leu Gly Pro Leu Val Asp Leu Lys Ile Pro Ala Asn Lys Thr
            980                 985                 990

Arg Trp Thr Leu Lys Asn Leu Asn Phe Ser Thr Arg Tyr Lys Phe Tyr
        995                 1000                1005

Phe Tyr Ala Gln Thr Ser Ala Gly Ser Gly Ser Gln Ile Thr Glu
    1010                1015                1020

Glu Ala Val Thr Thr Val Asp Glu Ala Met Ala Ser Arg Gln Val
    1025                1030                1035

Asp Ile Ala Thr Gln Gly Trp Phe Ile Gly Leu Met Cys Ala Val
    1040                1045                1050

Ala Leu Leu Ile Leu Ile Leu Leu Ile Val Cys Phe Ile Arg Arg
    1055                1060                1065

Asn Lys Gly Gly Lys Tyr Pro Val Lys Glu Lys Glu Asp Ala His
    1070                1075                1080

Ala Asp Pro Glu Ile Gln Pro Met Lys Glu Asp Gly Thr Phe
    1085                1090                1095

Gly Glu Tyr Ser Asp Ala Glu Asp His Lys Pro Leu Lys Lys Gly
    1100                1105                1110

Ser Arg Thr Pro Ser Asp Arg Thr Val Lys Lys Glu Asp Ser Asp
    1115                1120                1125

Asp Ser Leu Val Asp Tyr Gly Glu Gly Val Asn Gly Gln Phe Asn
    1130                1135                1140

Glu Asp Gly Ser Phe Ile Gly Gln Tyr Ser Gly Lys Lys Glu Lys
    1145                1150                1155

Glu Pro Ala Glu Gly Asn Glu Ser Ser Glu Ala Pro Ser Pro Val
    1160                1165                1170

Asn Ala Met Asn Ser Phe Val
    1175                1180

<210> SEQ ID NO 26
<211> LENGTH: 1183
<212> TYPE: PRT
<213> ORGANISM: Homo sapiens

<400> SEQUENCE: 26

Met Gln Leu Lys Ile Met Pro Lys Lys Arg Leu Ser Ala Gly Arg
1               5                   10                  15

Val Pro Leu Ile Leu Phe Leu Cys Gln Met Ile Ser Ala Leu Glu Val
            20                  25                  30

Pro Leu Asp Leu Val Gln Pro Thr Ile Thr Gln Ser Pro Lys
        35                  40                  45

Asp Tyr Ile Ile Asp Pro Arg Glu Asn Ile Val Ile Gln Cys Glu Ala
        50                  55                  60

Lys Gly Lys Pro Pro Pro Ser Phe Ser Trp Thr Arg Asn Gly Thr His

```
                65                  70                  75                  80
        Phe Asp Ile Asp Lys Asp Pro Leu Val Thr Met Lys Pro Gly Thr Gly
                            85                  90                  95
        Thr Leu Ile Ile Asn Ile Met Ser Glu Gly Lys Ala Glu Thr Tyr Glu
                            100                 105                 110
        Gly Val Tyr Gln Cys Thr Ala Arg Asn Glu Arg Gly Ala Ala Val Ser
                            115                 120                 125
        Asn Asn Ile Val Val Arg Pro Ser Arg Ser Pro Leu Trp Thr Lys Glu
                    130                 135                 140
        Lys Leu Glu Pro Ile Thr Leu Gln Ser Gly Gln Ser Leu Val Leu Pro
        145                 150                 155                 160
        Cys Arg Pro Pro Ile Gly Leu Pro Pro Ile Ile Phe Trp Met Asp
                                165                 170                 175
        Asn Ser Phe Gln Arg Leu Pro Gln Ser Glu Arg Val Ser Gln Gly Leu
                    180                 185                 190
        Asn Gly Asp Leu Tyr Phe Ser Asn Val Leu Pro Glu Asp Thr Arg Glu
                    195                 200                 205
        Asp Tyr Ile Cys Tyr Ala Arg Phe Asn His Thr Gln Thr Ile Gln Gln
                    210                 215                 220
        Lys Gln Pro Ile Ser Val Lys Val Ile Ser Val Asp Glu Leu Asn Asp
        225                 230                 235                 240
        Thr Ile Ala Ala Asn Leu Ser Asp Thr Glu Phe Tyr Gly Ala Lys Ser
                            245                 250                 255
        Ser Arg Glu Arg Pro Pro Thr Phe Leu Thr Pro Glu Gly Asn Ala Ser
                            260                 265                 270
        Asn Lys Glu Glu Leu Arg Gly Asn Val Leu Ser Leu Glu Cys Ile Ala
                    275                 280                 285
        Glu Gly Leu Pro Thr Pro Ile Ile Tyr Trp Ala Lys Glu Asp Gly Met
                    290                 295                 300
        Leu Pro Lys Asn Arg Thr Val Tyr Lys Asn Phe Glu Lys Thr Leu Gln
        305                 310                 315                 320
        Ile Ile His Val Ser Glu Ala Asp Ser Gly Asn Tyr Gln Cys Ile Ala
                            325                 330                 335
        Lys Asn Ala Leu Gly Ala Ile His His Thr Ile Ser Val Arg Val Lys
                    340                 345                 350
        Ala Ala Pro Tyr Trp Ile Thr Ala Pro Gln Asn Leu Val Leu Ser Pro
                    355                 360                 365
        Gly Glu Asp Gly Thr Leu Ile Cys Arg Ala Asn Gly Asn Pro Lys Pro
                    370                 375                 380
        Arg Ile Ser Trp Leu Thr Asn Gly Val Pro Ile Glu Ile Ala Pro Asp
        385                 390                 395                 400
        Asp Pro Ser Arg Lys Ile Asp Gly Asp Thr Ile Ile Phe Ser Asn Val
                            405                 410                 415
        Gln Glu Arg Ser Ser Ala Val Tyr Gln Cys Asn Ala Ser Asn Glu Tyr
                            420                 425                 430
        Gly Tyr Leu Leu Ala Asn Ala Phe Val Asn Val Leu Ala Glu Pro Pro
                    435                 440                 445
        Arg Ile Leu Thr Pro Ala Asn Thr Leu Tyr Gln Val Ile Ala Asn Arg
                    450                 455                 460
        Pro Ala Leu Leu Asp Cys Ala Phe Phe Gly Ser Pro Leu Pro Thr Ile
        465                 470                 475                 480
        Glu Trp Phe Lys Gly Ala Lys Gly Ser Ala Leu His Glu Asp Ile Tyr
                            485                 490                 495
```

```
Val Leu His Glu Asn Gly Thr Leu Glu Ile Pro Val Ala Gln Lys Asp
            500                 505                 510

Ser Thr Gly Thr Tyr Thr Cys Val Ala Arg Asn Lys Leu Gly Met Ala
            515                 520                 525

Lys Asn Glu Val His Leu Glu Ile Lys Asp Pro Thr Trp Ile Val Lys
            530                 535                 540

Gln Pro Glu Tyr Ala Val Val Gln Arg Gly Ser Met Val Ser Phe Glu
545                 550                 555                 560

Cys Lys Val Lys His Asp His Thr Leu Ser Leu Thr Val Leu Trp Leu
                565                 570                 575

Lys Asp Asn Arg Glu Leu Pro Ser Asp Glu Arg Phe Thr Val Asp Lys
            580                 585                 590

Asp His Leu Val Val Ala Asp Val Ser Asp Asp Ser Gly Thr Tyr
            595                 600                 605

Thr Cys Val Ala Asn Thr Thr Leu Asp Ser Val Ser Ala Ser Ala Val
            610                 615                 620

Leu Ser Val Val Asp Val Pro Asn Pro Pro Phe Asp Leu Glu Leu Thr
625                 630                 635                 640

Asp Gln Leu Asp Lys Ser Val Gln Leu Ser Trp Thr Pro Gly Asp Asp
                645                 650                 655

Asn Asn Ser Pro Ile Thr Lys Phe Ile Ile Glu Tyr Glu Asp Ala Met
            660                 665                 670

His Lys Pro Gly Leu Trp His His Gln Thr Glu Val Ser Gly Thr Gln
            675                 680                 685

Thr Thr Ala Gln Leu Lys Leu Ser Pro Tyr Val Asn Tyr Ser Phe Arg
            690                 695                 700

Val Met Ala Val Asn Ser Ile Gly Lys Ser Leu Pro Ser Glu Ala Ser
705                 710                 715                 720

Glu Gln Tyr Leu Thr Lys Ala Ser Glu Pro Asp Lys Asn Pro Thr Ala
                725                 730                 735

Val Glu Gly Leu Gly Ser Glu Pro Asp Asn Leu Val Ile Thr Trp Lys
            740                 745                 750

Pro Leu Asn Gly Phe Glu Ser Asn Gly Pro Gly Leu Gln Tyr Lys Val
            755                 760                 765

Ser Trp Arg Gln Lys Asp Gly Asp Asp Glu Trp Thr Ser Val Val Val
770                 775                 780

Ala Asn Val Ser Lys Tyr Ile Val Ser Gly Thr Pro Thr Phe Val Pro
785                 790                 795                 800

Tyr Leu Ile Lys Val Gln Ala Leu Asn Asp Met Gly Phe Ala Pro Glu
                805                 810                 815

Pro Ala Val Val Met Gly His Ser Gly Glu Asp Leu Pro Met Val Ala
            820                 825                 830

Pro Gly Asn Val Arg Val Asn Val Val Asn Ser Thr Leu Ala Glu Val
            835                 840                 845

His Trp Asp Pro Val Pro Leu Lys Ser Ile Arg Gly His Leu Gln Gly
            850                 855                 860

Tyr Arg Ile Tyr Tyr Trp Lys Thr Gln Ser Ser Ser Lys Arg Asn Arg
865                 870                 875                 880

Arg His Ile Glu Lys Lys Ile Leu Thr Phe Gln Gly Ser Lys Thr His
                885                 890                 895

Gly Met Leu Pro Gly Leu Glu Pro Phe Ser His Tyr Thr Leu Asn Val
            900                 905                 910
```

-continued

```
Arg Val Val Asn Gly Lys Gly Glu Gly Pro Ala Ser Pro Asp Arg Val
            915                 920                 925

Phe Asn Thr Pro Glu Gly Val Pro Ser Ala Pro Ser Ser Leu Lys Ile
        930                 935                 940

Val Asn Pro Thr Leu Asp Ser Leu Thr Leu Glu Trp Asp Pro Pro Ser
945                 950                 955                 960

His Pro Asn Gly Ile Leu Thr Glu Tyr Thr Leu Lys Tyr Gln Pro Ile
                965                 970                 975

Asn Ser Thr His Glu Leu Gly Pro Leu Val Asp Leu Lys Ile Pro Ala
            980                 985                 990

Asn Lys Thr Arg Trp Thr Leu Lys Asn Leu Asn Phe Ser Thr Arg Tyr
        995                 1000                1005

Lys Phe Tyr Phe Tyr Ala Gln Thr Ser Ala Gly Ser Gly Ser Gln
    1010                1015                1020

Ile Thr Glu Glu Ala Val Thr Thr Val Asp Glu Ala Met Ala Ser
    1025                1030                1035

Arg Gln Val Asp Ile Ala Thr Gln Gly Trp Phe Ile Gly Leu Met
    1040                1045                1050

Cys Ala Val Ala Leu Leu Ile Leu Ile Leu Leu Ile Val Cys Phe
    1055                1060                1065

Ile Arg Arg Asn Lys Gly Gly Lys Tyr Pro Val Lys Glu Lys Glu
    1070                1075                1080

Asp Ala His Ala Asp Pro Glu Ile Gln Pro Met Lys Glu Asp Asp
    1085                1090                1095

Gly Thr Phe Gly Glu Tyr Ser Asp Ala Glu Asp His Lys Pro Leu
    1100                1105                1110

Lys Lys Gly Ser Arg Thr Pro Ser Asp Arg Thr Val Lys Lys Glu
    1115                1120                1125

Asp Ser Asp Asp Ser Leu Val Asp Tyr Gly Glu Gly Val Asn Gly
    1130                1135                1140

Gln Phe Asn Glu Asp Gly Ser Phe Ile Gly Gln Tyr Ser Gly Lys
    1145                1150                1155

Lys Glu Lys Glu Pro Ala Glu Gly Asn Glu Ser Ser Glu Ala Pro
    1160                1165                1170

Ser Pro Val Asn Ala Met Asn Ser Phe Val
    1175                1180

<210> SEQ ID NO 27
<211> LENGTH: 1308
<212> TYPE: PRT
<213> ORGANISM: Homo sapiens

<400> SEQUENCE: 27

Met Gln Leu Lys Ile Met Pro Lys Lys Lys Arg Leu Ser Ala Gly Arg
1               5                   10                  15

Val Pro Leu Ile Leu Phe Leu Cys Gln Met Ile Ser Ala Leu Glu Val
            20                  25                  30

Pro Leu Asp Pro Lys Leu Leu Glu Asp Leu Val Gln Pro Pro Thr Ile
        35                  40                  45

Thr Gln Gln Ser Pro Lys Asp Tyr Ile Ile Asp Pro Arg Glu Asn Ile
    50                  55                  60

Val Ile Gln Cys Glu Ala Lys Gly Lys Pro Pro Pro Ser Phe Ser Trp
65                  70                  75                  80

Thr Arg Asn Gly Thr His Phe Asp Ile Asp Lys Asp Pro Leu Val Thr
                85                  90                  95
```

```
Met Lys Pro Gly Thr Gly Thr Leu Ile Ile Asn Ile Met Ser Glu Gly
            100                 105                 110

Lys Ala Glu Thr Tyr Glu Gly Val Tyr Gln Cys Thr Ala Arg Asn Glu
            115                 120                 125

Arg Gly Ala Ala Val Ser Asn Asn Ile Val Val Arg Pro Ser Arg Ser
            130                 135                 140

Pro Leu Trp Thr Lys Glu Lys Leu Glu Pro Ile Thr Leu Gln Ser Gly
145                 150                 155                 160

Gln Ser Leu Val Leu Pro Cys Arg Pro Pro Ile Gly Leu Pro Pro Pro
                165                 170                 175

Ile Ile Phe Trp Met Asp Asn Ser Phe Gln Arg Leu Pro Gln Ser Glu
            180                 185                 190

Arg Val Ser Gln Gly Leu Asn Gly Asp Leu Tyr Phe Ser Asn Val Leu
            195                 200                 205

Pro Glu Asp Thr Arg Glu Asp Tyr Ile Cys Tyr Ala Arg Phe Asn His
            210                 215                 220

Thr Gln Thr Ile Gln Gln Lys Gln Pro Ile Ser Val Lys Val Ile Ser
225                 230                 235                 240

Val Asp Glu Leu Asn Asp Thr Ile Ala Ala Asn Leu Ser Asp Thr Glu
                245                 250                 255

Phe Tyr Gly Ala Lys Ser Ser Arg Glu Arg Pro Pro Thr Phe Leu Thr
            260                 265                 270

Pro Glu Gly Asn Ala Ser Asn Lys Glu Glu Leu Arg Gly Asn Val Leu
            275                 280                 285

Ser Leu Glu Cys Ile Ala Glu Gly Leu Pro Thr Pro Ile Ile Tyr Trp
290                 295                 300

Ala Lys Glu Asp Gly Met Leu Pro Lys Asn Arg Thr Val Tyr Lys Asn
305                 310                 315                 320

Phe Glu Lys Thr Leu Gln Ile Ile His Val Ser Glu Ala Asp Ser Gly
            325                 330                 335

Asn Tyr Gln Cys Ile Ala Lys Asn Ala Leu Gly Ala Ile His His Thr
            340                 345                 350

Ile Ser Val Arg Val Lys Ala Ala Pro Tyr Trp Ile Thr Ala Pro Gln
            355                 360                 365

Asn Leu Val Leu Ser Pro Gly Glu Asp Gly Thr Leu Ile Cys Arg Ala
370                 375                 380

Asn Gly Asn Pro Lys Pro Arg Ile Ser Trp Leu Thr Asn Gly Val Pro
385                 390                 395                 400

Ile Glu Ile Ala Pro Asp Asp Pro Ser Arg Lys Ile Asp Gly Asp Thr
            405                 410                 415

Ile Ile Phe Ser Asn Val Gln Glu Arg Ser Ser Ala Val Tyr Gln Cys
            420                 425                 430

Asn Ala Ser Asn Glu Tyr Gly Tyr Leu Leu Ala Asn Ala Phe Val Asn
            435                 440                 445

Val Leu Ala Glu Pro Pro Arg Ile Leu Thr Pro Ala Asn Thr Leu Tyr
450                 455                 460

Gln Val Ile Ala Asn Arg Pro Ala Leu Leu Asp Cys Ala Phe Phe Gly
465                 470                 475                 480

Ser Pro Leu Pro Thr Ile Glu Trp Phe Lys Gly Ala Lys Gly Ser Ala
                485                 490                 495

Leu His Glu Asp Ile Tyr Val Leu His Glu Asn Gly Thr Leu Glu Ile
            500                 505                 510
```

```
Pro Val Ala Gln Lys Asp Ser Thr Gly Thr Tyr Thr Cys Val Ala Arg
            515                 520                 525

Asn Lys Leu Gly Met Ala Lys Asn Glu Val His Leu Glu Ile Lys Asp
        530                 535                 540

Pro Thr Trp Ile Val Lys Gln Pro Glu Tyr Ala Val Val Gln Arg Gly
545                 550                 555                 560

Ser Met Val Ser Phe Glu Cys Lys Val Lys His Asp His Thr Leu Ser
                565                 570                 575

Leu Thr Val Leu Trp Leu Lys Asp Asn Arg Glu Leu Pro Ser Asp Glu
            580                 585                 590

Arg Phe Thr Val Asp Lys Asp His Leu Val Val Ala Asp Val Ser Asp
        595                 600                 605

Asp Asp Ser Gly Thr Tyr Thr Cys Val Ala Asn Thr Thr Leu Asp Ser
610                 615                 620

Val Ser Ala Ser Ala Val Leu Ser Val Val Ala Pro Thr Pro Thr Pro
625                 630                 635                 640

Ala Pro Val Tyr Asp Val Pro Asn Pro Pro Phe Asp Leu Glu Leu Thr
                645                 650                 655

Asp Gln Leu Asp Lys Ser Val Gln Leu Ser Trp Thr Pro Gly Asp Asp
            660                 665                 670

Asn Asn Ser Pro Ile Thr Lys Phe Ile Ile Glu Tyr Glu Asp Ala Met
        675                 680                 685

His Lys Pro Gly Leu Trp His His Gln Thr Glu Val Ser Gly Thr Gln
690                 695                 700

Thr Thr Ala Gln Leu Lys Leu Ser Pro Tyr Val Asn Tyr Ser Phe Arg
705                 710                 715                 720

Val Met Ala Val Asn Ser Ile Gly Lys Ser Leu Pro Ser Glu Ala Ser
                725                 730                 735

Glu Gln Tyr Leu Thr Lys Ala Ser Glu Pro Asp Lys Asn Pro Thr Ala
            740                 745                 750

Val Glu Gly Leu Gly Ser Glu Pro Asp Asn Leu Val Ile Thr Trp Lys
        755                 760                 765

Pro Leu Asn Gly Phe Glu Ser Asn Gly Pro Gly Leu Gln Tyr Lys Val
770                 775                 780

Ser Trp Arg Gln Lys Asp Gly Asp Glu Trp Thr Ser Val Val Val
785                 790                 795                 800

Ala Asn Val Ser Lys Tyr Ile Val Ser Gly Thr Pro Thr Phe Val Pro
                805                 810                 815

Tyr Leu Ile Lys Val Gln Ala Leu Asn Asp Met Gly Phe Ala Pro Glu
            820                 825                 830

Pro Ala Val Val Met Gly His Ser Gly Glu Asp Leu Pro Met Val Ala
        835                 840                 845

Pro Gly Asn Val Arg Val Asn Val Asn Ser Thr Leu Ala Glu Val
850                 855                 860

His Trp Asp Pro Val Pro Leu Lys Ser Ile Arg Gly His Leu Gln Gly
                865                 870                 875                 880

Tyr Arg Ile Tyr Tyr Trp Lys Thr Gln Ser Ser Ser Lys Arg Asn Arg
            885                 890                 895

Arg His Ile Glu Lys Lys Ile Leu Thr Phe Gln Gly Ser Lys Thr His
        900                 905                 910

Gly Met Leu Pro Gly Leu Glu Pro Phe Ser His Tyr Thr Leu Asn Val
915                 920                 925

Arg Val Val Asn Gly Lys Gly Glu Gly Pro Ala Ser Pro Asp Arg Val
```

930                 935                 940
Phe Asn Thr Pro Glu Gly Val Pro Ser Ala Pro Ser Ser Leu Lys Ile
945                 950                 955                 960

Val Asn Pro Thr Leu Asp Ser Leu Thr Leu Glu Trp Asp Pro Pro Ser
                965                 970                 975

His Pro Asn Gly Ile Leu Thr Glu Tyr Thr Leu Lys Tyr Gln Pro Ile
                980                 985                 990

Asn Ser Thr His Glu Leu Gly Pro Leu Val Asp Leu Lys Ile Pro Ala
                995                 1000                1005

Asn Lys Thr Arg Trp Thr Leu Lys Asn Leu Asn Phe Ser Thr Arg
    1010                1015                1020

Tyr Lys Phe Tyr Phe Tyr Ala Gln Thr Ser Ala Gly Ser Gly Ser
    1025                1030                1035

Gln Ile Thr Glu Glu Ala Val Thr Thr Val Asp Glu Ala Gly Ile
    1040                1045                1050

Leu Pro Pro Asp Val Gly Ala Gly Lys Val Gln Ala Val Asn Pro
    1055                1060                1065

Arg Ile Ser Asn Leu Thr Ala Ala Ala Glu Thr Tyr Ala Asn
    1070                1075                1080

Ile Ser Trp Glu Tyr Glu Gly Pro Glu His Val Asn Phe Tyr Val
    1085                1090                1095

Glu Tyr Gly Val Ala Gly Ser Lys Glu Glu Trp Arg Lys Glu Ile
    1100                1105                1110

Val Asn Gly Ser Arg Ser Phe Phe Gly Leu Lys Gly Leu Met Pro
    1115                1120                1125

Gly Thr Ala Tyr Lys Val Arg Val Gly Ala Val Gly Asp Ser Gly
    1130                1135                1140

Phe Val Ser Ser Glu Asp Val Phe Glu Thr Gly Pro Ala Met Ala
    1145                1150                1155

Ser Arg Gln Val Asp Ile Ala Thr Gln Gly Trp Phe Ile Gly Leu
    1160                1165                1170

Met Cys Ala Val Ala Leu Leu Ile Leu Ile Leu Leu Ile Val Cys
    1175                1180                1185

Phe Ile Arg Arg Asn Lys Gly Gly Lys Tyr Pro Val Lys Glu Lys
    1190                1195                1200

Glu Asp Ala His Ala Asp Pro Glu Ile Gln Pro Met Lys Glu Asp
    1205                1210                1215

Asp Gly Thr Phe Gly Glu Tyr Arg Ser Leu Glu Ser Asp Ala Glu
    1220                1225                1230

Asp His Lys Pro Leu Lys Lys Gly Ser Arg Thr Pro Ser Asp Arg
    1235                1240                1245

Thr Val Lys Lys Glu Asp Ser Asp Asp Ser Leu Val Asp Tyr Gly
    1250                1255                1260

Glu Gly Val Asn Gly Gln Phe Asn Glu Asp Gly Ser Phe Ile Gly
    1265                1270                1275

Gln Tyr Ser Gly Lys Lys Glu Lys Glu Pro Ala Glu Gly Asn Glu
    1280                1285                1290

Ser Ser Glu Ala Pro Ser Pro Val Asn Ala Met Asn Ser Phe Val
    1295                1300                1305

<210> SEQ ID NO 28
<211> LENGTH: 1192
<212> TYPE: PRT
<213> ORGANISM: Homo sapiens

<400> SEQUENCE: 28

```
Met Gln Leu Lys Ile Met Pro Lys Lys Arg Leu Ser Ala Gly Arg
1               5                   10                  15

Val Pro Leu Ile Leu Phe Leu Cys Gln Met Ile Ser Ala Leu Glu Val
            20                  25                  30

Pro Leu Asp Pro Lys Leu Leu Glu Asp Leu Val Gln Pro Thr Ile
        35                  40                  45

Thr Gln Gln Ser Pro Lys Asp Tyr Ile Ile Asp Pro Arg Glu Asn Ile
    50                  55                      60

Val Ile Gln Cys Glu Ala Lys Gly Lys Pro Pro Ser Phe Ser Trp
65              70                  75                  80

Thr Arg Asn Gly Thr His Phe Asp Ile Asp Lys Asp Pro Leu Val Thr
                85                  90                  95

Met Lys Pro Gly Thr Gly Thr Leu Ile Ile Asn Ile Met Ser Glu Gly
            100                 105                 110

Lys Ala Glu Thr Tyr Glu Gly Val Tyr Gln Cys Thr Ala Arg Asn Glu
            115                 120                 125

Arg Gly Ala Ala Val Ser Asn Asn Ile Val Val Arg Pro Ser Arg Ser
130                 135                 140

Pro Leu Trp Thr Lys Glu Lys Leu Glu Pro Ile Thr Leu Gln Ser Gly
145                 150                 155                 160

Gln Ser Leu Val Leu Pro Cys Arg Pro Pro Ile Gly Leu Pro Pro Pro
                165                 170                 175

Ile Ile Phe Trp Met Asp Asn Ser Phe Gln Arg Leu Pro Gln Ser Glu
            180                 185                 190

Arg Val Ser Gln Gly Leu Asn Gly Asp Leu Tyr Phe Ser Asn Val Leu
            195                 200                 205

Pro Glu Asp Thr Arg Glu Asp Tyr Ile Cys Tyr Ala Arg Phe Asn His
    210                 215                 220

Thr Gln Thr Ile Gln Gln Lys Gln Pro Ile Ser Val Lys Val Ile Ser
225                 230                 235                 240

Ala Lys Ser Ser Arg Glu Arg Pro Pro Thr Phe Leu Thr Pro Glu Gly
                245                 250                 255

Asn Ala Ser Asn Lys Glu Glu Leu Arg Gly Asn Val Leu Ser Leu Glu
            260                 265                 270

Cys Ile Ala Glu Gly Leu Pro Thr Pro Ile Ile Tyr Trp Ala Lys Glu
        275                 280                 285

Asp Gly Met Leu Pro Lys Asn Arg Thr Val Tyr Lys Asn Phe Glu Lys
290                 295                 300

Thr Leu Gln Ile Ile His Val Ser Glu Ala Asp Ser Gly Asn Tyr Gln
305                 310                 315                 320

Cys Ile Ala Lys Asn Ala Leu Gly Ala Ile His His Thr Ile Ser Val
                325                 330                 335

Arg Val Lys Ala Ala Pro Tyr Trp Ile Thr Ala Pro Gln Asn Leu Val
            340                 345                 350

Leu Ser Pro Gly Glu Asp Gly Thr Leu Ile Cys Arg Ala Asn Gly Asn
        355                 360                 365

Pro Lys Pro Arg Ile Ser Trp Leu Thr Asn Gly Val Pro Ile Glu Ile
    370                 375                 380

Ala Pro Asp Asp Pro Ser Arg Lys Ile Asp Gly Asp Thr Ile Ile Phe
385                 390                 395                 400

Ser Asn Val Gln Glu Arg Ser Ser Ala Val Tyr Gln Cys Asn Ala Ser
```

```
                405             410             415
Asn Glu Tyr Gly Tyr Leu Leu Ala Asn Ala Phe Val Asn Val Leu Ala
        420             425             430

Glu Pro Pro Arg Ile Leu Thr Pro Ala Asn Thr Leu Tyr Gln Val Ile
        435             440             445

Ala Asn Arg Pro Ala Leu Leu Asp Cys Ala Phe Phe Gly Ser Pro Leu
450             455             460

Pro Thr Ile Glu Trp Phe Lys Gly Ala Lys Gly Ser Ala Leu His Glu
465             470             475             480

Asp Ile Tyr Val Leu His Glu Asn Gly Thr Leu Glu Ile Pro Val Ala
            485             490             495

Gln Lys Asp Ser Thr Gly Thr Tyr Thr Cys Val Ala Arg Asn Lys Leu
        500             505             510

Gly Met Ala Lys Asn Glu Val His Leu Glu Ile Lys Asp Pro Thr Trp
        515             520             525

Ile Val Lys Gln Pro Glu Tyr Ala Val Val Gln Arg Gly Ser Met Val
        530             535             540

Ser Phe Glu Cys Lys Val Lys His Asp His Thr Leu Ser Leu Thr Val
545             550             555             560

Leu Trp Leu Lys Asp Asn Arg Glu Leu Pro Ser Asp Glu Arg Phe Thr
            565             570             575

Val Asp Lys Asp His Leu Val Val Ala Asp Val Ser Asp Asp Asp Ser
        580             585             590

Gly Thr Tyr Thr Cys Val Ala Asn Thr Thr Leu Asp Ser Val Ser Ala
        595             600             605

Ser Ala Val Leu Ser Val Val Ala Pro Thr Pro Thr Pro Ala Pro Val
610             615             620

Tyr Asp Val Pro Asn Pro Pro Phe Asp Leu Glu Leu Thr Asp Gln Leu
625             630             635             640

Asp Lys Ser Val Gln Leu Ser Trp Thr Pro Gly Asp Asp Asn Asn Ser
            645             650             655

Pro Ile Thr Lys Phe Ile Ile Glu Tyr Glu Asp Ala Met His Lys Pro
        660             665             670

Gly Leu Trp His His Gln Thr Glu Val Ser Gly Thr Gln Thr Thr Ala
        675             680             685

Gln Leu Lys Leu Ser Pro Tyr Val Asn Tyr Ser Phe Arg Val Met Ala
        690             695             700

Val Asn Ser Ile Gly Lys Ser Leu Pro Ser Glu Ala Ser Glu Gln Tyr
705             710             715             720

Leu Thr Lys Ala Ser Glu Pro Asp Lys Asn Pro Thr Ala Val Glu Gly
            725             730             735

Leu Gly Ser Glu Pro Asp Asn Leu Val Ile Thr Trp Lys Pro Leu Asn
        740             745             750

Gly Phe Glu Ser Asn Gly Pro Gly Leu Gln Tyr Lys Val Ser Trp Arg
        755             760             765

Gln Lys Asp Gly Asp Glu Trp Thr Ser Val Val Val Ala Asn Val
        770             775             780

Ser Lys Tyr Ile Val Ser Gly Thr Pro Thr Phe Val Pro Tyr Leu Ile
785             790             795             800

Lys Val Gln Ala Leu Asn Asp Met Gly Phe Ala Pro Glu Pro Ala Val
            805             810             815

Val Met Gly His Ser Gly Glu Asp Leu Pro Met Val Ala Pro Gly Asn
        820             825             830
```

Val Arg Val Asn Val Val Asn Ser Thr Leu Ala Glu Val His Trp Asp
        835                 840                 845

Pro Val Pro Leu Lys Ser Ile Arg Gly His Leu Gln Gly Tyr Arg Ile
    850                 855                 860

Tyr Tyr Trp Lys Thr Gln Ser Ser Ser Lys Arg Asn Arg Arg His Ile
865                 870                 875                 880

Glu Lys Lys Ile Leu Thr Phe Gln Gly Ser Lys Thr His Gly Met Leu
                885                 890                 895

Pro Gly Leu Glu Pro Phe Ser His Tyr Thr Leu Asn Val Arg Val Val
            900                 905                 910

Asn Gly Lys Gly Glu Gly Pro Ala Ser Pro Asp Arg Val Phe Asn Thr
            915                 920                 925

Pro Glu Gly Val Pro Ser Ala Pro Ser Ser Leu Lys Ile Val Asn Pro
    930                 935                 940

Thr Leu Asp Ser Leu Thr Leu Glu Trp Asp Pro Pro Ser His Pro Asn
945                 950                 955                 960

Gly Ile Leu Thr Glu Tyr Thr Leu Lys Tyr Gln Pro Ile Asn Ser Thr
                965                 970                 975

His Glu Leu Gly Pro Leu Val Asp Leu Lys Ile Pro Ala Asn Lys Thr
            980                 985                 990

Arg Trp Thr Leu Lys Asn Leu Asn Phe Ser Thr Arg Tyr Lys Phe Tyr
            995                 1000                1005

Phe Tyr Ala Gln Thr Ser Ala Gly Ser Gly Ser Gln Ile Thr Glu
    1010                1015                1020

Glu Ala Val Thr Thr Val Asp Glu Ala Gly Ile Leu Pro Pro Asp
    1025                1030                1035

Val Gly Ala Gly Lys Ala Met Ala Ser Arg Gln Val Asp Ile Ala
    1040                1045                1050

Thr Gln Gly Trp Phe Ile Gly Leu Met Cys Ala Val Ala Leu Leu
    1055                1060                1065

Ile Leu Ile Leu Leu Ile Val Cys Phe Ile Arg Arg Asn Lys Gly
    1070                1075                1080

Gly Lys Tyr Pro Val Lys Glu Lys Glu Asp Ala His Ala Asp Pro
    1085                1090                1095

Glu Ile Gln Pro Met Lys Glu Asp Asp Gly Thr Phe Gly Glu Tyr
    1100                1105                1110

Ser Asp Ala Glu Asp His Lys Pro Leu Lys Lys Gly Ser Arg Thr
    1115                1120                1125

Pro Ser Asp Arg Thr Val Lys Lys Glu Asp Ser Asp Asp Ser Leu
    1130                1135                1140

Val Asp Tyr Gly Glu Gly Val Asn Gly Gln Phe Asn Glu Asp Gly
    1145                1150                1155

Ser Phe Ile Gly Gln Tyr Ser Gly Lys Lys Glu Lys Glu Pro Ala
    1160                1165                1170

Glu Gly Asn Glu Ser Ser Glu Ala Pro Ser Pro Val Asn Ala Met
    1175                1180                1185

Asn Ser Phe Val
    1190

<210> SEQ ID NO 29
<211> LENGTH: 788
<212> TYPE: PRT
<213> ORGANISM: Homo sapiens

```
<400> SEQUENCE: 29

Met Thr Ile His Gln Phe Leu Leu Phe Leu Phe Trp Val Cys Leu
1               5                   10                  15

Pro His Phe Cys Ser Pro Glu Ile Met Phe Arg Arg Thr Pro Val Pro
                20                  25                  30

Gln Gln Arg Ile Leu Ser Ser Arg Val Pro Arg Ser Asp Gly Lys Ile
            35                  40                  45

Leu His Arg Gln Lys Arg Gly Trp Met Trp Asn Gln Phe Phe Leu Leu
    50                  55                      60

Glu Glu Tyr Thr Gly Ser Asp Tyr Gln Tyr Val Gly Lys Leu His Ser
65              70                  75                      80

Asp Gln Asp Lys Gly Asp Gly Ser Leu Lys Tyr Ile Leu Ser Gly Asp
                85                  90                  95

Gly Ala Gly Thr Leu Phe Ile Ile Asp Glu Lys Thr Gly Asp Ile His
            100                 105                 110

Ala Thr Arg Arg Ile Asp Arg Glu Lys Ala Phe Tyr Thr Leu Arg
            115                 120                 125

Ala Gln Ala Ile Asn Arg Arg Thr Leu Arg Pro Val Glu Pro Glu Ser
        130                 135                 140

Glu Phe Val Ile Lys Ile His Asp Ile Asn Asp Asn Glu Pro Thr Phe
145                 150                 155                 160

Pro Glu Glu Ile Tyr Thr Ala Ser Val Pro Glu Met Ser Val Val Gly
                165                 170                 175

Thr Ser Val Val Gln Val Thr Ala Thr Asp Ala Asp Asp Pro Ser Tyr
            180                 185                 190

Gly Asn Ser Ala Arg Val Ile Tyr Ser Ile Leu Gln Gly Gln Pro Tyr
        195                 200                 205

Phe Ser Val Glu Pro Glu Thr Gly Ile Ile Arg Thr Ala Leu Pro Asn
        210                 215                 220

Met Asn Arg Glu Asn Arg Glu Gln Tyr Gln Val Val Ile Gln Ala Lys
225                 230                 235                 240

Asp Met Gly Gly Gln Met Gly Gly Leu Ser Gly Thr Thr Thr Val Asn
                245                 250                 255

Ile Thr Leu Thr Asp Val Asn Asp Asn Pro Pro Arg Phe Pro Gln Asn
            260                 265                 270

Thr Ile His Leu Arg Val Leu Glu Ser Ser Pro Val Gly Thr Ala Ile
        275                 280                 285

Gly Ser Val Lys Ala Thr Asp Ala Asp Thr Gly Lys Asn Ala Glu Val
        290                 295                 300

Glu Tyr Arg Ile Ile Asp Gly Asp Gly Thr Asp Met Phe Asp Ile Val
305                 310                 315                 320

Thr Glu Lys Asp Thr Gln Glu Gly Ile Ile Thr Val Lys Lys Pro Leu
                325                 330                 335

Asp Tyr Glu Ser Arg Arg Leu Tyr Thr Leu Lys Val Glu Ala Glu Asn
            340                 345                 350

Thr His Val Asp Pro Arg Phe Tyr Tyr Leu Gly Pro Phe Lys Asp Thr
        355                 360                 365

Thr Ile Val Lys Ile Ser Ile Glu Asp Val Asp Glu Pro Pro Val Phe
    370                 375                 380

Ser Arg Ser Ser Tyr Leu Phe Glu Val His Glu Asp Ile Glu Val Gly
385                 390                 395                 400

Thr Ile Ile Gly Thr Val Met Ala Arg Asp Pro Asp Ser Ile Ser Ser
                405                 410                 415
```

Pro Ile Arg Phe Ser Leu Asp Arg His Thr Asp Leu Asp Arg Ile Phe
                420                 425                 430

Asn Ile His Ser Gly Asn Gly Ser Leu Tyr Thr Ser Lys Pro Leu Asp
            435                 440                 445

Arg Glu Leu Ser Gln Trp His Asn Leu Thr Val Ile Ala Ala Glu Ile
450                 455                 460

Asn Asn Pro Lys Glu Thr Thr Arg Val Ala Val Phe Val Arg Ile Leu
465                 470                 475                 480

Asp Val Asn Asp Asn Ala Pro Gln Phe Ala Val Phe Tyr Asp Thr Phe
                485                 490                 495

Val Cys Glu Asn Ala Arg Pro Gly Gln Leu Ile Gln Thr Ile Ser Ala
                500                 505                 510

Val Asp Lys Asp Asp Pro Leu Gly Gly Gln Lys Phe Phe Phe Ser Leu
            515                 520                 525

Ala Ala Val Asn Pro Asn Phe Thr Val Gln Asp Asn Glu Asp Asn Thr
530                 535                 540

Ala Arg Ile Leu Thr Arg Lys Asn Gly Phe Asn Arg His Glu Ile Ser
545                 550                 555                 560

Thr Tyr Leu Leu Pro Val Val Ile Ser Asp Asn Asp Tyr Pro Ile Gln
                565                 570                 575

Ser Ser Thr Gly Thr Leu Thr Ile Arg Val Cys Ala Cys Asp Ser Gln
                580                 585                 590

Gly Asn Met Gln Ser Cys Ser Ala Glu Ala Leu Leu Leu Pro Ala Gly
            595                 600                 605

Leu Ser Thr Gly Ala Leu Ile Ala Ile Leu Leu Cys Ile Ile Ile Leu
            610                 615                 620

Leu Val Ile Val Val Leu Phe Ala Ala Leu Lys Arg Gln Arg Lys Lys
625                 630                 635                 640

Glu Pro Leu Ile Leu Ser Lys Glu Asp Ile Arg Asp Asn Ile Val Ser
                645                 650                 655

Tyr Asn Asp Glu Gly Gly Gly Glu Glu Asp Thr Gln Ala Phe Asp Ile
                660                 665                 670

Gly Thr Leu Arg Asn Pro Ala Ala Ile Glu Glu Lys Lys Leu Arg Arg
            675                 680                 685

Asp Ile Ile Pro Glu Thr Leu Phe Ile Pro Arg Arg Thr Pro Thr Ala
690                 695                 700

Pro Asp Asn Thr Asp Val Arg Asp Phe Ile Asn Glu Arg Leu Lys Glu
705                 710                 715                 720

His Asp Leu Asp Pro Thr Ala Pro Pro Tyr Asp Ser Leu Ala Thr Tyr
                725                 730                 735

Ala Tyr Glu Gly Asn Asp Ser Ile Ala Glu Ser Leu Ser Ser Leu Glu
            740                 745                 750

Ser Gly Thr Thr Glu Gly Asp Gln Asn Tyr Asp Tyr Leu Arg Glu Trp
            755                 760                 765

Gly Pro Arg Phe Asn Lys Leu Ala Glu Met Tyr Gly Gly Gly Glu Ser
770                 775                 780

Asp Lys Asp Ser
785

<210> SEQ ID NO 30
<211> LENGTH: 944
<212> TYPE: PRT
<213> ORGANISM: Homo sapiens

```
<400> SEQUENCE: 30

Met Gly Pro Lys Thr Leu Pro Gln Leu Ala Gly Lys Trp Gln Val Leu
1               5                   10                  15

Cys Met Leu Ser Leu Cys Cys Trp Gly Trp Val Ser Gly Gln Leu Arg
            20                  25                  30

Tyr Ser Val Val Glu Glu Ser Glu Pro Gly Thr Leu Val Gly Asn Val
        35                  40                  45

Ala Gln Asp Leu Gly Leu Lys Met Thr Asp Leu Leu Ser Arg Arg Leu
    50                  55                  60

Gln Leu Gly Ser Glu Glu Asn Gly Arg Tyr Phe Ser Leu Ser Leu Met
65                  70                  75                  80

Ser Gly Ala Leu Ala Val Asn Gln Lys Ile Asp Arg Glu Ser Leu Cys
                85                  90                  95

Gly Ala Ser Thr Ser Cys Leu Leu Pro Val Gln Val Val Thr Glu His
            100                 105                 110

Pro Leu Glu Leu Ile Arg Val Glu Val Glu Ile Leu Asp Leu Asn Asp
        115                 120                 125

Asn Ser Pro Ser Phe Ala Thr Pro Glu Arg Glu Met Arg Ile Ser Glu
    130                 135                 140

Ser Ala Ala Ser Gly Ala Arg Phe Pro Leu Asp Ser Ala Gln Asp Pro
145                 150                 155                 160

Asp Val Gly Thr Asn Thr Val Ser Phe Tyr Thr Leu Ser Pro Asn Ser
                165                 170                 175

His Phe Ser Leu Asn Val Lys Thr Leu Lys Asp Gly Lys Pro Phe Pro
            180                 185                 190

Glu Leu Val Leu Glu Gln Gln Leu Asp Arg Glu Ala Gln Ala Arg His
        195                 200                 205

Gln Leu Val Leu Thr Ala Val Asp Gly Gly Thr Pro Ala Arg Ser Gly
    210                 215                 220

Thr Thr Leu Ile Ser Val Ile Val Leu Asp Ile Asn Asp Asn Ala Pro
225                 230                 235                 240

Thr Phe Gln Ser Ser Val Leu Arg Val Gly Ile Pro Glu Asn Ala Pro
                245                 250                 255

Ile Gly Thr Leu Leu Leu Arg Leu Asn Ala Thr Asp Pro Asp Glu Gly
            260                 265                 270

Thr Asn Gly Gln Leu Asp Tyr Ser Phe Gly Asp His Thr Ser Glu Ala
        275                 280                 285

Val Arg Asn Leu Phe Gly Leu Asp Pro Ser Ser Gly Ala Ile His Val
    290                 295                 300

Leu Gly Pro Ile Asp Phe Glu Glu Ser Arg Phe Tyr Glu Ile His Ala
305                 310                 315                 320

Arg Ala Arg Asp Gln Gly Gln Pro Ala Met Glu Gly His Cys Val Ile
                325                 330                 335

Gln Val Asp Val Gly Asp Val Asn Asp Asn Ala Pro Glu Val Leu Leu
            340                 345                 350

Ala Ser Leu Ala Asn Pro Val Leu Glu Ser Thr Pro Val Gly Thr Val
        355                 360                 365

Val Gly Leu Phe Asn Val Arg Asp Arg Asp Ser Gly Arg Asn Gly Glu
    370                 375                 380

Val Ser Leu Asp Ile Ser Pro Asp Leu Pro Phe Gln Ile Lys Pro Ser
385                 390                 395                 400

Glu Asn His Tyr Ser Leu Leu Thr Ser Gln Pro Leu Asp Arg Glu Ala
                405                 410                 415
```

```
Thr Ser His Tyr Ile Ile Glu Leu Leu Ala Ser Asp Ala Gly Ser Pro
            420                 425                 430

Ser Leu His Lys His Leu Thr Ile Arg Leu Asn Ile Ser Asp Val Asn
            435                 440                 445

Asp Asn Ala Pro Arg Phe Asn Gln Gln Leu Tyr Thr Ala Tyr Ile Leu
450                 455                 460

Glu Asn Arg Pro Pro Gly Ser Leu Leu Cys Thr Val Ala Ala Ser Asp
465                 470                 475                 480

Pro Asp Thr Gly Asp Asn Ala Arg Leu Thr Tyr Ser Ile Val Gly Asn
                485                 490                 495

Gln Val Gln Gly Ala Pro Ala Ser Ser Phe Val Tyr Val Asn Pro Glu
            500                 505                 510

Asp Gly Arg Ile Phe Ala Gln Arg Thr Phe Asp Tyr Glu Leu Leu Gln
            515                 520                 525

Met Leu Gln Ile Val Val Gly Val Arg Asp Ser Gly Ser Pro Pro Leu
            530                 535                 540

His Ala Asn Thr Ser Leu His Val Phe Val Leu Asp Glu Asn Asp Asn
545                 550                 555                 560

Ala Pro Ala Val Leu His Pro Arg Pro Asp Trp Glu His Ser Ala Pro
                565                 570                 575

Gln Arg Leu Pro Arg Ser Ala Pro Pro Gly Ser Leu Val Thr Lys Val
            580                 585                 590

Thr Ala Val Asp Ala Asp Ala Gly His Asn Ala Trp Leu Ser Tyr Ser
            595                 600                 605

Leu Leu Pro Gln Ser Thr Ala Pro Gly Leu Phe Leu Val Ser Thr His
            610                 615                 620

Thr Gly Glu Val Arg Thr Ala Arg Ala Leu Leu Glu Asp Asp Ser Asp
625                 630                 635                 640

Thr Gln Gln Val Val Leu Val Arg Asp Asn Gly Asp Pro Ser Leu
                645                 650                 655

Ser Ser Thr Ala Thr Val Leu Val Leu Glu Asp Glu Asp Pro Glu
            660                 665                 670

Glu Met Pro Lys Ser Ser Asp Phe Leu Ile His Pro Glu Arg Ser
            675                 680                 685

Asp Leu Thr Leu Tyr Leu Ile Val Ala Leu Ala Thr Val Ser Leu Leu
            690                 695                 700

Ser Leu Val Thr Phe Thr Phe Leu Ser Ala Lys Cys Leu Gln Gly Asn
705                 710                 715                 720

Ala Asp Gly Asp Gly Gly Gly Gln Cys Cys Arg Gln Asp Ser
                725                 730                 735

Pro Ser Pro Asp Phe Tyr Lys Gln Ser Ser Pro Asn Leu Gln Val Ser
            740                 745                 750

Ser Asp Gly Thr Leu Lys Tyr Met Glu Val Thr Leu Arg Pro Thr Asp
            755                 760                 765

Ser Gln Ser His Cys Tyr Arg Thr Cys Phe Ser Pro Ala Ser Asp Gly
            770                 775                 780

Ser Asp Phe Thr Phe Leu Arg Pro Leu Ser Val Gln Gln Pro Thr Ala
785                 790                 795                 800

Leu Ala Leu Glu Pro Asp Ala Ile Arg Ser Arg Ser Asn Thr Leu Arg
                805                 810                 815

Glu Arg Ser Gln Gln Ala Pro Pro Asn Thr Asp Trp Arg Phe Ser Gln
            820                 825                 830
```

-continued

```
Ala Gln Arg Pro Gly Thr Ser Gly Ser Gln Asn Gly Asp Asp Thr Gly
            835                 840                 845

Thr Trp Pro Asn Asn Gln Phe Asp Thr Glu Met Leu Gln Ala Met Ile
850                 855                 860

Leu Ala Ser Ala Ser Glu Ala Ala Asp Gly Ser Ser Thr Leu Gly Gly
865                 870                 875                 880

Gly Ala Gly Thr Met Gly Leu Ser Ala Arg Tyr Gly Pro Gln Phe Thr
                885                 890                 895

Leu Gln His Val Pro Asp Tyr Arg Gln Asn Val Tyr Ile Pro Gly Ser
            900                 905                 910

Asn Ala Thr Leu Thr Asn Ala Ala Gly Lys Arg Asp Gly Lys Ala Pro
        915                 920                 925

Ala Gly Gly Asn Gly Asn Lys Lys Lys Ser Gly Lys Lys Glu Lys Lys
    930                 935                 940

<210> SEQ ID NO 31
<211> LENGTH: 878
<212> TYPE: PRT
<213> ORGANISM: Homo sapiens

<400> SEQUENCE: 31

Met Gly Pro Lys Thr Leu Pro Gln Leu Ala Gly Lys Trp Gln Val Leu
1               5                   10                  15

Cys Met Leu Ser Leu Cys Cys Trp Gly Trp Val Ser Gly Gln Leu Arg
            20                  25                  30

Tyr Ser Val Val Glu Glu Ser Glu Pro Gly Thr Leu Val Gly Asn Val
        35                  40                  45

Ala Gln Asp Leu Gly Leu Lys Met Thr Asp Leu Leu Ser Arg Arg Leu
    50                  55                  60

Gln Leu Gly Ser Glu Glu Asn Gly Arg Tyr Phe Ser Leu Ser Leu Met
65                  70                  75                  80

Ser Gly Ala Leu Ala Val Asn Gln Lys Ile Asp Arg Glu Ser Leu Cys
                85                  90                  95

Gly Ala Ser Thr Ser Cys Leu Leu Pro Val Gln Val Val Thr Glu His
            100                 105                 110

Pro Leu Glu Leu Ile Arg Val Glu Val Glu Ile Leu Asp Leu Asn Asp
        115                 120                 125

Asn Ser Pro Ser Phe Ala Thr Pro Glu Arg Glu Met Arg Ile Ser Glu
    130                 135                 140

Ser Ala Ala Ser Gly Ala Arg Phe Pro Leu Asp Ser Ala Gln Asp Pro
145                 150                 155                 160

Asp Val Gly Thr Asn Thr Val Ser Phe Tyr Thr Leu Ser Pro Asn Ser
                165                 170                 175

His Phe Ser Leu Asn Val Lys Thr Leu Lys Asp Gly Lys Pro Phe Pro
            180                 185                 190

Glu Leu Val Leu Glu Gln Gln Leu Asp Arg Glu Ala Gln Ala Arg His
        195                 200                 205

Gln Leu Val Leu Thr Ala Val Asp Gly Gly Thr Pro Ala Arg Ser Gly
    210                 215                 220

Thr Thr Leu Ile Ser Val Ile Val Leu Asp Ile Asn Asp Asn Ala Pro
225                 230                 235                 240

Thr Phe Gln Ser Ser Val Leu Arg Val Gly Ile Pro Glu Asn Ala Pro
                245                 250                 255

Ile Gly Thr Leu Leu Leu Arg Leu Asn Ala Thr Asp Pro Asp Glu Gly
            260                 265                 270
```

```
Thr Asn Gly Gln Leu Asp Tyr Ser Phe Gly Asp His Thr Ser Glu Ala
    275                 280                 285

Val Arg Asn Leu Phe Gly Leu Asp Pro Ser Ser Gly Ala Ile His Val
    290                 295                 300

Leu Gly Pro Ile Asp Phe Glu Glu Ser Arg Phe Tyr Glu Ile His Ala
305                 310                 315                 320

Arg Ala Arg Asp Gln Gly Gln Pro Ala Met Glu Gly His Cys Val Ile
                325                 330                 335

Gln Val Asp Val Gly Asp Val Asn Asp Asn Ala Pro Glu Val Leu Leu
                340                 345                 350

Ala Ser Leu Ala Asn Pro Val Leu Glu Ser Thr Pro Val Gly Thr Val
            355                 360                 365

Val Gly Leu Phe Asn Val Arg Asp Arg Asp Ser Gly Arg Asn Gly Glu
        370                 375                 380

Val Ser Leu Asp Ile Ser Pro Asp Leu Pro Phe Gln Ile Lys Pro Ser
385                 390                 395                 400

Glu Asn His Tyr Ser Leu Leu Thr Ser Gln Pro Leu Asp Arg Glu Ala
                405                 410                 415

Thr Ser His Tyr Ile Ile Glu Leu Leu Ala Ser Asp Ala Gly Ser Pro
            420                 425                 430

Ser Leu His Lys His Leu Thr Ile Arg Leu Asn Ile Ser Asp Val Asn
        435                 440                 445

Asp Asn Ala Pro Arg Phe Asn Gln Gln Leu Tyr Thr Ala Tyr Ile Leu
    450                 455                 460

Glu Asn Arg Pro Pro Gly Ser Leu Leu Cys Thr Val Ala Ala Ser Asp
465                 470                 475                 480

Pro Asp Thr Gly Asp Asn Ala Arg Leu Thr Tyr Ser Ile Val Gly Asn
                485                 490                 495

Gln Val Gln Gly Ala Pro Ala Ser Ser Phe Val Tyr Val Asn Pro Glu
            500                 505                 510

Asp Gly Arg Ile Phe Ala Gln Arg Thr Phe Asp Tyr Glu Leu Leu Gln
        515                 520                 525

Met Leu Gln Ile Val Val Gly Val Arg Asp Ser Gly Ser Pro Pro Leu
    530                 535                 540

His Ala Asn Thr Ser Leu His Val Phe Val Leu Asp Glu Asn Asp Asn
545                 550                 555                 560

Ala Pro Ala Val Leu His Pro Arg Pro Asp Trp Glu His Ser Ala Pro
                565                 570                 575

Gln Arg Leu Pro Arg Ser Ala Pro Pro Gly Ser Leu Val Thr Lys Val
            580                 585                 590

Thr Ala Val Asp Ala Asp Ala Gly His Asn Ala Trp Leu Ser Tyr Ser
        595                 600                 605

Leu Leu Pro Gln Ser Thr Ala Pro Gly Leu Phe Leu Val Ser Thr His
    610                 615                 620

Thr Gly Glu Val Arg Thr Ala Arg Ala Leu Leu Glu Asp Asp Ser Asp
625                 630                 635                 640

Thr Gln Gln Val Val Leu Val Arg Asp Asn Gly Asp Pro Ser Leu
                645                 650                 655

Ser Ser Thr Ala Thr Val Leu Val Leu Glu Asp Glu Asp Pro Glu
            660                 665                 670

Glu Met Pro Lys Ser Ser Asp Phe Leu Ile His Pro Pro Glu Arg Ser
        675                 680                 685
```

Asp Leu Thr Leu Tyr Leu Ile Val Ala Leu Ala Thr Val Ser Leu Leu
690                 695                 700

Ser Leu Val Thr Phe Thr Phe Leu Ser Ala Lys Cys Leu Gln Gly Asn
705                 710                 715                 720

Ala Asp Gly Asp Gly Gly Gly Gln Cys Cys Arg Arg Gln Asp Ser
            725                 730                 735

Pro Ser Pro Asp Phe Tyr Lys Gln Ser Ser Pro Asn Leu Gln Val Ser
            740                 745                 750

Ser Asp Gly Thr Leu Lys Tyr Met Glu Val Thr Leu Arg Pro Thr Asp
        755                 760                 765

Ser Gln Ser His Cys Tyr Arg Thr Cys Phe Ser Pro Ala Ser Asp Gly
770                 775                 780

Ser Asp Phe Thr Phe Leu Arg Pro Leu Ser Val Gln Gln Pro Thr Ala
785                 790                 795                 800

Leu Ala Leu Glu Pro Asp Ala Ile Arg Ser Arg Ser Asn Thr Leu Arg
                805                 810                 815

Glu Arg Ser Gln Val Arg Gly Ser Ala Pro Pro Arg Ala Thr Pro Gly
            820                 825                 830

Gly Gly Thr Gly Glu Ala Ala Arg Pro His Lys Gly Leu Asn Leu His
        835                 840                 845

Pro Leu Leu Ser Gly Arg Leu Gly Arg Trp Leu Arg Ser Thr Arg Phe
850                 855                 860

Ser Gly Ser Leu Asp Arg Leu Arg Glu Thr Arg Val Ala Asp
865                 870                 875

<210> SEQ ID NO 32
<211> LENGTH: 193
<212> TYPE: PRT
<213> ORGANISM: Homo sapiens

<400> SEQUENCE: 32

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

```
<210> SEQ ID NO 33
<211> LENGTH: 208
<212> TYPE: PRT
<213> ORGANISM: Homo sapiens

<400> SEQUENCE: 33
```

Met Pro Glu Glu Gly Ser Gly Cys Ser Val Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
        130                 135                 140

Leu Ser Phe His Gln Gly Leu Phe Gly Phe Trp Asn Trp Gly Leu Lys
145                 150                 155                 160

Val Lys Cys Phe Leu Arg His Leu Ile Trp Thr Ala His Cys Phe Ile
                165                 170                 175

Pro Leu Thr Gln Leu Val Phe Met Gln Ala Leu Gln Ser Trp Arg Asn
            180                 185                 190

His His Cys Ser His Phe Thr Asp Glu Glu Asn Arg Gly Val Asn Arg
        195                 200                 205

```
<210> SEQ ID NO 34
<211> LENGTH: 566
<212> TYPE: PRT
<213> ORGANISM: Homo sapiens

<400> SEQUENCE: 34
```

Met Gly Arg Ala Gly Gly Gly Gly Pro Gly Arg Gly Pro Pro Leu
1               5                   10                  15

Leu Leu Phe Leu Gly Ala Ala Leu Val Leu Ala Ser Gly Ala Val Pro
            20                  25                  30

Ala Arg Glu Ala Gly Ser Ala Val Glu Ala Glu Leu Val Lys Gly
            35                  40                  45

Ser Pro Ala Trp Glu Pro Ala Asn Asp Thr Arg Glu Glu Ala Gly
    50                  55                  60

Pro Pro Ala Ala Gly Glu Asp Glu Ala Ser Trp Thr Ala Pro Gly Gly
65                  70                  75                  80

Glu Leu Ala Gly Pro Glu Glu Val Leu Gln Glu Ser Ala Ala Val Thr
                85                  90                  95

Gly Thr Ala Trp Leu Glu Ala Asp Ser Pro Gly Leu Gly Gly Val Thr
            100                 105                 110

-continued

```
Ala Glu Ala Gly Ser Gly Asp Ala Gln Ala Leu Pro Ala Thr Leu Gln
            115                 120                 125

Ala Pro His Glu Val Leu Gly Gln Ser Ile Met Pro Ala Ile Pro
130                 135                 140

Glu Ala Thr Glu Ala Ser Gly Pro Pro Ser Pro Thr Pro Gly Asp Lys
145                 150                 155                 160

Leu Ser Pro Ala Ser Glu Leu Pro Lys Glu Ser Pro Leu Glu Val Trp
                165                 170                 175

Leu Asn Leu Gly Gly Ser Thr Pro Asp Pro Gln Gly Pro Glu Leu Thr
                180                 185                 190

Tyr Pro Phe Gln Gly Thr Leu Glu Pro Gln Pro Ala Ser Asp Ile Ile
            195                 200                 205

Asp Ile Asp Tyr Phe Glu Gly Leu Asp Gly Glu Gly Arg Gly Ala Asp
210                 215                 220

Leu Gly Ser Phe Pro Gly Ser Pro Gly Thr Ser Glu Asn His Pro Asp
225                 230                 235                 240

Thr Glu Gly Glu Thr Pro Ser Trp Ser Leu Leu Asp Leu Tyr Asp Asp
                245                 250                 255

Phe Thr Pro Phe Asp Glu Ser Asp Phe Tyr Pro Thr Thr Ser Phe Tyr
            260                 265                 270

Asp Asp Leu Asp Glu Glu Glu Glu Glu Asp Asp Lys Asp Ala
            275                 280                 285

Val Gly Gly Asp Leu Glu Asp Glu Asn Glu Leu Leu Val Pro Thr
            290                 295                 300

Gly Lys Pro Gly Leu Gly Pro Gly Thr Gly Gln Pro Thr Ser Arg Trp
305                 310                 315                 320

His Ala Val Pro Pro Gln His Thr Leu Gly Ser Val Pro Gly Ser Ser
                325                 330                 335

Ile Ala Leu Arg Pro Arg Pro Gly Glu Pro Gly Arg Asp Leu Ala Ser
                340                 345                 350

Ser Glu Asn Gly Thr Glu Cys Arg Ser Gly Phe Val Arg His Asn Gly
                355                 360                 365

Ser Cys Arg Ser Val Cys Asp Leu Phe Pro Ser Tyr Cys His Asn Gly
370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Gln Val Met Cys Val Ala Val Gly Ser Ala Ala Leu Val
            420                 425                 430

Leu Leu Leu Leu Phe Met Met Thr Val Phe Phe Ala Lys Lys Leu Tyr
            435                 440                 445

Leu Leu Lys Thr Glu Asn Thr Lys Leu Arg Arg Thr Asn Lys Phe Arg
450                 455                 460

Thr Pro Ser Glu Leu His Asn Asp Asn Phe Ser Leu Ser Thr Ile Ala
465                 470                 475                 480

Glu Gly Ser His Pro Asn Val Arg Lys Leu Cys Asn Thr Pro Arg Thr
                485                 490                 495

Ser Ser Pro His Ala Arg Ala Leu Ala His Tyr Asp Asn Val Ile Cys
                500                 505                 510

Gln Asp Asp Pro Ser Ala Pro His Lys Ile Gln Glu Val Leu Lys Ser
                515                 520                 525

Cys Leu Lys Glu Glu Glu Ser Phe Asn Ile Gln Asn Ser Met Ser Pro
```

```
                530             535             540
Lys Leu Glu Gly Gly Lys Gly Asp Gln Ala Asp Leu Asp Val Asn Cys
545                 550                 555                 560

Leu Gln Asn Asn Leu Thr
                565

<210> SEQ ID NO 35
<211> LENGTH: 539
<212> TYPE: PRT
<213> ORGANISM: Homo sapiens

<400> SEQUENCE: 35

Met Gly Arg Ala Gly Gly Gly Pro Gly Arg Gly Pro Pro Leu
1               5                   10                  15

Leu Leu Phe Leu Gly Ala Ala Leu Val Leu Ala Ser Gly Ala Val Pro
                20                  25                  30

Ala Arg Glu Ala Gly Ser Ala Val Glu Ala Glu Leu Val Lys Gly
            35                  40                  45

Ser Pro Ala Trp Glu Pro Pro Ala Asn Asp Thr Arg Glu Glu Ala Gly
50                  55                  60

Pro Pro Ala Ala Gly Glu Asp Glu Ala Ser Trp Thr Ala Pro Gly Gly
65                  70                  75                  80

Glu Leu Ala Gly Pro Glu Glu Val Leu Gln Glu Ser Ala Ala Val Thr
                85                  90                  95

Gly Thr Ala Trp Leu Glu Ala Asp Ser Pro Gly Leu Gly Gly Val Thr
                100                 105                 110

Ala Glu Ala Gly Ser Gly Asp Ala Gln Ala Leu Pro Ala Thr Leu Gln
            115                 120                 125

Ala Pro His Glu Val Leu Gly Gln Ser Ile Met Pro Ala Ile Pro
130                 135                 140

Glu Ala Thr Glu Ala Ser Gly Pro Pro Ser Pro Thr Pro Gly Asp Lys
145                 150                 155                 160

Leu Ser Pro Ala Ser Glu Leu Pro Lys Glu Ser Pro Leu Glu Val Trp
                165                 170                 175

Leu Asn Leu Gly Gly Ser Thr Pro Asp Pro Gln Gly Pro Glu Leu Thr
            180                 185                 190

Tyr Pro Phe Gln Gly Thr Leu Glu Pro Gln Pro Ala Ser Asp Ile Ile
            195                 200                 205

Asp Ile Asp Tyr Phe Glu Gly Leu Asp Gly Glu Gly Arg Gly Ala Asp
210                 215                 220

Leu Gly Ser Phe Pro Gly Ser Pro Gly Thr Ser Glu Asn His Pro Asp
225                 230                 235                 240

Thr Glu Gly Glu Thr Pro Ser Trp Ser Leu Leu Asp Leu Tyr Asp Asp
                245                 250                 255

Phe Thr Pro Phe Asp Glu Ser Asp Phe Tyr Pro Thr Thr Ser Phe Tyr
            260                 265                 270

Asp Asp Leu Asp Glu Glu Glu Glu Glu Glu Asp Lys Asp Ala
            275                 280                 285

Val Gly Gly Gly Asp Leu Glu Asp Glu Asn Glu Leu Leu Val Pro Thr
290                 295                 300

Gly Lys Pro Gly Leu Gly Pro Gly Thr Gly Gln Pro Thr Ser Arg Trp
305                 310                 315                 320

His Ala Val Pro Pro Gln His Thr Leu Gly Ser Val Pro Gly Ser Ser
                325                 330                 335
```

Ile Ala Leu Arg Pro Arg Pro Gly Glu Pro Gly Arg Asp Leu Ala Ser
                340                 345                 350

Ser Glu Asn Gly Thr Glu Cys Arg Ser Gly Phe Val Arg His Asn Gly
            355                 360                 365

Ser Cys Arg Ser Val Cys Asp Leu Phe Pro Ser Tyr Cys His Asn Gly
        370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Gln Val Met Cys Val Ala Val Gly Ser Ala Ala Leu Val
            420                 425                 430

Leu Leu Leu Leu Phe Met Met Thr Val Phe Phe Ala Lys Lys Leu Tyr
        435                 440                 445

Leu Leu Lys Thr Glu Asn Thr Lys Leu Arg Arg Thr Asn Lys Phe Arg
450                 455                 460

Thr Pro Ser Glu Leu His Asn Asp Asn Phe Ser Leu Ser Thr Ile Ala
465                 470                 475                 480

Glu Gly Ser His Pro Asn Asp Asp Pro Ser Ala Pro His Lys Ile Gln
                485                 490                 495

Glu Val Leu Lys Ser Cys Leu Lys Glu Glu Ser Phe Asn Ile Gln
            500                 505                 510

Asn Ser Met Ser Pro Lys Leu Glu Gly Gly Lys Gly Asp Gln Ala Asp
                515                 520                 525

Leu Asp Val Asn Cys Leu Gln Asn Asn Leu Thr
530                 535

<210> SEQ ID NO 36
<211> LENGTH: 401
<212> TYPE: PRT
<213> ORGANISM: Homo sapiens

<400> SEQUENCE: 36

Met Pro Pro Ala Ile Pro Glu Ala Thr Glu Ala Ser Gly Pro Pro Ser
1               5                   10                  15

Pro Thr Pro Gly Asp Lys Leu Ser Pro Ala Ser Glu Leu Pro Lys Glu
                20                  25                  30

Ser Pro Leu Glu Val Trp Leu Asn Leu Gly Gly Ser Thr Pro Asp Pro
            35                  40                  45

Gln Gly Pro Glu Leu Thr Tyr Pro Phe Gln Gly Thr Leu Glu Pro Gln
        50                  55                  60

Pro Ala Ser Asp Ile Ile Asp Ile Asp Tyr Phe Glu Gly Leu Asp Gly
65                  70                  75                  80

Glu Gly Arg Gly Ala Asp Leu Gly Ser Phe Pro Gly Ser Pro Gly Thr
                85                  90                  95

Ser Glu Asn His Pro Asp Thr Glu Gly Glu Thr Pro Ser Trp Ser Leu
            100                 105                 110

Leu Asp Leu Tyr Asp Asp Phe Thr Pro Phe Asp Glu Ser Asp Phe Tyr
        115                 120                 125

Pro Thr Thr Ser Phe Tyr Asp Asp Leu Asp Glu Glu Glu Glu Glu Glu
    130                 135                 140

Glu Asp Asp Lys Asp Ala Val Gly Gly Asp Leu Glu Asp Glu Asn
145                 150                 155                 160

Glu Leu Leu Val Pro Thr Gly Lys Pro Gly Leu Gly Pro Gly Thr Gly
                165                 170                 175

-continued

```
Gln Pro Thr Ser Arg Trp His Ala Val Pro Pro Gln His Thr Leu Gly
            180                 185                 190

Ser Val Pro Gly Ser Ser Ile Ala Leu Arg Pro Arg Pro Gly Glu Pro
            195                 200                 205

Gly Arg Asp Leu Ala Ser Ser Glu Asn Gly Thr Glu Cys Arg Ser Gly
            210                 215                 220

Phe Val Arg His Asn Gly Ser Cys Arg Ser Val Cys Asp Leu Phe Pro
225                 230                 235                 240

Ser Tyr Cys His Asn Gly Gly Gln Cys Tyr Leu Val Glu Asn Ile Gly
            245                 250                 255

Ala Phe Cys Arg Cys Asn Thr Gln Asp Tyr Ile Trp His Lys Gly Met
            260                 265                 270

Arg Cys Glu Ser Ile Ile Thr Asp Phe Gln Val Met Cys Val Ala Val
            275                 280                 285

Gly Ser Ala Ala Leu Val Leu Leu Leu Phe Met Met Thr Val Phe
            290                 295                 300

Phe Ala Lys Lys Leu Tyr Leu Leu Lys Thr Glu Asn Thr Lys Leu Arg
305                 310                 315                 320

Arg Thr Asn Lys Phe Arg Thr Pro Ser Glu Leu His Asn Asp Asn Phe
                325                 330                 335

Ser Leu Ser Thr Ile Ala Glu Gly Ser His Pro Asn Asp Pro Ser
            340                 345                 350

Ala Pro His Lys Ile Gln Glu Val Leu Lys Ser Cys Leu Lys Glu Glu
            355                 360                 365

Glu Ser Phe Asn Ile Gln Asn Ser Met Ser Pro Lys Leu Glu Gly Gly
            370                 375                 380

Lys Gly Asp Gln Ala Asp Leu Asp Val Asn Cys Leu Gln Asn Asn Leu
385                 390                 395                 400

Thr

<210> SEQ ID NO 37
<211> LENGTH: 911
<212> TYPE: PRT
<213> ORGANISM: Homo sapiens

<400> SEQUENCE: 37

Met Ala Gln Leu Phe Leu Pro Leu Leu Ala Ala Leu Val Leu Ala Gln
1               5                   10                  15

Ala Pro Ala Ala Leu Ala Asp Val Leu Glu Gly Asp Ser Ser Glu Asp
            20                  25                  30

Arg Ala Phe Arg Val Arg Ile Ala Gly Asp Ala Pro Leu Gln Gly Val
            35                  40                  45

Leu Gly Gly Ala Leu Thr Ile Pro Cys His Val His Tyr Leu Arg Pro
        50                  55                  60

Pro Pro Ser Arg Arg Ala Val Leu Gly Ser Pro Arg Val Lys Trp Thr
65                  70                  75                  80

Phe Leu Ser Arg Gly Arg Glu Ala Glu Val Leu Val Ala Arg Gly Val
                85                  90                  95

Arg Val Lys Val Asn Glu Ala Tyr Arg Phe Arg Val Ala Leu Pro Ala
            100                 105                 110

Tyr Pro Ala Ser Leu Thr Asp Val Ser Leu Ala Leu Ser Glu Leu Arg
            115                 120                 125

Pro Asn Asp Ser Gly Ile Tyr Arg Cys Glu Val Gln His Gly Ile Asp
        130                 135                 140
```

```
Asp Ser Ser Asp Ala Val Glu Val Lys Val Lys Gly Val Val Phe Leu
145                 150                 155                 160

Tyr Arg Glu Gly Ser Ala Arg Tyr Ala Phe Ser Phe Ser Gly Ala Gln
                165                 170                 175

Glu Ala Cys Ala Arg Ile Gly Ala His Ile Ala Thr Pro Glu Gln Leu
            180                 185                 190

Tyr Ala Ala Tyr Leu Gly Gly Tyr Glu Gln Cys Asp Ala Gly Trp Leu
            195                 200                 205

Ser Asp Gln Thr Val Arg Tyr Pro Ile Gln Thr Pro Arg Glu Ala Cys
210                 215                 220

Tyr Gly Asp Met Asp Gly Phe Pro Gly Val Arg Asn Tyr Gly Val Val
225                 230                 235                 240

Asp Pro Asp Asp Leu Tyr Asp Val Tyr Cys Tyr Ala Glu Asp Leu Asn
                245                 250                 255

Gly Glu Leu Phe Leu Gly Asp Pro Pro Glu Lys Leu Thr Leu Glu Glu
                260                 265                 270

Ala Arg Ala Tyr Cys Gln Glu Arg Gly Ala Glu Ile Ala Thr Thr Gly
            275                 280                 285

Gln Leu Tyr Ala Ala Trp Asp Gly Gly Leu Asp His Cys Ser Pro Gly
            290                 295                 300

Trp Leu Ala Asp Gly Ser Val Arg Tyr Pro Ile Val Thr Pro Ser Gln
305                 310                 315                 320

Arg Cys Gly Gly Gly Leu Pro Gly Val Lys Thr Leu Phe Leu Phe Pro
                325                 330                 335

Asn Gln Thr Gly Phe Pro Asn Lys His Ser Arg Phe Asn Val Tyr Cys
                340                 345                 350

Phe Arg Asp Ser Ala Gln Pro Ser Ala Ile Pro Glu Ala Ser Asn Pro
                355                 360                 365

Ala Ser Asn Pro Ala Ser Asp Gly Leu Glu Ala Ile Val Thr Val Thr
            370                 375                 380

Glu Thr Leu Glu Glu Leu Gln Leu Pro Gln Glu Ala Thr Glu Ser Glu
385                 390                 395                 400

Ser Arg Gly Ala Ile Tyr Ser Ile Pro Ile Met Glu Asp Gly Gly Gly
                405                 410                 415

Gly Ser Ser Thr Pro Glu Asp Pro Ala Glu Ala Pro Arg Thr Leu Leu
                420                 425                 430

Glu Phe Glu Thr Gln Ser Met Val Pro Pro Thr Gly Phe Ser Glu Glu
                435                 440                 445

Glu Gly Lys Ala Leu Glu Glu Glu Lys Tyr Glu Asp Glu Glu Glu
                450                 455                 460

Lys Glu Glu Glu Glu Glu Glu Val Glu Asp Glu Ala Leu Trp
465                 470                 475                 480

Ala Trp Pro Ser Glu Leu Ser Ser Pro Gly Pro Glu Ala Ser Leu Pro
                485                 490                 495

Thr Glu Pro Ala Ala Gln Glu Glu Ser Leu Ser Gln Ala Pro Ala Arg
                500                 505                 510

Ala Val Leu Gln Pro Gly Ala Ser Pro Leu Pro Asp Gly Glu Ser Glu
            515                 520                 525

Ala Ser Arg Pro Pro Arg Val His Gly Pro Pro Thr Glu Thr Leu Pro
530                 535                 540

Thr Pro Arg Glu Arg Asn Leu Ala Ser Pro Ser Pro Ser Thr Leu Val
545                 550                 555                 560
```

Glu Ala Arg Glu Val Gly Glu Ala Thr Gly Gly Pro Glu Leu Ser Gly
                565                 570                 575

Val Pro Arg Gly Glu Ser Glu Gly Thr Gly Ser Ser Glu Gly Ala Pro
            580                 585                 590

Ser Leu Leu Pro Ala Thr Arg Ala Pro Glu Gly Thr Arg Glu Leu Glu
        595                 600                 605

Ala Pro Ser Glu Asp Asn Ser Gly Arg Thr Ala Pro Ala Gly Thr Ser
    610                 615                 620

Val Gln Ala Gln Pro Val Leu Pro Thr Asp Ser Ala Ser Arg Gly Gly
625                 630                 635                 640

Val Ala Val Val Pro Ala Ser Gly Asp Cys Val Pro Ser Pro Cys His
                645                 650                 655

Asn Gly Gly Thr Cys Leu Glu Glu Glu Gly Val Arg Cys Leu Cys
            660                 665                 670

Leu Pro Gly Tyr Gly Gly Asp Leu Cys Asp Val Gly Leu Arg Phe Cys
        675                 680                 685

Asn Pro Gly Trp Asp Ala Phe Gln Gly Ala Cys Tyr Lys His Phe Ser
    690                 695                 700

Thr Arg Arg Ser Trp Glu Glu Ala Glu Thr Gln Cys Arg Met Tyr Gly
705                 710                 715                 720

Ala His Leu Ala Ser Ile Ser Thr Pro Glu Glu Gln Asp Phe Ile Asn
                725                 730                 735

Asn Arg Tyr Arg Glu Tyr Gln Trp Ile Gly Leu Asn Asp Arg Thr Ile
            740                 745                 750

Glu Gly Asp Phe Leu Trp Ser Asp Gly Val Pro Leu Leu Tyr Glu Asn
        755                 760                 765

Trp Asn Pro Gly Gln Pro Asp Ser Tyr Phe Leu Ser Gly Glu Asn Cys
    770                 775                 780

Val Val Met Val Trp His Asp Gln Gly Gln Trp Ser Asp Val Pro Cys
785                 790                 795                 800

Asn Tyr His Leu Ser Tyr Thr Cys Lys Met Gly Leu Val Ser Cys Gly
                805                 810                 815

Pro Pro Pro Glu Leu Pro Leu Ala Gln Val Phe Gly Arg Pro Arg Leu
            820                 825                 830

Arg Tyr Glu Val Asp Thr Val Leu Arg Tyr Arg Cys Arg Glu Gly Leu
        835                 840                 845

Ala Gln Arg Asn Leu Pro Leu Ile Arg Cys Gln Glu Asn Gly Arg Trp
    850                 855                 860

Glu Ala Pro Gln Ile Ser Cys Val Pro Arg Arg Pro Ala Arg Ala Leu
865                 870                 875                 880

His Pro Glu Glu Asp Pro Glu Gly Arg Gln Gly Arg Leu Leu Gly Arg
                885                 890                 895

Trp Lys Ala Leu Leu Ile Pro Pro Ser Ser Pro Met Pro Gly Pro
            900                 905                 910

<210> SEQ ID NO 38
<211> LENGTH: 671
<212> TYPE: PRT
<213> ORGANISM: Homo sapiens

<400> SEQUENCE: 38

Met Ala Gln Leu Phe Leu Pro Leu Leu Ala Ala Leu Val Leu Ala Gln
1               5                   10                  15

Ala Pro Ala Ala Leu Ala Asp Val Leu Glu Gly Asp Ser Ser Glu Asp
                20                  25                  30

-continued

```
Arg Ala Phe Arg Val Arg Ile Ala Gly Asp Ala Pro Leu Gln Gly Val
            35                  40                  45

Leu Gly Gly Ala Leu Thr Ile Pro Cys His Val His Tyr Leu Arg Pro
 50                  55                  60

Pro Pro Ser Arg Arg Ala Val Leu Gly Ser Pro Arg Val Lys Trp Thr
 65              70                  75                  80

Phe Leu Ser Arg Gly Arg Glu Ala Glu Val Leu Val Ala Arg Gly Val
                85                  90                  95

Arg Val Lys Val Asn Glu Ala Tyr Arg Phe Arg Val Ala Leu Pro Ala
            100                 105                 110

Tyr Pro Ala Ser Leu Thr Asp Val Ser Leu Ala Leu Ser Glu Leu Arg
            115                 120                 125

Pro Asn Asp Ser Gly Ile Tyr Arg Cys Glu Val Gln His Gly Ile Asp
130                 135                 140

Asp Ser Ser Asp Ala Val Glu Val Lys Val Lys Gly Val Val Phe Leu
145                 150                 155                 160

Tyr Arg Glu Gly Ser Ala Arg Tyr Ala Phe Ser Phe Ser Gly Ala Gln
                165                 170                 175

Glu Ala Cys Ala Arg Ile Gly Ala His Ile Ala Thr Pro Glu Gln Leu
            180                 185                 190

Tyr Ala Ala Tyr Leu Gly Gly Tyr Glu Gln Cys Asp Ala Gly Trp Leu
            195                 200                 205

Ser Asp Gln Thr Val Arg Tyr Pro Ile Gln Thr Pro Arg Glu Ala Cys
210                 215                 220

Tyr Gly Asp Met Asp Gly Phe Pro Gly Val Arg Asn Tyr Gly Val Val
225                 230                 235                 240

Asp Pro Asp Asp Leu Tyr Asp Val Tyr Cys Tyr Ala Glu Asp Leu Asn
                245                 250                 255

Gly Glu Leu Phe Leu Gly Asp Pro Pro Glu Lys Leu Thr Leu Glu Glu
            260                 265                 270

Ala Arg Ala Tyr Cys Gln Glu Arg Gly Ala Glu Ile Ala Thr Thr Gly
            275                 280                 285

Gln Leu Tyr Ala Ala Trp Asp Gly Gly Leu Asp His Cys Ser Pro Gly
290                 295                 300

Trp Leu Ala Asp Gly Ser Val Arg Tyr Pro Ile Val Thr Pro Ser Gln
305                 310                 315                 320

Arg Cys Gly Gly Gly Leu Pro Gly Val Lys Thr Leu Phe Leu Phe Pro
                325                 330                 335

Asn Gln Thr Gly Phe Pro Asn Lys His Ser Arg Phe Asn Val Tyr Cys
            340                 345                 350

Phe Arg Asp Ser Ala Gln Pro Ser Ala Ile Pro Glu Ala Ser Asn Pro
            355                 360                 365

Ala Ser Asn Pro Ala Ser Asp Gly Leu Glu Ala Ile Val Thr Val Thr
370                 375                 380

Glu Thr Leu Glu Glu Leu Gln Leu Pro Gln Glu Ala Thr Glu Ser Glu
385                 390                 395                 400

Ser Arg Gly Ala Ile Tyr Ser Ile Pro Ile Met Glu Asp Gly Gly Gly
                405                 410                 415

Gly Ser Ser Thr Pro Glu Asp Pro Ala Glu Ala Pro Arg Thr Leu Leu
            420                 425                 430

Glu Phe Glu Thr Gln Ser Met Val Pro Pro Thr Gly Phe Ser Glu Glu
            435                 440                 445
```

```
Glu Gly Lys Ala Leu Glu Glu Glu Lys Tyr Glu Asp Glu Glu Glu
    450                 455                 460
Lys Glu Glu Glu Glu Glu Glu Glu Val Glu Asp Glu Ala Leu Trp
465                 470                 475                 480
Ala Trp Pro Ser Glu Leu Ser Ser Pro Gly Pro Glu Ala Ser Leu Pro
            485                 490                 495
Thr Glu Pro Ala Ala Gln Glu Glu Ser Leu Ser Gln Ala Pro Ala Arg
        500                 505                 510
Ala Val Leu Gln Pro Gly Ala Ser Pro Leu Pro Asp Gly Glu Ser Glu
            515                 520                 525
Ala Ser Arg Pro Pro Arg Val His Gly Pro Pro Thr Glu Thr Leu Pro
    530                 535                 540
Thr Pro Arg Glu Arg Asn Leu Ala Ser Pro Ser Pro Ser Thr Leu Val
545                 550                 555                 560
Glu Ala Arg Glu Val Gly Glu Ala Thr Gly Gly Pro Glu Leu Ser Gly
                565                 570                 575
Val Pro Arg Gly Glu Ser Glu Glu Thr Gly Ser Ser Glu Gly Ala Pro
            580                 585                 590
Ser Leu Leu Pro Ala Thr Arg Ala Pro Glu Gly Thr Arg Glu Leu Glu
    595                 600                 605
Ala Pro Ser Glu Asp Asn Ser Gly Arg Thr Ala Pro Ala Gly Thr Ser
    610                 615                 620
Val Gln Ala Gln Pro Val Leu Pro Thr Asp Ser Ala Ser Arg Gly Gly
625                 630                 635                 640
Val Ala Val Val Pro Ala Ser Gly Asn Ser Ala Gln Gly Ser Thr Ala
                645                 650                 655
Leu Ser Ile Leu Leu Leu Phe Phe Pro Leu Gln Leu Trp Val Thr
            660                 665                 670

<210> SEQ ID NO 39
<211> LENGTH: 879
<212> TYPE: PRT
<213> ORGANISM: Homo sapiens

<400> SEQUENCE: 39

Met Lys Met Leu Thr Arg Leu Gln Val Leu Thr Leu Ala Leu Phe Ser
1               5                   10                  15
Lys Gly Phe Leu Leu Ser Leu Gly Asp His Asn Phe Leu Arg Arg Glu
            20                  25                  30
Ile Lys Ile Glu Gly Asp Leu Val Leu Gly Gly Leu Phe Pro Ile Asn
        35                  40                  45
Glu Lys Gly Thr Gly Thr Glu Glu Cys Gly Arg Ile Asn Glu Asp Arg
    50                  55                  60
Gly Ile Gln Arg Leu Glu Ala Met Leu Phe Ala Ile Asp Glu Ile Asn
65                  70                  75                  80
Lys Asp Asp Tyr Leu Leu Pro Gly Val Lys Leu Gly Val His Ile Leu
                85                  90                  95
Asp Thr Cys Ser Arg Asp Thr Tyr Ala Leu Glu Gln Ser Leu Glu Phe
            100                 105                 110
Val Arg Ala Ser Leu Thr Lys Val Asp Glu Ala Glu Tyr Met Cys Pro
        115                 120                 125
Asp Gly Ser Tyr Ala Ile Gln Glu Asn Ile Pro Leu Leu Ile Ala Gly
    130                 135                 140
Val Ile Gly Gly Ser Tyr Ser Ser Val Ser Ile Gln Val Ala Asn Leu
145                 150                 155                 160
```

```
Leu Arg Leu Phe Gln Ile Pro Gln Ile Ser Tyr Ala Ser Thr Ser Ala
             165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Phe Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
            260                 265                 270

Val Leu Phe Met Arg Ser Asp Asp Ser Arg Glu Leu Ile Ala Ala Ala
        275                 280                 285

Ser Arg Ala Asn Ala Ser Phe Thr Trp Val Ala Ser Asp Gly Trp Gly
    290                 295                 300

Ala Gln Glu Ser Ile Ile Lys Gly Ser Glu His Val Ala Tyr Gly Ala
305                 310                 315                 320

Ile Thr Leu Glu Leu Ala Ser Gln Pro Val Arg Gln Phe Asp Arg Tyr
                325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
        355                 360                 365

His Arg Arg Val Cys Asp Lys His Leu Ala Ile Asp Ser Ser Asn Tyr
    370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415

Lys Leu Cys Asp Ala Met Lys Ile Leu Asp Gly Lys Lys Leu Tyr Lys
            420                 425                 430

Asp Tyr Leu Leu Lys Ile Asn Phe Thr Ala Pro Phe Asn Pro Asn Lys
        435                 440                 445

Asp Ala Asp Ser Ile Val Lys Phe Asp Thr Phe Gly Asp Gly Met Gly
    450                 455                 460

Arg Tyr Asn Val Phe Asn Phe Gln Asn Val Gly Gly Lys Tyr Ser Tyr
465                 470                 475                 480

Leu Lys Val Gly His Trp Ala Glu Thr Leu Ser Leu Asp Val Asn Ser
                485                 490                 495

Ile His Trp Ser Arg Asn Ser Val Pro Thr Ser Gln Cys Ser Asp Pro
            500                 505                 510

Cys Ala Pro Asn Glu Met Lys Asn Met Gln Pro Gly Asp Val Cys Cys
        515                 520                 525

Trp Ile Cys Ile Pro Cys Glu Pro Tyr Glu Tyr Leu Ala Asp Glu Phe
    530                 535                 540

Thr Cys Met Asp Cys Gly Ser Gly Gln Trp Pro Thr Ala Asp Leu Thr
545                 550                 555                 560

Gly Cys Tyr Asp Leu Pro Glu Asp Tyr Ile Arg Trp Glu Asp Ala Trp
                565                 570                 575
```

```
Ala Ile Gly Pro Val Thr Ile Ala Cys Leu Phe Met Cys Thr Cys
            580                 585                 590

Met Val Val Thr Val Phe Ile Lys His Asn Asn Thr Pro Leu Val Lys
            595                 600                 605

Ala Ser Gly Arg Glu Leu Cys Tyr Ile Leu Leu Phe Gly Val Gly Leu
            610                 615                 620

Ser Tyr Cys Met Thr Phe Phe Phe Ile Ala Lys Pro Ser Pro Val Ile
625                 630                 635                 640

Cys Ala Leu Arg Arg Leu Gly Leu Gly Ser Ser Phe Ala Ile Cys Tyr
            645                 650                 655

Ser Ala Leu Leu Thr Lys Thr Asn Cys Ile Ala Arg Ile Phe Asp Gly
            660                 665                 670

Val Lys Asn Gly Ala Gln Arg Pro Lys Phe Ile Ser Pro Ser Ser Gln
            675                 680                 685

Val Phe Ile Cys Leu Gly Leu Ile Leu Val Gln Ile Val Met Val Ser
            690                 695                 700

Val Trp Leu Ile Leu Glu Ala Pro Gly Thr Arg Arg Tyr Thr Leu Ala
705                 710                 715                 720

Glu Lys Arg Glu Thr Val Ile Leu Lys Cys Asn Val Lys Asp Ser Ser
            725                 730                 735

Met Leu Ile Ser Leu Thr Tyr Asp Val Ile Leu Val Ile Leu Cys Thr
            740                 745                 750

Val Tyr Ala Phe Lys Thr Arg Lys Cys Pro Glu Asn Phe Asn Glu Ala
            755                 760                 765

Lys Phe Ile Gly Phe Thr Met Tyr Thr Thr Cys Ile Ile Trp Leu Ala
            770                 775                 780

Phe Leu Pro Ile Phe Tyr Val Thr Ser Ser Asp Tyr Arg Val Gln Thr
785                 790                 795                 800

Thr Thr Met Cys Ile Ser Val Ser Leu Ser Gly Phe Val Val Leu Gly
            805                 810                 815

Cys Leu Phe Ala Pro Lys Val His Ile Ile Leu Phe Gln Pro Gln Lys
            820                 825                 830

Asn Val Val Thr His Arg Leu His Leu Asn Arg Phe Ser Val Ser Gly
            835                 840                 845

Thr Gly Thr Thr Tyr Ser Gln Ser Ser Ala Ser Thr Tyr Val Pro Thr
850                 855                 860

Val Cys Asn Gly Arg Glu Val Leu Asp Ser Thr Thr Ser Ser Leu
865                 870                 875

<210> SEQ ID NO 40
<211> LENGTH: 537
<212> TYPE: PRT
<213> ORGANISM: Homo sapiens

<400> SEQUENCE: 40

Met Lys Met Leu Thr Arg Leu Gln Val Leu Thr Leu Ala Leu Phe Ser
1               5                   10                  15

Lys Gly Phe Leu Leu Ser Leu Gly Asp His Asn Phe Leu Arg Arg Glu
                20                  25                  30

Ile Lys Ile Glu Gly Asp Leu Val Leu Gly Gly Leu Phe Pro Ile Asn
            35                  40                  45

Glu Lys Gly Thr Gly Thr Glu Glu Cys Gly Arg Ile Asn Glu Asp Arg
        50                  55                  60

Gly Ile Gln Arg Leu Glu Ala Met Leu Phe Ala Ile Asp Glu Ile Asn
65                  70                  75                  80
```

```
Lys Asp Asp Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Phe Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
            260                 265                 270

Val Leu Phe Met Arg Ser Asp Ser Arg Glu Leu Ile Ala Ala Ala
        275                 280                 285

Ser Arg Ala Asn Ala Ser Phe Thr Trp Val Ala Ser Asp Gly Trp Gly
    290                 295                 300

Ala Gln Glu Ser Ile Ile Lys Gly Ser Glu His Val Ala Tyr Gly Ala
305                 310                 315                 320

Ile Thr Leu Glu Leu Ala Ser Gln Pro Val Arg Gln Phe Asp Arg Tyr
                325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
        355                 360                 365

His Arg Arg Val Cys Asp Lys His Leu Ala Ile Asp Ser Ser Asn Tyr
    370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415

Lys Leu Cys Asp Ala Met Lys Ile Leu Asp Gly Lys Lys Leu Tyr Lys
            420                 425                 430

Asp Tyr Leu Leu Lys Ile Asn Phe Thr Gly Ala Asp Asn His Val
        435                 440                 445

His Leu Cys Gln Pro Glu Trp Leu Cys Gly Leu Gly Leu Phe Val Cys
    450                 455                 460

Thr Gln Gly Ser His His Pro Val Ser Thr Pro Glu Glu Cys Cys His
465                 470                 475                 480

Thr Gln Thr Ala Pro Gln Gln Val Gln Cys Gln Trp Asn Trp Asp His
                485                 490                 495
```

```
Ile Leu Ser Val Leu Cys Lys His Val Cys Ala Asn Gly Val Gln Trp
            500                 505                 510

Ala Gly Ser Pro Arg Leu His His Leu Ile Ser Val Ile Val Asn Cys
            515                 520                 525

Ser Ser Val Leu Val Phe Leu Asp Cys
    530                 535

<210> SEQ ID NO 41
<211> LENGTH: 1406
<212> TYPE: PRT
<213> ORGANISM: Homo sapiens

<400> SEQUENCE: 41

Met Ala Leu Lys Asn Ile Asn Tyr Leu Leu Ile Phe Tyr Leu Ser Phe
1               5                   10                  15

Ser Leu Leu Ile Tyr Ile Lys Asn Ser Phe Cys Asn Lys Asn Asn Thr
            20                  25                  30

Arg Cys Leu Ser Asn Ser Cys Gln Asn Asn Ser Thr Cys Lys Asp Phe
        35                  40                  45

Ser Lys Asp Asn Asp Cys Ser Cys Ser Asp Thr Ala Asn Asn Leu Asp
    50                  55                  60

Lys Asp Cys Asp Asn Met Lys Asp Pro Cys Phe Ser Asn Pro Cys Gln
65                  70                  75                  80

Gly Ser Ala Thr Cys Val Asn Thr Pro Gly Glu Arg Ser Phe Leu Cys
                85                  90                  95

Lys Cys Pro Pro Gly Tyr Ser Gly Thr Ile Cys Glu Thr Thr Ile Gly
            100                 105                 110

Ser Cys Gly Lys Asn Ser Cys Gln His Gly Ile Cys His Gln Asp
        115                 120                 125

Pro Ile Tyr Pro Val Cys Ile Cys Pro Ala Gly Tyr Ala Gly Arg Phe
    130                 135                 140

Cys Glu Ile Asp His Asp Glu Cys Ala Ser Ser Pro Cys Gln Asn Gly
145                 150                 155                 160

Ala Val Cys Gln Asp Gly Ile Asp Gly Tyr Ser Cys Phe Cys Val Pro
                165                 170                 175

Gly Tyr Gln Gly Arg His Cys Asp Leu Glu Val Asp Glu Cys Ala Ser
            180                 185                 190

Asp Pro Cys Lys Asn Glu Ala Thr Cys Leu Asn Glu Ile Gly Arg Tyr
        195                 200                 205

Thr Cys Ile Cys Pro His Asn Tyr Ser Gly Val Asn Cys Glu Leu Glu
    210                 215                 220

Ile Asp Glu Cys Trp Ser Gln Pro Cys Leu Asn Gly Ala Thr Cys Gln
225                 230                 235                 240

Asp Ala Leu Gly Ala Tyr Phe Cys Asp Cys Ala Pro Gly Phe Leu Gly
                245                 250                 255

Asp His Cys Glu Leu Asn Thr Asp Glu Cys Ala Ser Gln Pro Cys Leu
            260                 265                 270

His Gly Gly Leu Cys Val Asp Gly Glu Asn Arg Tyr Ser Cys Asn Cys
        275                 280                 285

Thr Gly Ser Gly Phe Thr Gly Thr His Cys Glu Thr Leu Met Pro Leu
    290                 295                 300

Cys Trp Ser Lys Pro Cys His Asn Asn Ala Thr Cys Glu Asp Ser Val
305                 310                 315                 320

Asp Asn Tyr Thr Cys His Cys Trp Pro Gly Tyr Thr Gly Ala Gln Cys
                325                 330                 335
```

```
Glu Ile Asp Leu Asn Glu Cys Asn Ser Asn Pro Cys Gln Ser Asn Gly
            340                 345                 350

Glu Cys Val Glu Leu Ser Ser Glu Lys Gln Tyr Gly Arg Ile Thr Gly
            355                 360                 365

Leu Pro Ser Ser Phe Ser Tyr His Glu Ala Ser Gly Tyr Val Cys Ile
            370                 375                 380

Cys Gln Pro Gly Phe Thr Gly Ile His Cys Glu Glu Asp Val Asn Glu
385                 390                 395                 400

Cys Ser Ser Asn Pro Cys Gln Asn Gly Gly Thr Cys Glu Asn Leu Pro
                405                 410                 415

Gly Asn Tyr Thr Cys His Cys Pro Phe Asp Asn Leu Ser Arg Thr Phe
            420                 425                 430

Tyr Gly Gly Arg Asp Cys Ser Asp Ile Leu Leu Gly Cys Thr His Gln
            435                 440                 445

Gln Cys Leu Asn Asn Gly Thr Cys Ile Pro His Phe Gln Asp Gly Gln
            450                 455                 460

His Gly Phe Ser Cys Leu Cys Pro Ser Gly Tyr Thr Gly Ser Leu Cys
465                 470                 475                 480

Glu Ile Ala Thr Thr Leu Ser Phe Glu Gly Asp Gly Phe Leu Trp Val
            485                 490                 495

Lys Ser Gly Ser Val Thr Thr Lys Gly Ser Val Cys Asn Ile Ala Leu
            500                 505                 510

Arg Phe Gln Thr Val Gln Pro Met Ala Leu Leu Phe Arg Ser Asn
            515                 520                 525

Arg Asp Val Phe Val Lys Leu Glu Leu Leu Ser Gly Tyr Ile His Leu
            530                 535                 540

Ser Ile Gln Val Asn Asn Gln Ser Lys Val Leu Leu Phe Ile Ser His
545                 550                 555                 560

Asn Thr Ser Asp Gly Glu Trp His Phe Val Glu Val Ile Phe Ala Glu
            565                 570                 575

Ala Val Thr Leu Thr Leu Ile Asp Asp Ser Cys Lys Glu Lys Cys Ile
            580                 585                 590

Ala Lys Ala Pro Thr Pro Leu Glu Ser Asp Gln Ser Ile Cys Ala Phe
            595                 600                 605

Gln Asn Ser Phe Leu Gly Gly Leu Pro Val Gly Met Thr Ser Asn Gly
            610                 615                 620

Val Ala Leu Leu Asn Phe Tyr Asn Met Pro Ser Thr Pro Ser Phe Val
625                 630                 635                 640

Gly Cys Leu Gln Asp Ile Lys Ile Asp Trp Asn His Ile Thr Leu Glu
            645                 650                 655

Asn Ile Ser Ser Gly Ser Ser Leu Asn Val Lys Ala Gly Cys Val Arg
            660                 665                 670

Lys Asp Trp Cys Glu Ser Gln Pro Cys Gln Ser Arg Gly Arg Cys Ile
            675                 680                 685

Asn Leu Trp Leu Ser Tyr Gln Cys Asp Cys His Arg Pro Tyr Glu Gly
            690                 695                 700

Pro Asn Cys Leu Arg Glu Tyr Val Ala Gly Arg Phe Gly Gln Asp Asp
705                 710                 715                 720

Ser Thr Gly Tyr Val Ile Phe Thr Leu Asp Glu Ser Tyr Gly Asp Thr
            725                 730                 735

Ile Ser Leu Ser Met Phe Val Arg Thr Leu Gln Pro Ser Gly Leu Leu
            740                 745                 750
```

```
Leu Ala Leu Glu Asn Ser Thr Tyr Gln Tyr Ile Arg Val Trp Leu Glu
            755                 760                 765

Arg Gly Arg Leu Ala Met Leu Thr Pro Asn Ser Pro Lys Leu Val Val
        770                 775                 780

Lys Phe Val Leu Asn Asp Gly Asn Val His Leu Ile Ser Leu Lys Ile
785                 790                 795                 800

Lys Pro Tyr Lys Ile Glu Leu Tyr Gln Ser Ser Gln Asn Leu Gly Phe
            805                 810                 815

Ile Ser Ala Ser Thr Trp Lys Ile Glu Lys Gly Asp Val Ile Tyr Ile
            820                 825                 830

Gly Gly Leu Pro Asp Lys Gln Glu Thr Glu Leu Asn Gly Gly Phe Phe
        835                 840                 845

Lys Gly Cys Ile Gln Asp Val Arg Leu Asn Asn Gln Asn Leu Glu Phe
850                 855                 860

Phe Pro Asn Pro Thr Asn Asn Ala Ser Leu Asn Pro Val Leu Val Asn
865                 870                 875                 880

Val Thr Gln Gly Cys Ala Gly Asp Asn Ser Cys Lys Ser Asn Pro Cys
            885                 890                 895

His Asn Gly Gly Val Cys His Ser Arg Trp Asp Asp Phe Ser Cys Ser
        900                 905                 910

Cys Pro Ala Leu Thr Ser Gly Lys Ala Cys Glu Glu Val Gln Trp Cys
        915                 920                 925

Gly Phe Ser Pro Cys Pro His Gly Ala Gln Cys Gln Pro Val Leu Gln
        930                 935                 940

Gly Phe Glu Cys Ile Ala Asn Ala Val Phe Asn Gly Gln Ser Gly Gln
945                 950                 955                 960

Ile Leu Phe Arg Ser Asn Gly Asn Ile Thr Arg Glu Leu Thr Asn Ile
            965                 970                 975

Thr Phe Gly Phe Arg Thr Arg Asp Ala Asn Val Ile Ile Leu His Ala
        980                 985                 990

Glu Lys Glu Pro Glu Phe Leu Asn Ile Ser Ile Gln Asp Ser Arg Leu
        995                 1000                1005

Phe Phe Gln Leu Gln Ser Gly Asn Ser Phe Tyr Met Leu Ser Leu
    1010                1015                1020

Thr Ser Leu Gln Ser Val Asn Asp Gly Thr Trp His Glu Val Thr
    1025                1030                1035

Leu Ser Met Thr Asp Pro Leu Ser Gln Thr Ser Arg Trp Gln Met
    1040                1045                1050

Glu Val Asp Asn Glu Thr Pro Phe Val Thr Ser Thr Ile Ala Thr
    1055                1060                1065

Gly Ser Leu Asn Phe Leu Lys Asp Asn Thr Asp Ile Tyr Val Gly
    1070                1075                1080

Asp Arg Ala Ile Asp Asn Ile Lys Gly Leu Gln Gly Cys Leu Ser
    1085                1090                1095

Thr Ile Glu Ile Gly Gly Ile Tyr Leu Ser Tyr Phe Glu Asn Val
    1100                1105                1110

His Gly Phe Ile Asn Lys Pro Gln Glu Glu Gln Phe Leu Lys Ile
    1115                1120                1125

Ser Thr Asn Ser Val Val Thr Gly Cys Leu Gln Leu Asn Val Cys
    1130                1135                1140

Asn Ser Asn Pro Cys Leu His Gly Gly Asn Cys Glu Asp Ile Tyr
    1145                1150                1155

Ser Ser Tyr His Cys Ser Cys Pro Leu Gly Trp Ser Gly Lys His
```

```
             1160                1165                1170

Cys Glu Leu Asn Ile Asp Glu Cys Phe Ser Asn Pro Cys Ile His
    1175                1180                1185

Gly Asn Cys Ser Asp Arg Val Ala Ala Tyr His Cys Thr Cys Glu
    1190                1195                1200

Pro Gly Tyr Thr Gly Val Asn Cys Glu Val Asp Ile Asp Asn Cys
    1205                1210                1215

Gln Ser His Gln Cys Ala Asn Gly Ala Thr Cys Ile Ser His Thr
    1220                1225                1230

Asn Gly Tyr Ser Cys Leu Cys Phe Gly Asn Phe Thr Gly Lys Phe
    1235                1240                1245

Cys Arg Gln Ser Arg Leu Pro Ser Thr Val Cys Gly Asn Glu Lys
    1250                1255                1260

Thr Asn Leu Thr Cys Tyr Asn Gly Gly Asn Cys Thr Glu Phe Gln
    1265                1270                1275

Thr Glu Leu Lys Cys Met Cys Arg Pro Gly Phe Thr Gly Glu Trp
    1280                1285                1290

Cys Glu Lys Asp Ile Asp Glu Cys Ala Ser Asp Pro Cys Val Asn
    1295                1300                1305

Gly Gly Leu Cys Gln Asp Leu Leu Asn Lys Phe Gln Cys Leu Cys
    1310                1315                1320

Asp Val Ala Phe Ala Gly Glu Arg Cys Glu Val Asp Leu Ala Asp
    1325                1330                1335

Asp Leu Ile Ser Asp Ile Phe Thr Thr Ile Gly Ser Val Thr Val
    1340                1345                1350

Ala Leu Leu Leu Ile Leu Leu Leu Ala Ile Val Ala Ser Val Val
    1355                1360                1365

Thr Ser Asn Lys Arg Ala Thr Gln Gly Thr Tyr Ser Pro Ser Arg
    1370                1375                1380

Gln Glu Lys Glu Gly Ser Arg Val Glu Met Trp Asn Leu Met Pro
    1385                1390                1395

Pro Pro Ala Met Glu Arg Leu Ile
    1400                1405

<210> SEQ ID NO 42
<211> LENGTH: 1376
<212> TYPE: PRT
<213> ORGANISM: Homo sapiens

<400> SEQUENCE: 42

Met Ala Leu Lys Asn Ile Asn Tyr Leu Leu Ile Phe Tyr Leu Ser Phe
1               5                   10                  15

Ser Leu Leu Ile Tyr Ile Lys Asn Ser Phe Cys Asn Lys Asn Asn Thr
                20                  25                  30

Arg Cys Leu Ser Asn Ser Cys Gln Asn Asn Ser Thr Cys Lys Asp Phe
            35                  40                  45

Ser Lys Asp Asn Asp Cys Ser Cys Ser Asp Thr Ala Asn Asn Leu Asp
        50                  55                  60

Lys Asp Cys Asp Asn Met Lys Asp Pro Cys Phe Ser Asn Pro Cys Gln
65                  70                  75                  80

Gly Ser Ala Thr Cys Val Asn Thr Pro Gly Glu Arg Ser Phe Leu Cys
                85                  90                  95

Lys Cys Pro Pro Gly Tyr Ser Gly Thr Ile Cys Glu Thr Thr Ile Gly
            100                 105                 110
```

```
Ser Cys Gly Lys Asn Ser Cys Gln His Gly Gly Ile Cys His Gln Asp
            115                 120                 125
Pro Ile Tyr Pro Val Cys Ile Cys Pro Ala Gly Tyr Ala Gly Arg Phe
        130                 135                 140
Cys Glu Ile Asp His Asp Glu Cys Ala Ser Ser Pro Cys Gln Asn Gly
145                 150                 155                 160
Ala Val Cys Gln Asp Gly Ile Asp Gly Tyr Ser Cys Phe Cys Val Pro
                165                 170                 175
Gly Tyr Gln Gly Arg His Cys Asp Leu Glu Val Asp Glu Cys Ala Ser
                180                 185                 190
Asp Pro Cys Lys Asn Glu Ala Thr Cys Leu Asn Glu Ile Gly Arg Tyr
            195                 200                 205
Thr Cys Ile Cys Pro His Asn Tyr Ser Gly Val Asn Cys Glu Leu Glu
        210                 215                 220
Ile Asp Glu Cys Trp Ser Gln Pro Cys Leu Asn Gly Ala Thr Cys Gln
225                 230                 235                 240
Asp Ala Leu Gly Ala Tyr Phe Cys Asp Cys Ala Pro Gly Phe Leu Gly
                245                 250                 255
Asp His Cys Glu Leu Asn Thr Asp Glu Cys Ala Ser Gln Pro Cys Leu
                260                 265                 270
His Gly Gly Leu Cys Val Asp Gly Glu Asn Arg Tyr Ser Cys Asn Cys
            275                 280                 285
Thr Gly Ser Gly Phe Thr Gly Thr His Cys Glu Thr Leu Met Pro Leu
        290                 295                 300
Cys Trp Ser Lys Pro Cys His Asn Asn Ala Thr Cys Glu Asp Ser Val
305                 310                 315                 320
Asp Asn Tyr Thr Cys His Cys Trp Pro Gly Tyr Thr Gly Ala Gln Cys
                325                 330                 335
Glu Ile Asp Leu Asn Glu Cys Asn Ser Asn Pro Cys Gln Ser Asn Gly
                340                 345                 350
Glu Cys Val Glu Leu Ser Ser Glu Lys Gln Tyr Gly Arg Ile Thr Gly
            355                 360                 365
Leu Pro Ser Ser Phe Ser Tyr His Glu Ala Ser Gly Tyr Val Cys Ile
        370                 375                 380
Cys Gln Pro Gly Phe Thr Gly Ile His Cys Glu Glu Asp Val Asn Glu
385                 390                 395                 400
Cys Ser Ser Asn Pro Cys Gln Asn Gly Gly Thr Cys Glu Asn Leu Pro
                405                 410                 415
Gly Asn Tyr Thr Cys His Cys Pro Phe Asp Asn Leu Ser Arg Thr Phe
                420                 425                 430
Tyr Gly Gly Arg Asp Cys Ser Asp Ile Leu Leu Gly Cys Thr His Gln
            435                 440                 445
Gln Cys Leu Asn Asn Gly Thr Cys Ile Pro His Phe Gln Asp Gly Gln
        450                 455                 460
His Gly Phe Ser Cys Leu Cys Pro Ser Gly Tyr Thr Gly Ser Leu Cys
465                 470                 475                 480
Glu Ile Ala Thr Thr Leu Ser Phe Gly Asp Gly Phe Leu Trp Val
                485                 490                 495
Lys Ser Gly Ser Val Thr Thr Lys Gly Ser Val Cys Asn Ile Ala Leu
                500                 505                 510
Arg Phe Gln Thr Val Gln Pro Met Ala Leu Leu Leu Phe Arg Ser Asn
            515                 520                 525
Arg Asp Val Phe Val Lys Leu Glu Leu Leu Ser Gly Tyr Ile His Leu
```

```
              530                 535                 540
Ser Ile Gln Val Asn Asn Gln Ser Lys Val Leu Leu Phe Ile Ser His
545                 550                 555                 560

Asn Thr Ser Asp Gly Glu Trp His Phe Val Glu Val Ile Phe Ala Glu
                    565                 570                 575

Ala Val Thr Leu Thr Leu Ile Asp Asp Ser Cys Lys Glu Lys Cys Ile
                580                 585                 590

Ala Lys Ala Pro Thr Pro Leu Glu Ser Asp Gln Ser Ile Cys Ala Phe
            595                 600                 605

Gln Asn Ser Phe Leu Gly Gly Leu Pro Val Gly Met Thr Ser Asn Gly
        610                 615                 620

Val Ala Leu Leu Asn Phe Tyr Asn Met Pro Ser Thr Pro Ser Phe Val
625                 630                 635                 640

Gly Cys Leu Gln Asp Ile Lys Ile Asp Trp Asn His Ile Thr Leu Glu
                    645                 650                 655

Asn Ile Ser Ser Gly Ser Ser Leu Asn Val Lys Ala Gly Cys Val Arg
                660                 665                 670

Lys Asp Trp Cys Glu Ser Gln Pro Cys Gln Ser Arg Gly Arg Cys Ile
            675                 680                 685

Asn Leu Trp Leu Ser Tyr Gln Cys Asp Cys His Arg Pro Tyr Glu Gly
        690                 695                 700

Pro Asn Cys Leu Arg Glu Tyr Val Ala Gly Arg Phe Gly Gln Asp Asp
705                 710                 715                 720

Ser Thr Gly Tyr Val Ile Phe Thr Leu Asp Glu Ser Tyr Gly Asp Thr
                    725                 730                 735

Ile Ser Leu Ser Met Phe Val Arg Thr Leu Gln Pro Ser Gly Leu Leu
                740                 745                 750

Leu Ala Leu Glu Asn Ser Thr Tyr Gln Tyr Ile Arg Val Trp Leu Glu
            755                 760                 765

Arg Gly Arg Leu Ala Met Leu Thr Pro Asn Ser Pro Lys Leu Val Val
        770                 775                 780

Lys Phe Val Leu Asn Asp Gly Asn Val His Leu Ile Ser Leu Lys Ile
785                 790                 795                 800

Lys Pro Tyr Lys Ile Glu Leu Tyr Gln Ser Ser Gln Asn Leu Gly Phe
                    805                 810                 815

Ile Ser Ala Ser Thr Trp Lys Ile Glu Lys Gly Asp Val Ile Tyr Ile
                820                 825                 830

Gly Gly Leu Pro Asp Lys Gln Glu Thr Glu Leu Asn Gly Gly Phe Phe
            835                 840                 845

Lys Gly Cys Ile Gln Asp Val Arg Leu Asn Asn Gln Asn Leu Glu Phe
        850                 855                 860

Phe Pro Asn Pro Thr Asn Ala Ser Leu Asn Pro Val Leu Val Asn
865                 870                 875                 880

Val Thr Gln Gly Cys Ala Gly Asp Asn Ser Cys Lys Ser Asn Pro Cys
                    885                 890                 895

His Asn Gly Gly Val Cys His Ser Arg Trp Asp Asp Phe Ser Cys Ser
                900                 905                 910

Cys Pro Ala Leu Thr Ser Gly Lys Ala Cys Glu Glu Val Gln Trp Cys
            915                 920                 925

Gly Phe Ser Pro Cys Pro His Gly Ala Gln Cys Gln Pro Val Leu Gln
        930                 935                 940

Gly Phe Glu Cys Ile Ala Asn Ala Val Phe Asn Gly Gln Ser Gly Gln
945                 950                 955                 960
```

-continued

```
Ile Leu Phe Arg Ser Asn Gly Asn Ile Thr Arg Glu Leu Thr Asn Ile
            965                 970                 975

Thr Phe Gly Phe Arg Thr Arg Asp Ala Asn Val Ile Ile Leu His Ala
            980                 985                 990

Glu Lys Glu Pro Glu Phe Leu Asn Ile Ser Ile Gln Asp Ser Arg Leu
            995                1000                1005

Phe Phe Gln Leu Gln Ser Gly Asn Ser Phe Tyr Met Leu Ser Leu
       1010                1015                1020

Thr Ser Leu Gln Ser Val Asn Asp Gly Thr Trp His Glu Val Thr
       1025                1030                1035

Leu Ser Met Thr Asp Pro Leu Ser Gln Thr Ser Arg Trp Gln Met
       1040                1045                1050

Glu Val Asp Asn Glu Thr Pro Phe Val Thr Ser Thr Ile Ala Thr
       1055                1060                1065

Gly Ser Leu Asn Phe Leu Lys Asp Asn Thr Asp Ile Tyr Val Gly
       1070                1075                1080

Asp Arg Ala Ile Asp Asn Ile Lys Gly Leu Gln Gly Cys Leu Ser
       1085                1090                1095

Thr Ile Glu Ile Gly Gly Ile Tyr Leu Ser Tyr Phe Glu Asn Val
       1100                1105                1110

His Gly Phe Ile Asn Lys Pro Gln Glu Glu Gln Phe Leu Lys Ile
       1115                1120                1125

Ser Thr Asn Ser Val Val Thr Gly Cys Leu Gln Leu Asn Val Cys
       1130                1135                1140

Asn Ser Asn Pro Cys Leu His Gly Gly Asn Cys Glu Asp Ile Tyr
       1145                1150                1155

Ser Ser Tyr His Cys Ser Cys Pro Leu Gly Trp Ser Gly Lys His
       1160                1165                1170

Cys Glu Leu Asn Ile Asp Glu Cys Phe Ser Asn Pro Cys Ile His
       1175                1180                1185

Gly Asn Cys Ser Asp Arg Val Ala Ala Tyr His Cys Thr Cys Glu
       1190                1195                1200

Pro Gly Tyr Thr Gly Val Asn Cys Glu Val Asp Ile Asp Asn Cys
       1205                1210                1215

Gln Ser His Gln Cys Ala Asn Gly Ala Thr Cys Ile Ser His Thr
       1220                1225                1230

Asn Gly Tyr Ser Cys Leu Cys Phe Gly Asn Phe Thr Gly Lys Phe
       1235                1240                1245

Cys Arg Gln Ser Arg Leu Pro Ser Thr Val Cys Gly Asn Glu Lys
       1250                1255                1260

Thr Asn Leu Thr Cys Tyr Asn Gly Gly Asn Cys Thr Glu Phe Gln
       1265                1270                1275

Thr Glu Leu Lys Cys Met Cys Arg Pro Gly Phe Thr Gly Glu Trp
       1280                1285                1290

Cys Glu Lys Asp Ile Asp Glu Cys Ala Ser Asp Pro Cys Val Asn
       1295                1300                1305

Gly Gly Leu Cys Gln Asp Leu Leu Asn Lys Phe Gln Cys Leu Cys
       1310                1315                1320

Asp Val Ala Phe Ala Gly Glu Arg Cys Glu Val Asp Val Ser Ser
       1325                1330                1335

Leu Ser Phe Tyr Val Ser Leu Phe Trp Gln Asn Leu Phe Gln
       1340                1345                1350
```

-continued

Leu Leu Ser Tyr Leu Ile Leu Arg Met Asn Asp Glu Pro Val Val
    1355                1360                1365

Glu Trp Gly Glu Gln Glu Asp Tyr
    1370            1375

<210> SEQ ID NO 43
<211> LENGTH: 1294
<212> TYPE: PRT
<213> ORGANISM: Homo sapiens

<400> SEQUENCE: 43

Met Ala Leu Lys Asn Ile Asn Tyr Leu Leu Ile Phe Tyr Leu Ser Phe
1               5                   10                  15

Ser Leu Leu Ile Tyr Ile Lys Asn Ser Phe Cys Asn Lys Asn Asn Thr
            20                  25                  30

Arg Cys Leu Ser Asn Ser Cys Gln Asn Asn Ser Thr Cys Lys Asp Phe
        35                  40                  45

Ser Lys Asp Asn Asp Cys Ser Cys Ser Asp Thr Ala Asn Asn Leu Asp
50                  55                  60

Lys Asp Cys Asp Asn Met Lys Asp Pro Cys Phe Ser Asn Pro Cys Gln
65                  70                  75                  80

Gly Ser Ala Thr Cys Val Asn Thr Pro Gly Glu Arg Ser Phe Leu Cys
                85                  90                  95

Lys Cys Pro Pro Gly Tyr Ser Gly Thr Ile Cys Glu Thr Thr Ile Gly
            100                 105                 110

Ser Cys Gly Lys Asn Ser Cys Gln His Gly Gly Ile Cys His Gln Asp
        115                 120                 125

Pro Ile Tyr Pro Val Cys Ile Cys Pro Ala Gly Tyr Ala Gly Arg Phe
130                 135                 140

Cys Glu Ile Asp His Asp Glu Cys Ala Ser Ser Pro Cys Gln Asn Gly
145                 150                 155                 160

Ala Val Cys Gln Asp Gly Ile Asp Gly Tyr Ser Cys Phe Cys Val Pro
                165                 170                 175

Gly Tyr Gln Gly Arg His Cys Asp Leu Glu Val Asp Glu Cys Ala Ser
            180                 185                 190

Asp Pro Cys Lys Asn Glu Ala Thr Cys Leu Asn Glu Ile Gly Arg Tyr
        195                 200                 205

Thr Cys Ile Cys Pro His Asn Tyr Ser Gly Tyr Thr Gly Ala Gln Cys
210                 215                 220

Glu Ile Asp Leu Asn Glu Cys Asn Ser Asn Pro Cys Gln Ser Asn Gly
225                 230                 235                 240

Glu Cys Val Glu Leu Ser Ser Glu Lys Gln Tyr Gly Arg Ile Thr Gly
                245                 250                 255

Leu Pro Ser Ser Phe Ser Tyr His Glu Ala Ser Gly Tyr Val Cys Ile
            260                 265                 270

Cys Gln Pro Gly Phe Thr Gly Ile His Cys Glu Glu Asp Val Asn Glu
        275                 280                 285

Cys Ser Ser Asn Pro Cys Gln Asn Gly Gly Thr Cys Glu Asn Leu Pro
290                 295                 300

Gly Asn Tyr Thr Cys His Cys Pro Phe Asp Asn Leu Ser Arg Thr Phe
305                 310                 315                 320

Tyr Gly Gly Arg Asp Cys Ser Asp Ile Leu Leu Gly Cys Thr His Gln
                325                 330                 335

Gln Cys Leu Asn Asn Gly Thr Cys Ile Pro His Phe Gln Asp Gly Gln
            340                 345                 350

```
His Gly Phe Ser Cys Leu Cys Pro Ser Gly Tyr Thr Gly Ser Leu Cys
            355                 360                 365

Glu Ile Ala Thr Thr Leu Ser Phe Glu Gly Asp Gly Phe Leu Trp Val
370                 375                 380

Lys Ser Gly Ser Val Thr Thr Lys Gly Ser Val Cys Asn Ile Ala Leu
385                 390                 395                 400

Arg Phe Gln Thr Val Gln Pro Met Ala Leu Leu Phe Arg Ser Asn
                405                 410                 415

Arg Asp Val Phe Val Lys Leu Glu Leu Leu Ser Gly Tyr Ile His Leu
                420                 425                 430

Ser Ile Gln Val Asn Asn Gln Ser Lys Val Leu Leu Phe Ile Ser His
            435                 440                 445

Asn Thr Ser Asp Gly Glu Trp His Phe Val Glu Val Ile Phe Ala Glu
450                 455                 460

Ala Val Thr Leu Thr Leu Ile Asp Asp Ser Cys Lys Glu Lys Cys Ile
465                 470                 475                 480

Ala Lys Ala Pro Thr Pro Leu Glu Ser Asp Gln Ser Ile Cys Ala Phe
                485                 490                 495

Gln Asn Ser Phe Leu Gly Gly Leu Pro Val Gly Met Thr Ser Asn Gly
            500                 505                 510

Val Ala Leu Leu Asn Phe Tyr Asn Met Pro Ser Thr Pro Ser Phe Val
            515                 520                 525

Gly Cys Leu Gln Asp Ile Lys Ile Asp Trp Asn His Ile Thr Leu Glu
        530                 535                 540

Asn Ile Ser Ser Gly Ser Ser Leu Asn Val Lys Ala Gly Cys Val Arg
545                 550                 555                 560

Lys Asp Trp Cys Glu Ser Gln Pro Cys Gln Ser Arg Gly Arg Cys Ile
                565                 570                 575

Asn Leu Trp Leu Ser Tyr Gln Cys Asp Cys His Arg Pro Tyr Glu Gly
            580                 585                 590

Pro Asn Cys Leu Arg Glu Tyr Val Ala Gly Arg Phe Gly Gln Asp Asp
        595                 600                 605

Ser Thr Gly Tyr Val Ile Phe Thr Leu Asp Glu Ser Tyr Gly Asp Thr
        610                 615                 620

Ile Ser Leu Ser Met Phe Val Arg Thr Leu Gln Pro Ser Gly Leu Leu
625                 630                 635                 640

Leu Ala Leu Glu Asn Ser Thr Tyr Gln Tyr Ile Arg Val Trp Leu Glu
                645                 650                 655

Arg Gly Arg Leu Ala Met Leu Thr Pro Asn Ser Pro Lys Leu Val Val
            660                 665                 670

Lys Phe Val Leu Asn Asp Gly Asn Val His Leu Ile Ser Leu Lys Ile
                675                 680                 685

Lys Pro Tyr Lys Ile Glu Leu Tyr Gln Ser Ser Gln Asn Leu Gly Phe
        690                 695                 700

Ile Ser Ala Ser Thr Trp Lys Ile Glu Lys Gly Asp Val Ile Tyr Ile
705                 710                 715                 720

Gly Gly Leu Pro Asp Lys Gln Glu Thr Glu Leu Asn Gly Gly Phe Phe
                725                 730                 735

Lys Gly Cys Ile Gln Asp Val Arg Leu Asn Asn Gln Asn Leu Glu Phe
            740                 745                 750

Phe Pro Asn Pro Thr Asn Asn Ala Ser Leu Asn Pro Val Leu Val Asn
        755                 760                 765
```

-continued

```
Val Thr Gln Gly Cys Ala Gly Asp Asn Ser Cys Lys Ser Asn Pro Cys
    770                 775                 780

His Asn Gly Gly Val Cys His Ser Arg Trp Asp Asp Phe Ser Cys Ser
785                 790                 795                 800

Cys Pro Ala Leu Thr Ser Gly Lys Ala Cys Glu Glu Val Gln Trp Cys
                805                 810                 815

Gly Phe Ser Pro Cys Pro His Gly Ala Gln Cys Gln Pro Val Leu Gln
                820                 825                 830

Gly Phe Glu Cys Ile Ala Asn Ala Val Phe Asn Gly Gln Ser Gly Gln
            835                 840                 845

Ile Leu Phe Arg Ser Asn Gly Asn Ile Thr Arg Glu Leu Thr Asn Ile
    850                 855                 860

Thr Phe Gly Phe Arg Thr Arg Asp Ala Asn Val Ile Ile Leu His Ala
865                 870                 875                 880

Glu Lys Glu Pro Glu Phe Leu Asn Ile Ser Ile Gln Asp Ser Arg Leu
                885                 890                 895

Phe Phe Gln Leu Gln Ser Gly Asn Ser Phe Tyr Met Leu Ser Leu Thr
                900                 905                 910

Ser Leu Gln Ser Val Asn Asp Gly Thr Trp His Glu Val Thr Leu Ser
            915                 920                 925

Met Thr Asp Pro Leu Ser Gln Thr Ser Arg Trp Gln Met Glu Val Asp
930                 935                 940

Asn Glu Thr Pro Phe Val Thr Ser Thr Ile Ala Thr Gly Ser Leu Asn
945                 950                 955                 960

Phe Leu Lys Asp Asn Thr Asp Ile Tyr Val Gly Asp Arg Ala Ile Asp
                965                 970                 975

Asn Ile Lys Gly Leu Gln Gly Cys Leu Ser Thr Ile Glu Ile Gly Gly
            980                 985                 990

Ile Tyr Leu Ser Tyr Phe Glu Asn Val His Gly Phe Ile Asn Lys Pro
    995                 1000                1005

Gln Glu Glu Gln Phe Leu Lys Ile Ser Thr Asn Ser Val Val Thr
    1010            1015                1020

Gly Cys Leu Gln Leu Asn Val Cys Asn Ser Asn Pro Cys Leu His
    1025            1030                1035

Gly Gly Asn Cys Glu Asp Ile Tyr Ser Ser Tyr His Cys Ser Cys
    1040            1045                1050

Pro Leu Gly Trp Ser Gly Lys His Cys Glu Leu Asn Ile Asp Glu
    1055            1060                1065

Cys Phe Ser Asn Pro Cys Ile His Gly Asn Cys Ser Asp Arg Val
    1070            1075                1080

Ala Ala Tyr His Cys Thr Cys Glu Pro Gly Tyr Thr Gly Val Asn
    1085            1090                1095

Cys Glu Val Asp Ile Asp Asn Cys Gln Ser His Gln Cys Ala Asn
    1100            1105                1110

Gly Ala Thr Cys Ile Ser His Thr Asn Gly Tyr Ser Cys Leu Cys
    1115            1120                1125

Phe Gly Asn Phe Thr Gly Lys Phe Cys Arg Gln Ser Arg Leu Pro
    1130            1135                1140

Ser Thr Val Cys Gly Asn Glu Lys Thr Asn Leu Thr Cys Tyr Asn
    1145            1150                1155

Gly Gly Asn Cys Thr Glu Phe Gln Thr Glu Leu Lys Cys Met Cys
    1160            1165                1170

Arg Pro Gly Phe Thr Gly Glu Trp Cys Glu Lys Asp Ile Asp Glu
```

-continued

```
                1175                1180                1185
Cys Ala Ser Asp Pro Cys Val Asn Gly Gly Leu Cys Gln Asp Leu
            1190                1195                1200
Leu Asn Lys Phe Gln Cys Leu Cys Asp Val Ala Phe Ala Gly Glu
            1205                1210                1215
Arg Cys Glu Val Asp Leu Ala Asp Asp Leu Ile Ser Asp Ile Phe
            1220                1225                1230
Thr Thr Ile Gly Ser Val Val Ala Leu Leu Ile Leu Leu
            1235                1240                1245
Leu Ala Ile Val Ala Ser Val Val Thr Ser Asn Lys Arg Ala Thr
            1250                1255                1260
Gln Gly Thr Tyr Ser Pro Ser Arg Gln Glu Lys Glu Gly Ser Arg
            1265                1270                1275
Val Glu Met Trp Asn Leu Met Pro Pro Pro Ala Met Glu Arg Leu
            1280                1285                1290
Ile

<210> SEQ ID NO 44
<211> LENGTH: 942
<212> TYPE: PRT
<213> ORGANISM: Homo sapiens

<400> SEQUENCE: 44

Met Ile Arg Asn Ser Leu Cys Gln Pro Ser Arg Cys Leu Asp Glu Tyr
1               5                   10                  15
Leu Phe Phe Asn Arg Lys Met Phe Gly Ala Arg Thr His Gly Phe His
            20                  25                  30
Ile Leu Met Ala Met Leu Ile Gly Ile His Cys Glu Glu Asp Val Asn
        35                  40                  45
Glu Cys Ser Ser Asn Pro Cys Gln Asn Gly Gly Thr Cys Glu Asn Leu
    50                  55                  60
Pro Gly Asn Tyr Thr Cys His Cys Pro Phe Asp Asn Leu Ser Arg Thr
65                  70                  75                  80
Phe Tyr Gly Gly Arg Asp Cys Ser Asp Ile Leu Leu Gly Cys Thr His
                85                  90                  95
Gln Gln Cys Leu Asn Asn Gly Thr Cys Ile Pro His Phe Gln Asp Gly
            100                 105                 110
Gln His Gly Phe Ser Cys Leu Cys Pro Ser Gly Tyr Thr Gly Ser Leu
        115                 120                 125
Cys Glu Ile Ala Thr Thr Leu Ser Phe Glu Gly Asp Gly Phe Leu Trp
    130                 135                 140
Val Lys Ser Gly Ser Val Thr Thr Lys Gly Ser Val Cys Asn Ile Ala
145                 150                 155                 160
Leu Arg Phe Gln Thr Val Gln Pro Met Ala Leu Leu Leu Phe Arg Ser
                165                 170                 175
Asn Arg Asp Val Phe Val Lys Leu Glu Leu Leu Ser Gly Tyr Ile His
            180                 185                 190
Leu Ser Ile Gln Val Asn Asn Gln Ser Lys Val Leu Leu Phe Ile Ser
        195                 200                 205
His Asn Thr Ser Asp Gly Glu Trp His Phe Val Glu Val Ile Phe Ala
    210                 215                 220
Glu Ala Val Thr Leu Thr Leu Ile Asp Asp Ser Cys Lys Glu Lys Cys
225                 230                 235                 240
Ile Ala Lys Ala Pro Thr Pro Leu Glu Ser Asp Gln Ser Ile Cys Ala
```

```
                245              250              255
Phe Gln Asn Ser Phe Leu Gly Gly Leu Pro Val Gly Met Thr Ser Asn
            260              265              270
Gly Val Ala Leu Leu Asn Phe Tyr Asn Met Pro Ser Thr Pro Ser Phe
            275              280              285
Val Gly Cys Leu Gln Asp Ile Lys Ile Asp Trp Asn His Ile Thr Leu
            290              295              300
Glu Asn Ile Ser Ser Gly Ser Ser Leu Asn Val Lys Ala Gly Cys Val
305              310              315              320
Arg Lys Asp Trp Cys Glu Ser Gln Pro Cys Gln Ser Arg Gly Arg Cys
                325              330              335
Ile Asn Leu Trp Leu Ser Tyr Gln Cys Asp Cys His Arg Pro Tyr Glu
            340              345              350
Gly Pro Asn Cys Leu Arg Glu Tyr Val Ala Gly Arg Phe Gly Gln Asp
            355              360              365
Asp Ser Thr Gly Tyr Val Ile Phe Thr Leu Asp Glu Ser Tyr Gly Asp
        370              375              380
Thr Ile Ser Leu Ser Met Phe Val Arg Thr Leu Gln Pro Ser Gly Leu
385              390              395              400
Leu Leu Ala Leu Glu Asn Ser Thr Tyr Gln Tyr Ile Arg Val Trp Leu
                405              410              415
Glu Arg Gly Arg Leu Ala Met Leu Thr Pro Asn Ser Pro Lys Leu Val
            420              425              430
Val Lys Phe Val Leu Asn Asp Gly Asn Val His Leu Ile Ser Leu Lys
            435              440              445
Ile Lys Pro Tyr Lys Ile Glu Leu Tyr Gln Ser Ser Gln Asn Leu Gly
        450              455              460
Phe Ile Ser Ala Ser Thr Trp Lys Ile Glu Lys Gly Asp Val Ile Tyr
465              470              475              480
Ile Gly Gly Leu Pro Asp Lys Gln Glu Thr Glu Leu Asn Gly Gly Phe
                485              490              495
Phe Lys Gly Cys Ile Gln Asp Val Arg Leu Asn Asn Gln Asn Leu Glu
            500              505              510
Phe Phe Pro Asn Pro Thr Asn Asn Ala Ser Leu Asn Pro Val Leu Val
        515              520              525
Asn Val Thr Gln Gly Cys Ala Gly Asp Asn Ser Cys Lys Ser Asn Pro
    530              535              540
Cys His Asn Gly Gly Val Cys His Ser Arg Trp Asp Asp Phe Ser Cys
545              550              555              560
Ser Cys Pro Ala Leu Thr Ser Gly Lys Ala Cys Glu Glu Val Gln Trp
                565              570              575
Cys Gly Phe Ser Pro Cys Pro His Gly Ala Gln Cys Gln Pro Val Leu
            580              585              590
Gln Gly Phe Glu Cys Ile Ala Asn Ala Val Phe Asn Gly Gln Ser Gly
            595              600              605
Gln Ile Leu Phe Arg Ser Asn Gly Asn Ile Thr Arg Glu Leu Thr Asn
        610              615              620
Ile Thr Phe Gly Phe Arg Thr Arg Asp Ala Asn Val Ile Ile Leu His
625              630              635              640
Ala Glu Lys Glu Pro Glu Phe Leu Asn Ile Ser Ile Gln Asp Ser Arg
                645              650              655
Leu Phe Phe Gln Leu Gln Ser Gly Asn Ser Phe Tyr Met Leu Ser Leu
            660              665              670
```

```
Thr Ser Leu Gln Ser Val Asn Asp Gly Thr Trp His Glu Val Thr Leu
            675                 680                 685

Ser Met Thr Asp Pro Leu Ser Gln Thr Ser Arg Trp Gln Met Glu Val
        690                 695                 700

Asp Asn Glu Thr Pro Phe Val Thr Ser Thr Ile Ala Thr Gly Ser Leu
705                 710                 715                 720

Asn Phe Leu Lys Asp Asn Thr Asp Ile Tyr Val Gly Asp Arg Ala Ile
                725                 730                 735

Asp Asn Ile Lys Gly Leu Gln Gly Cys Leu Ser Thr Ile Glu Ile Gly
                740                 745                 750

Gly Ile Tyr Leu Ser Tyr Phe Glu Asn Val His Gly Phe Ile Asn Lys
            755                 760                 765

Pro Gln Glu Gln Phe Leu Lys Ile Ser Thr Asn Ser Val Val Thr
        770                 775                 780

Gly Cys Leu Gln Leu Asn Val Cys Asn Ser Asn Pro Cys Leu His Gly
785                 790                 795                 800

Gly Asn Cys Glu Asp Ile Tyr Ser Ser Tyr His Cys Ser Cys Pro Leu
                805                 810                 815

Gly Trp Ser Gly Lys His Cys Glu Leu Asn Ile Asp Glu Cys Phe Ser
            820                 825                 830

Asn Pro Cys Ile His Gly Asn Cys Ser Asp Arg Val Ala Ala Tyr His
                835                 840                 845

Cys Thr Cys Glu Pro Gly Tyr Thr Gly Val Asn Cys Glu Val Asp Ile
        850                 855                 860

Asp Asn Cys Gln Ser His Gln Cys Ala Asn Gly Ala Thr Cys Ile Ser
865                 870                 875                 880

His Thr Asn Gly Tyr Ser Cys Leu Cys Phe Gly Asn Phe Thr Gly Lys
                885                 890                 895

Phe Cys Arg Gln Ser Arg Leu Pro Ser Thr Val Cys Gly Asn Glu Lys
            900                 905                 910

Thr Asn Leu Thr Cys Tyr Asn Gly Gly Asn Cys Thr Glu Phe Gln Thr
        915                 920                 925

Glu Leu Lys Cys Met Cys Arg Pro Gly Phe Thr Gly Glu Trp
    930                 935                 940

<210> SEQ ID NO 45
<211> LENGTH: 870
<212> TYPE: PRT
<213> ORGANISM: Homo sapiens

<400> SEQUENCE: 45

Met Ala Leu Lys Asn Ile Asn Tyr Leu Leu Ile Phe Tyr Leu Ser Phe
1               5                   10                  15

Ser Leu Leu Ile Tyr Ile Lys Asn Ser Phe Cys Asn Lys Asn Asn Thr
            20                  25                  30

Arg Cys Leu Ser Asn Ser Cys Gln Asn Asn Ser Thr Cys Lys Asp Phe
        35                  40                  45

Ser Lys Asp Asn Asp Cys Ser Cys Ser Asp Thr Ala Asn Asn Leu Asp
    50                  55                  60

Lys Asp Cys Asp Asn Met Lys Asp Pro Cys Phe Ser Asn Pro Cys Gln
65                  70                  75                  80

Gly Ser Ala Thr Cys Val Asn Thr Pro Gly Glu Arg Ser Phe Leu Cys
                85                  90                  95

Lys Cys Pro Pro Gly Tyr Ser Gly Thr Ile Cys Glu Thr Thr Ile Gly
```

```
                100                 105                 110
Ser Cys Gly Lys Asn Ser Cys Gln His Gly Gly Ile Cys His Gln Asp
            115                 120                 125

Pro Ile Tyr Pro Val Cys Ile Cys Pro Ala Gly Tyr Ala Gly Arg Phe
            130                 135                 140

Cys Glu Ile Asp His Asp Glu Cys Ala Ser Ser Pro Cys Gln Asn Gly
145                 150                 155                 160

Ala Val Cys Gln Asp Gly Ile Asp Gly Tyr Ser Cys Phe Cys Val Pro
            165                 170                 175

Gly Tyr Gln Gly Arg His Cys Asp Leu Glu Val Asp Glu Cys Ala Ser
            180                 185                 190

Asp Pro Cys Lys Asn Glu Ala Thr Cys Leu Asn Glu Ile Gly Arg Tyr
            195                 200                 205

Thr Cys Ile Cys Pro His Asn Tyr Ser Gly Val Asn Cys Glu Leu Glu
            210                 215                 220

Ile Asp Glu Cys Trp Ser Gln Pro Cys Leu Asn Gly Ala Thr Cys Gln
225                 230                 235                 240

Asp Ala Leu Gly Ala Tyr Phe Cys Asp Cys Ala Pro Gly Phe Leu Gly
            245                 250                 255

Asp His Cys Glu Leu Asn Thr Asp Glu Cys Ala Ser Gln Pro Cys Leu
            260                 265                 270

His Gly Gly Leu Cys Val Asp Gly Glu Asn Arg Tyr Ser Cys Asn Cys
            275                 280                 285

Thr Gly Ser Gly Phe Thr Gly Thr His Cys Glu Thr Leu Met Pro Leu
            290                 295                 300

Cys Trp Ser Lys Pro Cys His Asn Asn Ala Thr Cys Glu Asp Ser Val
305                 310                 315                 320

Asp Asn Tyr Thr Cys His Cys Trp Pro Gly Tyr Thr Gly Ala Gln Cys
            325                 330                 335

Glu Ile Asp Leu Asn Glu Cys Asn Ser Asn Pro Cys Gln Ser Asn Gly
            340                 345                 350

Glu Cys Val Glu Leu Ser Ser Glu Lys Gln Tyr Gly Arg Ile Thr Gly
            355                 360                 365

Leu Pro Ser Ser Phe Ser Tyr His Glu Ala Ser Gly Tyr Val Cys Ile
            370                 375                 380

Cys Gln Pro Gly Phe Thr Gly Ile His Cys Glu Glu Asp Val Asn Glu
385                 390                 395                 400

Cys Ser Ser Asn Pro Cys Gln Asn Gly Gly Thr Cys Glu Asn Leu Pro
            405                 410                 415

Gly Asn Tyr Thr Cys His Cys Pro Phe Asp Asn Leu Ser Arg Thr Phe
            420                 425                 430

Tyr Gly Gly Arg Asp Cys Ser Asp Ile Leu Leu Gly Cys Thr His Gln
            435                 440                 445

Gln Cys Leu Asn Asn Gly Thr Cys Ile Pro His Phe Gln Asp Gly Gln
            450                 455                 460

His Gly Phe Ser Cys Leu Cys Pro Ser Gly Tyr Thr Gly Ser Leu Cys
465                 470                 475                 480

Glu Ile Ala Thr Thr Leu Ser Phe Glu Gly Asp Gly Phe Leu Trp Val
            485                 490                 495

Lys Ser Gly Ser Val Thr Thr Lys Gly Ser Val Cys Asn Ile Ala Leu
            500                 505                 510

Arg Phe Gln Thr Val Gln Pro Met Ala Leu Leu Leu Phe Arg Ser Asn
            515                 520                 525
```

Arg Asp Val Phe Val Lys Leu Glu Leu Leu Ser Gly Tyr Ile His Leu
530                535                540

Ser Ile Gln Val Asn Asn Gln Ser Lys Val Leu Leu Phe Ile Ser His
545                550                555                560

Asn Thr Ser Asp Gly Glu Trp His Phe Val Glu Val Ile Phe Ala Glu
                565                570                575

Ala Val Thr Leu Thr Leu Ile Asp Asp Ser Cys Lys Glu Lys Cys Ile
                580                585                590

Ala Lys Ala Pro Thr Pro Leu Glu Ser Asp Gln Ser Ile Cys Ala Phe
        595                600                605

Gln Asn Ser Phe Leu Gly Gly Leu Pro Val Gly Met Thr Ser Asn Gly
        610                615                620

Val Ala Leu Leu Asn Phe Tyr Asn Met Pro Ser Thr Pro Ser Phe Val
625                630                635                640

Gly Cys Leu Gln Asp Ile Lys Ile Asp Trp Asn His Ile Thr Leu Glu
                645                650                655

Asn Ile Ser Ser Gly Ser Ser Leu Asn Val Lys Ala Gly Cys Val Arg
                660                665                670

Lys Asp Trp Cys Glu Ser Gln Pro Cys Gln Ser Arg Gly Arg Cys Ile
        675                680                685

Asn Leu Trp Leu Ser Tyr Gln Cys Asp Cys His Arg Pro Tyr Glu Gly
        690                695                700

Pro Asn Cys Leu Arg Gly Lys Phe Cys Arg Gln Ser Arg Leu Pro Ser
705                710                715                720

Thr Val Cys Gly Asn Glu Lys Thr Asn Leu Thr Cys Tyr Asn Gly Gly
                725                730                735

Asn Cys Thr Glu Phe Gln Thr Glu Leu Lys Cys Met Cys Arg Pro Gly
                740                745                750

Phe Thr Gly Glu Trp Cys Glu Lys Asp Ile Asp Glu Cys Ala Ser Asp
        755                760                765

Pro Cys Val Asn Gly Gly Leu Cys Gln Asp Leu Leu Asn Lys Phe Gln
        770                775                780

Cys Leu Cys Asp Val Ala Phe Ala Gly Glu Arg Cys Glu Val Asp Leu
785                790                795                800

Ala Asp Asp Leu Ile Ser Asp Ile Phe Thr Thr Ile Gly Ser Val Thr
                805                810                815

Val Ala Leu Leu Leu Ile Leu Leu Ala Ile Val Ala Ser Val Val
                820                825                830

Thr Ser Asn Lys Arg Ala Thr Gln Gly Thr Tyr Ser Pro Ser Arg Gln
        835                840                845

Glu Lys Glu Gly Ser Arg Val Glu Met Trp Asn Leu Met Pro Pro Pro
        850                855                860

Ala Met Glu Arg Leu Ile
865                870

<210> SEQ ID NO 46
<211> LENGTH: 238
<212> TYPE: PRT
<213> ORGANISM: Homo sapiens

<400> SEQUENCE: 46

Met Leu Cys Cys Met Arg Arg Thr Lys Gln Val Glu Lys Asn Asp Asp
1                5                10                15

Asp Gln Lys Ile Glu Gln Asp Gly Ile Lys Pro Glu Asp Lys Ala His

```
                20                  25                  30
Lys Ala Ala Thr Lys Ile Gln Ala Ser Phe Arg Gly His Ile Thr Arg
             35                  40                  45

Lys Lys Leu Lys Gly Glu Lys Lys Asp Asp Val Gln Ala Ala Glu Ala
 50                  55                  60

Glu Ala Asn Lys Lys Asp Glu Ala Pro Val Ala Asp Gly Val Glu Lys
 65                  70                  75                  80

Lys Gly Glu Gly Thr Thr Thr Ala Glu Ala Ala Pro Ala Thr Gly Ser
                 85                  90                  95

Lys Pro Asp Glu Pro Gly Lys Ala Gly Glu Thr Pro Ser Glu Glu Lys
            100                 105                 110

Lys Gly Glu Gly Asp Ala Ala Thr Glu Gln Ala Ala Pro Gln Ala Pro
        115                 120                 125

Ala Ser Ser Glu Glu Lys Ala Gly Ser Ala Glu Thr Glu Ser Ala Thr
        130                 135                 140

Lys Ala Ser Thr Asp Asn Ser Pro Ser Ser Lys Ala Glu Asp Ala Pro
145                 150                 155                 160

Ala Lys Glu Glu Pro Lys Gln Ala Asp Val Pro Ala Ala Val Thr Ala
                165                 170                 175

Ala Ala Ala Thr Thr Pro Ala Ala Glu Asp Ala Ala Lys Ala Thr
                180                 185                 190

Ala Gln Pro Pro Thr Glu Thr Gly Glu Ser Ser Gln Ala Glu Glu Asn
        195                 200                 205

Ile Glu Ala Val Asp Glu Thr Lys Pro Lys Glu Ser Ala Arg Gln Asp
        210                 215                 220

Glu Gly Lys Glu Glu Glu Pro Glu Ala Asp Gln Glu His Ala
225                 230                 235

<210> SEQ ID NO 47
<211> LENGTH: 274
<212> TYPE: PRT
<213> ORGANISM: Homo sapiens

<400> SEQUENCE: 47

Met Thr Lys Ser Cys Ser Glu Leu Cys His Pro Ala Leu His Phe Leu
 1               5                  10                  15

Pro Cys Leu Gly Gly Leu Arg Lys Asn Leu Gln Arg Ala Val Arg Pro
            20                  25                  30

Ser Pro Tyr Ser Leu Gly Phe Leu Thr Phe Trp Ile Ser Arg Val Glu
        35                  40                  45

Lys Asn Asp Asp Asp Gln Lys Ile Glu Gln Asp Gly Ile Lys Pro Glu
 50                  55                  60

Asp Lys Ala His Lys Ala Ala Thr Lys Ile Gln Ala Ser Phe Arg Gly
 65                  70                  75                  80

His Ile Thr Arg Lys Lys Leu Lys Gly Glu Lys Lys Asp Asp Val Gln
                 85                  90                  95

Ala Ala Glu Ala Glu Ala Asn Lys Lys Asp Glu Ala Pro Val Ala Asp
            100                 105                 110

Gly Val Glu Lys Lys Gly Glu Gly Thr Thr Thr Ala Glu Ala Ala Pro
        115                 120                 125

Ala Thr Gly Ser Lys Pro Asp Glu Pro Gly Lys Ala Gly Glu Thr Pro
        130                 135                 140

Ser Glu Glu Lys Lys Gly Glu Gly Asp Ala Ala Thr Glu Gln Ala Ala
145                 150                 155                 160
```

```
Pro Gln Ala Pro Ala Ser Ser Glu Glu Lys Ala Gly Ser Ala Glu Thr
                165                 170                 175

Glu Ser Ala Thr Lys Ala Ser Thr Asp Asn Ser Pro Ser Ser Lys Ala
            180                 185                 190

Glu Asp Ala Pro Ala Lys Glu Glu Pro Lys Gln Ala Asp Val Pro Ala
        195                 200                 205

Ala Val Thr Ala Ala Ala Thr Thr Pro Ala Ala Glu Asp Ala Ala
    210                 215                 220

Ala Lys Ala Thr Ala Gln Pro Pro Thr Glu Thr Gly Glu Ser Ser Gln
225                 230                 235                 240

Ala Glu Glu Asn Ile Glu Ala Val Asp Glu Thr Lys Pro Lys Glu Ser
                245                 250                 255

Ala Arg Gln Asp Glu Gly Lys Glu Glu Glu Pro Glu Ala Asp Gln Glu
            260                 265                 270

His Ala

<210> SEQ ID NO 48
<211> LENGTH: 290
<212> TYPE: PRT
<213> ORGANISM: Homo sapiens

<400> SEQUENCE: 48

Met Val Ile Gln Lys Glu Lys Ser Cys Gly Gln Val Val Glu Glu
1               5                   10                  15

Trp Lys Glu Phe Val Trp Asn Pro Arg Thr His Gln Phe Met Gly Arg
                20                  25                  30

Thr Gly Thr Ser Trp Ala Phe Ile Leu Leu Phe Tyr Leu Val Phe Tyr
            35                  40                  45

Gly Phe Leu Thr Ala Met Phe Thr Leu Thr Met Trp Val Met Leu Gln
    50                  55                  60

Thr Val Ser Asp His Thr Pro Lys Tyr Gln Asp Arg Leu Ala Thr Pro
65                  70                  75                  80

Gly Leu Met Ile Arg Pro Lys Thr Glu Asn Leu Asp Val Ile Val Asn
                85                  90                  95

Val Ser Asp Thr Glu Ser Trp Asp Gln His Val Gln Lys Leu Asn Lys
            100                 105                 110

Phe Leu Glu Pro Tyr Asn Asp Ser Ile Gln Ala Gln Lys Asn Asp Val
        115                 120                 125

Cys Arg Pro Gly Arg Tyr Tyr Glu Gln Pro Asp Asn Gly Val Leu Asn
    130                 135                 140

Tyr Pro Lys Arg Ala Cys Gln Phe Asn Arg Thr Gln Leu Gly Asn Cys
145                 150                 155                 160

Ser Gly Ile Gly Asp Ser Thr His Tyr Gly Tyr Ser Thr Gly Gln Pro
                165                 170                 175

Cys Val Phe Ile Lys Met Asn Arg Val Ile Asn Phe Tyr Ala Gly Ala
            180                 185                 190

Asn Gln Ser Met Asn Val Thr Cys Ala Gly Lys Arg Asp Glu Asp Ala
        195                 200                 205

Glu Asn Leu Gly Asn Phe Val Met Phe Pro Ala Asn Gly Asn Ile Asp
    210                 215                 220

Leu Met Tyr Phe Pro Tyr Tyr Gly Lys Lys Phe His Val Asn Tyr Thr
225                 230                 235                 240

Gln Pro Leu Val Ala Val Lys Phe Leu Asn Val Thr Pro Asn Val Glu
                245                 250                 255
```

```
Val Asn Val Glu Cys Arg Ile Asn Ala Ala Asn Ile Ala Thr Asp Asp
                260                 265                 270

Glu Arg Asp Lys Phe Ala Gly Arg Val Ala Phe Lys Leu Arg Ile Asn
            275                 280                 285

Lys Thr
    290

<210> SEQ ID NO 49
<211> LENGTH: 1390
<212> TYPE: PRT
<213> ORGANISM: Homo sapiens

<400> SEQUENCE: 49

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335
```

```
Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
                530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
                610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750
```

-continued

Phe Ile Ser Gly Gly Ser Thr Ile Thr Gly Val Gly Lys Asn Leu Asn
    755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala  Thr Phe Pro
        995                 1000                1005

Glu Asp  Gln Phe Pro Asn Ser  Ser Gln Asn Gly Ser  Cys Arg Gln
    1010                1015                1020

Val Gln  Tyr Pro Leu Thr Asp  Met Ser Pro Ile Leu  Thr Ser Gly
    1025                1030                1035

Asp Ser  Asp Ile Ser Ser Pro  Leu Leu Gln Asn Thr  Val His Ile
    1040                1045                1050

Asp Leu  Ser Ala Leu Asn Pro  Glu Leu Val Gln Ala  Val Gln His
    1055                1060                1065

Val Val  Ile Gly Pro Ser Ser  Leu Ile Val His Phe  Asn Glu Val
    1070                1075                1080

Ile Gly  Arg Gly His Phe Gly  Cys Val Tyr His Gly  Thr Leu Leu
    1085                1090                1095

Asp Asn  Asp Gly Lys Lys Ile  His Cys Ala Val Lys  Ser Leu Asn
    1100                1105                1110

Arg Ile  Thr Asp Ile Gly Glu  Val Ser Gln Phe Leu  Thr Glu Gly
    1115                1120                1125

Ile Ile  Met Lys Asp Phe Ser  His Pro Asn Val Leu  Ser Leu Leu
    1130                1135                1140

Gly Ile  Cys Leu Arg Ser Glu  Gly Ser Pro Leu Val  Val Leu Pro
    1145                1150                1155

Tyr Met  Lys His Gly Asp Leu  Arg Asn Phe Ile Arg  Asn Glu Thr

```
                1160                1165                1170

His Asn Pro Thr Val Lys Asp Leu Ile Gly Phe Gly Leu Gln Val
    1175                1180                1185

Ala Lys Gly Met Lys Tyr Leu Ala Ser Lys Lys Phe Val His Arg
    1190                1195                1200

Asp Leu Ala Ala Arg Asn Cys Met Leu Asp Glu Lys Phe Thr Val
    1205                1210                1215

Lys Val Ala Asp Phe Gly Leu Ala Arg Asp Met Tyr Asp Lys Glu
    1220                1225                1230

Tyr Tyr Ser Val His Asn Lys Thr Gly Ala Lys Leu Pro Val Lys
    1235                1240                1245

Trp Met Ala Leu Glu Ser Leu Gln Thr Gln Lys Phe Thr Thr Lys
    1250                1255                1260

Ser Asp Val Trp Ser Phe Gly Val Leu Leu Trp Glu Leu Met Thr
    1265                1270                1275

Arg Gly Ala Pro Pro Tyr Pro Asp Val Asn Thr Phe Asp Ile Thr
    1280                1285                1290

Val Tyr Leu Leu Gln Gly Arg Arg Leu Leu Gln Pro Glu Tyr Cys
    1295                1300                1305

Pro Asp Pro Leu Tyr Glu Val Met Leu Lys Cys Trp His Pro Lys
    1310                1315                1320

Ala Glu Met Arg Pro Ser Phe Ser Glu Leu Val Ser Arg Ile Ser
    1325                1330                1335

Ala Ile Phe Ser Thr Phe Ile Gly Glu His Tyr Val His Val Asn
    1340                1345                1350

Ala Thr Tyr Val Asn Val Lys Cys Val Ala Pro Tyr Pro Ser Leu
    1355                1360                1365

Leu Ser Ser Glu Asp Asn Ala Asp Asp Glu Val Asp Thr Arg Pro
    1370                1375                1380

Ala Ser Phe Trp Glu Thr Ser
    1385                1390

<210> SEQ ID NO 50
<211> LENGTH: 1408
<212> TYPE: PRT
<213> ORGANISM: Homo sapiens

<400> SEQUENCE: 50

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125
```

```
Gln Leu Ile Ser Cys Gly Ser Val Asn Arg Gly Thr Cys Gln Arg His
            130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                    165                 170                 175

Val Ser Ala Leu Gly Ala Lys Val Leu Ser Ser Val Lys Asp Arg Phe
                180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
                260                 265                 270

Thr Phe His Thr Arg Ile Ile Arg Phe Cys Ser Ile Asn Ser Gly Leu
            275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
            435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
```

-continued

```
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
        610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
        690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Thr Trp Trp Lys Glu Pro Leu Asn Ile Val Ser Phe Leu
        755                 760                 765

Phe Cys Phe Ala Ser Gly Gly Ser Thr Ile Thr Gly Val Gly Lys Asn
        770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro
                820                 825                 830

Leu Lys Thr Lys Ala Phe Phe Met Leu Asp Gly Ile Leu Ser Lys Tyr
        835                 840                 845

Phe Asp Leu Ile Tyr Val His Asn Pro Val Phe Lys Pro Phe Glu Lys
850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
                900                 905                 910

Thr Val Pro Asn Asp Leu Leu Lys Leu Asn Ser Glu Leu Asn Ile Glu
        915                 920                 925

Trp Lys Gln Ala Ile Ser Ser Thr Val Leu Gly Lys Val Ile Val Gln
        930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                965                 970                 975
```

-continued

```
Lys Gln Ile Lys Asp Leu Gly Ser Glu Leu Val Arg Tyr Asp Ala Arg
                980             985                 990

Val His Thr Pro His Leu Asp Arg  Leu Val Ser Ala Arg  Ser Val Ser
            995             1000                 1005

Pro Thr  Thr Glu Met Val Ser  Asn Glu Ser Val Asp  Tyr Arg Ala
    1010             1015                 1020

Thr Phe  Pro Glu Asp Gln Phe  Pro Asn Ser Ser Gln  Asn Gly Ser
    1025             1030                 1035

Cys Arg  Gln Val Gln Tyr Pro  Leu Thr Asp Met Ser  Pro Ile Leu
    1040             1045                 1050

Thr Ser  Gly Asp Ser Asp Ile  Ser Ser Pro Leu Leu  Gln Asn Thr
    1055             1060                 1065

Val His  Ile Asp Leu Ser Ala  Leu Asn Pro Glu Leu  Val Gln Ala
    1070             1075                 1080

Val Gln  His Val Val Ile Gly  Pro Ser Ser Leu Ile  Val His Phe
    1085             1090                 1095

Asn Glu  Val Ile Gly Arg Gly  His Phe Gly Cys Val  Tyr His Gly
    1100             1105                 1110

Thr Leu  Leu Asp Asn Asp Gly  Lys Lys Ile His Cys  Ala Val Lys
    1115             1120                 1125

Ser Leu  Asn Arg Ile Thr Asp  Ile Gly Glu Val Ser  Gln Phe Leu
    1130             1135                 1140

Thr Glu  Gly Ile Ile Met Lys  Asp Phe Ser His Pro  Asn Val Leu
    1145             1150                 1155

Ser Leu  Leu Gly Ile Cys Leu  Arg Ser Glu Gly Ser  Pro Leu Val
    1160             1165                 1170

Val Leu  Pro Tyr Met Lys His  Gly Asp Leu Arg Asn  Phe Ile Arg
    1175             1180                 1185

Asn Glu  Thr His Asn Pro Thr  Val Lys Asp Leu Ile  Gly Phe Gly
    1190             1195                 1200

Leu Gln  Val Ala Lys Gly Met  Lys Tyr Leu Ala Ser  Lys Lys Phe
    1205             1210                 1215

Val His  Arg Asp Leu Ala Ala  Arg Asn Cys Met Leu  Asp Glu Lys
    1220             1225                 1230

Phe Thr  Val Lys Val Ala Asp  Phe Gly Leu Ala Arg  Asp Met Tyr
    1235             1240                 1245

Asp Lys  Glu Tyr Tyr Ser Val  His Asn Lys Thr Gly  Ala Lys Leu
    1250             1255                 1260

Pro Val  Lys Trp Met Ala Leu  Glu Ser Leu Gln Thr  Gln Lys Phe
    1265             1270                 1275

Thr Thr  Lys Ser Asp Val Trp  Ser Phe Gly Val Leu  Leu Trp Glu
    1280             1285                 1290

Leu Met  Thr Arg Gly Ala Pro  Pro Tyr Pro Asp Val  Asn Thr Phe
    1295             1300                 1305

Asp Ile  Thr Val Tyr Leu Leu  Gln Gly Arg Arg Leu  Leu Gln Pro
    1310             1315                 1320

Glu Tyr  Cys Pro Asp Pro Leu  Tyr Glu Val Met Leu  Lys Cys Trp
    1325             1330                 1335

His Pro  Lys Ala Glu Met Arg  Pro Ser Phe Ser Glu  Leu Val Ser
    1340             1345                 1350

Arg Ile  Ser Ala Ile Phe Ser  Thr Phe Ile Gly Glu  His Tyr Val
    1355             1360                 1365
```

His Val Asn Ala Thr Tyr Val Asn Val Lys Cys Val Ala Pro Tyr
    1370            1375            1380

Pro Ser Leu Leu Ser Ser Glu Asp Asn Ala Asp Asp Glu Val Asp
    1385            1390            1395

Thr Arg Pro Ala Ser Phe Trp Glu Thr Ser
    1400            1405

<210> SEQ ID NO 51
<211> LENGTH: 764
<212> TYPE: PRT
<213> ORGANISM: Homo sapiens

<400> SEQUENCE: 51

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

```
Leu Asn Asp Asp Ile Leu Phe Gly Val Phe Ala Gln Ser Lys Pro Asp
                340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Asn Val Arg
                370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
                450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
                530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
                610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750
```

```
Phe Ile Arg His Val Asn Ile Ala Leu Ile Gln Arg
        755                 760

<210> SEQ ID NO 52
<211> LENGTH: 976
<212> TYPE: PRT
<213> ORGANISM: Homo sapiens

<400> SEQUENCE: 52

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
    210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
    290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365
```

```
Cys Trp Pro Glu Ser Gly Glu Cys Gly Pro Cys Glu Ala Ser Val Arg
    370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                    405                 410                 415

Gly Val Ser Gly Leu Val Thr Ser Arg Ser Phe Arg Thr Ala Ser Val
                420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Gln Gln Ser
450                 455                 460

Arg Val Trp Lys Tyr Glu Val Thr Tyr Arg Lys Lys Gly Asp Ser Asn
465             470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
                500                 505                 510

Glu Gly Gln Gly Ala Gly Ser Lys Val His Glu Phe Gly Thr Leu Ser
        515                 520                 525

Pro Glu Gly Ser Gly Asn Leu Ala Val Ile Gly Gly Val Ala Val Gly
        530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
        595                 600                 605

His Pro Ser Cys Val Thr Arg Gln Lys Val Ile Gly Ala Gly Glu Phe
    610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
            660                 665                 670

His Asn Ile Ile Arg Leu Glu Gly Val Ile Ser Lys Tyr Lys Pro Met
    675                 680                 685

Met Ile Ile Thr Glu Tyr Met Glu Asn Gly Ala Leu Asp Lys Phe Leu
    690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
                740                 745                 750

Cys Lys Val Ser Asp Phe Gly Leu Ser Arg Val Leu Glu Asp Asp Pro
        755                 760                 765

Glu Ala Thr Tyr Thr Thr Ser Gly Gly Lys Ile Pro Ile Arg Trp Thr
770                 775                 780
```

-continued

```
Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
    850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
                900                 905                 910

Leu Glu Ser Ile Lys Met Gln Gln Tyr Thr Glu His Phe Met Ala Ala
            915                 920                 925

Gly Tyr Thr Ala Ile Glu Lys Val Val Gln Met Thr Asn Asp Asp Ile
        930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 53
<211> LENGTH: 497
<212> TYPE: PRT
<213> ORGANISM: Homo sapiens

<400> SEQUENCE: 53

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu Leu
                20                  25                  30

Asp Phe Ala Ala Ala Gly Gly Glu Leu Gly Trp Leu Thr His Pro Tyr
            35                  40                  45

Gly Lys Gly Trp Asp Leu Met Gln Asn Ile Met Asn Asp Met Pro Ile
        50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
    130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190
```

```
Ser Val Arg Val Tyr Tyr Lys Lys Cys Pro Glu Leu Leu Gln Gly Leu
            195                 200                 205

Ala His Phe Pro Glu Thr Ile Ala Gly Ser Asp Ala Pro Ser Leu Ala
            210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
            245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
            275                 280                 285

Pro Cys Leu Glu Cys Pro Glu His Thr Leu Pro Ser Pro Glu Gly Ala
            290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
            325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
            355                 360                 365

Cys Trp Pro Glu Ser Gly Glu Cys Gly Pro Cys Glu Ala Ser Val Arg
            370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
            405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
            435                 440                 445

Thr Thr Ser Leu Ser Val Ser Trp Ser Ile Pro Pro Pro Gln Gln Ser
            450                 455                 460

Arg Val Trp Lys Tyr Glu Val Thr Tyr Arg Lys Lys Val Thr Pro Arg
465                 470                 475                 480

Gly Ala Gly Leu Ala Leu Ala Gly Pro Thr Ala Gly Asp Arg Leu Val
            485                 490                 495

Thr

<210> SEQ ID NO 54
<211> LENGTH: 253
<212> TYPE: PRT
<213> ORGANISM: Homo sapiens

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Ser Ser Ser Tyr Pro
                 85                  90                  95

Trp Thr Phe Gly Gln Gly Thr Lys Val Glu Ile Lys Arg Thr Gly Gly
            100                 105                 110

Gly Gly Ser Gly Ala Gly Gly Ser Gly Gly Gly Thr Gly Gly
            115                 120                 125      Gly

Gly Ser Glu Val Asp Leu Leu Glu Ser Gly Gly Leu Val Gln Pro
            130                 135             140

Gly Gly Ser Leu Arg Leu Ser Cys Ala Ala Ser Gly Phe Thr Phe Ser
145                 150                 155                 160

Arg Tyr Trp Met His Trp Val Arg Gln Ala Pro Gly Lys Gly Leu Glu
                165                 170                 175

Trp Val Ser Ser Ile Ser Pro Tyr Asp Gly Glu Thr Asn Tyr Ala Asp
                180                 185                 190

Ser Val Lys Gly Arg Phe Thr Ile Ser Arg Asp Asn Ser Lys Asn Thr
                195                 200                 205

Leu Tyr Leu Gln Met Asn Ser Leu Arg Ala Glu Asp Thr Ala Val Tyr
            210                 215                 220

Tyr Cys Ala Arg Ile Ser Glu Trp Tyr Asn Trp Ala Val Asp Val Phe
225                 230                 235                 240

Asp Tyr Trp Gly Gln Gly Thr Leu Val Thr Val Ser Ser
                245                 250

<210> SEQ ID NO 55
<211> LENGTH: 237
<212> TYPE: PRT
<213> ORGANISM: Homo sapiens

<400> SEQUENCE: 55

Gln Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Thr Met Ser Trp Val Arg Gln Ala Pro Gly Gln Ala Leu Glu Trp Met
          35                  40                  45

Gly Thr Ile Ser Ser Gly Gly Thr Tyr Thr Tyr Tyr Pro Asp Ser Val
       50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Glu Ala Ile Phe Thr Tyr Trp Gly Arg Gly Thr Leu Val Thr
          100                 105                 110

Ser Ser Gly Gly Gly Gly Ser Gly Gly Gly Gly Ser Gly Gly Gly Gly
          115                 120                 125

Ser Asp Ile Gln Leu Thr Gln Ser Pro Ser Ser Leu Ser Ala Ser Val
          130                 135                 140

Gly Asp Arg Val Thr Ile Thr Cys Lys Ala Ser Gln Asp Ile Asn Asn
145                 150                 155                 160

Tyr Leu Ser Trp Tyr Gln Gln Lys Pro Gly Gln Ala Pro Arg Leu Leu
                165                 170                 175

Ile Tyr Arg Ala Asn Arg Leu Val Asp Gly Val Pro Asp Arg Phe Ser
```

```
              180                 185                 190
Gly Ser Gly Tyr Gly Thr Asp Phe Thr Leu Thr Ile Asn Asn Ile Glu
            195                 200                 205

Ser Glu Asp Ala Ala Tyr Tyr Phe Cys Leu Lys Tyr Asp Val Phe Pro
        210                 215                 220

Tyr Thr Phe Gly Gln Gly Thr Lys Val Glu Ile Lys Ser
225                 230                 235

<210> SEQ ID NO 56
<211> LENGTH: 983
<212> TYPE: PRT
<213> ORGANISM: Homo sapiens

<400> SEQUENCE: 56

Met Asp Cys Gln Leu Ser Ile Leu Leu Leu Ser Cys Ser Val Leu
1               5                  10                  15

Asp Ser Phe Gly Glu Leu Ile Pro Gln Pro Ser Asn Glu Val Asn Leu
                20                  25                  30

Leu Asp Ser Lys Thr Ile Gln Gly Glu Leu Gly Trp Ile Ser Tyr Pro
            35                  40                  45

Ser His Gly Trp Glu Glu Ile Ser Gly Val Asp Glu His Tyr Thr Pro
        50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
                100                 105                 110

Leu Gly Thr Cys Lys Glu Thr Phe Asn Leu Tyr Tyr Met Glu Ser Asp
            115                 120                 125

Asp Asp His Gly Val Lys Phe Arg Glu His Gln Phe Thr Lys Ile Asp
        130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Lys Cys Pro Phe Thr Val Lys Asn
        195                 200                 205

Leu Ala Met Phe Pro Asp Thr Val Pro Met Asp Ser Gln Ser Leu Val
    210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln Ala
            260                 265                 270

Cys Arg Pro Gly Phe Tyr Lys Ala Leu Asp Gly Asn Met Lys Cys Ala
        275                 280                 285

Lys Cys Pro Pro His Ser Ser Thr Gln Glu Asp Gly Ser Met Asn Cys
    290                 295                 300

Arg Cys Glu Asn Asn Tyr Phe Arg Ala Asp Lys Asp Pro Pro Ser Met
305                 310                 315                 320
```

```
Ala Cys Thr Arg Pro Pro Ser Ser Pro Arg Asn Val Ile Ser Asn Ile
            325                 330                 335

Asn Glu Thr Ser Val Ile Leu Asp Trp Ser Trp Pro Leu Asp Thr Gly
            340                 345                 350

Gly Arg Lys Asp Val Thr Phe Asn Ile Ile Cys Lys Lys Cys Gly Trp
            355                 360                 365

Asn Ile Lys Gln Cys Glu Pro Cys Ser Pro Asn Val Arg Phe Leu Pro
        370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
            405                 410                 415

Glu Leu Ser Ser Pro Pro Arg Gln Phe Ala Ala Val Ser Ile Thr Thr
            420                 425                 430

Asn Gln Ala Ala Pro Ser Pro Val Leu Thr Ile Lys Lys Asp Arg Thr
            435                 440                 445

Ser Arg Asn Ser Ile Ser Leu Ser Trp Gln Pro Glu His Pro Asn
            450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
            485                 490                 495

Ser Ser Leu Lys Pro Asp Thr Ile Tyr Val Phe Gln Ile Arg Ala Arg
            500                 505                 510

Thr Ala Ala Gly Tyr Gly Thr Asn Ser Arg Lys Phe Glu Phe Glu Thr
            515                 520                 525

Ser Pro Asp Ser Phe Ser Ile Ser Gly Glu Ser Ser Gln Val Val Met
            530                 535                 540

Ile Ala Ile Ser Ala Ala Val Ala Ile Ile Leu Leu Thr Val Val Ile
545                 550                 555                 560

Tyr Val Leu Ile Gly Arg Phe Cys Gly Tyr Lys Ser Lys His Gly Ala
            565                 570                 575

Asp Glu Lys Arg Leu His Phe Gly Asn Gly His Leu Lys Leu Pro Gly
            580                 585                 590

Leu Arg Thr Tyr Val Asp Pro His Thr Tyr Glu Asp Pro Thr Gln Ala
            595                 600                 605

Val His Glu Phe Ala Lys Glu Leu Asp Ala Thr Asn Ile Ser Ile Asp
            610                 615                 620

Lys Val Val Gly Ala Gly Glu Phe Gly Glu Val Cys Ser Gly Arg Leu
625                 630                 635                 640

Lys Leu Pro Ser Lys Lys Glu Ile Ser Val Ala Ile Lys Thr Leu Lys
            645                 650                 655

Val Gly Tyr Thr Glu Lys Gln Arg Arg Asp Phe Leu Gly Glu Ala Ser
            660                 665                 670

Ile Met Gly Gln Phe Asp His Pro Asn Ile Ile Arg Leu Glu Gly Val
            675                 680                 685

Val Thr Lys Ser Lys Pro Val Met Ile Val Thr Glu Tyr Met Glu Asn
            690                 695                 700

Gly Ser Leu Asp Ser Phe Leu Arg Lys His Asp Ala Gln Phe Thr Val
705                 710                 715                 720

Ile Gln Leu Val Gly Met Leu Arg Gly Ile Ala Ser Gly Met Lys Tyr
            725                 730                 735

Leu Ser Asp Met Gly Tyr Val His Arg Asp Leu Ala Ala Arg Asn Ile
```

```
                740                 745                 750
Leu Ile Asn Ser Asn Leu Val Cys Lys Val Ser Asp Phe Gly Leu Ser
            755                 760                 765

Arg Val Leu Glu Asp Pro Glu Ala Ala Tyr Thr Thr Arg Gly Gly
        770                 775                 780

Lys Ile Pro Ile Arg Trp Thr Ser Pro Glu Ala Ile Ala Tyr Arg Lys
785                 790                 795                 800

Phe Thr Ser Ala Ser Asp Val Trp Ser Tyr Gly Ile Val Leu Trp Glu
                805                 810                 815

Val Met Ser Tyr Gly Glu Arg Pro Tyr Trp Glu Met Ser Asn Gln Asp
            820                 825                 830

Val Ile Lys Ala Val Asp Glu Gly Tyr Arg Leu Pro Pro Pro Met Asp
        835                 840                 845

Cys Pro Ala Ala Leu Tyr Gln Leu Met Leu Asp Cys Trp Gln Lys Asp
    850                 855                 860

Arg Asn Asn Arg Pro Lys Phe Glu Gln Ile Val Ser Ile Leu Asp Lys
865                 870                 875                 880

Leu Ile Arg Asn Pro Gly Ser Leu Lys Ile Ile Thr Ser Ala Ala Ala
                885                 890                 895

Arg Pro Ser Asn Leu Leu Leu Asp Gln Ser Asn Val Asp Ile Thr Thr
            900                 905                 910

Phe Arg Thr Thr Gly Asp Trp Leu Asn Gly Val Trp Thr Ala His Cys
        915                 920                 925

Lys Glu Ile Phe Thr Gly Val Glu Tyr Ser Ser Cys Asp Thr Ile Ala
    930                 935                 940

Lys Ile Ser Thr Asp Asp Met Lys Lys Val Gly Val Thr Val Val Gly
945                 950                 955                 960

Pro Gln Lys Lys Ile Ile Ser Ser Ile Lys Ala Leu Glu Thr Gln Ser
                965                 970                 975

Lys Asn Gly Pro Val Pro Val
            980

<210> SEQ ID NO 57
<211> LENGTH: 539
<212> TYPE: PRT
<213> ORGANISM: Homo sapiens

<400> SEQUENCE: 57

Met Asp Cys Gln Leu Ser Ile Leu Leu Leu Leu Ser Cys Ser Val Leu
1               5                   10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
        35                  40                  45

Ser His Gly Trp Glu Glu Ile Ser Gly Val Asp Glu His Tyr Thr Pro
    50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
        115                 120                 125
```

-continued

```
Asp Asp His Gly Val Lys Phe Arg Glu His Gln Phe Thr Lys Ile Asp
130                 135                 140
Thr Ile Ala Ala Asp Glu Ser Phe Thr Gln Met Asp Leu Gly Asp Arg
145                 150                 155                 160
Ile Leu Lys Leu Asn Thr Glu Ile Arg Glu Val Gly Pro Val Asn Lys
                165                 170                 175
Lys Gly Phe Tyr Leu Ala Phe Gln Asp Val Gly Ala Cys Val Ala Leu
            180                 185                 190
Val Ser Val Arg Val Tyr Phe Lys Lys Cys Pro Phe Thr Val Lys Asn
        195                 200                 205
Leu Ala Met Phe Pro Asp Thr Val Pro Met Asp Ser Gln Ser Leu Val
210                 215                 220
Glu Val Arg Gly Ser Cys Val Asn Asn Ser Lys Glu Asp Pro Pro
225                 230                 235                 240
Arg Met Tyr Cys Ser Thr Gly Glu Trp Leu Val Pro Ile Gly Lys
                245                 250                 255
Cys Ser Cys Asn Ala Gly Tyr Glu Glu Arg Gly Phe Met Cys Gln Ala
            260                 265                 270
Cys Arg Pro Gly Phe Tyr Lys Ala Leu Asp Gly Asn Met Lys Cys Ala
        275                 280                 285
Lys Cys Pro Pro His Ser Ser Thr Gln Glu Asp Gly Ser Met Asn Cys
290                 295                 300
Arg Cys Glu Asn Asn Tyr Phe Arg Ala Asp Lys Asp Pro Pro Ser Met
305                 310                 315                 320
Ala Cys Thr Arg Pro Pro Ser Ser Pro Arg Asn Val Ile Ser Asn Ile
                325                 330                 335
Asn Glu Thr Ser Val Ile Leu Asp Trp Ser Trp Pro Leu Asp Thr Gly
            340                 345                 350
Gly Arg Lys Asp Val Thr Phe Asn Ile Ile Cys Lys Lys Cys Gly Trp
        355                 360                 365
Asn Ile Lys Gln Cys Glu Pro Cys Ser Pro Asn Val Arg Phe Leu Pro
370                 375                 380
Arg Gln Phe Gly Leu Thr Asn Thr Thr Val Thr Val Thr Asp Leu Leu
385                 390                 395                 400
Ala His Thr Asn Tyr Thr Phe Glu Ile Asp Ala Val Asn Gly Val Ser
                405                 410                 415
Glu Leu Ser Ser Pro Pro Arg Gln Phe Ala Ala Val Ser Ile Thr Thr
            420                 425                 430
Asn Gln Ala Ala Pro Ser Pro Val Leu Thr Ile Lys Lys Asp Arg Thr
        435                 440                 445
Ser Arg Asn Ser Ile Ser Leu Ser Trp Gln Glu Pro Glu His Pro Asn
450                 455                 460
Gly Ile Ile Leu Asp Tyr Glu Val Lys Tyr Tyr Glu Lys Gln Glu Gln
465                 470                 475                 480
Glu Thr Ser Tyr Thr Ile Leu Arg Ala Arg Gly Thr Asn Val Thr Ile
                485                 490                 495
Ser Ser Leu Lys Pro Asp Thr Ile Tyr Val Phe Gln Ile Arg Ala Arg
            500                 505                 510
Thr Ala Ala Gly Tyr Gly Thr Asn Ser Arg Lys Phe Glu Phe Glu Thr
        515                 520                 525
Ser Pro Asp Cys Met Tyr Tyr Phe Asn Ala Val
530                 535
```

```
<210> SEQ ID NO 58
<211> LENGTH: 146
<212> TYPE: PRT
<213> ORGANISM: Homo sapiens

<400> SEQUENCE: 58

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Arg
    130                 135                 140

Phe Asn
145

<210> SEQ ID NO 59
<211> LENGTH: 122
<212> TYPE: PRT
<213> ORGANISM: Artificial sequence
<220> FEATURE:
<223> OTHER INFORMATION: synthetic polypeptide sequence

<400> SEQUENCE: 59

Leu Thr Cys Leu Gly Gly Phe Ala Ser Pro Gly Pro Val Pro Pro Ser
1               5                   10                  15

Thr Ala Leu Arg Lys Leu Ile Glu Glu Leu Val Asn Ile Thr Gln Asn
            20                  25                  30

Gln Lys Ala Pro Leu Cys Asn Gly Ser Met Val Trp Ser Ile Asn Leu
        35                  40                  45

Thr Ala Gly Met Tyr Cys Ala Ala Leu Glu Ser Leu Ile Asn Val Ser
    50                  55                  60

Gly Cys Ser Ala Ile Glu Lys Thr Gln Arg Met Leu Ser Gly Phe Cys
65                  70                  75                  80

Pro His Lys Val Ser Ala Gly Gln Phe Ser Ser Leu His Val Arg Asp
                85                  90                  95

Thr Lys Ile Glu Val Ala Gln Phe Val Lys Asp Leu Leu Leu His Leu
            100                 105                 110

Arg Lys Leu Phe Arg Glu Gly Arg Phe Asn
        115                 120

<210> SEQ ID NO 60
<211> LENGTH: 1210
<212> TYPE: PRT
<213> ORGANISM: Homo sapiens

<400> SEQUENCE: 60
```

-continued

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
                35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
```

```
                420              425              430
His Gly Gln Phe Ser Leu Ala Val Val Ser Leu Asn Ile Thr Ser Leu
            435              440              445
Gly Leu Arg Ser Leu Lys Glu Ile Ser Asp Gly Asp Val Ile Ile Ser
            450              455              460
Gly Asn Lys Asn Leu Cys Tyr Ala Asn Thr Ile Asn Trp Lys Lys Leu
465              470              475              480
Phe Gly Thr Ser Gly Gln Lys Thr Lys Ile Ile Ser Asn Arg Gly Glu
                485              490              495
Asn Ser Cys Lys Ala Thr Gly Gln Val Cys His Ala Leu Cys Ser Pro
            500              505              510
Glu Gly Cys Trp Gly Pro Glu Pro Arg Asp Cys Val Ser Cys Arg Asn
            515              520              525
Val Ser Arg Gly Arg Glu Cys Val Asp Lys Cys Asn Leu Leu Glu Gly
            530              535              540
Glu Pro Arg Glu Phe Val Glu Asn Ser Glu Cys Ile Gln Cys His Pro
545              550              555              560
Glu Cys Leu Pro Gln Ala Met Asn Ile Thr Cys Thr Gly Arg Gly Pro
                565              570              575
Asp Asn Cys Ile Gln Cys Ala His Tyr Ile Asp Gly Pro His Cys Val
            580              585              590
Lys Thr Cys Pro Ala Gly Val Met Gly Glu Asn Asn Thr Leu Val Trp
            595              600              605
Lys Tyr Ala Asp Ala Gly His Val Cys His Leu Cys His Pro Asn Cys
            610              615              620
Thr Tyr Gly Cys Thr Gly Pro Gly Leu Glu Gly Cys Pro Thr Asn Gly
625              630              635              640
Pro Lys Ile Pro Ser Ile Ala Thr Gly Met Val Gly Ala Leu Leu Leu
                645              650              655
Leu Leu Val Val Ala Leu Gly Ile Gly Leu Phe Met Arg Arg Arg His
            660              665              670
Ile Val Arg Lys Arg Thr Leu Arg Arg Leu Leu Gln Glu Arg Glu Leu
            675              680              685
Val Glu Pro Leu Thr Pro Ser Gly Glu Ala Pro Asn Gln Ala Leu Leu
            690              695              700
Arg Ile Leu Lys Glu Thr Glu Phe Lys Lys Ile Lys Val Leu Gly Ser
705              710              715              720
Gly Ala Phe Gly Thr Val Tyr Lys Gly Leu Trp Ile Pro Glu Gly Glu
                725              730              735
Lys Val Lys Ile Pro Val Ala Ile Lys Glu Leu Arg Glu Ala Thr Ser
            740              745              750
Pro Lys Ala Asn Lys Glu Ile Leu Asp Glu Ala Tyr Val Met Ala Ser
            755              760              765
Val Asp Asn Pro His Val Cys Arg Leu Leu Gly Ile Cys Leu Thr Ser
            770              775              780
Thr Val Gln Leu Ile Thr Gln Leu Met Pro Phe Gly Cys Leu Leu Asp
785              790              795              800
Tyr Val Arg Glu His Lys Asp Asn Ile Gly Ser Gln Tyr Leu Leu Asn
                805              810              815
Trp Cys Val Gln Ile Ala Lys Gly Met Asn Tyr Leu Glu Asp Arg Arg
            820              825              830
Leu Val His Arg Asp Leu Ala Ala Arg Asn Val Leu Val Lys Thr Pro
            835              840              845
```

```
Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 61
<211> LENGTH: 405
<212> TYPE: PRT
<213> ORGANISM: Homo sapiens
```

```
<400> SEQUENCE: 61

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Leu Ser
            405
```

```
<210> SEQ ID NO 62
<211> LENGTH: 705
<212> TYPE: PRT
<213> ORGANISM: Homo sapiens

<400> SEQUENCE: 62
```

| | | | | | | | | | | | | | | |
|---|---|---|---|---|---|---|---|---|---|---|---|---|---|---|
| Met | Arg | Pro | Ser | Gly | Thr | Ala | Gly | Ala | Ala | Leu | Leu | Ala | Leu | Leu |
| 1 | | | | 5 | | | | | 10 | | | | | 15 |
| Ala | Leu | Cys | Pro | Ala | Ser | Arg | Ala | Leu | Glu | Glu | Lys | Lys | Val | Cys | Gln |
| | | | 20 | | | | | 25 | | | | | 30 | | |
| Gly | Thr | Ser | Asn | Lys | Leu | Thr | Gln | Leu | Gly | Thr | Phe | Glu | Asp | His | Phe |
| | | | 35 | | | | | 40 | | | | | 45 | | |
| Leu | Ser | Leu | Gln | Arg | Met | Phe | Asn | Asn | Cys | Glu | Val | Val | Leu | Gly | Asn |
| | 50 | | | | | 55 | | | | | 60 | | | | |
| Leu | Glu | Ile | Thr | Tyr | Val | Gln | Arg | Asn | Tyr | Asp | Leu | Ser | Phe | Leu | Lys |
| 65 | | | | | 70 | | | | | 75 | | | | | 80 |
| Thr | Ile | Gln | Glu | Val | Ala | Gly | Tyr | Val | Leu | Ile | Ala | Leu | Asn | Thr | Val |
| | | | | 85 | | | | | 90 | | | | | 95 | |
| Glu | Arg | Ile | Pro | Leu | Glu | Asn | Leu | Gln | Ile | Ile | Arg | Gly | Asn | Met | Tyr |
| | | | 100 | | | | | 105 | | | | | 110 | | |
| Tyr | Glu | Asn | Ser | Tyr | Ala | Leu | Ala | Val | Leu | Ser | Asn | Tyr | Asp | Ala | Asn |
| | | 115 | | | | | 120 | | | | | 125 | | | |
| Lys | Thr | Gly | Leu | Lys | Glu | Leu | Pro | Met | Arg | Asn | Leu | Gln | Glu | Ile | Leu |
| | 130 | | | | | 135 | | | | | 140 | | | | |
| His | Gly | Ala | Val | Arg | Phe | Ser | Asn | Asn | Pro | Ala | Leu | Cys | Asn | Val | Glu |
| 145 | | | | | 150 | | | | | 155 | | | | | 160 |
| Ser | Ile | Gln | Trp | Arg | Asp | Ile | Val | Ser | Ser | Asp | Phe | Leu | Ser | Asn | Met |
| | | | | 165 | | | | | 170 | | | | | 175 | |
| Ser | Met | Asp | Phe | Gln | Asn | His | Leu | Gly | Ser | Cys | Gln | Lys | Cys | Asp | Pro |
| | | | 180 | | | | | 185 | | | | | 190 | | |
| Ser | Cys | Pro | Asn | Gly | Ser | Cys | Trp | Gly | Ala | Gly | Glu | Glu | Asn | Cys | Gln |
| | | 195 | | | | | 200 | | | | | 205 | | | |
| Lys | Leu | Thr | Lys | Ile | Ile | Cys | Ala | Gln | Gln | Cys | Ser | Gly | Arg | Cys | Arg |
| | 210 | | | | | 215 | | | | | 220 | | | | |
| Gly | Lys | Ser | Pro | Ser | Asp | Cys | Cys | His | Asn | Gln | Cys | Ala | Ala | Gly | Cys |
| 225 | | | | | 230 | | | | | 235 | | | | | 240 |
| Thr | Gly | Pro | Arg | Glu | Ser | Asp | Cys | Leu | Val | Cys | Arg | Lys | Phe | Arg | Asp |
| | | | | 245 | | | | | 250 | | | | | 255 | |
| Glu | Ala | Thr | Cys | Lys | Asp | Thr | Cys | Pro | Pro | Leu | Met | Leu | Tyr | Asn | Pro |
| | | | 260 | | | | | 265 | | | | | 270 | | |
| Thr | Thr | Tyr | Gln | Met | Asp | Val | Asn | Pro | Glu | Gly | Lys | Tyr | Ser | Phe | Gly |
| | | 275 | | | | | 280 | | | | | 285 | | | |
| Ala | Thr | Cys | Val | Lys | Lys | Cys | Pro | Arg | Asn | Tyr | Val | Val | Thr | Asp | His |
| | 290 | | | | | 295 | | | | | 300 | | | | |
| Gly | Ser | Cys | Val | Arg | Ala | Cys | Gly | Ala | Asp | Ser | Tyr | Glu | Met | Glu | Glu |
| 305 | | | | | 310 | | | | | 315 | | | | | 320 |
| Asp | Gly | Val | Arg | Lys | Cys | Lys | Lys | Cys | Glu | Gly | Pro | Cys | Arg | Lys | Val |
| | | | | 325 | | | | | 330 | | | | | 335 | |
| Cys | Asn | Gly | Ile | Gly | Ile | Gly | Glu | Phe | Lys | Asp | Ser | Leu | Ser | Ile | Asn |
| | | | 340 | | | | | 345 | | | | | 350 | | |
| Ala | Thr | Asn | Ile | Lys | His | Phe | Lys | Asn | Cys | Thr | Ser | Ile | Ser | Gly | Asp |
| | | 355 | | | | | 360 | | | | | 365 | | | |
| Leu | His | Ile | Leu | Pro | Val | Ala | Phe | Arg | Gly | Asp | Ser | Phe | Thr | His | Thr |

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
                660                 665                 670

Ser Leu Leu Pro Ser Glu Phe Gln Leu Gly Trp Gly Gly Cys Ser His
            675                 680                 685

Leu His Ala Trp Pro Ser Ala Ser Val Ile Ile Thr Ala Ser Ser Cys
690                 695                 700

His
705

<210> SEQ ID NO 63
<211> LENGTH: 628
<212> TYPE: PRT
<213> ORGANISM: Homo sapiens

<400> SEQUENCE: 63

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

```
Gly Thr Ser Asn Lys Leu Thr Gln Leu Gly Thr Phe Glu Asp His Phe
             35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
            130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
            195                 200                 205

Lys Leu Thr Lys Ile Ile Cys Ala Gln Gln Cys Ser Gly Arg Cys Arg
            210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
```

```
                450                 455                 460
Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Ser
625

<210> SEQ ID NO 64
<211> LENGTH: 1255
<212> TYPE: PRT
<213> ORGANISM: Homo sapiens

<400> SEQUENCE: 64

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190
```

-continued

His Pro Cys Ser Pro Met Cys Lys Gly Ser Arg Cys Trp Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
        260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
    355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
        420                 425                 430

Gly Arg Ile Leu His Asn Gly Ala Tyr Ser Leu Thr Leu Gln Gly Leu
    435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
        500                 505                 510

Gln Leu Cys Ala Arg Gly His Cys Trp Gly Pro Gly Pro Thr Gln Cys
    515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
        580                 585                 590

Pro Pro Phe Cys Val Ala Arg Cys Pro Ser Gly Val Lys Pro Asp Leu
    595                 600                 605

Ser Tyr Met Pro Ile Trp Lys Phe Pro Asp Glu Glu Gly Ala Cys Gln

```
            610                 615                 620
Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                    645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu  Asp Ser Thr Phe Tyr  Arg Ser Leu
            995                 1000                 1005

Leu Glu  Asp Asp Asp Met Gly  Asp Leu Val Asp Ala  Glu Glu Tyr
        1010                1015                 1020

Leu Val  Pro Gln Gln Gly Phe  Phe Cys Pro Asp Pro  Ala Pro Gly
        1025                1030                 1035
```

```
Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 65
<211> LENGTH: 645
<212> TYPE: PRT
<213> ORGANISM: Homo sapiens

<400> SEQUENCE: 65

Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
            20                  25                  30

Pro Ala Glu Gln Arg Ala Ser Pro Leu Thr Ser Ile Ile Ser Ala Val
        35                  40                  45

Val Gly Ile Leu Leu Val Val Val Leu Gly Val Val Phe Gly Ile Leu
    50                  55                  60

Ile Lys Arg Arg Gln Gln Lys Ile Arg Lys Tyr Thr Met Arg Arg Leu
65                  70                  75                  80

Leu Gln Glu Thr Glu Leu Val Glu Pro Leu Thr Pro Ser Gly Ala Met
                85                  90                  95

Pro Asn Gln Ala Gln Met Arg Ile Leu Lys Glu Thr Glu Leu Arg Lys
            100                 105                 110

Val Lys Val Leu Gly Ser Gly Ala Phe Gly Thr Val Tyr Lys Gly Ile
        115                 120                 125

Trp Ile Pro Asp Gly Glu Asn Val Lys Ile Pro Val Ala Ile Lys Val
```

```
            130                 135                 140
Leu Arg Glu Asn Thr Ser Pro Lys Ala Asn Lys Glu Ile Leu Asp Glu
145                 150                 155                 160

Ala Tyr Val Met Ala Gly Val Gly Ser Pro Tyr Val Ser Arg Leu Leu
                165                 170                 175

Gly Ile Cys Leu Thr Ser Thr Val Gln Leu Val Thr Gln Leu Met Pro
            180                 185                 190

Tyr Gly Cys Leu Leu Asp His Val Arg Glu Asn Arg Gly Arg Leu Gly
        195                 200                 205

Ser Gln Asp Leu Leu Asn Trp Cys Met Gln Ile Ala Lys Gly Met Ser
    210                 215                 220

Tyr Leu Glu Asp Val Arg Leu Val His Arg Asp Leu Ala Ala Arg Asn
225                 230                 235                 240

Val Leu Val Lys Ser Pro Asn His Val Lys Ile Thr Asp Phe Gly Leu
                245                 250                 255

Ala Arg Leu Leu Asp Ile Asp Glu Thr Glu Tyr His Ala Asp Gly Gly
            260                 265                 270

Lys Val Pro Ile Lys Trp Met Ala Leu Glu Ser Ile Leu Arg Arg Arg
        275                 280                 285

Phe Thr His Gln Ser Asp Val Trp Ser Tyr Gly Val Thr Val Trp Glu
    290                 295                 300

Leu Met Thr Phe Gly Ala Lys Pro Tyr Asp Gly Ile Pro Ala Arg Glu
305                 310                 315                 320

Ile Pro Asp Leu Leu Glu Lys Gly Glu Arg Leu Pro Gln Pro Pro Ile
                325                 330                 335

Cys Thr Ile Asp Val Tyr Met Ile Met Val Lys Cys Trp Met Ile Asp
            340                 345                 350

Ser Glu Cys Arg Pro Arg Phe Arg Glu Leu Val Ser Glu Phe Ser Arg
        355                 360                 365

Met Ala Arg Asp Pro Gln Arg Phe Val Val Ile Gln Asn Glu Asp Leu
    370                 375                 380

Gly Pro Ala Ser Pro Leu Asp Ser Thr Phe Tyr Arg Ser Leu Leu Glu
385                 390                 395                 400

Asp Asp Asp Met Gly Asp Leu Val Asp Ala Glu Glu Tyr Leu Val Pro
                405                 410                 415

Gln Gln Gly Phe Phe Cys Pro Asp Pro Ala Pro Gly Ala Gly Gly Met
            420                 425                 430

Val His His Arg His Arg Ser Ser Ser Thr Arg Ser Gly Gly Gly Asp
        435                 440                 445

Leu Thr Leu Gly Leu Glu Pro Ser Glu Glu Glu Ala Pro Arg Ser Pro
450                 455                 460

Leu Ala Pro Ser Glu Gly Ala Gly Ser Asp Val Phe Asp Gly Asp Leu
465                 470                 475                 480

Gly Met Gly Ala Ala Lys Gly Leu Gln Ser Leu Pro Thr His Asp Pro
                485                 490                 495

Ser Pro Leu Gln Arg Tyr Ser Glu Asp Pro Thr Val Pro Leu Pro Ser
            500                 505                 510

Glu Thr Asp Gly Tyr Val Ala Pro Leu Thr Cys Ser Pro Gln Pro Glu
        515                 520                 525

Tyr Val Asn Gln Pro Asp Val Arg Pro Gln Pro Ser Pro Arg Glu
    530                 535                 540

Gly Pro Leu Pro Ala Ala Arg Pro Ala Gly Ala Thr Leu Glu Arg Pro
545                 550                 555                 560
```

```
Lys Thr Leu Ser Pro Gly Lys Asn Gly Val Lys Asp Val Phe Ala
                565                 570                 575

Phe Gly Gly Ala Val Glu Asn Pro Glu Tyr Leu Thr Pro Gln Gly Gly
            580                 585                 590

Ala Ala Pro Gln Pro His Pro Pro Ala Phe Ser Pro Ala Phe Asp
        595                 600                 605

Asn Leu Tyr Tyr Trp Asp Gln Asp Pro Pro Glu Arg Gly Ala Pro Pro
    610                 615                 620

Ser Thr Phe Lys Gly Thr Pro Thr Ala Glu Asn Pro Glu Tyr Leu Gly
625                 630                 635                 640

Leu Asp Val Pro Val
                645

<210> SEQ ID NO 66
<211> LENGTH: 569
<212> TYPE: PRT
<213> ORGANISM: Homo sapiens

<400> SEQUENCE: 66

Met Arg Arg Leu Leu Gln Glu Thr Glu Leu Val Glu Pro Leu Thr Pro
1               5                   10                  15

Ser Gly Ala Met Pro Asn Gln Ala Gln Met Arg Ile Leu Lys Glu Thr
            20                  25                  30

Glu Leu Arg Lys Val Lys Val Leu Gly Ser Gly Ala Phe Gly Thr Val
        35                  40                  45

Tyr Lys Gly Ile Trp Ile Pro Asp Gly Glu Asn Val Lys Ile Pro Val
    50                  55                  60

Ala Ile Lys Val Leu Arg Glu Asn Thr Ser Pro Lys Ala Asn Lys Glu
65                  70                  75                  80

Ile Leu Asp Glu Ala Tyr Val Met Ala Gly Val Gly Ser Pro Tyr Val
                85                  90                  95

Ser Arg Leu Leu Gly Ile Cys Leu Thr Ser Thr Val Gln Leu Val Thr
            100                 105                 110

Gln Leu Met Pro Tyr Gly Cys Leu Leu Asp His Val Arg Glu Asn Arg
        115                 120                 125

Gly Arg Leu Gly Ser Gln Asp Leu Leu Asn Trp Cys Met Gln Ile Ala
    130                 135                 140

Lys Gly Met Ser Tyr Leu Glu Asp Val Arg Leu Val His Arg Asp Leu
145                 150                 155                 160

Ala Ala Arg Asn Val Leu Val Lys Ser Pro Asn His Val Lys Ile Thr
                165                 170                 175

Asp Phe Gly Leu Ala Arg Leu Leu Asp Ile Asp Glu Thr Glu Tyr His
            180                 185                 190

Ala Asp Gly Gly Lys Val Pro Ile Lys Trp Met Ala Leu Glu Ser Ile
        195                 200                 205

Leu Arg Arg Arg Phe Thr His Gln Ser Asp Val Trp Ser Tyr Gly Val
    210                 215                 220

Thr Val Trp Glu Leu Met Thr Phe Gly Ala Lys Pro Tyr Asp Gly Ile
225                 230                 235                 240

Pro Ala Arg Glu Ile Pro Asp Leu Leu Glu Lys Gly Glu Arg Leu Pro
                245                 250                 255

Gln Pro Pro Ile Cys Thr Ile Asp Val Tyr Met Ile Met Val Lys Cys
            260                 265                 270

Trp Met Ile Asp Ser Glu Cys Arg Pro Arg Phe Arg Glu Leu Val Ser
```

```
                         275                 280                 285
    Glu Phe Ser Arg Met Ala Arg Asp Pro Gln Arg Phe Val Val Ile Gln
    290                 295                 300

Asn Glu Asp Leu Gly Pro Ala Ser Pro Leu Asp Ser Thr Phe Tyr Arg
305                 310                 315                 320

Ser Leu Leu Glu Asp Asp Met Gly Asp Leu Val Asp Ala Glu Glu
                    325                 330                 335

Tyr Leu Val Pro Gln Gln Gly Phe Phe Cys Pro Asp Pro Ala Pro Gly
                340                 345                 350

Ala Gly Gly Met Val His His Arg His Arg Ser Ser Thr Arg Ser
                    355                 360                 365

Gly Gly Gly Asp Leu Thr Leu Gly Leu Glu Pro Ser Glu Glu Ala
                370                 375                 380

Pro Arg Ser Pro Leu Ala Pro Ser Glu Gly Ala Gly Ser Asp Val Phe
385                 390                 395                 400

Asp Gly Asp Leu Gly Met Gly Ala Ala Lys Gly Leu Gln Ser Leu Pro
                    405                 410                 415

Thr His Asp Pro Ser Pro Leu Gln Arg Tyr Ser Glu Asp Pro Thr Val
                420                 425                 430

Pro Leu Pro Ser Glu Thr Asp Gly Tyr Val Ala Pro Leu Thr Cys Ser
                435                 440                 445

Pro Gln Pro Glu Tyr Val Asn Gln Pro Asp Val Arg Pro Gln Pro Pro
                450                 455                 460

Ser Pro Arg Glu Gly Pro Leu Pro Ala Ala Arg Pro Ala Gly Ala Thr
465                 470                 475                 480

Leu Glu Arg Pro Lys Thr Leu Ser Pro Gly Lys Asn Gly Val Val Lys
                    485                 490                 495

Asp Val Phe Ala Phe Gly Gly Ala Val Glu Asn Pro Glu Tyr Leu Thr
                    500                 505                 510

Pro Gln Gly Gly Ala Ala Pro Gln Pro His Pro Pro Ala Phe Ser
                515                 520                 525

Pro Ala Phe Asp Asn Leu Tyr Tyr Trp Asp Gln Asp Pro Pro Glu Arg
                530                 535                 540

Gly Ala Pro Pro Ser Thr Phe Lys Gly Thr Pro Thr Ala Glu Asn Pro
545                 550                 555                 560

Glu Tyr Leu Gly Leu Asp Val Pro Val
                    565

<210> SEQ ID NO 67
<211> LENGTH: 1240
<212> TYPE: PRT
<213> ORGANISM: Homo sapiens

<400> SEQUENCE: 67

Met Pro Arg Gly Ser Trp Lys Pro Gln Val Cys Thr Gly Thr Asp Met
    1               5                   10                  15

Lys Leu Arg Leu Pro Ala Ser Pro Glu Thr His Leu Asp Met Leu Arg
                    20                  25                  30

His Leu Tyr Gln Gly Cys Gln Val Val Gln Gly Asn Leu Glu Leu Thr
                    35                  40                  45

Tyr Leu Pro Thr Asn Ala Ser Leu Ser Phe Leu Gln Asp Ile Gln Glu
                50                  55                  60

Val Gln Gly Tyr Val Leu Ile Ala His Asn Gln Val Arg Gln Val Pro
    65                  70                  75                  80
```

```
Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
            115                 120                 125

Ser Leu Thr Glu Ile Leu Lys Gly Gly Val Leu Ile Gln Arg Asn Pro
130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
            195                 200                 205

Cys Ala Arg Cys Lys Gly Pro Leu Pro Thr Asp Cys Cys His Glu Gln
            210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
            275                 280                 285

Leu Ser Thr Asp Val Gly Ser Cys Thr Leu Val Cys Pro Leu His Asn
290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
            355                 360                 365

Asp Pro Ala Ser Asn Thr Ala Pro Leu Gln Pro Glu Gln Leu Gln Val
            370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
            435                 440                 445

Gly Leu Ala Leu Ile His His Asn Thr His Leu Cys Phe Val His Thr
            450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
```

```
                500                 505                 510
        Cys Val Asn Cys Ser Gln Phe Leu Arg Gly Gln Glu Cys Val Glu Glu
                    515                 520                 525
        Cys Arg Val Leu Gln Gly Leu Pro Arg Glu Tyr Val Asn Ala Arg His
                530                 535                 540
        Cys Leu Pro Cys His Pro Glu Cys Gln Pro Gln Asn Gly Ser Val Thr
        545                 550                 555                 560
        Cys Phe Gly Pro Glu Ala Asp Gln Cys Val Ala Cys Ala His Tyr Lys
                            565                 570                 575
        Asp Pro Pro Phe Cys Val Ala Arg Cys Pro Ser Gly Val Lys Pro Asp
                        580                 585                 590
        Leu Ser Tyr Met Pro Ile Trp Lys Phe Pro Asp Glu Glu Gly Ala Cys
                    595                 600                 605
        Gln Pro Cys Pro Ile Asn Cys Thr His Ser Cys Val Asp Leu Asp Asp
                610                 615                 620
        Lys Gly Cys Pro Ala Glu Gln Arg Ala Ser Pro Leu Thr Ser Ile Ile
        625                 630                 635                 640
        Ser Ala Val Val Gly Ile Leu Leu Val Val Val Leu Gly Val Val Phe
                            645                 650                 655
        Gly Ile Leu Ile Lys Arg Arg Gln Gln Lys Ile Arg Lys Tyr Thr Met
                        660                 665                 670
        Arg Arg Leu Leu Gln Glu Thr Glu Leu Val Glu Pro Leu Thr Pro Ser
                    675                 680                 685
        Gly Ala Met Pro Asn Gln Ala Gln Met Arg Ile Leu Lys Glu Thr Glu
                690                 695                 700
        Leu Arg Lys Val Lys Val Leu Gly Ser Gly Ala Phe Gly Thr Val Tyr
        705                 710                 715                 720
        Lys Gly Ile Trp Ile Pro Asp Gly Glu Asn Val Lys Ile Pro Val Ala
                            725                 730                 735
        Ile Lys Val Leu Arg Glu Asn Thr Ser Pro Lys Ala Asn Lys Glu Ile
                        740                 745                 750
        Leu Asp Glu Ala Tyr Val Met Ala Gly Val Gly Ser Pro Tyr Val Ser
                    755                 760                 765
        Arg Leu Leu Gly Ile Cys Leu Thr Ser Thr Val Gln Leu Val Thr Gln
                770                 775                 780
        Leu Met Pro Tyr Gly Cys Leu Leu Asp His Val Arg Glu Asn Arg Gly
        785                 790                 795                 800
        Arg Leu Gly Ser Gln Asp Leu Leu Asn Trp Cys Met Gln Ile Ala Lys
                            805                 810                 815
        Gly Met Ser Tyr Leu Glu Asp Val Arg Leu Val His Arg Asp Leu Ala
                        820                 825                 830
        Ala Arg Asn Val Leu Val Lys Ser Pro Asn His Val Lys Ile Thr Asp
                    835                 840                 845
        Phe Gly Leu Ala Arg Leu Leu Asp Ile Asp Glu Thr Glu Tyr His Ala
                850                 855                 860
        Asp Gly Gly Lys Val Pro Ile Lys Trp Met Ala Leu Glu Ser Ile Leu
        865                 870                 875                 880
        Arg Arg Arg Phe Thr His Gln Ser Asp Val Trp Ser Tyr Gly Val Thr
                            885                 890                 895
        Val Trp Glu Leu Met Thr Phe Gly Ala Lys Pro Tyr Asp Gly Ile Pro
                        900                 905                 910
        Ala Arg Glu Ile Pro Asp Leu Leu Glu Lys Gly Glu Arg Leu Pro Gln
                    915                 920                 925
```

```
Pro Pro Ile Cys Thr Ile Asp Val Tyr Met Ile Met Val Lys Cys Trp
        930                 935                 940

Met Ile Asp Ser Glu Cys Arg Pro Arg Phe Arg Glu Leu Val Ser Glu
945                 950                 955                 960

Phe Ser Arg Met Ala Arg Asp Pro Gln Arg Phe Val Ile Gln Asn
                965                 970                 975

Glu Asp Leu Gly Pro Ala Ser Pro Leu Asp Ser Thr Phe Tyr Arg Ser
            980                 985                 990

Leu Leu Glu Asp Asp Asp Met Gly Asp Leu Val Asp Ala Glu Glu Tyr
        995                 1000                1005

Leu Val Pro Gln Gln Gly Phe Phe Cys Pro Asp Pro Ala Pro Gly
    1010                1015                1020

Ala Gly Gly Met Val His His Arg His Arg Ser Ser Ser Thr Arg
    1025                1030                1035

Ser Gly Gly Gly Asp Leu Thr Leu Gly Leu Glu Pro Ser Glu Glu
    1040                1045                1050

Glu Ala Pro Arg Ser Pro Leu Ala Pro Ser Glu Gly Ala Gly Ser
    1055                1060                1065

Asp Val Phe Asp Gly Asp Leu Gly Met Gly Ala Ala Lys Gly Leu
    1070                1075                1080

Gln Ser Leu Pro Thr His Asp Pro Ser Pro Leu Gln Arg Tyr Ser
    1085                1090                1095

Glu Asp Pro Thr Val Pro Leu Pro Ser Glu Thr Asp Gly Tyr Val
    1100                1105                1110

Ala Pro Leu Thr Cys Ser Pro Gln Pro Glu Tyr Val Asn Gln Pro
    1115                1120                1125

Asp Val Arg Pro Gln Pro Pro Ser Pro Arg Glu Gly Pro Leu Pro
    1130                1135                1140

Ala Ala Arg Pro Ala Gly Ala Thr Leu Glu Arg Pro Lys Thr Leu
    1145                1150                1155

Ser Pro Gly Lys Asn Gly Val Val Lys Asp Val Phe Ala Phe Gly
    1160                1165                1170

Gly Ala Val Glu Asn Pro Glu Tyr Leu Thr Pro Gln Gly Gly Ala
    1175                1180                1185

Ala Pro Gln Pro His Pro Pro Ala Phe Ser Pro Ala Phe Asp
    1190                1195                1200

Asn Leu Tyr Tyr Trp Asp Gln Asp Pro Pro Glu Arg Gly Ala Pro
    1205                1210                1215

Pro Ser Thr Phe Lys Gly Thr Pro Thr Ala Glu Asn Pro Glu Tyr
    1220                1225                1230

Leu Gly Leu Asp Val Pro Val
    1235                1240

<210> SEQ ID NO 68
<211> LENGTH: 1225
<212> TYPE: PRT
<213> ORGANISM: Homo sapiens

<400> SEQUENCE: 68

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
                20                  25                  30

Thr Tyr Leu Pro Thr Asn Ala Ser Leu Ser Phe Leu Gln Asp Ile Gln
```

-continued

```
             35                  40                  45
Glu Val Gln Gly Tyr Val Leu Ile Ala His Asn Gln Val Arg Gln Val
 50                  55                  60
Pro Leu Gln Arg Leu Arg Ile Val Arg Gly Thr Gln Leu Phe Glu Asp
 65                  70                  75                  80
Asn Tyr Ala Leu Ala Val Leu Asp Asn Gly Asp Pro Leu Asn Asn Thr
                 85                  90                  95
Thr Pro Val Thr Gly Ala Ser Pro Gly Gly Leu Arg Glu Leu Gln Leu
            100                 105                 110
Arg Ser Leu Thr Glu Ile Leu Lys Gly Gly Val Leu Ile Gln Arg Asn
            115                 120                 125
Pro Gln Leu Cys Tyr Gln Asp Thr Ile Leu Trp Lys Asp Ile Phe His
130                 135                 140
Lys Asn Asn Gln Leu Ala Leu Thr Leu Ile Asp Thr Asn Arg Ser Arg
145                 150                 155                 160
Ala Cys His Pro Cys Ser Pro Met Cys Lys Gly Ser Arg Cys Trp Gly
                165                 170                 175
Glu Ser Ser Glu Asp Cys Gln Ser Leu Thr Arg Thr Val Cys Ala Gly
            180                 185                 190
Gly Cys Ala Arg Cys Lys Gly Pro Leu Pro Thr Asp Cys Cys His Glu
            195                 200                 205
Gln Cys Ala Ala Gly Cys Thr Gly Pro Lys His Ser Asp Cys Leu Ala
210                 215                 220
Cys Leu His Phe Asn His Ser Gly Ile Cys Glu Leu His Cys Pro Ala
225                 230                 235                 240
Leu Val Thr Tyr Asn Thr Asp Thr Phe Glu Ser Met Pro Asn Pro Glu
                245                 250                 255
Gly Arg Tyr Thr Phe Gly Ala Ser Cys Val Thr Ala Cys Pro Tyr Asn
            260                 265                 270
Tyr Leu Ser Thr Asp Val Gly Ser Cys Thr Leu Val Cys Pro Leu His
            275                 280                 285
Asn Gln Glu Val Thr Ala Glu Asp Gly Thr Gln Arg Cys Glu Lys Cys
290                 295                 300
Ser Lys Pro Cys Ala Arg Val Cys Tyr Gly Leu Gly Met Glu His Leu
305                 310                 315                 320
Arg Glu Val Arg Ala Val Thr Ser Ala Asn Ile Gln Glu Phe Ala Gly
                325                 330                 335
Cys Lys Lys Ile Phe Gly Ser Leu Ala Phe Leu Pro Glu Ser Phe Asp
            340                 345                 350
Gly Asp Pro Ala Ser Asn Thr Ala Pro Leu Gln Pro Glu Gln Leu Gln
            355                 360                 365
Val Phe Glu Thr Leu Glu Glu Ile Thr Gly Tyr Leu Tyr Ile Ser Ala
370                 375                 380
Trp Pro Asp Ser Leu Pro Asp Leu Ser Val Phe Gln Asn Leu Gln Val
385                 390                 395                 400
Ile Arg Gly Arg Ile Leu His Asn Gly Ala Tyr Ser Leu Thr Leu Gln
                405                 410                 415
Gly Leu Gly Ile Ser Trp Leu Gly Leu Arg Ser Leu Arg Glu Leu Gly
            420                 425                 430
Ser Gly Leu Ala Leu Ile His His Asn Thr His Leu Cys Phe Val His
            435                 440                 445
Thr Val Pro Trp Asp Gln Leu Phe Arg Asn Pro His Gln Ala Leu Leu
450                 455                 460
```

```
His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
    610                 615                 620

Ile Ser Ala Val Val Gly Ile Leu Leu Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880
```

```
Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
        995                 1000                1005

Ala Gly Gly Met Val His His Arg His Arg Ser Ser Ser Thr Arg
        1010                1015                1020

Ser Gly Gly Gly Asp Leu Thr Leu Gly Leu Glu Pro Ser Glu Glu
        1025                1030                1035

Glu Ala Pro Arg Ser Pro Leu Ala Pro Ser Glu Gly Ala Gly Ser
        1040                1045                1050

Asp Val Phe Asp Gly Asp Leu Gly Met Gly Ala Ala Lys Gly Leu
        1055                1060                1065

Gln Ser Leu Pro Thr His Asp Pro Ser Pro Leu Gln Arg Tyr Ser
        1070                1075                1080

Glu Asp Pro Thr Val Pro Leu Pro Ser Glu Thr Asp Gly Tyr Val
        1085                1090                1095

Ala Pro Leu Thr Cys Ser Pro Gln Pro Glu Tyr Val Asn Gln Pro
        1100                1105                1110

Asp Val Arg Pro Gln Pro Pro Ser Pro Arg Glu Gly Pro Leu Pro
        1115                1120                1125

Ala Ala Arg Pro Ala Gly Ala Thr Leu Glu Arg Pro Lys Thr Leu
        1130                1135                1140

Ser Pro Gly Lys Asn Gly Val Val Lys Asp Val Phe Ala Phe Gly
        1145                1150                1155

Gly Ala Val Glu Asn Pro Glu Tyr Leu Thr Pro Gln Gly Gly Ala
        1160                1165                1170

Ala Pro Gln Pro His Pro Pro Ala Phe Ser Pro Ala Phe Asp
        1175                1180                1185

Asn Leu Tyr Tyr Trp Asp Gln Asp Pro Pro Glu Arg Gly Ala Pro
        1190                1195                1200

Pro Ser Thr Phe Lys Gly Thr Pro Thr Ala Glu Asn Pro Glu Tyr
        1205                1210                1215

Leu Gly Leu Asp Val Pro Val
        1220                1225

<210> SEQ ID NO 69
<211> LENGTH: 888
<212> TYPE: PRT
<213> ORGANISM: Homo sapiens

<400> SEQUENCE: 69

Met Glu Leu Ala Ala Leu Cys Arg Trp Gly Leu Leu Leu Ala Leu Leu
1               5                   10                  15
```

```
Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430
```

```
Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                    485                 490                 495

Ala Asn Arg Pro Glu Asp Glu Cys Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Pro Leu Thr Ser Ile Ile Ser
625                 630                 635                 640

Ala Val Val Gly Ile Leu Leu Val Val Leu Gly Val Val Phe Gly
                645                 650                 655

Ile Leu Ile Lys Arg Arg Gln Gln Lys Ile Arg Lys Tyr Thr Met Arg
            660                 665                 670

Arg Leu Leu Gln Glu Thr Glu Leu Val Glu Pro Leu Thr Pro Ser Gly
                675                 680                 685

Ala Met Pro Asn Gln Ala Gln Met Arg Ile Leu Lys Glu Thr Glu Leu
690                 695                 700

Arg Lys Val Lys Val Leu Gly Ser Gly Ala Phe Gly Thr Val Tyr Lys
705                 710                 715                 720

Gly Ile Trp Ile Pro Asp Gly Glu Asn Val Lys Ile Pro Val Ala Ile
                    725                 730                 735

Lys Val Leu Arg Glu Asn Thr Ser Pro Lys Ala Asn Lys Glu Ile Leu
                740                 745                 750

Asp Glu Thr Ile Ser Asn Leu Phe Ser Asn Phe Ala Pro Arg Gly Pro
            755                 760                 765

Ser Ala Cys Cys Glu Pro Thr Cys Trp Cys His Ser Gly Lys Gly Gln
        770                 775                 780

Asp Ser Leu Pro Arg Glu Glu Trp Gly Arg Gln Arg Phe Cys Leu
785                 790                 795                 800

Trp Gly Cys Arg Gly Glu Pro Arg Val Leu Asp Thr Pro Gly Arg Ser
                805                 810                 815

Cys Pro Ser Ala Pro Pro Ser Ser Cys Leu Gln Pro Ser Leu Arg Gln
            820                 825                 830

Pro Leu Leu Leu Gly Pro Gly Pro Thr Arg Ala Gly Gly Ser Thr Gln
                835                 840                 845

His Leu Gln Arg Asp Thr Tyr Gly Arg Glu Pro Arg Val Pro Gly Ser
```

```
                850                 855                 860
Gly Arg Ala Ser Val Asn Gln Lys Ala Lys Ser Ala Glu Ala Leu Met
865                 870                 875                 880

Cys Pro Gln Gly Ala Gly Lys Ala
                885

<210> SEQ ID NO 70
<211> LENGTH: 186
<212> TYPE: PRT
<213> ORGANISM: Homo sapiens

<400> SEQUENCE: 70

Met Glu Pro Thr Arg Asp Cys Pro Leu Phe Gly Gly Ala Phe Ser Ala
1               5                   10                  15

Ile Leu Pro Met Gly Ala Ile Asp Val Ser Asp Leu Arg Pro Val Pro
                20                  25                  30

Asp Asn Gln Glu Val Phe Cys His Pro Val Thr Asp Gln Ser Leu Ile
            35                  40                  45

Val Glu Leu Leu Glu Leu Gln Ala His Val Arg Gly Glu Ala Ala Ala
        50                  55                  60

Arg Tyr His Phe Glu Asp Val Gly Gly Val Gln Gly Ala Arg Ala Val
65                  70                  75                  80

His Val Glu Ser Val Gln Pro Leu Ser Leu Glu Asn Leu Ala Leu Arg
                85                  90                  95

Gly Arg Cys Gln Glu Ala Trp Val Leu Ser Gly Lys Gln Gln Ile Ala
            100                 105                 110

Lys Glu Asn Gln Gln Val Ala Lys Asp Val Thr Leu His Gln Ala Leu
        115                 120                 125

Leu Arg Leu Pro Gln Tyr Gln Thr Asp Leu Leu Leu Thr Phe Asn Gln
130                 135                 140

Pro Pro Pro Asp Asn Arg Ser Ser Leu Gly Pro Glu Asn Leu Ser Pro
145                 150                 155                 160

Ala Pro Trp Ser Leu Gly Asp Phe Glu Gln Leu Val Thr Ser Leu Thr
                165                 170                 175

Leu His Asp Pro Asn Ile Phe Gly Pro Gln
            180                 185

<210> SEQ ID NO 71
<211> LENGTH: 146
<212> TYPE: PRT
<213> ORGANISM: Homo sapiens

<400> SEQUENCE: 71

Met Glu Pro Thr Arg Asp Cys Pro Leu Phe Gly Gly Ala Phe Ser Ala
1               5                   10                  15

Ile Leu Pro Met Gly Ala Ile Asp Val Ser Asp Leu Arg Pro Val Pro
                20                  25                  30

Asp Asn Gln Glu Val Phe Cys His Pro Val Thr Asp Gln Ser Leu Ile
            35                  40                  45

Val Glu Leu Leu Glu Leu Gln Ala His Val Arg Gly Glu Ala Ala Ala
        50                  55                  60

Arg Tyr His Phe Glu Asp Val Gly Gly Val Gln Gly Ala Arg Ala Val
65                  70                  75                  80

His Val Glu Ser Val Gln Pro Leu Ser Leu Glu Asn Leu Ala Leu Arg
                85                  90                  95

Gly Arg Cys Gln Glu Ala Trp Val Leu Ser Gly Lys Gln Gln Ile Ala
```

```
            100                 105                 110
Lys Glu Asn Gln Gln Val Ala Lys Asp Val Thr Leu His Gln Ala Leu
        115                 120                 125

Leu Arg Leu Pro Gln Tyr Gln Thr Asp Leu Leu Leu Thr Phe Asn Gln
        130                 135                 140

Pro Pro
145

<210> SEQ ID NO 72
<211> LENGTH: 165
<212> TYPE: PRT
<213> ORGANISM: Homo sapiens

<400> SEQUENCE: 72

Met Glu Pro Thr Arg Asp Cys Pro Leu Phe Gly Gly Ala Phe Ser Ala
1               5                   10                  15

Ile Leu Pro Met Gly Ala Ile Asp Val Ser Asp Leu Arg Pro Val Pro
            20                  25                  30

Asp Asn Gln Glu Val Phe Cys His Pro Val Thr Asp Gln Ser Leu Ile
        35                  40                  45

Val Glu Leu Leu Glu Leu Gln Ala His Val Arg Gly Glu Ala Ala Ala
    50                  55                  60

Arg Tyr His Phe Glu Asp Val Gly Gly Val Gln Gly Ala Arg Ala Val
65                  70                  75                  80

His Val Glu Ser Val Gln Pro Leu Ser Leu Glu Asn Leu Ala Leu Arg
                85                  90                  95

Gly Arg Cys Gln Glu Ala Trp Val Leu Ser Gly Lys Gln Gln Ile Ala
            100                 105                 110

Lys Glu Asn Gln Gln Val Arg Ala Arg Glu Cys Val Met Ser Trp Lys
        115                 120                 125

Gly Gly Ser Gly Asp Ala Glu Ile Gln Val Ser Ile Leu Thr Leu Ile
    130                 135                 140

Pro Leu Gly Ser Lys Gly Arg Asp Thr Ser Ser Gly Leu Ala Glu Ala
145                 150                 155                 160

Ala Pro Val Pro Asp
                165

<210> SEQ ID NO 73
<211> LENGTH: 118
<212> TYPE: PRT
<213> ORGANISM: Homo sapiens

<400> SEQUENCE: 73

Met Glu Pro Thr Arg Asp Cys Pro Leu Phe Gly Gly Ala Phe Ser Ala
1               5                   10                  15

Ile Leu Pro Met Gly Ala Ile Asp Val Ser Asp Leu Arg Pro Val Pro
            20                  25                  30

Asp Asn Gln Glu Val Phe Cys His Pro Val Thr Asp Gln Ser Leu Ile
        35                  40                  45

Val Glu Leu Leu Glu Leu Gln Ala His Val Arg Gly Glu Ala Ala Ala
    50                  55                  60

Arg Tyr His Phe Glu Asp Val Gly Gly Val Gln Gly Ala Arg Ala Val
65                  70                  75                  80

His Val Glu Ser Val Gln Pro Leu Ser Leu Glu Asn Leu Ala Leu Arg
                85                  90                  95
```

```
Gly Arg Cys Gln Glu Ala Trp Val Leu Ser Gly Lys Gln Gln Ile Ala
            100                 105                 110

Lys Glu Asn Gln Gln Pro
            115
```